United States Patent
Clelland et al.

(10) Patent No.: US 11,814,681 B2
(45) Date of Patent: Nov. 14, 2023

(54) METHOD FOR PREDICTING A SUBJECTS RESPONSE TO SLC MODULATOR THERAPY

(71) Applicants: THE TRUSTEES OF COLUMBIA UNIVERSITY IN THE CITY OF NEW YORK, New York, NY (US); RESEARCH FOUNDATION FOR MENTAL HYGIENE, INC., Menands, NY (US)

(72) Inventors: Catherine L. Clelland, New York, NY (US); James D. Clelland, New York, NY (US)

(73) Assignees: THE TRUSTEES OF COLUMBIA UNIVERSITY IN THE CITY OF NEW YORK, New York, NY (US); RESEARCH FOUNDATION FOR MENTAL HYGIENE, INC., Menands, NY (US)

( * ) Notice: Subject to any disclaimer, the term of this patent is extended or adjusted under 35 U.S.C. 154(b) by 663 days.

(21) Appl. No.: 16/805,410

(22) Filed: Feb. 28, 2020

(65) Prior Publication Data

US 2021/0254158 A1 Aug. 19, 2021

Related U.S. Application Data

(63) Continuation-in-part of application No. PCT/US2018/048345, filed on Aug. 28, 2018.
(60) Provisional application No. 62/550,879, filed on Aug. 28, 2017.

(51) Int. Cl.
| | |
|---|---|
| *C12Q 1/6883* | (2018.01) |
| *A61P 25/18* | (2006.01) |
| *A61K 31/429* | (2006.01) |
| *A61K 31/439* | (2006.01) |
| *A61K 31/506* | (2006.01) |
| *G01N 33/68* | (2006.01) |

(52) U.S. Cl.
CPC .......... *C12Q 1/6883* (2013.01); *A61K 31/429* (2013.01); *A61K 31/439* (2013.01); *A61K 31/506* (2013.01); *A61P 25/18* (2018.01); *G01N 33/6896* (2013.01); *C12Q 2600/156* (2013.01); *C12Q 2600/158* (2013.01); *G01N 2800/302* (2013.01); *G01N 2800/304* (2013.01); *G01N 2800/52* (2013.01)

(58) Field of Classification Search
CPC .................................................. G01N 33/6896
See application file for complete search history.

(56) References Cited

PUBLICATIONS

Allen NC, et al. Systematic meta-analyses and field synopsis of genetic association studies in schizophrenia: the SzGene database. Nat Genet 2008; 40(7):827-34.
Baker KD, Skuse DH. Adolescents and young adults with 22q11 deletion syndrome: psychopathology in an at-risk group. Br J Psychiatry 2005; 186:115-20.
Baxter CF, et al. High proline levels in the brains of mice as related to specific learning deficits. Pharmacol Biochem Behav 1985; 22(6):1053-9.
Bender HU, et al. Functional consequences of PRODH missense mutations. Am J Hum Genet 2005; 76:409-20.
Bilder RM, et al. The catechol-O-methyltransferase polymorphism: relations to the tonic-phasic dopamine hypothesis and neuropsychiatric phenotypes. Neuropsychopharmacology 2004; 29(11):1943-61.
Blanchard JJ, et al. Toward the next generation of negative symptom assessments: the collaboration to advance negative symptom assessment in schizophrenia. Schizophr Bull 2011; 37(2):291-9.
Chen J, et al. Functional analysis of genetic variation in catechol-O-methyltransferase (COMT): effects on mRNA, protein, and enzyme activity in postmortem human brain. Am J Hum Genet 2004; 75(5):807-21.
Clelland CL, et al. Evidence for association of hyperprolinemia with schizophrenia and a measure of clinical outcome. Schizophr Res 2011; 131(1-3):139-45.
Clelland CL, et al. Evidence that COMT genotype and proline interact on negative-symptom outcomes in schizophrenia and bipolar disorder. Translational Psychiatry 2016. In press.
Cohen SM, Nadler JV. Proline-induced inhibition of glutamate release in hippocampal area CA1. Brain Res 1997; 769:333-9.
Cohen SM, Nadler JV. Proline-induced potentiation of glutamate transmission. Brain Res 1997; 761:271-82.
Crabtree GW, et al. Cytosolic Accumulation of L-Proline Disrupts GABA-Ergic Transmission through GAD Blockade. Cell Rep Oct. 4, 2016;17(2):570-582.
Dingman W, Sporn MB. The penetration of proline and proline derivatives into brain. J Neurochem 1959; 4(2):148-53.
Donnelly CL, McEvoy JP, Wilson WH, Narasimhachari N. (1996) A study of the potential confounding effects of diet, caffeine, nicotine and lorazepam on the stability of plasma and urinary homovanillic acid levels in patients with schizophrenia. Biol Psychiatry. Dec. 15;40(12):1218-21.
Drake RE, Mueser KT. Co-occurring alcohol use disorder and schizophrenia. Alcohol Research & Health 2002; 26(2): 99-102.
Drew LJ, et al. The 22q11.2 microdeletion: fifteen years of insights into the genetic and neural complexity of psychiatric disorders. Int J Dev Neurosci 2011; 29(3):259-81.
Efrom ML. Familial hyperprolinemia. Report of a second case, associated with congenital renal malformations, hereditary hematuria and mild mental retardation, with demonstration of an enzyme defect. N Engl J Med 1965; 272:1243-54.
Fernandez-Garcimartin H, et al. Is it possible to combine different psychotic symptom scales in bipolar disorder? Psychiatry Res 2014; 220(3):1090-3.

(Continued)

*Primary Examiner* — Kevin E Weddington
(74) *Attorney, Agent, or Firm* — Bryan Cave Leighton Paisner, LLP

(57) ABSTRACT

The present invention provides, inter alia, methods for treating or ameliorating the effects of a disorder, such as schizophrenia or bipolar disorder, by increasing or decreasing proline levels. Further provided are methods of predicting and monitoring the clinical response in a patient, and diagnostic systems for identifying a patient likely to benefit from proline modulation.

10 Claims, 8 Drawing Sheets
(7 of 8 Drawing Sheet(s) Filed in Color)

Specification includes a Sequence Listing.

(56) References Cited

PUBLICATIONS

Fine SE, et al. Autism spectrum disorders and symptoms in children with molecularly confirmed 22q11.2 deletion syndrome. J Autism Dev Disord 2005; 35(4):461-70.

Goghari VM, Sponheim SR. Differential association of the COMT Val158Met polymorphism with clinical phenotypes in schizophrenia and bipolar disorder. Schizophr Res 2008; 103(1-3):186-91.

Gogos JA, et al. The gene encoding proline dehydrogenase modulates sensorimotor gating in mice. Nat Genet 1999; 21(4):434-9.

Gothelf D, et al. Obsessive-compulsive disorder in patients with velocardiofacial (22q11 deletion) syndrome. Am J Med Genet B Neuropsychiatr Genet. 2004; 126B(1):99-105.

Grainger DJ, Aitken S. A microtitre format assay for proline in human serum or plasma. Clin Chim Acta. 2004; 343(1-2):1 13-8.

Guillot CR, et al. COMT Associations with Disordered Gambling and Drinking Measures. J Gambl Stud. Jun. 2015; 31(2): 513-524.

Hashimoto K, et al. Decreased serum levels of D-serine in patients with schizophrenia: evidence in support of the N-methyl-D-aspartate receptor hypofunction hypothesis of schizophrenia. Arch Gen Psychiatry Jun. 2003; 60(6):572-6.

Huber-Smith MJ, Nesse R, Mazhar M, McCann DS. (1986) Evaluation of plasma 3-methoxy-4- hydroxyphenylglycol. J Chromatogr. Apr. 25, 1986;377:91-9.

Imaizumi, A., Adachi, Y., Kawaguchi, T et al. Genetic basis for plasma amino acid concentrations based on absolute quantification: a genome-wide association study in the Japanese population. *Eur J Hum Genet* 27, 621-630 (2019).

Inoue H, et al. Determination of total hydroxyproline and proline in human serum and urine by HPLC with fluorescence detection. Biol Pharm Bull. 1996;19(2):163-6.

Jacquet H, et al. Hyperprolinemia is a risk factor for schizoaffective disorder. Mol Psychiatry 2005; 10(5):479-85.

Jiménez-Jiménez FJ, et al. Neurotransmitter amino acids in cerebrospinal fluid of patients with Alzheimer's disease. J Neural Transm (Vienna) 1998; 105(2-3):269-77.

Joober R, et al. Catechol-O-methyltransferase Val-108/158-Met gene variants associated with performance on the Wisconsin Card Sorting Test. Arch Gen Psychiatry 2002; 59(7):662-3.

Kane J, et al. Clozapine for the treatment-resistant schizophrenic. A double-blind comparison with chlorpromazine. Arch Gen Psychiatry 1988; 45(9):789-96.

Karayiorgou M, et al. 22q11.2 microdeletions: linking DNA structural variation to brain dysfunction and schizophrenia. Nat Rev Neurosci 2010; 11:402-16.

Lachman HM, et al. Human catechol-O-methyltransferase pharmacogenetics: description of a functional polymorphism and its potential application to neuropsychiatric disorders. Pharmacogenetics 1996;6(3):243-50.

Le Boucher J, Charret C, Coudray-Lucas C, Giboudeau J, Cynober L. Amino acid determination in biological fluids by automated ion-exchange chromatography: performance of Hitachi L-8500A. Clin Chem. 1997; 43(8 Pt 1 ):1421-8.

Lewis DA, et al. Dopamine transporter immunoreactivity in monkey cerebral cortex: regional, laminar, and ultrastructural localization. J Comp Neurol 2001; 432(1):119-36.

Liang S, et al. Determination of proline in human serum by a robust LC-MS/MS method: application to identification of human metabolites as candidate biomarkers for esophageal cancer early detection and risk stratification. Biomed. Chromatogr. 2015, 29: 570-577.

Lindenmayer JP, et al. Dimensions of psychosis in patients with bipolar mania as measured by the positive and negative syndrome scale. Psychopathology 2008; 41(4):264-70.

Lorenz M, Paul F, Moobed M, Baumann G, Zimmermann BF, Stangl K, Stangl V. (2014) The activity of catechol-O-methyltransferase (COMT) is not impaired by high doses of epigallocatechin-3-gallate (EGCG) in vivo. Eur J Pharmacol. Oct. 5, 2014;740:645-51. doi: 10.1016/j.ejphar.2014.06.014. Epub Jun. 24, 2014.

Luykx JJ, et al. D-amino acid aberrations in cerebrospinal fluid and plasma of smokers. Neuropsychopharmacology Sep. 2013; 38(10):2019-26.

Luykx JJ, et al. Genome-wide association study of NMDA receptor coagonists in human cerebrospinal fluid and plasma. Mol Psychiatry. 2015; doi: 10.1038/mp.2014.190.

Masuda M, Tsunoda M, Yusa Y, Yamada S, Imai K.(2002) Assay of catechol-O-methyltransferase activity in human erythrocytes using norepinephrine as a natural substrate. Ann Clin Biochem. Nov;39(Pt 6):589-94.

McBride KL, Belmont JW, O'Brien WE, Amin TJ, Carter S, Lee BH. (2007) Heritability of plasma amino acid levels in different nutritional states. Mol Genet Metab;90(2):217-20.

Mohammad MG et al. Immune cell trafficking from the brain maintains CNS immunetolerance. J Clin Invest. Mar. 2014;124(3):1228-41. doi: 10.1172/JCI71544.Nadler JV. Sodium-dependent proline uptake in the rat hippocampal formation: association with ipsilateral-commissural projections of CA3 pyramidal cells. J Neurochem 1987; 49:1155-60.

Nackley AG, Shabalina SA, Tchivileva IE, Satterfield K, Korchynskyi O, Makarov SS, Maixner W, Diatchenko L. (2006) Human catechol-O-methyltransferase haplotypes modulate protein expression by altering mRNA secondary structure. Science. Dec. 22;314(5807):1930-3.

Nickolson VJ. "On" and "off" responses of K+-induced synaptosomal proline release: involvement of the sodium pump. J Neurochem 1982; 38:289-92.

Orešič M, et al. Metabolome in schizophrenia and other psychotic disorders: a general population-based study. Genome Med 2011; 3(3):19.

Paterlini M, et al. Transcriptional and behavioral interaction between 22q11.2 orthologs modulates schizophrenia-related phenotypes in mice. Nat Neurosci 2005; 8(11):1586-94.

Phang JM, et al. Disorders of proline and hydroxyproline metabolism, in Metabolic and molecular basis of inherited disease. New York, McGraw-Hill Press, 2001, pp. 1821-1838.

Pomara N, et al. Glutamate and other CSF amino acids in Alzheimer's disease. Am J Psychiatry Feb. 1992;149(2):251-4.

Raux G, et al. Involvement of hyperprolinemia in cognitive and psychiatric features of the 22q11 deletion syndrome. Hum Mol Genet 2007; 16(1):83-91.

Renick SE, et al. The mammalian brain high-affinity L-proline transporter is enriched preferentially in synaptic vesicles in a subpopulation of excitatory nerve terminals in rat forebrain. J Neurosci 1999; 19:21-33.

Rhee EP, et al. A genome-wide association study of the human metabolome in a community-based cohort. Cell Metab Jul. 2, 2013;18(1):130-43.

Scholl-Bürgi S, et al. The relation of cerebrospinal fluid and plasma glycine levels in propionic acidaemia, a 'ketotic hyperglycinaemia'. J Inherit Metab Dis Jun. 2008; 31(3):395-8.

Segall SK, Nackley AG, Diatchenko L, Lariviere WR, Lu X, Marron JS, Grabowski-Boase L, Walker JR, Slade G, Gauthier J, Bailey JS, Steffy BM, Maynard TM, Tarantino LM, Wiltshire T. (2010) Comt1 genotype and expression predicts anxiety and nociceptive sensitivity in inbred strains of mice. Genes Brain Behav. Nov;9(8):933-46. doi: 10.1111/j.1601-183X.2010.00633.x.

Shifman S, et al. A highly significant association between a COMT haplotype and schizophrenia. Am J Hum Genet 2002; 71(6):1296-302.

Shifman S, et al. COMT: a common susceptibility gene in bipolar disorder and schizophrenia. Am J Med Genet B Neuropsychiatr Genet 2004; 128B(1):61-4.

Sonne SC, Brady KT. Bipolar Disorder and Alcoholism. NIAAA publication Nov. 2002; http://pubs.niaaa.nih.gov/publications/arh26-2/103-108.htm.

Tomiya M, et al. Alterations in serum amino acid concentrations in male and female schizophrenic patients. Clin Chim Acta 2007; 380(1-2):186-90.

Tunbridge EM, et al. Catechol-o-methyltransferase, cognition, and psychosis: Val158Met and beyond. Biol Psychiatry 2006; 60:141-151.

(56) References Cited

PUBLICATIONS

Vorstman JA, et al. Proline affects brain function in 22q11DS children with the low activity COMT 158 allele. Neuropsychopharmacology 2009; 34(3):739-46.

Wu, G. Determination of proline by reversed-phase high-performance liquid chromatography with automated pre-column o-phthaldialdehyde derivatization. Journal of Chromatography A. vol. 641, Issue 1, 1993, pp. 168-175.

Yoneda Y, Roberts E. A new synaptosomal biosynthetic pathway of proline from ornithine and its negative feedback inhibition by proline. Brain Res 1982; 239:479-88.

Zarchi O, et al. Schizophrenia-like neurophysiological abnormalities in 22q11.2 deletion syndrome and their association to COMT and PRODH genotypes. J Psychiatr Res 2013; 47(11):1623-9.

SEQUENCE LISTING

```
<160> NUMBER OF SEQ ID NOS: 5

<210> SEQ ID NO 1
<211> LENGTH: 3651
<212> TYPE: DNA
<213> ORGANISM: Homo sapiens

<400> SEQUENCE: 1
agtattgctg ttcagatagc ctttatttgg gtatatattc tacactgttt ttaaatatgg      60
agagtaacca aaatggccca ttatctgacc acacaaatac tagtagtcat tatagataaa     120
ccatagcaga taaataatag taaacaaagc aacaggctgt gtcattggaa atccccacca     180
tgaagaaagg agcaaggtga aaacttctgg ctgcttcagg tcatgcatgg tccctctcca     240
ccatcgttcc ccctgtcatc ttcctgccag aataaggacc ctggtacctt agggaagcac     300
catctcttgt tttttcccca cgagccctgt gggtcatggc acgtcctgcc ccgctgggaa     360
aacacagtgg gccacgggtt tccctgcagg cctgaccct tcccagggt agcagcagaa      420 ggcagcacga ttcccactcc tgcagctgtg acagggcacc cccactgtca ctgagccctg     480
caccgggttc catcacctgc tcgggctct gcctttggcc ttttcctgtg aactgcatgt      540
tggccactgt acctatctgt ctctcatctt tttttcttac gggtttgggt atgttcttgg     600
taaaccagcc cttggtctta cacatcattt ccaaggtact aaggactctt caggggaaat     660
acaacttgag cagagtggtt ccctcctctt gtggttcaca aggtgcaggt gcacacacac     720
ataccacagg gcagtgtgac aggaccagag actgccctg gggtccctgg ctgggggaca      780
ctagtaggga tgtcccttgc ctctctgagg ccttctgctg tctcttctga ggccggaaag     840
gcgaagcact gccctcgccc tgctagggaa ggctcaggcc aggctggccc tatccgggga     900
aggggctcag gtatctggac cttggtcatc gccaggttag ggtttatgtt gatgattatc     960 caaagcaaa attgatttcc acagaaataa catctgcttt gctgccgagc cagaggagac      1020
cccagacccc tcccgcagcc agagggctgg agcctgctca gaggtgcttt gaaggtgagt     1080
tggccaacgg aagccgggc agtgccaggg tgggacagaa gaggcacaca cctgctctgt      1140
ctacccgagg gcaccagagg gcacgagaag gctggctccc tggcgctgac acgtcaggca     1200
actgaggcac aaggctggca tttctgaacc ttgcccctct gcgaacacaa ggggcgatg      1260 gtggcactcc aagcaaaggg gcgtgtgggt gctgcaggag gagcacagag cactggcgcc     1320
cctcccctcc cgccctgcag atgccggagg ccccgcctct gctgttggca gctgtgttgc     1380
tgggcctggt gctgctggtg gtgctgctgc tgcttctgag gcactggggc tggggcctgt     1440
gccttatcgg ctggaacgag ttcatcctgc agccatcca caacctgctc atgggtgaca     1500
ccaaggagca gcgcatcctg aaccacgtgc tgcagcatgc ggagcccggg aacgcacaga     1560
gcgtgctgga ggccattgac acctactgcg agcagaagga gtgggccatg aacgtgggcg     1620
```

-continued

```
acaagaaagg ttggggttcc gggccagcag gtgctcagct ctgggacagg gacccaggac    1680
caggcatcaa atcccgtgcc tggggatcca agttcccctc tctccacctg tgctcacctc    1740
tcctccgtcc ccaaccctgc acaggcaaga tcgtggacgc cgtgattcag gagcaccagc    1800
cctccgtgct gctggagctg ggggcctact gtggctactc agctgtgcgc atggcccgcc    1860
tgctgtcacc aggggcgagg ctcatcacca tcgagatcaa ccccgactgt gccgccatca    1920
cccagcggat ggtggatttc gctggcgtga aggacaaggt gtgcatgcct gacccgttgt    1980
cagacctgga aaaagggccg gctgtgggca gggcgggcat gcgcactttg atcctcccca    2040
ccaggtgttc acaccacgtt cactgaaaac ccactatcac cagggtcatc ccagaaccct    2100
aaagaaaact gatgaatgct tgtatgggtg tgtaaagatg gcctcctgtc tgtgtgggcg    2160
tgggcactga caggcgctgt tgtataggtg tgtagggatg gcctcctgtc tgtgaggacg    2220
tgggcactga caggcgctgt tccaggtcac ccttgtggtt ggagcgtccc aggacatcat    2280
cccccagctg aagaagaagt atgatgtgga cacactggac atggtcttcc tcgaccactg    2340
gaaggaccgg tacctgccgg acacgcttct cttggaggtg agccccaacc aggatggcat    2400
ccgtgccagc tgctgcccag agcccattca gtcagcctca gcctctccaa agagccaggc    2460
attccagtag agccctgtgt ggacacagct cgctctggag gcaccacctg aggtctggga    2520
gtgtggggga ctgaggaggc cctgtggtgg gtggagatgg gtggggagct gggccagggg    2580
ctggctgggt ggcctgttgg gaactgggga gccaagcggt ccctgtcctc acggggccca    2640
tgttctgaag gtggcaccca agtcttgtac agtcctttcc tgcaggagtc acgctgggca    2700
ggaagtggaa acctggcccc aggggctagg cacaggcagt ggtgccgtgg cctagtgagg    2760
agcacccatc ctggtttggg gcaggttctc tgggcacctc tgacctctca cctcccccac    2820
cccccggtct gtttgcagga atgtggcctg ctgcggaagg ggacagtgct actggctgac    2880
aacgtgatct gcccaggtgc gccagacttc ctagcacacg tgcgcgggag cagctgcttt    2940
gagtgcacac actaccaatc gttcctggaa tacaggagg tggtggacgg cctggagaag    3000
gccatctaca agggcccagg cagcgaagca gggccctgac tgcccccccg gccccctct    3060
cgggctctct cacccagcct ggtactgaag gtgccagacg tgctcctgct gaccttctgc    3120
ggctccgggc tgtgtcctaa atgcaaagca cacctcggcc gaggcctgcg ccctgacatg    3180
ctaacctctc tgaactgcaa cactggattg ttcttttta agactcaatc atgacttctt    3240
tactaacact ggctagctat attatcttat atactaatat catgttttaa aaatataaaa    3300
tagaaattaa gaatctaaat atttagatat aactcgactt agtacatcct tctcaactgc    3360
cattcccctg ctgcccttga cttgggcacc aaacattcaa agctcccctt gacggacgct    3420
aacgctaagg gcgggccct agctggctgg gttctgggtg gcacgcctgg cccactggcc    3480
tcccagccac agtggtgcag aggtcagccc tcctgcagct aggccagggg cacctgttag    3540
ccccatgggg acgactgccg gcctgggaaa cgaagaggag tcagccaagc attcacacct    3600
ttctgaccaa gcaggcgctg gggacaggtg gacccgcagc agcaccagcc c             3651
```

<210> SEQ ID NO 2
<211> LENGTH: 221
<212> TYPE: PRT
<213> ORGANISM: Homo sapiens

<400> SEQUENCE: 2

```
Met Gly Asp Thr Lys Glu Gln Arg Ile Leu Asn His Val Leu Gln His
1               5                   10                  15
```

Ala Glu Pro Gly Asn Ala Gln Ser Val Leu Glu Ala Ile Asp Thr Tyr
            20                  25                  30

Cys Glu Gln Lys Glu Trp Ala Met Asn Val Gly Asp Lys Lys Gly Lys
        35                  40                  45

Ile Val Asp Ala Val Ile Gln Glu His Gln Pro Ser Val Leu Leu Glu
    50                  55                  60

Leu Gly Ala Tyr Cys Gly Tyr Ser Ala Val Arg Met Ala Arg Leu Leu
65                  70                  75                  80

Ser Pro Gly Ala Arg Leu Ile Thr Ile Glu Ile Asn Pro Asp Cys Ala
                85                  90                  95

Ala Ile Thr Gln Arg Met Val Asp Phe Ala Gly Val Lys Asp Lys Val
            100                 105                 110

Thr Leu Val Val Gly Ala Ser Gln Asp Ile Ile Pro Gln Leu Lys Lys
        115                 120                 125

Lys Tyr Asp Val Asp Thr Leu Asp Met Val Phe Leu Asp His Trp Lys
    130                 135                 140

Asp Arg Tyr Leu Pro Asp Thr Leu Leu Leu Glu Glu Cys Gly Leu Leu
145                 150                 155                 160

Arg Lys Gly Thr Val Leu Leu Ala Asp Asn Val Ile Cys Pro Gly Ala
                165                 170                 175

Pro Asp Phe Leu Ala His Val Arg Gly Ser Ser Cys Phe Glu Cys Thr
            180                 185                 190

His Tyr Gln Ser Phe Leu Glu Tyr Arg Glu Val Val Asp Gly Leu Glu
        195                 200                 205

Lys Ala Ile Tyr Lys Gly Pro Gly Ser Glu Ala Gly Pro
    210                 215                 220

<210> SEQ ID NO 3
<211> LENGTH: 271
<212> TYPE: PRT
<213> ORGANISM: Homo sapiens

<400> SEQUENCE: 3

Met Pro Glu Ala Pro Leu Leu Leu Ala Ala Val Leu Leu Gly Leu
1               5                   10                  15

Val Leu Leu Val Val Leu Leu Leu Leu Arg His Trp Gly Trp Gly
            20                  25                  30

Leu Cys Leu Ile Gly Trp Asn Glu Phe Ile Leu Gln Pro Ile His Asn
        35                  40                  45

Leu Leu Met Gly Asp Thr Lys Glu Gln Arg Ile Leu Asn His Val Leu
    50                  55                  60

Gln His Ala Glu Pro Gly Asn Ala Gln Ser Val Leu Glu Ala Ile Asp
65                  70                  75                  80

Thr Tyr Cys Glu Gln Lys Glu Trp Ala Met Asn Val Gly Asp Lys Lys
                85                  90                  95

Gly Lys Ile Val Asp Ala Val Ile Gln Glu His Gln Pro Ser Val Leu
            100                 105                 110

Leu Glu Leu Gly Ala Tyr Cys Gly Tyr Ser Ala Val Arg Met Ala Arg
        115                 120                 125

Leu Leu Ser Pro Gly Ala Arg Leu Ile Thr Ile Glu Ile Asn Pro Asp
    130                 135                 140

Cys Ala Ala Ile Thr Gln Arg Met Val Asp Phe Ala Gly Val Lys Asp
145                 150                 155                 160

```
Lys Val Thr Leu Val Val Gly Ala Ser Gln Asp Ile Ile Pro Gln Leu
            165                 170                 175

Lys Lys Lys Tyr Asp Val Asp Thr Leu Asp Met Val Phe Leu Asp His
            180                 185                 190

Trp Lys Asp Arg Tyr Leu Pro Asp Thr Leu Leu Leu Glu Glu Cys Gly
            195                 200                 205

Leu Leu Arg Lys Gly Thr Val Leu Leu Ala Asp Asn Val Ile Cys Pro
            210                 215                 220

Gly Ala Pro Asp Phe Leu Ala His Val Arg Gly Ser Ser Cys Phe Glu
225                 230                 235                 240

Cys Thr His Tyr Gln Ser Phe Leu Glu Tyr Arg Glu Val Val Asp Gly
                245                 250                 255

Leu Glu Lys Ala Ile Tyr Lys Gly Pro Gly Ser Glu Ala Gly Pro
                260                 265                 270

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
actgtggcta ctcagctgtg                                              20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cctttttcca ggtctgacaa                                              20
```

METHOD FOR PREDICTING A SUBJECTS RESPONSE TO SLC MODULATOR THERAPY

CROSS REFERENCE TO RELATED APPLICATIONS

The present application is a continuation in part of PCT international application no. PCT/US2018/048345, filed Aug. 28, 2018, which claims benefit of U.S. Provisional Patent Application Ser. No. 62/550,879, filed on Aug. 28, 2017 which applications are incorporated by reference herein in their entireties.

FIELD OF THE INVENTION

The present invention provides, inter alia, methods for treating or ameliorating the effects of a disorder, such as schizophrenia or bipolar disorder, in a subject. Methods and diagnostic systems for identifying subjects with such a disorder, and for predicting clinical response to treatments of such disorders, are also provided herein.

INCORPORATION BY REFERENCE OF SEQUENCE LISTING

This application contains references to amino acids and/or nucleic acid sequences that have been filed as sequence listing text file "1035795-000660-seq.txt", file size of 10 KB, created on Jun. 30, 2020. The aforementioned sequence listing is hereby incorporated by reference in its entirety pursuant to 37 C.F.R. § 1.52(e)(5).

BACKGROUND OF THE INVENTION

Negative symptoms, including avolition, blunted affect and social withdrawal, are amongst the most persistent and debilitating in schizophrenia, and are largely unaddressed by current medications (Blanchard et al., 2011). Negative symptoms, which are present across psychiatric disorders (Lindenmayer et al., 2008; Fernandez-Garcimartin et al., 2014), contribute significantly to the huge personal and economic costs of severe psychiatric illness and other disorders.

Proline is a precursor of the neurotransmitter glutamate and may function as a central nervous system (CNS) neuromodulator (Phang et al., 2001; and references therein). Peripheral hyperprolinemia, which reflects CNS proline elevation (Dingman and Sporn, 1959; Efrom, 1965; Baxter et al., 1985; Gogos et al., 1999; Paterlini et al., 2005; Luykx et al., 2015), has been associated with psychiatric disorders including schizophrenia (Tomiya et al., 2007; Clelland et al., 2011; Orešič et al., 2011). The proline dehydrogenase gene (PRODH) encodes proline oxidase (POX), the enzyme that catalyzes the first step in proline catabolism. The direct consequences of elevated proline for neurotransmission have been demonstrated by work on the hyperprolinemic Prodh null model (Gogos et al., 1999; Paterlini et al., 2005). In the presence of POX deficiency and elevated proline (peripheral and CNS), the mouse exhibits altered glutamate and dopamine (DA) signaling, including an enhancement of glutamatergic synaptic transmission, prefrontal DA transmission, and functional hyper-DA responses (Paterlini et al., 2005).

PRODH maps to chromosome 22q11, a region associated with the highest known genetic risk for schizophrenia, aside from that shared by monozygotic twins. In addition, this location is also associated with the hemizygous microdeletion found in 22q11 deletion syndrome (22q11DS), and there is an increased risk of schizophrenia as well as other psychotic, mood-, obsessive compulsive-, and autism spectrum disorders in 22q11DS patients (Karayiorgou et al., 2010; Baker and Skuse, 2005; Fine et al., 2005; Gothelf et al., 2004). Approximately 37-50% of 22q11DS patients have significant elevation of fasting plasma proline, and proline levels inversely correlate with intelligence quotient in 22q11DS (Raux et al., 2007).

The catechol-O-methyltransferase gene (COMT) encodes the eponymous enzyme that methylates and inactivates catecholamines including DA, and also maps to 22q11, distal to PRODH. The COMT $Val^{158/108}Met$ functional polymorphism (substitution of valine (Val) to methionine (Met) at codon 158 (or at codon 108 for soluble catechol-O-methyltransferase (S-COMT)), has been studied with regards to DA neurotransmission because Val/Val homozygotes have pre-frontal cortex (PFC) enzyme activity approximately 40% higher than Met/Met homozygotes and are considered to have concomitant lower PFC DA levels (Lachman et al., 1996; Chen et al., 2004). It has thus been suggested that the $Val^{158/108}Met$ polymorphism modulates cognitive functioning (Bilder et al., 2004; and references therein). Whilst COMT has been associated with psychotic and mood disorders including schizophrenia and bipolar disorder (Shifman et al., 2002; Shifman et al., 2004), results have been inconsistent (Allen et al., 2008).

A CNS functional interaction between COMT and PRODH has been proposed by Paterlini et al. (2005), who suggested that significant cortical Comt upregulation in the Prodh null mouse represents a compensatory response to increased PFC DA transmission, arising as a consequence of PRODH deficiency enhancing glutamatergic synaptic transmission. In addition, high levels of plasma proline in 22q11DS with the low activity Met allele have been associated with psychosis with positive symptoms (Raux et al., 2007), and significantly decreased smooth pursuit eye movement (SPEM) (Vorstman et al., 2009).

Recent reports have shown significantly elevated fasting peripheral proline in schizophrenia patients versus healthy controls (Clelland et al., 2011). Given the finding of increased COMT expression in the Prodh null mouse (Paterlini et al., 2005), and the significant interaction between proline and COMT genotype on psychosis risk in 22q11DS patients (Raux et al., 2007), this data suggests that COMT genotype and proline levels could be employed for treatment decisions for schizophrenia and other psychiatric disorders.

SUMMARY OF THE INVENTION

The present invention provides a method for predicting the clinical response of a subject with a disorder to a solute carrier (SLC) modulator comprising:
  a) obtaining a biological sample from the subject;
  b) determining the identity of the allele(s) of the $Val^{158/108}Met$ locus associated with the COMT gene in the sample;
    wherein the presence of Val/Val is indicative of a subject who will benefit from an SLC modulator that increases proline levels, and wherein the presence of at least one Met allele is indicative of a subject who will benefit from an SLC modulator that decreases proline levels; and
  c) administering, if appropriate based on the results of step b), an effective amount of an SLC modulator to the subject to achieve an appropriate clinical response.

The present invention also provides a method for monitoring the treatment of a subject in need thereof, the method comprising:
  a) obtaining a biological sample from the subject;
  b) determining the genotype for the allele(s) of the COMT gene at codon 158 (and/or codon 108 for S-COMT) in the biological sample;
  c) determining the subject's proline level; and
  d) modifying the course of treatment, if necessary, including administering a solute carrier (SLC) modulator to the subject, or stopping or omitting treatment with an SLC modulator, or administering a different SLC modulator to the subject, based upon the presence or absence of a $Val^{158/108}Met$ polymorphism in the COMT gene, and/or an increase or decrease in the subject's proline level.

The present invention also provides a diagnostic system for identifying a subject with a disorder who will benefit from a solute carrier (SLC) modulator that increases or decreases proline levels comprising:
  a) obtaining a biological sample from the subject; and
  b) determining the identity of alleles of the $Val^{158/108}Met$ locus associated with the COMT gene in the sample;
  wherein the presence of Val/Val at codon 158 (and/or codon 108 for S-COMT) is indicative of a subject who will benefit from an SLC modulator that increases proline levels and wherein the presence of at least one Met allele at codon 158 (and/or codon 108 for S-COMT) is indicative of a subject who will benefit from an SLC modulator that decreases proline levels. Kits comprising the diagnostic systems of the present invention packaged together with instructions for use are also provided.

The present invention also provides a method for predicting the clinical response of a subject with a disorder to a solute carrier (SLC) modulator comprising:
  a) determining the identity of the allele(s) of the $Val^{158/108}Met$ locus associated with the COMT gene using a biological sample of the subject; wherein the presence of Val/Val at the locus is indicative of a subject who will benefit from an SLC modulator that increases proline levels, and wherein the presence of at least one Met allele at the locus is indicative of a subject who will benefit from an SLC modulator that decreases proline levels; and
  b) administering, if appropriate based on the results of step (a), an effective amount of an SLC modulator to the subject to achieve a clinically appropriate response.

The present invention also provides a method for monitoring the treatment of a subject with a disorder, the method comprising:
  a) determining the genotype for the allele(s) of the COMT gene at codon 158 (and/or codon 108 for S-COMT) in a biological sample of the subject;
  b) determining the proline level of the subject; and
  c) modifying the course of treatment of the subject, if necessary, including administering a solute carrier (SLC) modulator to the subject or stopping or omitting treatment with an SLC modulator, or administering a different SLC modulator to the subject, based upon the presence or absence of a $Val^{158/108}Met$ polymorphism in the COMT gene.

The present invention also provides a diagnostic system for identifying a subject with a disorder who will benefit from treatment with a solute carrier (SLC) modulator that increases or decreases proline levels comprising: determining the identity of the allele(s) of the $Val^{158/108}Met$ locus associated with the COMT gene using a biological sample from the subject; wherein the presence of Val/Val at the locus is indicative of a subject who will benefit from an SLC modulator that increases proline levels and wherein the presence of at least one Met allele at the locus is indicative of a subject who will benefit from an SLC modulator that decreases proline levels.

The present invention also provides a method for treating or ameliorating the effects of a disorder in a subject in need thereof comprising:
  a) obtaining a biological sample from the subject;
  b) determining, in the biological sample, the presence or absence of a $Val^{158/108}Met$ polymorphism in the COMT gene; and
  ci) administering to the subject, if appropriate based on the results of step (b), an effective amount of a solute carrier (SLC) modulator that increases proline levels if the subject is determined from step (b) to have a Val/Val genotype at codon 158 (and/or codon 108 for S-COMT); or
  cii) administering to the subject, if appropriate based on the results of step (b), an effective amount of an SLC modulator that decreases proline levels if the subject is determined from step (b) to have a Val/Met or Met/Met genotype at codon 158 (and/or codon 108 for S-COMT).

The present invention also provides a method for treating or ameliorating the effects of a disorder in a subject in need thereof comprising:
  a) determining, using a biological sample of the subject, the presence or absence of a $Val^{158/108}Met$ polymorphism in the COMT gene of the subject; and
  bi) administering to the subject, if clinically appropriate, an effective amount of a solute carrier (SLC) modulator that increases proline levels if the subject is determined from step (a) to have a Val/Val genotype at codon 158 (and/or codon 108 for S-COMT); or
  bii) administering to the subject, if clinically appropriate, an effective amount of an SLC modulator that decreases proline levels if the subject is determined from step (a) to have a Val/Met or Met/Met genotype at codon 158 (and/or codon 108 for S-COMT).

The present invention also provides a method for eradicating or reducing a negative symptom experienced by a subject who suffers from a disorder comprising:
  a) obtaining a biological sample from the subject;
  b) determining, in the biological sample, the presence or absence of a $Val^{158/108}Met$ polymorphism in the COMT gene; and
  ci) administering to the subject, if clinically appropriate, an effective amount of a solute carrier (SLC) modulator that increases proline levels if the subject is determined from step (b) to have a Val/Val genotype at codon 158 (and/or codon 108 for S-COMT); or
  cii) administering to the subject, if clinically appropriate, an effective amount of an SLC modulator that decreases proline levels if the subject is determined from step (b) to have at least one Met allele at codon 158 (and/or codon 108 for S-COMT); or
  ciii) modifying the course of treatment of the subject, if clinically appropriate, including stopping or omitting treatment with an SLC modulator, based upon the presence or absence of a $Val^{158/108}Met$ polymorphism in the COMT gene.

The present invention also provides a method for monitoring the treatment of a subject with a disorder, the method comprising:
  a) determining the genotype for the allele(s) of the COMT gene at codon 158 (and/or codon 108 for S-COMT) in a biological sample of the subject;
  b) determining the proline level of the subject;
  c) determining the level of one or more of glycine, serine, GABA, glutamate of the subject; and
  d) modifying the course of treatment of the subject, if necessary, including administering a solute carrier (SLC) modulator to the subject or stopping or omitting treatment with an SLC modulator, or administering a different SLC modulator to the subject, based upon the presence or absence of a $Val^{158/108}Met$ polymorphism in the COMT gene.

The present invention also provides a method for monitoring the treatment of a subject with a disorder, the method comprising:
  a) determining the genotype for the allele(s) of the COMT gene at codon 158 (and/or codon 108 for S-COMT) in a biological sample of the subject;
  b) determining the level of one or more of glycine, serine, GABA, glutamate of the subject; and
    modifying the course of treatment of the subject, if necessary, including administering a solute carrier (SLC) modulator to the subject or stopping or omitting treatment with an SLC modulator, or administering a different SLC modulator to the subject, based upon the presence or absence of a $Val^{158/108}Met$ polymorphism in the COMT gene.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
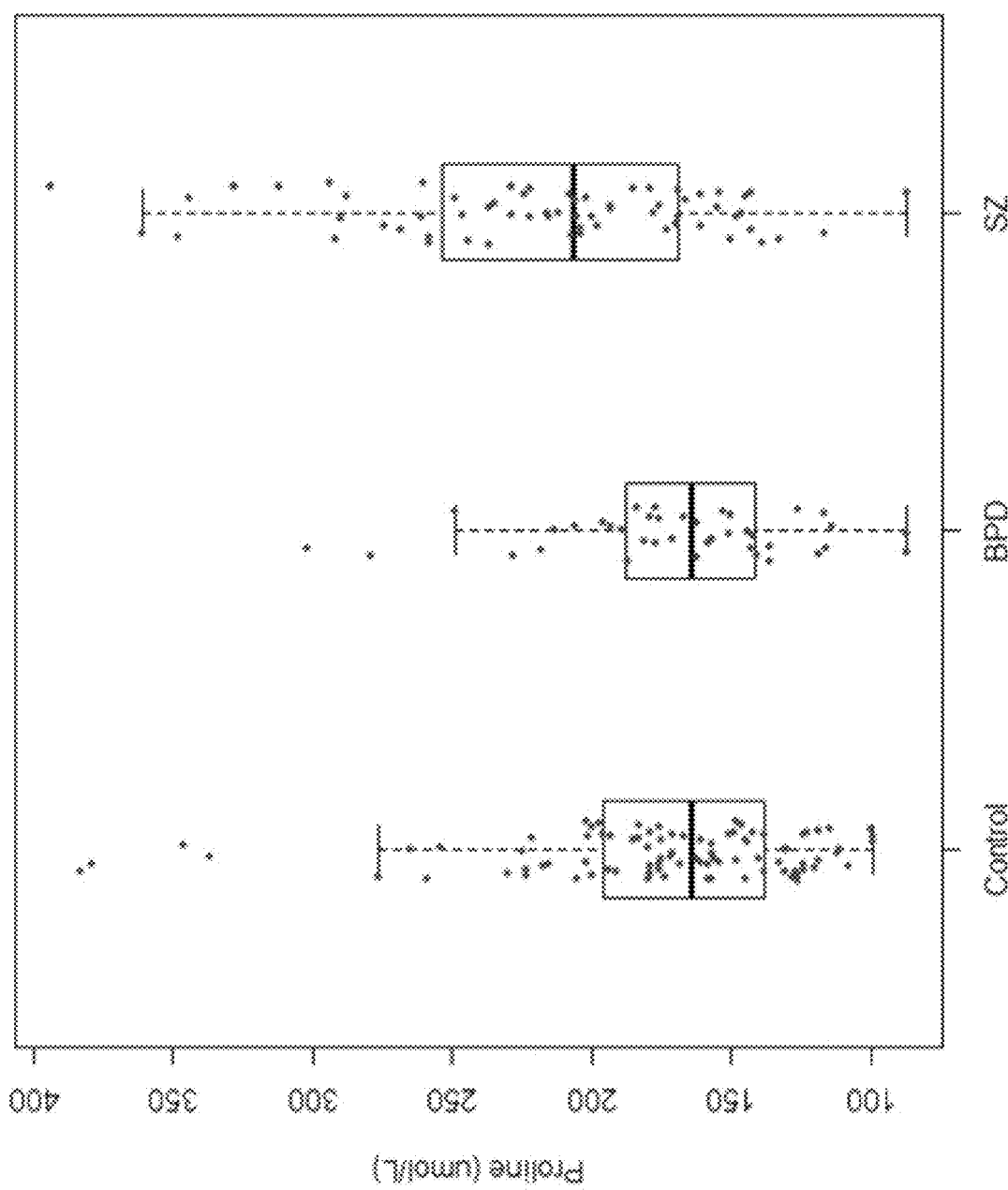
FIG. 1 shows a boxplot of fasting plasma proline levels plotted for controls (174.28±55.97, n=90), bipolar disorder patients (168.75±45.50, n=40) and schizophrenia patients (215.84±63.00, n=64). Red jittered points represent individual data. The horizontal line within each box represents the group mean (mean±SD reported). The box indicates the interquartile range (IQR). The whiskers extend to the most extreme data point which is 1.5 times the IQR. While hyperprolinemia was present in 26.6% of schizophrenia (SZ) patients (17/64), the proportion of bipolar disorder (BPD) patients exhibiting peripheral hyperprolinemia (3/37; 7.5%) was not significantly different to controls (5/85; 5.6%) (Fisher's exact p=0.70).

One embodiment of the present invention is a method for predicting the clinical response of a subject with a disorder to a solute carrier (SLC) modulator comprising:
  a) obtaining a biological sample from the subject;
  b) determining the identity of the allele(s) of the Val$^{158/}$$_{108}$Met locus associated with the COMT gene in the sample;
    wherein the presence of Val/Val at codon 158 (and/or codon 108 for S-COMT) is indicative of a subject who will benefit from an SLC modulator that increases proline levels, and wherein the presence of at least one Met allele at codon 158 (and/or codon 108 for S-COMT) is indicative of a subject who will benefit from an SLC modulator that decreases proline levels; and
  c) administering, if appropriate based on the results of step b), an effective amount of an SLC modulator to the subject to achieve an appropriate clinical response.

As used herein, the term "disorder" broadly refers to a syndrome, condition, chronic illness or a particular disease. For example, the disorder may be a psychiatric disorder. In the present invention, a "psychiatric disorder" is one of a number of disorders that affect mood, thinking, and behavior. Thus, as used herein, "psychiatric disorder" includes but is not limited to: schizophrenia, bipolar disorder, schizoaffective disorders, schizophreniform disorders, schizotypal and schizoid personality disorders, delusional disorders, 22q11.2 deletion syndrome, mood disorders, anxiety disorders, substance use disorders, and personality disorders.

Other non-limiting examples of disorders according to the present invention include: schizophrenia, bipolar disorder, schizophrenia spectrum and other psychotic disorders, 22q11.2 deletion syndrome, depressive disorders, mood disorders, Alzheimer's disease, alcohol use disorder, substance use disorders, addictive disorders, anxiety disorders, obsessive-compulsive disorders, and trauma and stressor-related disorders. In a preferred embodiment, the disorder is e.g., schizophrenia or bipolar disorder.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment. The term "clinical response" as used herein means a reduction of the severity or number of symptoms or characteristics of a disorder, during or following treatment.

In some aspects of this and other embodiments, the subject is a mammal. Preferably, the mammal is selected from the group consisting of humans, primates, farm animals, and domestic animals. More preferably, the mammal is a human.

As used herein, a "biological sample" means a biological specimen, which may be a bodily fluid or a tissue. Biological samples include, for example, whole blood, serum, plasma, cerebro-spinal fluid, leukocytes or leukocyte subtype cells (e.g. neutrophils, basophils, and eosinophils, lymphocytes, monocytes, macrophages), fibroblast sample, olfactory neuron sample, and tissues from the central nervous system, such as the cortex and hippocampus, and cells previously exposed to the CNS environment, such as dendritic cells trafficked from the brain, or other immune or other cell types (Mohamed-M G et al., 2014). Examples of preferred biological samples include, e.g., a blood sample, a biopsy sample, a plasma sample, a saliva sample, a tissue sample, a serum sample, a tear sample, a sweat sample, a skin sample, a cell sample, a hair sample, an excretion sample, a waste sample, a bodily fluid sample, a nail sample, a cheek swab, a cheek cell sample, or a mucous sample.

There is one single gene for COMT, which codes for both soluble COMT (S-COMT) and membrane-bound COMT (MB-COMT) using two separate promoters. The nucleic acid sequence for the human COMT gene is set forth in GenBank Accession Number Z26491 (see, e.g., SEQ ID NO: 1). Human S-COMT contains 221 amino acids (see, e.g., SEQ ID NO: 2), and the molecular mass is 24.4 kDa. Human MB-COMT (see, e.g., SEQ ID NO: 3) contains 50 additional amino acids, of which 20 are hydrophobic membrane anchors. The remainder of the MB-COMT molecule is suspended on the cytoplasmic side of the intracellular membranes. The corresponding molecular mass is 30.0 kDa.

A single nucleotide polymorphism (SNP) in the COMT gene causes a trimodal distribution of low, intermediate, and high activity. That polymorphism is caused by autosomal codominant alleles and leads to 3- to 4-fold differences in COMT activity. It has been shown that the molecular basis for this variation in activity is due to a transition of guanine to adenine at codon 158 (and/or codon 108 for S-COMT) of the COMT gene that results in a substitution of valine (Val) by methionine (Met) at codon 158 in MB-COMT (SEQ ID NO: 3) or the corresponding amino acid 108 in S-COMT (SEQ ID NO: 2). The SNP polymorphism is referred to interchangeably herein as "rs4680" or "G158A" or "Val$^{158}$Met" or Val$^{158/108}$Met or Val$^{108/158}$Met. In subjects with 22q11.2 deletion syndrome (22q11DS), there is only one allele which determines COMT activity.

COMT Enzyme Activity can also be measured as a separate and/or additional measure of COMT activity with or without without COMT genotyping. Different methods can be utilized to assay COMT activity in a patient/person, these include but are not limited to assay of COMT enzyme activity in erythrocytes using a method developed by Masuda et al., which is based upon the conversion to normetanephrine (NML) using norepinephrine as a substrate, and which has good inter-, and intra-day precision (Masuda et al. 2002). This assay has recently been set-up in the Clelland lab, and is briefly described as follows: After blood draw, erythrocytes were obtained via gradient centration and cell pellets stored at −80° C. prior to downstream assay. Cell pellets were then lysed and protein concentrations assayed. COMT activity was determined via the Normetanephrine (Plasma) ELISA (IBL America), according to the manufacturer's instructions. Specific COMT activity was calculated after subtracting out the amount of product resulting from endogenous cellular methyltransferase activity in parallel reaction using a COMT inhibitor (OR486). To date all values have obtained have been within the range of internal standard controls. This COMT activity assay has been successfully employed to assay COMT activity in human erythrocytes (Segall et al. 2010), CNS tissue from murine models (Lorenz et al. 2014), and in vitro cell lines (Nackley et al. 2006).

Dopaminergic activity may also be measured with or without assay of COMT genotype: Estimation of dopamine activity can be assayed via methods including but not limited to: MRI, functional MRI, MRS, PET and/or SPECT imaging of CNS. Other methods include but are not limited to biochemical assays such as plasma HVA and MHPH: Fasting pHVA is considered a good indicator of central dopaminergic neuronal activity, particularly when fasting MHPG are also considered. pHVA and Pmhpg will be assayed via HPLC assays. Both assays are robust and reproducible (Donnelly et al. 1996; Huber-Smith et al. 1986).

Exemplary methods which may be used for the determination/identification of the COMT genotype or Val$^{158/108}$Met polymorphism in the present invention are disclosed, for example, in US2003/0100476, which is incorporated herein by reference. Further examples of such methods include, but are not limited to, PCR-based restriction fragment length polymorphism analysis using the restriction enzyme αIII, allele specific hybridization, use of a primer in a polymerase chain reaction (PCR), such as, for example, anchor PCR or RACE PCR or in a ligase chain reaction (LCR), identification of alterations in restriction enzyme cleavage patterns, sequencing reactions, analysis of the protection from cleavage agents (such as, for example, nuclease, hydroxylamine or osmium tetroxide and with piperidine), recognition of mismatched base pairs in double strand DNA by specific enzymes, alterations in electrophoretic mobility, analysis of the movement of polymorphic fragments in polyacrylamide gels containing gradients of denaturant (denaturing gradient gel electrophoresis, DGGE), selective oligonucleotide hybridization (for example using a specialized exonuclease-resistance nucleotide), selective amplification depending on selective PCR or selective primer extension, oligonucleotide ligation assays, expansion methods using dideoxynucleotides derivatives, and Genetic Bit Analysis (GBA™). The detection of a variant in the COMT protein sequence can also be determined by methods such as in situ detection using an antibody specific to a variant sequence, immunoassays such as, for example, EIA or ELISA, immunofluorescence and the like. A preferred method for determining a COMT genotype is disclosed in Example 1.

As set forth above, the determination/identification of the COMT genotype or mutation in the COMT protein of a subject may be carried out by methods known to the skilled artisan. Such methods may be carried out, e.g., on a biological sample obtained from the subject, such as for example, a blood sample or a sample obtained after a biopsy has been carried out on the subject. Furthermore, any cell type or tissue may be utilized in the detection procedures described above. In a preferred embodiment, a bodily fluid, e.g., blood, is obtained from the subject to determine the presence of the allelic variant of a polymorphic region, such as the region including the Val$^{158/108}$Met, in the COMT gene. A bodily fluid, e.g., blood, can be obtained by known techniques (e.g., venipuncture). Alternatively, nucleic acid tests can be performed on dry samples (e.g., skin).

As used herein, "a solute carrier (SLC)" means any member in the solute carrier family of membrane transport proteins, which transport various solutes including both charged and uncharged organic molecules such as amino acids as well as inorganic ions and the gas ammonia. Non-limiting examples of SLCs include SLC6A7, SLC6A17, SLC6A20, SLC6A9, SLC7A11, SLC1A1, SLC1A2, SLC1A3, SLC1A4, SLC1A5, SLC1A6, SLC3A2, SLC7A5, SLC7A8, SLC7A13, SLC7A10, SLC17A6, SLC17A7, SLC17A8, SLC32A1, SLC36A1, SLC36A2, SLC36A4, SLC38A2, SLC38A4, SLC38A9, SLC6A1, SLC6A13, SLC6A11, SLC6A12, SLC6A5, SLC6A14, SLC6A15, SLC6A18, and SLC6A19. As used herein, "a solute carrier modulator" or "an SLC modulator" means any drug or other composition that inhibits/modulates/affects specific SLC transporter to increase or decrease the plasma levels of certain solutes (e.g., D- and/or L-forms of proline, glycine, glutamate, serine, alanine, threonine, glutamine, and GABA, etc.) in a subject. Such SLC modulators and their formulations and/or derivatives with stability and/or CNS transport characteristics may be administered to a subject as therapeutics, e.g. via incorporation of stable isotopes including Carbon-13, Oxygen-18, and/or methylation, acetylation, glycosylation and/or other derivatization or decoration, and/or incorporation into nanoparticles and/or liposomes and/or other carriers, including conjugation to carrier moieties, for example polyamines and/or pyrene and/or pyrene derivatives. In the present invention, combinations of such SLC modulators are also contemplated.

Examples of SLC6A7 modulator include, but are not limited to, LX-6171, Benztropine, LP-403812, 2',3,3',4',5-pentachloro-4-hydroxybiphenyl, Dronabinol, ethanol, N-Methyl-3,4-methylenedioxyamphetamine, Methionine-enkephalin, [D-Ser$^2$]Leu-enkephalin-Thr, Leucine enkephalin, (des-Tyr)-Leucine enkephalin, Leucine enkephalinamide, [D-ser$^2$]Leu-enkephalin-Thr, [D-Ala2, D-Leu5]Leu-enkephalin, SLC6A7(PROT) inhibiting peptides and modified peptides and derivatives, including (denoted in amino acid single letter codes) GGFL, YGGFL, YGGFM, GFL, GGFL-NH2, YGGFLR, YGGFLRRI (dynorphin A1-8), GGFLRRI (des-Tyr-dynorphinA1-8), L-pipecolate (PIP), L-norleucine, sarcosine, Ammonium Chloride, bisphenol A, Copper, Morphine, Nicotine, Propylthiouracil, pyrachlostrobin, Imatinib mesylate, Fluoxetine, miR-205, microRNA-140, Imatinib, hsa-miR-490-3p, hsa-miR-143, hsa-miR-874, hsa-miR-491-5p, hsa-miR-485-5p, hsa-miR-128, hsa-miR-339-5p, hsa-miR-324-5p, hsa-miR-3064-5p, hsa-miR-6504-5p, hsa-miR-138-5p, hsa-miR-150-5p, hsa-miR-4319, hsa-miR-125b-5p, hsa-miR-125a-5p, hsa-miR-122-5p, hsa-miR-876-5p, hsa-miR-3167, hsa-miR-532-3p, hsa-miR-1287-5p, hsa-miR-3135b, hsa-miR-152-5p, hsa-miR-133a-5p, hsa-miR-550a-3p, hsa-miR-200c-5p, hsa-miR-132-5p, hsa-miR-874-3p, hsa-miR-3692-5p, hsa-miR-597-3p, hsa-miR-873-5p.2, and combinations thereof.

The entities below have also been found to effect SLC6A7: the transporter regulatory molecules named Compound 1, Compound 2, Compound 3, Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, Compound 23, Compound 24, Compound 25, Compound 26, Compound 27, Compound 28, Compound 29, Compound 30, Compound 31, Compound 32, Compound 33, Compound 34, Compound 35, Compound 36, Compound 37, Compound 38, Compound 39, Compound 40, Compound 41, Compound 42, Compound 43, Compound 44, Compound 45, Compound 46, Compound 47, Compound 48, Compound 49, Compound 50, Compound 51, Compound 52, Compound 53, Compound 54, Compound 55, Compound 56, Compound 57 and Compound 58 disclosed in Zipp et al 2014 (PMID:25037917 DOI:10.1016/j.bmcl.2014.06.049).

Examples of SLC6A17 modulator include, but are not limited to, Fluoxetine, bupropion, N-Methyl-D-Glucosamine tartrate, Resveratrol, pioglitazone, 2,2',3',4,4',5-hexachlorobiphenyl, 2',3,3',4',5-pentachloro-4-hydroxybiphenyl, bisphenol A, furan, Gentamicins, jinfukang, Paraquat, Soman, hsa-miR-140-3p.1, hsa-miR-15b-5p, hsa-miR-16-5p, hsa-miR-195-5p, hsa-miR-6838-5p, hsa-miR-424-5p, hsa-miR-497-5p, hsa-miR-15a-5p, hsa-miR-141-3p, hsa-miR-200a-3p, hsa-miR-183-5p.2, hsa-miR-424-5p, hsa-miR-497-5p, hsa-miR-16-5p, hsa-miR-195-5p, hsa-miR-15a-5p, hsa-miR-15b-5p, hsa-miR-6838-5p, hsa-miR-449a, hsa-miR-34a-5p, hsa-miR-449b-5p, hsa-miR-34c-5p, hsa-miR-218-5p, hsa-miR-218-5p, hsa-miR-29a-3p, hsa-miR-29b-3p, hsa-miR-29c-3p, hsa-miR-22-3p, hsa-miR-138-5p, hsa-miR-218-5p, hsa-miR-218-5p, hsa-miR-137, hsa-miR-200c-3p, hsa-miR-429, hsa-miR-200b-3p, hsa-miR-144-3p, hsa-miR-4319, hsa-miR-125a-5p, hsa-miR-125b-5p, hsa-miR-367, hsa-miR-32, hsa-miR-363, hsa-miR-92a, hsa-miR-92b, hsa-miR-25, hsa-miR-144, hsa-miR-374a, hsa-miR-374b, hsa-miR-222, hsa-miR-449a, hsa-miR-449b, hsa-miR-34a, hsa-miR-34c-5p, and combinations thereof.

Examples of SLC6A20 modulator include, but are not limited to, Pipecolate, N-methyl-l-proline, N-methylaminoisobutyrate (MeAIB), sarcosine (N-methylglycine), α-methylamino-isobutyric acid (MeAIB), 2-Aminobicyclo[2.2.1]heptane-2-carboxylic acid (BCH), d-proline, miR-221, Imatinib mesylate, Creatine, zinc, miR-122, High phosphate, Estradiol, Cyclosporine, oxaliplatin, Topotecan, Acetaminophen, Amiodarone, Ammonium Chloride, AZM551248, beta-Naphthoflavone, Benzo(a)pyrene, bisphenol A, Chlorpromazine, Diethylstilbestrol, Ethinyl Estradiol, Fonofos, Hydrogen Peroxide, (+)-JQ1 compound, octylphenol, Paclitaxel, Paraquat, Parathion, Propylthiouracil, terbufos, Tetracycline, Thioacetamide, Valproic Acid, Vancomycin, zoledronic acid, hsa-miR-138-5p, hsa-miR-1-3p, hsa-miR-203a-3p.1, hsa-miR-204-5p, hsa-miR-206, hsa-miR-208a-3p, hsa-miR-208b-3p, hsa-miR-211-5p, hsa-miR-613, hsa-miR-448, hsa-miR-133a, hsa-miR-133b, hsa-miR-19a, hsa-miR-19b, hsa-miR-125a-3p, hsa-miR-376a, hsa-miR-376b, hsa-miR-599, hsa-miR-149, hsa-miR-214, hsa-miR-194 hsa-miR-539, hsa-miR-129-5p, hsa-miR-124, hsa-miR-506, and combinations thereof.

Examples of SLC6A9 modulator include, but are not limited to, ASP2535, Bitopertin (RG1678), Org 25935, PF-03463275, RG1678 (R 1678, R1678, RG 1678, RO 4917838, RO49 17838, RO4917838), SCH900435 (Org 25935, Org25935, SCH 900435, SCH900435), SSR103800 (SSR 103800), SSR504734 (SSR 504734), AMG747 (AMG 747), AMR-GLY-3 (GlyT 1 inhibitor ALBANY), B1425809 (BI 425809), CST1200 (CSTI 200), DNS006 (DNS 006, GlyT1 Inhibitor DART, GlyT1 Program), GSK1018921 (1018921, GSK 1018921), JNJ17305600 (Glycine Reuptake Inhibitors, JNJ 17305600), Org26041 (Org 26041), PF03463275 (PF 03463275, PF 3463275, PF3463275), TASPO315003 (TASP 0315003). microRNA-128, Aldosterone, JQ1, miR-34, acrylamide, microRNA-140, Ribavirin, Tetrachlorodibenzodioxin, Benzo(a)pyrene, Nanotubes Carbon, bisphenol A, Phenobarbital, benzamide, benzyloxycarbonylleucyl-leucyl-leucine aldehyde, Cuprizone, Cyclosporine, decabromobiphenyl ether, Cisplatin, Diethylhexyl Phthalate, Ethinyl Estradiol, Fenofibrate, Flutamide, jinfukang, Monensin, nobiletin, oxaliplatin, Paraquat, Tetradecanoylphorbol Acetate, Topotecan, 1-(2-trifluoromethoxyphenyl)-2-nitroethanone, 1,4-bis(2-(3,5-dichloropyridyloxy))benzene, 2-(1'H-indolo-3'-carbonyl)thiazole-4-carboxylic acid methyl ester, 2,2',4,4'-tetrabromodiphenyl ether, 2,2-bis(4-hydroxyphenyl)-1,1,1-trichloroethane, 3,4,3',4'-tetrachlorobiphenyl, 3-biphenyl-4-yl-4-(2-fluorophenyl)-5-isopropyl-4H-1,2,4-triazole, Acetaminophen, adefovir dipivoxil, Amphetamine, Atrazine, Betaine, 8-Bromo Cyclic Adenosine Monophosphate, caffeic acid phenethyl ester, Cannabidiol, Cihorine, chloroacetaldehyde, Choline, cidofovir, Ciguatoxins, Clodronic Acid, Clofibric Acid, Copper, coumarin, Dronabinol, Dexamethasone, Diazinon, dibenzo(a,l)pyrene, Dibutyl Phthalate, Diethylnitrosamine, Disulfiram, Diuron, Ethanol, fipronil, Flavonoids, Folic Acid, Ibuprofen, ICG 001, Ifosfamide, (+)-JQ1 compound, lead acetate, Magnetite Nanoparticles, Metformin, Methamphetamine, Methionine, Methotrexate, 1-Methyl-4-phenylpyridinium, n-butoxyethanol, nefazodone, nimesulide, N-methyl-N-(6-methoxy-1-phenyl-1,2,3,4-tetrahydronaphthalen-2-ylmethyl)aminomethylcarboxylic acid, NSC668394, Oxycodone, Ozone, Pentachlorophenol, phorone, pirinixic acid, Pregnenolone Carbonitrile, Propylthiouracil, rosiglitazone, sevoflurane, Sodium Fluoride, Sodium Selenite, Tamoxifen, tauroursodeoxycholic acid, Thapsigargin, troglitazone, Tunicamycin, Vanadium, hsa-miR-184, hsa-miR-3064-5p, hsa-miR-6504-5p, hsa-miR-140-3p.2, hsa-miR-140-5p, hsa-miR-222-3p, hsa-miR-221-3p, hsa-miR-200a-3p, hsa-miR-141-3p, hsa-miR-520a-3p, hsa-miR-302e, hsa-miR-520d-3p, hsa-miR-372-3p, hsa-miR-302d-3p, hsa-miR-302c-3p.1, hsa-miR-302b-3p, hsa-miR-302a-3p, hsa-miR-520e, hsa-miR-520c-3p, hsa-miR-520b, hsa-miR-373-3p, hsa-miR-183-5p.2, hsa-miR-200a-3p, hsa-miR-302c-3p.2, hsa-miR-520f-3p, hsa-miR-7-5p, hsa-miR-182-5p, hsa-miR-519d-3p, hsa-miR-106b-5p, hsa-miR-20a-5p, hsa-miR-106a-5p, hsa-miR-93-5p, hsa-miR-17-5p, hsa-miR-20b-5p, hsa-miR-526b-3p, hsa-miR-1271-5p, hsa-miR-96-5p, hsa-miR-30b-5p, hsa-miR-30a-5p, hsa-miR-30d-5p, hsa-miR-30e-5p, hsa-miR-30c-5p, hsa-miR-137, hsa-miR-214-5p, hsa-miR-490-3p, hsa-miR-455-3p.2, hsa-miR-425-5p, hsa-miR-125a-5p, hsa-miR-193a-3p, hsa-miR-125b-5p, hsa-miR-193b-3p, hsa-miR-744-5p, hsa-miR-615-3p, and combinations thereof.

Examples of SLC7A11 modulator include, but are not limited to, SXC2023 (SXC 2023), PRO4051 (Cpd X, CpdX, PRO 4051), Glucosamine, Gamma-tocotrienol, miR-221/222, Ribavirin, Imatinib, 1,2,4-benzenetriol, Nickel, Camptothecin, Benzo(a)pyrene, Sulfasalazine, Cyclosporine, 4-(5-benzo(1,3)dioxol-5-yl-4-pyridin-2-yl-1H-imidazol-2-yl)benzamide, (6-(4-(2-piperidin-1-ylethoxy)phenyl))-3-pyridin-4-ylpyrazolo(1,5-a)pyrimidine, Valproic Acid, arsenic trioxide, Estradiol, bisphenol A, Glutathione, Tetrachlorodibenzodioxin, Cystine, Bilirubin, Paraquat, diethyl maleate, Hydrogen Peroxide, (+)-JQ1 compound, Tetradecanoylphorbol Acetate, Acetaminophen, aluminum citrate, Cadmium, Chlorpyrifos, Cocaine, Copper, Copper Sulfate, Cisplatin, lead acetate, Magnetite Nanoparticles, Phenobarbital, Succimer, trichostatin A, Zymosan, 1-(2-cyano-3,12-dioxooleana-1,9-dien-28-oyl) imidazole, 1,2-dihydroxynaphthalene, 1-(2-trifluoromethoxyphenyl)-2-nitroethanone, 2,2',4,4'-tetrabromodiphenyl ether, 2,3-bis(3'-hydroxybenzyl)butyrolactone, 3,4,5,3',4'-pentachlorobiphenyl, 4-(4-fluorophenyl)-2-(4-hydroxyphenyl)-5-(4-pyridyl)imidazole, Acetylcysteine, Air Pollutants, alpha-Tocopherol, Ampicillin, Azathioprine, 7,8-Dihydro-7,8-dihydroxybenzo(a)pyrene 9,10-oxide, tert-Butylhydroperoxide, p-Chloromercuribenzoic Acid, cinnamic aldehyde, Coumestrol, Cuprizone, Curcumin, Cyclophosphamide, Dronabinol, Diazinon, Diethylstilbestrol, elesclomol, entinostat, Formaldehyde, glycidamide, Lindane, Lipopolysaccharides, motexafin gadolinium, nickel chloride, panobinostat, pentabromodiphenyl ether, Phenylmercuric Acetate, Prednisolone, Quercetin, Reactive Oxygen Species, tetrabromobisphenol A, Tretinoin, tripterine, Vitamin K 3, vorinostat, Zinc Acetate, 1,2-diamino-4-nitrobenzene, 1,6-hexamethylenediisocyanate,2',3,3',4',5-pentachloro-4-hydroxybiphenyl, 2,3-dichloro-1-propanol, 2-amino-3,8-dimethylimidazo(4,5-f)quinoxaline, 2-amino-3-methylimidazo(4,5-f)quinolone, 2-amino-4-methylphenol, 2-chloromethylpyridine, 2-tert-butylhydroquinone, 2-xylene, 3,4,3',4'-tetrachlorobiphenyl, 4-anisidine, 4-carboxyphenylglycine, 4-hydroxy-2-nonenal, 7-aminocephalosporanic acid, Acrolein, Acrylamide, ammonium hexachloroplatinate, andrographolide, Arachidonic Acid, Crocidolite, Ascorbic Acid, Atrazine, belinostat, benz(a)anthracene, benzidine, benzyloxycarbonylleucyl-leucyl-leucine aldehyde, bicalutamide, BIRB 796, bis(tri-n-butyltin) oxide, 8-Bromo Cyclic Adenosine Monophosphate, butyraldehyde, candoxin, Cannabidiol, captax, Carbamazepine, Ceftriaxone, chlorantraniliprole, chloroacetaldehyde, chloropicrin, Chloroprene, chloroquine diphosphate, Choline, Coumaphos, cresidine, cyanoginosin LR, cypermethrin, DDT, Demecolcine, dibutyldichlorotin, Diclofenac, Dieldrin, Dimethylnitrosamine, Diquat, Endosulfan, Epichlorohydrin, Estriol, Estrone, Ethinyl Estradiol, ethyl acrylate, ethylbenzene, Ethyl Methanesulfonate, Eugenol, Zearalenone, Fluoxetine, Folic Acid, Maleic Anhydrides, gedunin, Genistein, glycidol, Gold Sodium Thiomalate, Hypochlorous Acid, Ibuprofen, ICG 001, Indomethacin, Ionomycin, K 7174, Metformin, Methionine, Methotrexate, Methylenebis(chloroaniline), Methylene Chloride, Methylmethacrylate, Methylprednisolone, Mitomycin, mono-(2-ethylhexyl)phthalate, monomethylarsonous acid, Mycophenolic Acid, Nanotubes Carbon, naphthalene, Naphthoquinones, n-butoxyethanol, nickel sulfate, N-methyl-4-aminophenol, nonylphenol, NSC668394, NSC 689534, ochratoxin A, Oxadiazoles, Ozone, PCI 5002, Phenol, Piroxicam, Polychlorinated Biphenyls, Potassium Dichromate, Progesterone, Propylthiouracil, racecadotril, Raloxifene Hydrochloride, resorcinol, S-(1,1,2,2-tetrafluoroethyl)cysteine, Silver, si-wu-tang, sodium bichromate, Sodium Selenite, tetrathiomolybdate, Thiram, triacsin C, Trichloroethylene, trimellitic anhydride, Tunicamycin, vanillin, Vincristine, Zinc, and combinations thereof.

Examples of SLC1A1 modulator include, but are not limited to, dihydrokaininc acid, kainic acid monohydrate, kainite, DL-Threo-β-Benzyloxyaspartic acid (DL-TBOA). Threo-β-benzyloxyaspartate (TBOA), dihydrokainic acid (DHK), Vemurafenib, Potassium chloride, FNA-1-2, Gamma-tocotrienol, Progesterone, Vitamin D, Interleukin-22, Valproic Acid, Tretinoin, Tetradecanoylphorbol Acetate, wortmannin, Benzo(a)pyrene, bisphenol A, chelerythrine, Staurosporine, 2-(4-morpholinyl)-8-phenyl-4H-1-benzopyran-4-one, Estradiol, Carbamazepine, 1-Methyl-4-phenyl-1,2,3,6-tetrahydropyridine, Pregabalin, tamibarotene, Tetrachlorodibenzodioxin, Acetylcysteine, Ammonia, tert-Butylhydroperoxide, 4-(5-benzo(1,3)dioxol-5-yl-4-pyridin-2-yl-1H-imidazol-2-yl)benzamide, (6-(4-(2-piperidin-1-ylethoxy)phenyl))-3-pyridin-4-ylpyrazolo(1,5-a) pyrimidine, Amino Acids, Caffeine, calphostin C, Cyclosporine, Cisplatin, Ethinyl Estradiol, HX 630, lead acetate, Nicotine, Phenobarbital, Phenylmercuric Acetate, Pilocarpine, Rotenone, trichostatin A, Zinc, 2,2',4,4'-tetrabromodiphenyl ether, Acetaminophen, afimoxifene, Ammonium Chloride, Androgen Antagonists, Antirheumatic Agents, Astemizole, 7,8-Dihydro-7,8-dihydroxybenzo(a)pyrene 9,10-oxide, butylparaben, caffeic acid phenethyl ester, Chlorodiphenyl (54% Chlorine), Chloroprene, Chlorpyrifos, Clozapine, Cycloheximide, diazepinylbenzoic acid, Diethylnitrosamine, Calcitriol, diphenyldiselenide, entinostat, enzacamene, Excitatory Amino Acid Agents, Fonofos, Haloperidol, Ibotenic Acid, Ibuprofen, Kainic Acid, Ketone Bodies, LE 540, N-Methyl-3,4-methylenedioxyamphetamine, Mitomycin, Nanotubes Carbon, 1-Naphthylisothiocyanate, octylmethoxycinnamate, Paclitaxel, panobinostat, Parathion, pentabromodiphenyl ether, pirinixic acid, potassium chromate(VI), Pregnanolone, Pregnenolone Carbonitrile, profenofos, Propofol, resveratrol, Selenium, St. Thomas' Hospital cardioplegic solution, terbufos, Thallium, titanium dioxide, Trinitrobenzenesulfonic Acid, Tunicamycin, undecane, Vanadium, Vitamin K 3, vorinostat, Win 55212-2, Zidovudine, zonisamide, hsa-miR-7-5p, hsa-miR-520f-3p, hsa-miR-302c-3p.2, hsa-miR-200b-3p, hsa-miR-429, hsa-miR-200c-3p, hsa-miR-203a-3p.1, hsa-miR-144-3p, hsa-miR-101-3p.2, hsa-miR-138-5p, hsa-miR-200a-3p, hsa-miR-141-3p, hsa-miR-23a-3p, hsa-miR-23b-3p, hsa-miR-23c, hsa-miR-130a-5p, hsa-miR-25-3p, hsa-miR-32-5p, hsa-miR-363-3p, hsa-miR-367-3p, hsa-miR-92b-3p, hsa-miR-92a-3p, hsa-miR-101-3p.1, hsa-miR-137, hsa-miR-182-5p, hsa-miR-183-5p.2, hsa-miR-9-5p, hsa-miR-1271-5p, hsa-miR-96-5p, hsa-miR-202-5p, hsa-miR-217, hsa-miR-6807-3p, hsa-miR-1271, hsa-miR-96, hsa-miR-23a, hsa-miR-23b, hsa-miR-146a, hsa-miR-146b-5p, hsa-miR-876-5p, hsa-miR-544, hsa-miR-101, hsa-miR-429, hsa-miR-200b, hsa-miR-200c, hsa-miR-193a-3p, hsa-miR-193b, hsa-miR-1297, hsa-miR-26a, hsa-miR-26b, hsa-miR-200a, hsa-miR-141, hsa-miR-374b, hsa-miR-374a, hsa-miR-485-5p, hsa-miR-212, hsa-miR-132, hsa-miR-542-3p, hsa-miR-211, hsa-miR-204, hsa-miR-203, hsa-miR-494, hsa-miR-182, hsa-miR-382, hsa-miR-33a, hsa-miR-33b, hsa-miR-384, hsa-miR-376a, hsa-miR-376b, hsa-miR-186, hsa-miR-340, hsa-miR-143, hsa-miR-145, hsa-miR-138, hsa-miR-9, and combinations thereof.

Examples of SLC1A2 modulator include, but are not limited to, LDN 212320, DL-TBOA, (+/−)-threo-3-Methylglutamic acid, Dihydrokainic acid, WAY 213613, TFB-TBOA, L-trans-2,4-PDC, 7-Chlorokynurenate. Cocaine, nicotine, heroin, alcohol, N-acetylcysteine, Dihydrokainic acid, L-trans-2,4-PDC, TFB-TBOA, (2S,4R)-4-methylglutamate, D-aspartic acid, L-aspartic acid, SYM2081, threo-3-methylglutamate, WAY-213613, (±)-HIP-A, (±)-HIP-B, (±)-threo-3-Methylglutamic acid, 7-Chlorokynurenic acid, cis-ACBD, Congo Red, L-(−)-threo-3-Hydroxyaspartic acid, L-CCG-III, LDN 212320, MPDC, UCPH, WAY 213613, Creatine, Fluoxetine, Ascorbic acid, 2,3,7,8-tetrachlorodibenzo-p-dioxin, miR-122, 1-(4-(6-bromobenzo(1,3) dioxol-5-yl)-3a,4,5,9b-tetrahydro-3H-cyclopenta(c)quinolin-8-yl)ethanone, Raloxifene Hydrochloride, Manganese, Valproic Acid, manganese chloride, Estradiol, Riluzole, trichostatin A, 1,3,5-tris(4-hydroxyphenyl)-4-propyl-1H-pyrazole, 2-(2-amino-3-methoxyphenyl)-4H-1-benzopyran-4-one, diarylpropionitrile, methylmercuric chloride, tyrphostin AG 1478, Ceftriaxone, Corticosterone, N-(2-(4- bromocinnamylamino)ethyl)-5-isoquinolinesulfonamide, pyrrolidine dithiocarbamic acid, 2-(4-morpholinyl)-8-phenyl-4H-1-benzopyran-4-one, 4-(5-benzo(1,3)dioxol-5-yl-4-pyridin-2-yl-1H-imidazol-2-yl)benzamide, 4-(6-bromo-1,3-benzodioxol-5-yl)-3a,4,5,9b-3H-cyclopenta(c)quinolone, (6-(4-(2-piperidin-1-ylethoxy)phenyl))-3-pyridin-4-ylpyrazolo(1,5-a)pyrimidine, bisphenol A, Clozapine, Cocaine, copper(II)(1,10-phenanthroline)3, fulvestrant, Kainic Acid, manganese sulfate, Pertussis Toxin, Phenobarbital, pirinixic acid, Vitamin A, Acetaminophen, Acetylcysteine, arsenic disulfide, Benzo(a)pyrene, Blood Glucose, Chlorodiphenyl (54% Chlorine), p-Chloromercuribenzoic Acid, Chlorpyrifos, decitabine, Ethanol, Ethinyl Estradiol, Excitatory Amino Acid Agents, furan, Hydrogen Peroxide, Methamphetamine, Paraoxon, Phenylmercuric Acetate, resveratrol, romidepsin, Tretinoin, vorinostat, 2-(1'H-indolo-3'-carbonyl)thiazole-4-carboxylic acid methyl ester, 2,3-dimethoxy-1,4-naphthoquinone, 3,4,3',4'-tetrachlorobiphenyl, 3-hydroxyacetanilide, 4-toluidine, AG 1879, Aldehydes, Ammonium Chloride, Ampicillin, Antirheumatic Agents, arsenic trioxide, Atorvastatin Calcium, benzo(k)fluoranthene, Bleomycin, butylparaben, butyraldehyde, Butyric Acid, Ethylene Chlorohydrin, cinnamic aldehyde, Clofibrate, Cobalt, Copper Sulfate, coumarin, Cuprizone, Cyclosporine, Diazinon, Dibutyl Phthalate, Cisplatin, Dichlorodiphenyl Dichloroethylene, Diethylhexyl Phthalate, dihydrokainic acid, Dithiothreitol, Levodopa, enzacamene, epoxiconazole, ethylene dichloride, Genistein, Haloperidol, indole-3-carbinol, lonomycin, (+)-JQ1 compound, Ketamine, Ketolides, KT 5720, lard, lead acetate, Linuron, Methoxychlor, 2-Methyl-4-chlorophenoxyacetic Acid, Nanotubes Carbon, N-methyl-N-(6-methoxy-1-phenyl-1,2,3,4-tetrahydronaphthalen-2-ylmethyl)aminomethylcarboxylic acid, N-nitrosomorpholine, ochratoxin A, octylmethoxycinnamate, Oxidopamine, Oxycodone, Paclitaxel, Penicillins, Pentachlorophenol, pentanal, perfluorooctane sulfonic acid, Potassium Dichromate, prochloraz, procymidone, Progesterone, propionaldehyde, Propylthiouracil, Quercetin, Quinazolines, sodium bisulfide, Soman, Triiodothyronine, Tamoxifen, Tetradecanoylphorbol Acetate, Trichloroethylene, tungsten carbide, U 0126, vinclozolin, Win 55212-2, Zinc, zinc chloride, hsa-miR-142-5p, hsa-miR-5590-3p, hsa-miR-221-3p, hsa-miR-222-3p, hsa-miR-31-5p, hsa-miR-182-5p, hsa-miR-145-5p, hsa-miR-5195-3p, hsa-miR-187-3p, hsa-miR-218-5p, hsa-miR-203a-3p.1, hsa-miR-16-5p, hsa-miR-195-5p, hsa-miR-6838-5p, hsa-miR-15b-5p, hsa-miR-424-5p, hsa-miR-15a-5p, hsa-miR-497-5p, hsa-miR-455-3p.1, hsa-miR-183-5p.1, hsa-miR-429, hsa-miR-200c-3p, hsa-miR-200b-3p, hsa-miR-1271-5p, hsa-miR-96-5p, hsa-miR-526b-3p, hsa-miR-93-5p, hsa-miR-106b-5p, hsa-miR-20a-5p, hsa-miR-20b-5p, hsa-miR-17-5p, hsa-miR-519d-3p, hsa-miR-106a-5p, hsa-miR-369-3p, hsa-miR-374c-5p, hsa-miR-655-3p, hsa-miR-542-3p, hsa-miR-376c, hsa-miR-186, and combinations thereof.

Examples of SLC1A3 modulator include, but are not limited to, 7-Chlorokynurenate. DL-TBOA, L-Glutamic Acid, 7-Chlorokynurenic acid sodium salt, Dihydrokainic acid, L-trans-2,4-PDC, TFB-TBOA, (2S,4R)-4-methylglutamate, D-aspartic acid, L-aspartic acid, UCPH-101, (±)-HIP-A 103, (±)-HIP-B, (±)-threo-3-Methylglutamic acid, 7-Chlorokynurenic acid, cis-ACBD, Congo Red, L-(−)-threo-3-Hydroxyaspartic acid, L-CCG-III, LDN 212320, MPDC, UCPH, WAY 213613, ETB-TBOA, DL-TBOA, Dihydrokainate, 13-cis retinoic acid, Potassium chloride, pioglitazone, olanzapine, Palmitate, Raloxifene Hydrochloride, Valproic Acid, Estradiol, manganese chloride, Streptozocin, Manganese, Riluzole, 4-(5-benzo(1,3)dioxol-5-yl-4-pyridin-2-yl-1H-imidazol-2-yl)benzamide, (6-(4-(2-piperidin-1-ylethoxy)phenyl))-3-pyridin-4-ylpyrazolo(1,5-a)pyrimidine, Tetrachlorodibenzodioxin, bisphenol A, Ethinyl Estradiol, Glucose, resveratrol, Tamoxifen, trichostatin A, manganese sulfate, perfluorooctane sulfonic acid, 1-(4-(6-bromobenzo(1,3)dioxol-5-yl)-3a,4,5,9b-tetrahydro-3H-cyclopenta(c)quinolin-8-yl)ethanone, 4-(6-bromo-1,3-benzodioxol-5-yl)-3a,4,5,9b-3H-cyclopenta(c)quinolone, Ammonium Chloride, Benzo(a)pyrene, butylparaben, Ethylene Chlorohydrin, Chlorpyrifos, Copper, Dexamethasone, enzacamene, Ethanol, Excitatory Amino Acid Agents, lead acetate, octylmethoxycinnamate, oxaliplatin, panobinostat, Paraoxon, Progesterone, pyrrolidine dithiocarbamic acid, vorinostat, 2-(1'H-indolo-3'-carbonyl)thiazole-4-carboxylic acid methyl ester, 2,2',3',4,4',5-hexachlorobiphenyl, 22,4,4-tetrabromodiphenyl ether, 2,4,5,2',4',5'-hexachlorobiphenyl, 2-amino-4-(4-methoxyphenyl)-7-(naphthalen-1-yl)-5-oxo-5,6,7,8-tetrahydro-4H-chromene-3-carbonitrile, 3,4,5,3',4'-pentachlorobiphenyl, Acetaminophen, Acrylamide, Amino Acids, Peptides, and Proteins, Androgen Antagonists, Crocidolite, Atorvastatin Calcium, belinostat, bexarotene, Chloroprene, Cholesterol, CI 1044, Curcumin, Diazepam, Diazinon, Dibutyl Phthalate, Cisplatin, 9,10-Dimethyl-1,2-benzanthracene, diphenyldiselenide, furan, Genistein, Haloperidol, Hydrogen Peroxide, Kanamycin, Medroxyprogesterone Acetate, Methamphetamine, N-Methyl-3,4-methylenedioxyamphetamine, Nanotubes Carbon, 1-Naphthylisothiocyanate, nitrosobenzylmethylamine, NSC 689534, ochratoxin A, Oxidopamine, Ozone, Paclitaxel, palm oil, perfluorooctanoic acid, Phenylephrine, pirinixic acid, Pregnenolone Carbonitrile, SCH 442416, titanium dioxide, Topotecan, Tretinoin, trimellitic anhydride, Tunicamycin, vinclozolin, zoledronic acid, hsa-miR-23a, hsa-miR-23b, hsa-miR-194, hsa-miR-361-5p, hsa-miR-142-3p, hsa-miR-382, hsa-miR-143, hsa-miR-203, hsa-miR-216b, hsa-miR-371-5p, hsa-miR-125a-3p, hsa-miR-486-5p, hsa-miR-370, hsa-miR-155, hsa-miR-499-5p, hsa-miR-384, hsa-miR-490-3p, hsa-miR-128, hsa-miR-190, hsa-miR-365, hsa-miR-410, hsa-miR-190b, hsa-miR-488, hsa-miR-22, hsa-miR-23b-3p, hsa-miR-23a-3p, hsa-miR-23c, hsa-miR-130a-5p, hsa-miR-155-5p, hsa-miR-203a-3p.1, hsa-miR-455-3p.1, hsa-miR-22-3p, hsa-miR-142-3p.1, hsa-miR-613, hsa-miR-206, hsa-miR-1-3p, hsa-miR-216a-5p, hsa-miR-142-3p.2, hsa-miR-194-5p, hsa-miR-140-3p.2, hsa-miR-499a-5p, hsa-miR-5195-3p, hsa-miR-145-5p, hsa-miR-153-3p, hsa-miR-143-3p, hsa-miR-6088, hsa-miR-4770, hsa-miR-365b-3p, hsa-miR-365a-3p, and combinations thereof.

Examples of SLC1A4 modulator include, but are not limited to, L-alanine, hydroxyproline, L-cystine, L-serine, L-threonine, L-proline, D-proline. d,l-threo-benzyloxy aspartate (d,l-TBOA), Glucosamine, Tretinoin, miR-122, dexamethasone, Gamma-tocotrienol, pregnenolone, 16alpha-carbonitrile, Tetrachlorodibenzodioxin, Valproic Acid, Estradiol, Cyclosporine, bisphenol A, pirinixic acid, Benzo(a)pyrene, Progesterone, 4-(5-benzo(1,3)dioxol-5-yl-4-pyridin-2-yl-1H-imidazol-2-yl)benzamide, (6-(4-(2-piperidin-1-ylethoxy)phenyl))-3-pyridin-4-ylpyrazolo(1,5-a) pyrimidine, Coumestrol, 1-(2-cyano-3,12-dioxooleana-1,9-dien-28-oyl) imidazole, andrographolide, Chlorpyrifos, Copper, Cuprizone, Cisplatin, Diethylnitrosamine, Ethanol, Genistein, motexafin gadolinium, pentabromodiphenyl ether, Phenylmercuric Acetate, Zidovudine, Zinc Acetate, 1-(2-trifluoromethoxyphenyl)-2-nitroethanone, 2-(1'H-indolo-3'-carbonyl)thiazole-4-carboxylic acid methyl ester, 2,2',4,4'-tetrabromodiphenyl ether, 2,3-bis(3'-hydroxybenzyl)butyrolactone, 2,4,5,2',4',5'-hexachlorobiphenyl, 3,4,5, 3',4'-pentachlorobiphenyl, Acetaminophen, AM 251, Crocidolite, Atrazine, benz(a)anthracene, beta-Naphthoflavone, 7,8-Dihydro-7,8-dihydroxybenzo(a)pyrene 9,10-oxide, tert-Butylhydroperoxide, Cannabidiol, Carbamazepine, chloroacetaldehyde, cidofovir, Clodronic Acid, Clofibrate, Cocaine, Copper Sulfate, Dasatinib, Dronabinol, Dexamethasone, Diazinon, dibenzothiophene, Dibutyl Phthalate, diethyl maleate, Ethinyl Estradiol, Ethyl Methanesulfonate, Formaldehyde, Ibuprofen, ICG 001, indole-3-carbinol, lonomycin, K 7174, lead acetate, Lucanthone, Magnetite Nanoparticles, Metformin, Methyl Methanesulfonate, N-Methyl-3,4-methylenedioxyamphetamine, Mitomycin, monomethylarsonous acid, N-methyl-N-(6-methoxy-1-phenyl-1,2,3,4-tetrahydronaphthalen-2-ylmethyl)aminomethylcarboxylic acid, NSC 689534, Orphenadrine, Phenobarbital, potassium chromate(VI), Potassium Dichromate, propiconazole, Propylthiouracil, resveratrol, S-(1,1,2,2-tetrafluoroethyl)cysteine, Succimer, Testosterone, Tetracycline, Tetradecanoylphorbol Acetate, Thapsigargin, Thiram, Lamivudine, Tunicamycin, Vanadium, vinclozolin, vorinostat, Zinc, hsa-miR-526b-3p, hsa-miR-20b-5p, hsa-miR-17-5p, hsa-miR-93-5p, hsa-miR-106b-5p, hsa-miR-20a-5p, hsa-miR-519d-3p, hsa-miR-106a-5p, hsa-miR-3064-5p, hsa-miR-6504-5p, hsa-miR-203a-3p.1, hsa-miR-124-3p.2, hsa-miR-506-3p, hsa-miR-124-3p.1, hsa-let-7d-5p, hsa-miR-4458, hsa-let-7b-5p, hsa-miR-98-5p, hsa-let-7c-5p, hsa-let-7e-5p, hsa-let-7a-5p, hsa-let-7i-5p, hsa-let-7f-5p, hsa-miR-4500, hsa-let-7g-5p, hsa-miR-135a, hsa-miR-135b, hsa-miR-214, hsa-miR-590-3p, hsa-miR-31, hsa-miR-382, hsa-miR-103, hsa-miR-107, hsa-miR-145, hsa-miR-26a, hsa-miR-26b, hsa-let-7f, hsa-let-7b, hsa-let-7g, hsa-let-7i, hsa-let-7a, hsa-let-7c, hsa-let-7e, hsa-miR-98, hsa-let-7d, hsa-miR-132, hsa-miR-212, hsa-miR-203, hsa-miR-326, hsa-miR-330-5p, hsa-miR-485-5p, hsa-miR-496, hsa-miR-1297, and combinations thereof.

Examples of SLC1A5 modulator include, but are not limited to, I-γ-glutamyl-p-nitroanilide, Benzylcysteine, benzylserine, p-nitrophenyl glutamyl anilide, L-glutamine, gamma-L-glutamyl-p-nitroanilide (GPNA), Ribavirin, Silica, miR-542-3p, Imatinib, Glucosamine, microRNA-140, Adriamycin, Tretinoin, bisphenol A, Cyclosporine, Progesterone, Tetrachlorodibenzodioxin, Benzo(a)pyrene, Cisplatin, Ethinyl Estradiol, Genistein, Estradiol, Chlorpyrifos, Ethanol, Manganese, Phenobarbital, Tetradecanoylphorbol Acetate, Thiazoles, Valproic Acid, 2-(1H-indazol-4-yl)-6-(4-methanesulfonylpiperazin-1-ylmethyl)-4-morpholin-4-ylthieno(3,2-d)pyrimidine, 2,2',3',4,4',5-hexachlorobiphenyl, 2,2',4,4'-tetrabromodiphenyl ether, 2',3,3',4',5-pentachloro-4-hydroxybiphenyl, 2,4,4'-trichlorobiphenyl, 2,4,5,2',4',5'-hexachlorobiphenyl, 2,4,5,2',5'-pentachlorobiphenyl, 2,5,2',5'-tetrachlorobiphenyl, 3,4,5,3',4'-pentachlorobiphenyl, 4,4'-diaminodiphenylmethane, 4'-cyanobiphenyl-4-sulfonic acid (6-aminopyridin-2-yl)amide, Acetaminophen, Ammonium Chloride, Beclomethasone, C646 compound, caffeic acid phenethyl ester, Cephaloridine, chloroacetaldehyde, chloropicrin, Chlorpromazine, Choline, cidofovir, Clodronic Acid, Colchicine, Copper, Cuprizone, Dronabinol, Dexamethasone, Diazinon, Dibutyl Phthalate, Dieldrin, Diethylnitrosamine, 9,10-Dimethyl-1,2-benzanthracene, Dithioerythritol, Etoposide, Zearalenone, Folic Acid, Gentamicins, Hydrocortisone, Hydroxyurea, Ifosfamide, indeno(1,2,3-cd)pyrene, Ionomycin, 1-Methyl-3-isobutylxanthine, K 7174, Lipopolysaccharides, Methionine, Mitomycin, 1-Naphthylisothiocyanate, Nickel, nonylphenol, NSC668394, o,p'-DDT, palm oil, PCB 180, pentabromodiphenyl ether, Pentachlorophenol, prochloraz, resveratrol, rosiglitazone, Sodium Selenite, Tamoxifen, Thioacetamide, Lamivudine, tolcapone, tributyltin, trichostatin A, Adenine, Zidovudine, zinc chloride, zoledronic acid, hsa-miR-122, hsa-miR-122-5p, hsa-miR-125a-5p, hsa-miR-125b, hsa-miR-137, hsa-miR-137 hsa-miR-146a, hsa-miR-146b-5p, hsa-miR-199a-5p, hsa-miR-199b-5p, hsa-miR-214 hsa-miR-302c-3p.2, hsa-miR-338-3p, hsa-miR-520f-3p, hsa-miR-542-3p, hsa-miR-590-3p, and combinations thereof.

Examples of SLC1A6 modulator include, but are not limited to, DL-TBOA, threo-3-methylglutamate, 7-Chlorokynurenic acid sodium salt, Dihydrokainic acid, L-trans-2,4-PDC, TFB-TBOA, 7-Chlorokynurenate, L-glutamic acid, glutamate, Potassium chloride, 4-nonylphenol, Aldosterone, cisplatin, Valproic Acid, 4-(5-benzo(1,3)dioxol-5-yl-4-pyridin-2-yl-1H-imidazol-2-yl)benzamide, (6-(4-(2-piperidin-1-ylethoxy)phenyl))-3-pyridin-4-ylpyrazolo(1,5-a)pyrimidine, trichostatin A, Phenylmercuric Acetate, Tetrachlorodibenzodioxin, Tretinoin, 2,2',3',4,4',5-hexachlorobiphenyl, 2,4,4'-trichlorobiphenyl, 2,4,5,2',4',5'-hexachlorobiphenyl, 2,4,5,2',5'-pentachlorobiphenyl, 2,5,2',5'-tetrachlorobiphenyl, 3,4-dichloroaniline, Acetaminophen, Ammonium Chloride, Androgen Antagonists, Atrazine, bisphenol A, butylparaben, Chlorine, Chlorpyrifos, Dibutyl Phthalate, Dichlorodiphenyl Dichloroethylene, Diethylhexyl Phthalate, Calcitriol, Diuron, enzacamene, epoxiconazole, Ethanol, Ethinyl Estradiol, Fatty Acids, Omega-3, furan, (+)-JQ1 compound, Linuron, Lipopolysaccharides, Methoxychlor, octylmethoxycinnamate, Fatty Acids, Omega-6, Ozone, PCB 180, Phthalic Acids, Potassium Dichromate, prochloraz, procymidone, Propylthiouracil, pyrachlostrobin, Soman, tamibarotene, Thioacetamide, Trichloroethylene, vinclozolin, hsa-miR-153-3p, hsa-miR-3064-5p, hsa-miR-6504-5p, hsa-miR-223-3p, hsa-miR-129-2-3p, hsa-miR-129-1-3p, hsa-miR-33a-5p, hsa-miR-33b-5p, hsa-miR-135a-5p, hsa-miR-135b-5p, hsa-miR-153, hsa-miR-186, hsa-miR-33a, hsa-miR-33b, hsa-miR-199b-5p, hsa-miR-495, hsa-miR-135a, hsa-miR-135b, hsa-miR-224, hsa-miR-223, hsa-miR-590-3p, hsa-miR-149, hsa-miR-302e, hsa-miR-373, hsa-miR-302a, hsa-miR-302b, hsa-miR-302c, hsa-miR-302d, hsa-miR-520a-3p, hsa-miR-520d-3p, hsa-miR-520e, hsa-miR-372, hsa-miR-520b, hsa-miR-520c-3p, and combinations thereof.

Examples of SLC3A2 modulator include, but are not limited to, Erastin, Erastin-A8, SAS, RSL3, and molecules numbered analog #s 3,4,5,6,7,8,9,10,11,12,13,14,15,16,17,18,19,20,21,22 (see Dixon-S J et al. PMID:24844246. Elife. 2014 May 203:e02523, FIG. 3), (S)-4-carboxyphenylglycine, glutamate, Glucosamine, cyclopamine, Dioxin, Probiotic Lactobacillus GG soluble factors, Palmitate, Ascorbic acid, Nickel, miR-221, miR-542-3p, Tetrachlorodibenzodioxin, Cyclosporine, Benzo(a)pyrene, Bilirubin, Cystine, Ethinyl Estradiol, Valproic Acid, 4-(5-benzo(1,3)dioxol-5-yl-4-pyridin-2-yl-1H-imidazol-2-yl)benzamide, (6-(4-(2-piperidin-1-ylethoxy)phenyl))-3-pyridin-4-ylpyrazolo(1,5-a)pyrimidine, Acetaminophen, Amino Acids, Peptides, and Proteins, Estradiol, Genistein, pirinixic acid, 2-methyl-2H-pyrazole-3-carboxylic acid (2-methyl-4-o-tolylazophenyl)amide, bisphenol A, Cisplatin, Ionomycin, Phenobarbital, Tetradecanoylphorbol Acetate, 1-(2-trifluoromethoxyphenyl)-2-nitroethanone, 2,2',4,4'-tetrabromodiphenyl ether, Chlorodiphenyl (54% Chlorine), p-Chloromercuribenzoic Acid, Choline, Cuprizone, Curcumin, Dronabinol, Dibutyl Phthalate, Diethylnitrosamine, entinostat, Estrogens, Fenofibrate, Fluorouracil, Flutamide, Folic Acid, Glutathione, Indomethacin, Methionine, motexafin gadolinium, Nanotubes Carbon, palm oil, pentabromodiphenyl ether, perfluorooctanoic acid, Phenylmercuric Acetate, rosiglitazone, Trichloroethylene, Zidovudine, Zinc Acetate, zoledronic acid, 2',3,3',4',5-pentachloro-4-hydroxybiphenyl, 2,4-dinitro 2,6-dinitro 2-tert-butylhydroquinone, 3,4,5,3',4'-pentachlorobiphenyl, 4,4'-diaminodiphenylmethane, (4-amino-1,4-dihydro-3-(2-pyridyl)-5-thioxo-1,2,4-triazole)copper(II), 4-amino-2,6-dinitro afimoxifene, AGN 194204, Amiodarone, arsenic trioxide, arsenite, Crocidolite, Atrazine, benz(a)anthracene, beta-Naphthoflavone, bicalutamide, 8-Bromo Cyclic Adenosine Monophosphate, C646 compound, Cadmium, Cannabidiol, Carbamazepine, Carmustine, CC-8490, chloroacetaldehyde, Chlorpromazine, chrysene, Cidofovir, Clodronic Acid, Clofibrate, Clofibric Acid, Copper, Copper Sulfate, Cycloheximide, Cyclophosphamide, Dactinomycin, decitabine, Dexamethasone, Diethylstilbestrol, Diuron, Drugs Ethyl Methanesulfonate, Zearalenone, fipronil, Formaldehyde, gamma-Linolenic Acid, gedunin, Heptachlor Epoxide, Fenretinide, Hydralazine, Hydrogen Peroxide, Ibuprofen, ICG 001, Ifosfamide, jinfukang, (+)-JQ1 compound, K 7174, lead acetate, leflunomide, Lindane, Lithium Chloride, Mercaptoethanol, Metformin, Methapyrilene, Methotrexate, Methyl Methanesulfonate, 1-Methyl-4-phenylpyridinium, monomethylarsonous acid, Naphthoquinones, 1-Naphthylisothiocyanate, n-butoxyethanol, nefazodone, nimesulide, NSC305787, NSC668394, NSC 689534, Paraquat, PCI 5002, Pentachlorophenol, phorone, Phosgene, Phthalic Acids, Piperonyl Butoxide, Piroxicam, Pregnenolone Carbonitrile, Proton Pump Inhibitors, pyrrolidine dithiocarbamic acid, Quercetin, quinocetone, Raloxifene Hydrochloride, roscovitine, S-(1,1,2,2-tetrafluoroethyl)cysteine, Selenium, sevoflurane, sodium bichromate, Sodium Fluoride, Sulfasalazine, Sulindac, sulindac sulfide, systhane, tallow, Tamoxifen, Thapsigargin, Thioacetamide, Thioguanine, Lamivudine, triadimefon, tripterine, troglitazone, Tunicamycin, valdecoxib, vinclozolin, Zinc, hsa-miR-7-5p, hsa-miR-425, hsa-miR-490-3p, hsa-miR-128, hsa-miR-7, and combinations thereof.

Examples of SLC7A5 modulator include, but are not limited to, Aminobicyclo[2.2.1]heptane-2-carboxylic acid (BCH), dexamethasone, JPH203/KYT-0353, D-leucine, D-phenylalanine, Imatinib mesylate, nickel, Glucosamine, Dioxin, Camptothecin, Ascorbic acid, Imatinib, ethanol, Tetrachlorodibenzodioxin, 4-(5-benzo(1,3)dioxol-5-yl-4-pyridin-2-yl-1H-imidazol-2-yl)benzamide, (6-(4-(2-piperidin-1-ylethoxy)phenyl))-3-pyridin-4-ylpyrazolo(1,5-a)pyrimidine, Estradiol, Benzo(a)pyrene, Cyclosporine, Valproic Acid, Genistein, bisphenol A, Coumestrol, Ethinyl Estradiol, Nanotubes Carbon, nickel sulfate, Tretinoin, trichostatin A, 2,3-dibromopropyl-2,4,6-tribromophenyl ether, 3,4,5,3',4'-pentachlorobiphenyl, Acetaminophen, 7,8-Dihydro-7,8-dihydroxybenzo(a)pyrene 9,10-oxide, p-Chloromercuribenzoic Acid, Cuprizone, Dexamethasone, Cisplatin, Diethylstilbestrol, entinostat, (+)-JQ1 compound, Mercury, Nickel, O,O-diethyl O-3,5,6-trichloro-2-pyridyl phosphate, oxaliplatin, panobinostat, Phenobarbital, Phenylmercuric Acetate, Topotecan, zoledronic acid, 1-(2-trifluoromethoxyphenyl)-2-nitroethanone, 1,3,5-tribromobenzene, 2,2',3',4,4',5-hexachlorobiphenyl, 2,2',4,4'-tetrabromodiphenyl ether, 2,2,5,7,8-pentamethyl-1-hydroxychroman, 2',3,3',4',5-pentachloro-4-hydroxybiphenyl, 2,3-bis(3'-hydroxybenzyl)butyrolactone, 2,4,4'-trichlorobiphenyl, 2,4,5,2',4',5'-hexachlorobiphenyl, 2,4,5,2',5'-pentachlorobiphenyl, 2,5,2',5'-tetrachlorobiphenyl, 2,6-dinitro 2-amino-3-(4-((5-amino-2-phenylbenzo(d)oxazol-7-yl)methoxy)-3,5-dichlorophenyl) propanoic acid, 2-methyl-2H-pyrazole-3-carboxylicacid(2-methyl-4-o-tolylazophenyl)amide, (4-amino-1,4-dihydro-3-(2-pyridyl)-5-thioxo-1,2,4-triazole)copper(II), 9,10-dihydroxy-9,10-dihydroxybenzo(a)pyrene, Acetylglucosamine, afimoxifene, Air Pollutants, Occupational, AM 251, Amino Acids, Peptides, and Proteins, Ammonium Chloride, Crocidolite, Atrazine, benz(a)anthracene, beta-Naphthoflavone, beta-methylcholine, bexarotene, Bortezomib, tert-Butylhydroperoxide, C646 compound, Carbamazepine, carbonyl sulfide, Cephaloridine, chloroacetaldehyde, chloropicrin, Chloroprene, Cholesterol, chrysene, cidofovir, Clodronic Acid, Clofibrate, Cycloheximide, Cysteine, Dactinomycin, daidzein, decitabine, Dinitrochlorobenzene, Estrone, Ethanol, Mestranol, Ethyl Methanesulfonate, Etoposide, Zearalenone, Fenofibrate, Flavonoids, Flutamide, fulvestrant, furan, gabapentin, Fenretinide, Hydrogen Peroxide, Ibuprofen, ICG 001, Ifosfamide, Indomethacin, lonomycin, K 7174, lipopolysaccharide, E. coli O55-B5, Lipopolysaccharides, Metformin, Methyl Methanesulfonate, 1-Methyl-4-phenylpyridinium, Mitoxantrone, nickel chloride, Nicotine, NSC668394, o,p'-DDT, Oxazolone, PCB 180, pentabromodiphenyl ether, Piperonyl Butoxide, pirinixic acid, Piroxicam, polyhexamethyleneguanidine, Progesterone, Propylthiouracil, Quercetin, quinocetone, Raloxifene Hydrochloride, resveratrol, Isotretinoin, riddelliine, roscovitine, rosiglitazone, S-(1,1,2,2-tetrafluoroethyl)cysteine, Selenium, Sodium Selenite, Tamoxifen, Tetradecanoylphorbol Acetate, Thapsigargin, Thioacetamide, Trichloroethylene, Tunicamycin, vinclozolin, Zidovudine, hsa-miR-124-3p.1, hsa-miR-506-3p, hsa-miR-124-3p.2, hsa-miR-199b-5p, hsa-miR-199a-5p, hsa-miR-3064-5p, hsa-miR-6504-5p, hsa-miR-27b-3p, hsa-miR-27a-3p, hsa-miR-148b-3p, hsa-miR-148a-3p, hsa-miR-152-3p, hsa-miR-194-5p, hsa-miR-126-3p.1, and combinations thereof.

Examples of SLC7A11 modulator include, but are not limited to, L-alanosine, Erastin, Erastin-A8, SAS, RSL3, and molecules numbered analog #s 3,4,5,6,7,8,9,10,11,12, 13,14,15,16,17,18,19,20,21,22 (see Dixon-S J et al. PMID: 24844246. Elife. 2014 May 20; 3:e02523, FIG. 3), Riluzole, Sulfasalazine, L-Cystine, Acetylcysteine, Rosuvastatin, Tauroursodeoxycholic acid, Taurocholic acid, L-Glutamic Acid, miR-221/222, Gamma-tocotrienol, Ribavirin, Imatinib, Nickel, Camptothecin, Palmitate, Sebacic acid, Glucosamine, Benzo(a)pyrene, Sulfasalazine, Cyclosporine, 4-(5-benzo(1,3)dioxol-5-yl-4-pyridin-2-yl-1H-imidazol-2-yl)benzamide, (6-(4-(2-piperidin-1-ylethoxy)phenyl))-3-pyridin-4-ylpyrazolo(1,5-a)pyrimidine, Valproic Acid, arsenic trioxide, Estradiol, bisphenol A, Glutathione, Tetrachlorodibenzodioxin, Cystine, Bilirubin, Paraquat, diethyl maleate, Hydrogen Peroxide, (+)-JQ1 compound, Tetradecanoylphorbol Acetate, Acetaminophen, aluminum citrate, Cadmium, Chlorpyrifos, Cocaine, Copper, Copper Sulfate, Cisplatin, lead acetate, Magnetite Nanoparticles, Phenobarbital, Succimer, trichostatin A, Zymosan, 1-(2-cyano-3,12-dioxooleana-1,9-dien-28-oyl) imidazole, 1,2-dihydroxynaphthalene, 1-(2-trifluoromethoxyphenyl)-2-nitroethanone, 2,2',4,4'-tetrabromodiphenyl ether, 2,3-bis(3'-hydroxybenzyl)butyrolactone, 3,4,5,3',4'-pentachlorobiphenyl, 4-(4-fluorophenyl)-2-(4-hydroxyphenyl)-5-(4-pyridyl)imidazole, Acetylcysteine, Air Pollutants, alpha-Tocopherol, Ampicillin, Azathioprine, 7,8-Dihydro-7,8-dihydroxybenzo(a)pyrene 9,10-oxide, tert-Butylhydroperoxide, p-Chloromercuribenzoic Acid, cinnamic aldehyde, Coumestrol, Cuprizone, Curcumin, Cyclophosphamide, Dronabinol, Diazinon, Diethylstilbestrol, elesclomol, entinostat, Formaldehyde, glycidamide, Lindane, Lipopolysaccharides, motexafin gadolinium, Nickel, nickel chloride, panobinostat, pentabromodiphenyl ether, Phenylmercuric Acetate, Prednisolone, Quercetin, Reactive Oxygen Species, tetrabromobisphenol A, Tretinoin, tripterine, Vitamin K3, vorinostat, Zinc Acetate, 1,2-diamino-4-nitrobenzene, 1,6-hexamethylene diisocyanate, 2',3,3',4',5-pentachloro-4-hydroxybiphenyl, 2,3-dichloro-1-propanol, 2-amino-3,8-dimethylimidazo(4,5-f)quinoxaline, 2-amino-3-methylimidazo(4,5-f)quinolone, 2-amino-4-methylphenol, 2-chloromethylpyridine, 2-tert-butylhydroquinone, 2-xylene, 3,4,3',4'-tetrachlorobiphenyl, 4-anisidine, 4-carboxyphenylglycine, 4-hydroxy-2-nonenal, 7-aminocephalosporanic acid, Acrolein, Acrylamide, ammonium hexachloroplatinate, andrographolide, Arachidonic Acid, Crocidolite, Ascorbic Acid, Atrazine, belinostat, benz(a)anthracene, benzidine, benzyloxycarbonylleucyl-leucyl-leucine aldehyde, bicalutamide, BIRB 796, bis(tri-n-butyltin)oxide, 8-Bromo Cyclic Adenosine Monophosphate, butyraldehyde, candoxin, Cannabidiol, captax, Carbamazepine, Ceftriaxone, chlorantranilipole, chloroacetaldehyde, chloropicrin, Chloroprene, chloroquine diphosphate, Choline, Coumaphos, cresidine, cyanoginosin LR, cypermethrin, DDT, Demecolcine, dibutyldichlorotin, Diclofenac, Dieldrin, Dimethylnitrosamine, Diquat, Drugs Endosulfan, Epichlorohydrin, Estriol, Estrone, Ethinyl Estradiol, ethyl acrylate, ethylbenzene, Ethyl Methanesulfonate, Eugenol, Zearalenone, Fluoxetine, Folic Acid, Maleic Anhydrides, gedunin, Genistein, glycidol, Gold Sodium Thiomalate, Hypochlorous Acid, Ibuprofen, ICG 001, Indomethacin, Ionomycin, K7174, Metformin, Methionine, Methotrexate, Methylenebis(chloroaniline), Methylene Chloride, Methylmethacrylate, Methylprednisolone, Mitomycin, mono-(2-ethylhexyl)phthalate, monomethylarsonous acid, Mycophenolic Acid, Nanotubes Carbon, naphthalene, Naphthoquinones, n-butoxyethanol, nickel sulfate, N-methyl-4-aminophenol, nonylphenol, NSC668394, NSC 689534, ochratoxin A, Oxadiazoles, Ozone, PCI 5002, Phenol, Piroxicam, Polychlorinated Biphenyls, Potassium Dichromate, Progesterone, Propylthiouracil, racecadotril, Raloxifene Hydrochloride, resorcinol, S-(1,1,2,2-tetrafluoroethyl)cysteine, Silver, si-wu-tang, sodium bichromate, Sodium Selenite, tetrathiomolybdate, Thiram, triacsin C, Trichloroethylene, trimellitic anhydride, Tunicamycin, vanillin, Vincristine, Zinc, hsa-miR-199b-5p, hsa-miR-199a-5p, hsa-miR-489-3p, hsa-miR-23c, hsa-miR-23b-3p, hsa-miR-23a-3p, hsa-miR-130a-5p, hsa-miR-338-3p, hsa-miR-142-3p.2, hsa-miR-3064-5p, hsa-miR-6504-5p, hsa-miR-3064-5p, hsa-miR-6504-5p, hsa-miR-155-5p, hsa-miR-375, hsa-miR-429, hsa-miR-200c-3p, hsa-miR-200b-3p, hsa-miR-375, hsa-miR-148b-3p, hsa-miR-148a-3p, hsa-miR-152-3p, hsa-miR-199b-3p, hsa-miR-199a-3p, hsa-miR-3129-5p, hsa-miR-148b-3p, hsa-miR-152-3p, hsa-miR-148a-3p, hsa-miR-30c-5p, hsa-miR-30b-5p, hsa-miR-30a-5p, hsa-miR-30e-5p, hsa-miR-30d-5p, hsa-miR-142-3p.1, hsa-miR-30b-5p, hsa-miR-30c-5p, hsa-miR-30d-5p, hsa-miR-30a-5p, hsa-miR-30e-5p, hsa-miR-3681-3p, hsa-miR-128-3p, hsa-miR-216a-3p, hsa-miR-30c-5p, hsa-miR-30b-5p, hsa-miR-30a-5p, hsa-miR-30d-5p, hsa-miR-30e-5p, hsa-miR-144-3p, hsa-miR-25-3p, hsa-miR-363-3p, hsa-miR-32-5p, hsa-miR-367-3p, hsa-miR-92b-3p, hsa-miR-92a-3p, hsa-miR-27b-3p, hsa-miR-27a-3p, and combinations thereof.

Examples of SLC7A8 modulator include, but are not limited to, BCH, JPH203, Acivicin, 3-iodo-L-tyrosine, ESK242, ESK246, Vitamin D, Imatinib, miR-122, Dopaminergic transcription factors, Valproic Acid, bisphenol A, Ethinyl Estradiol, Progesterone, Tetrachlorodibenzodioxin, Dibutyl Phthalate, Glucosamine, trichostatin A, 4-(5-benzo(1,3)dioxol-5-yl-4-pyridin-2-yl-1H-imidazol-2-yl)benzamide, (6-(4-(2-piperidin-1-ylethoxy)phenyl))-3-pyridin-4-ylpyrazolo(1,5-a)pyrimidine, Acetaminophen, Estradiol, Calcitriol, Nanotubes Carbon, 3,4,5,3',4'-pentachlorobiphenyl, Amino Acids, Peptides, and Proteins, Ammonium Chloride, arsenic trioxide, arsenite, Benzo(a)pyrene, Ciguatoxins, Copper, Cisplatin, Diclofenac, Dieldrin, Docosahexaenoic Acids, Ethanol, Ionomycin, lead acetate, lipopolysaccharide, E coli 055-B5, Manganese, Medroxyprogesterone Acetate, Methotrexate, N-Methyl-3,4-methylenedioxyamphetamine, MRK 003, nickel sulfate, nitrosobenzylmethylamine, NSC 689534, palm oil, Pentachlorophenol, Phthalic Acids, pirinixic acid, Piroxicam, Prednisolone, Selenium, Silver, Smoke, Tamoxifen, Testosterone, Tetradecanoylphorbol Acetate, titanium dioxide, Trichloroethylene, Vancomycin, Zidovudine, hsa-miR-124-3p.1, hsa-miR-124-3p.2, hsa-miR-1271-5p, hsa-miR-133a-3p.1, hsa-miR-133a-3p.2, hsa-miR-133b, hsa-miR-145-5p, hsa-miR-182-5p, hsa-miR-183-5p.2, hsa-miR-3064-5p, hsa-miR-506-3p, hsa-miR-5195-3p, hsa-miR-6504-5p, hsa-miR-9-5p, hsa-miR-96-5p, and combinations thereof.

Examples of SLC7A13 modulator include, but are not limited to, Acrylamide, resveratrol, antipsychotic drugs, olanzapine quetiapine, miR-221, cyclopamine, miR-365, Laccaic acid, microRNA-140, adrenocorticotropin zinc, amphotericin B deoxycholate drug combination, Aristolochic Acids, bisphenol A, Cyclosporine, furan, hsa-miR-3129-5p, hsa-miR-199a-3p, hsa-miR-199b-3p, and combinations thereof.

Examples of SLC7A10 modulator include, but are not limited to, BMS-466442, miR-122, Valproic Acid, 4-(5-benzo(1,3)dioxol-5-yl-4-pyridin-2-yl-1H-imidazol-2-yl)benzamide, (6-(4-(2-piperidin-1-ylethoxy)phenyl))-3-pyridin-4-ylpyrazolo(1,5-a)pyrimidine, entinostat, Cuprizone, Nanotubes Carbon, panobinostat, Zidovudine, Aldehydes, Ammonium Chloride, Atrazine, bisphenol A, butyraldehyde, Cephaloridine, Chloroprene, Copper Sulfate, decitabine, Dibutyl Phthalate, Cisplatin, Diethylstilbestrol, Gentamicins, Ketamine, lead acetate, palm oil, pentanal, Phosgene, propionaldehyde, Propylthiouracil, sevoflurane, Tetrachlorodibenzodioxin, titanium dioxide, trichostatin A, trimellitic anhydride, hsa-miR-455-3p.1, hsa-miR-30a-5p, hsa-miR-30e-5p, hsa-miR-30d-5p, hsa-miR-30c-5p, hsa-miR-30b-5p, and combinations thereof.

Examples of SLC17A6 modulator include, but are not limited to, Resveratrol, Dopaminergic transcription factors, Fluoxetine, Gonadotropin-releasing hormone, pioglitazone, microRNA-140, Valproic Acid, Clozapine, Estradiol, Ethanol, Haloperidol, Lithium, Risperidone, 2,2',3',4,4',5-hexachlorobiphenyl, 2',3,3',4',5-pentachloro-4-hydroxybiphenyl, 2,4,4'-trichlorobiphenyl, 2,4,5,2',4',5'-hexachlorobiphenyl, 2,4,5,2',5'-pentachlorobiphenyl, 2,5,2',5'-tetrachlorobiphenyl, Ammonium Chloride, arsenite, Atrazine, beta-Naphthoflavone, bisphenol A, Cocaine, Cytarabine, Dronabinol, Diethylnitrosamine, entinostat, fullerene C60, furan, glycidol, Ketone Bodies, lead acetate, Methotrexate, Methoxychlor, Morphine, nickel monoxide, Nicotine, PCB 180, Phencyclidine, pirinixic acid, Polyphenols, Progesterone, sevoflurane, T-2 Toxin, hsa-miR-7-5p, hsa-miR-130a-5p, hsa-miR-23c, hsa-miR-23a-3p, hsa-miR-23b-3p, hsa-miR-33b-5p, hsa-miR-33a-5p, hsa-miR-203a-3p.1, hsa-miR-200a-3p, hsa-miR-141-3p, hsa-miR-455-3p.1, hsa-miR-33b-5p, hsa-miR-33a-5p, hsa-miR-455-3p.2, hsa-miR-19b-3p, hsa-miR-19a-3p, hsa-miR-218-5p, hsa-miR-373-3p, hsa-miR-520e, hsa-miR-520a-3p, hsa-miR-520d-3p, hsa-miR-372-3p, hsa-miR-520b, hsa-miR-520c-3p, hsa-miR-302e, hsa-miR-302b-3p, hsa-miR-302c-3p.1, hsa-miR-302d-3p, hsa-miR-302a-3p, hsa-miR-32-5p, hsa-miR-92b-3p, hsa-miR-25-3p, hsa-miR-367-3p, hsa-miR-92a-3p, hsa-miR-363-3p, hsa-miR-137, and combinations thereof.

Examples of SLC17A7 modulator include, but are not limited to, Zinc, Vitamin D, Imatinib, miR-483, Imatinib mesylate, Fluoxetine, Valproic Acid, Excitatory Amino Acid Agents, bafilomycin A1, Cisplatin, bisphenol A, Clozapine, Desipramine, Folic Acid, lead acetate, Lithium, Silver, 2,2', 3',4,4',5-hexachlorobiphenyl, 2,2',4,4'-tetrabromodiphenyl ether, 2',3,3',4',5-pentachloro-4-hydroxybiphenyl, 2,5,2',5'-tetrachlorobiphenyl, Acetaminophen, Ammonium Chloride, Dextroamphetamine, Androgen Antagonists, Antirheumatic Agents, Benzo(a)pyrene, butylparaben, Cocaine, Cuprizone, diphenyldiselenide, enzacamene, Ethanol, furan, jinfukang, (+)-JQ1 compound, Ketamine, lipopolysaccharide, *E coli* 055-B5, Morphine, octylmethoxycinnamate, PCB 180, Phosphates, Pilocarpine, pirinixic acid, pyrachlostrobin, Raloxifene Hydrochloride, Riluzole, S-2-pentyl-4-pentynoic hydroxamic acid, Sodium, Tetrachlorodibenzodioxin, Trichloroethylene, trichostatin A, Valinomycin, hsa-miR-138-5p, hsa-miR-142-5p, hsa-miR-5590-3p, hsa-miR-4319, hsa-miR-125b-5p, hsa-miR-125a-5p, hsa-miR-520f-3p, hsa-miR-302c-3p.2, hsa-miR-125b-5p, hsa-miR-125a-5p, hsa-miR-4319, hsa-miR-93-5p, hsa-miR-20a-5p, hsa-miR-519d-3p, hsa-miR-526b-3p, hsa-miR-106b-5p, hsa-miR-106a-5p, hsa-miR-20b-5p, hsa-miR-17-5p, hsa-miR-138-5p, hsa-miR-17-5p, hsa-miR-106a-5p, hsa-miR-519d-3p, hsa-miR-93-5p, hsa-miR-20b-5p, hsa-miR-106b-5p, hsa-miR-526b-3p, hsa-miR-20a-5p, and combinations thereof.

Examples of SLC17A8 modulator include, but are not limited to, miR-122 antisense oligonucleotide, Homocysteine, Interleukin 6, Chlorpyrifos, Diethylnitrosamine, Folic Acid, Valproic Acid, Acetaminophen, Acetylcholine, Ammonium Chloride, Atrazine, bisphenol A, Bromodeoxyuridine, caffeic acid phenethyl ester, Choline, Cocaine, Diazinon, ethylene dichloride, Ethylnitrosourea, furan, Haloperidol, Maneb, Methionine, muraglitazar, Paraquat, pirinixic acid, Propylthiouracil, rosiglitazone, Tamoxifen, Tetrachlorodibenzodioxin, Trichloroethylene, troglitazone, Zidovudine, hsa-miR-31-5p, hsa-miR-203a-3p.1, and combinations thereof.

Examples of SLC32A1 modulator include, but are not limited to, Potassium chloride, Glycine, Vigabatrin, ultrafine particles, miR-124, bisphenol A, lead acetate, Pilocarpine, Valproic Acid, 1-anilino-4-methyl-2-methylthio-4-phenylimidazolin-5-one, 2,2',3',4,4',5-hexachlorobiphenyl, 2,2', 4,4'-tetrabromodiphenyl ether, 2',3,3',4',5-pentachloro-4-hydroxybiphenyl, 2,4,4'-trichlorobiphenyl, 2,4,5,2',4',5'-hexachlorobiphenyl, 2,4,5,2',5'-pentachlorobiphenyl, 2,5,2', 5'-tetrachlorobiphenyl, 4-(5-benzo(1,3)dioxol-5-yl-4-pyridin-2-yl-1H-imidazol-2-yl)benzamide, (6-(4-(2-piperidin-1-ylethoxy)phenyl))-3-pyridin-4-ylpyrazolo(1,5-a)pyrimidine, Ammonium Chloride, arsenite, Benzo(a) pyrene, butyraldehyde, Choline, Citalopram, Cocaine, Copper, Dibutyl Phthalate, Diethylhexyl Phthalate, Ethanol, Flavonoids, Fluoxetine, Folic Acid, gluconic acid, Sodium Oxybate, Ketamine, Methionine, Paraquat, PCB 180, pentabromodiphenyl ether, pentanal, Phenylmercuric Acetate, Propylthiouracil, sodium arsenate, Tretinoin, trichostatin A, hsa-miR-138-5p, hsa-miR-32-5p, hsa-miR-25-3p, hsa-miR-363-3p, hsa-miR-92b-3p, hsa-miR-92a-3p, hsa-miR-367-3p, and combinations thereof.

Examples of SLC36A1 modulator include, but are not limited to, Glycine, L-Alanine, L-Tryptophan, Oxitriptan, hydroxyproline, Acamprosate, Spaglumic acid, Vigabatrin, D-Proline, Gaboxadol, indole-3-propionic acid, 5-Hydroxytryptamine, Glycine-Sarcosine, Glycine-Glycine, δ-aminolevulinic acid, β-aminoethylglycine, δ-aminopentanoic acid, GABA, Glycine, Proline, miR-221, miR-221/222, Imatinib, 1,2,4-benzenetriol, Tretinoin, Valproic Acid, Tetrachlorodibenzodioxin, Acetaminophen, Dibutyl Phthalate, N-Methyl-3,4-methylenedioxyamphetamine, vinclozolin, Ammonium Chloride, Atrazine, Betaine, bisphenol A, Celecoxib, Choline, Cyclosporine, dibenzo(a,l)pyrene, Ethanol, Folic Acid, Methionine, Methyl Methanesulfonate, Nickel, pirinixic acid, Propylthiouracil, sodium bichromate, tamibarotene, testosterone-3-carboxymethyloxime-bovine serum albumin conjugate, Thapsigargin, Tunicamycin, Vancomycin, hsa-miR-205-5p, hsa-miR-6838-5p, hsa-miR-424-5p, hsa-miR-497-5p, hsa-miR-195-5p, hsa-miR-15b-5p, hsa-miR-15a-5p, hsa-miR-16-5p, hsa-miR-129-2-3p, hsa-miR-129-1-3p, hsa-miR-6504-5p, hsa-miR-3064-5p, hsa-miR-503-5p, hsa-miR-489-3p, hsa-miR-4770, hsa-miR-143-3p, hsa-miR-6088, hsa-miR-187-3p, hsa-miR-9-5p, hsa-miR-497-5p, hsa-miR-6838-5p, hsa-miR-195-5p, hsa-miR-424-5p, hsa-miR-203a-3p.1, hsa-miR-101-3p.1, hsa-miR-93-5p, hsa-miR-106a-5p, hsa-miR-20b-5p, hsa-miR-17-5p, hsa-miR-20a-5p, hsa-miR-106b-5p, hsa-miR-519d-3p, hsa-miR-526b-3p, hsa-miR-124-3p.2, hsa-miR-506-3p, hsa-miR-124-3p.1, hsa-miR-142-5p, hsa-miR-5590-3p, hsa-miR-208a-3p, hsa-miR-208b-3p, hsa-miR-142-3p.2, hsa-miR-30d-5p, hsa-miR-30a-5p, hsa-miR-30c-5p, hsa-miR-30b-5p, hsa-miR-30e-5p, hsa-miR-29a-3p, hsa-miR-29b-3p, hsa-miR-29c-3p, hsa-miR-101-3p.1, hsa-miR-101-3p.2, hsa-miR-144-3p, hsa-miR-140-3p.1, hsa-miR-1306-5p, hsa-miR-222-3p, hsa-miR-221-3p, hsa-miR-7-5p, hsa-miR-19a-3p, hsa-miR-19b-3p, and combinations thereof.

Examples of SLC36A2 modulator include, but are not limited to, D- and L-enantiomers of 2-azetidine-carboxylate, proline, cycloserine, sarcosine, betaine, alanine-O-methyl ester, Oxitriptan, Cycloserine, α-Methyl-DL-tryptophan, Sarcosine, lysophosphatidic acid, microRNA-140, miR-205, olanzapine, Tetrachlorodibenzodioxin, Ethinyl Estradiol, bisphenol A, Cisplatin, Nanotubes Carbon, 1,2,5,6-dibenzanthracene, 2-(1'H-indolo-3'-carbonyl)thiazole-4-carboxylic acid methyl ester, Aldrin, Ammonium Chloride, AZM551248, benz(a)anthracene, benzo(b)fluoranthene, Estradiol, Dibutyl Phthalate, Isoproterenol, jinfukang, palm oil, Tamoxifen, trimellitic anhydride, Vinyl Chloride, hsa-miR-6504-5p, hsa-miR-3064-5p, hsa-miR-183-5p.2, hsa-miR-23b-3p, hsa-miR-23a-3p, hsa-miR-130a-5p, hsa-miR-23c, hsa-miR-183-5p.2, hsa-miR-138-5p, and combinations thereof.

Examples of SLC36A4 modulator include, but are not limited to, miR-221, Ribavirin, Casiopeina-II-gly, Fluoxetine, Imatinib mesylate, Valproic Acid, Acetaminophen, bisphenol A, butyraldehyde, Copper Sulfate, Cyclosporine, Flutamide, Ionomycin, jinfukang, N-Methyl-3,4-methylenedioxyamphetamine, pentabromodiphenyl ether, potassium chromate(VI), Tetradecanoylphorbol Acetate, vinclozolin, hsa-miR-520e, hsa-miR-520c-3p, hsa-miR-520b, hsa-miR-520d-3p, hsa-miR-520a-3p, hsa-miR-372-3p, hsa-miR-373-3p, hsa-miR-302c-3p.1, hsa-miR-302d-3p, hsa-miR-302a-3p, hsa-miR-302b-3p, hsa-miR-302e, hsa-miR-7153-5p, hsa-miR-146b-5p, hsa-miR-146a-5p, hsa-miR-140-3p.1, hsa-miR-183-5p.2, hsa-miR-155-5p, hsa-miR-137, hsa-miR-199a-5p, hsa-miR-199b-5p, hsa-miR-208a-3p, hsa-miR-499a-5p, hsa-miR-208b-3p, hsa-miR-202-5p, hsa-miR-802, hsa-miR-142-3p.2, hsa-miR-30d-5p, hsa-miR-30a-5p, hsa-miR-30e-5p, hsa-miR-30c-5p, hsa-miR-30b-5p, hsa-miR-183-5p.1, hsa-miR-5590-3p, hsa-miR-142-5p, hsa-miR-455-3p.2, hsa-miR-433, hsa-miR-539, hsa-miR-653, hsa-miR-186, hsa-miR-204, hsa-miR-211, hsa-miR-137, hsa-miR-590-3p, hsa-miR-185, hsa-miR-200a, hsa-miR-141, hsa-miR-129-5p, hsa-miR-376a, hsa-miR-376b, and combinations thereof.

Examples of SLC38A2 modulator include, but are not limited to, Alanine, SRPIN803, Beta-catenin depletion, Ethanol, zinc deficiency, miR-203, Imatinib, arsenite, Acetaminophen, arsenic trioxide, 7,8-Dihydro-7,8-dihydroxybenzo(a)pyrene 9,10-oxide, Estradiol, motexafin gadolinium, Testosterone, Tetrachlorodibenzodioxin, titanium dioxide, Valproic Acid, Zinc Acetate, Benzo(a)pyrene, bisphenol A, Clofibrate, Diethylnitrosamine, Lipopolysaccharides, Magnetite Nanoparticles, methylformamide, Nanotubes Carbon, Nickel, pirinixic acid, Progesterone, Succimer, 1,4-bis(2-(3,5-dichloropyridyloxy))benzene, 2-(1'H-indolo-3'-carbonyl)thiazole-4-carboxylic acid methyl ester, 2,2,4,4-tetrabromodiphenyl ether, 2,2,5,7,8-pentamethyl-1-hydroxychroman, 2',3,3',4',5-pentachloro-4-hydroxybiphenyl, 2,4-dinitro 2-(methylamino)isobutyric acid, 2-xylene, 3,4,3',4'-tetrachlorobiphenyl, 3,4,5,3',4'-pentachlorobiphenyl, 3-(4'-hydroxy-3'-adamantylbiphenyl-4-yl)acrylic acid, 4-phenylbutyric acid, Acetylcysteine, Ammonium Chloride, arsenic disulfide, beta-Naphthoflavone, caffeic acid phenethyl ester, carbonyl sulfide, chloropicrin, Ciguatoxins, Copper Sulfate, Cuprizone, cyclonite, Cyclosporine, Dichlororibofuranosylbenzimidazole, 9,10-Dimethyl-1,2-benzanthracene, domoic acid, Doxorubicin, Drugs Erythromycin Estolate, ethylbenzene, Ethyl Methanesulfonate, Flavonoids, Formaldehyde, Gentamicins, ICG 001, Ionomycin, jinfukang, K 7174, lead acetate, Levofloxacin, lipopolysaccharide, *E coli* O55-B5, Manganese, methoxyacetic acid, Methylene Chloride, N-Methyl-3,4-methylenedioxyamphetamine, 1-Methyl-4-phenylpyridinium, monomethylarsonous acid, Naphthoquinones, PCI 5002, perfluorooctanoic acid, Phenobarbital, phorone, pinosylvin, propiconazole, Quercetin, Raloxifene Hydrochloride, Ranitidine, salubrinal, sevoflurane, sodium arsenate, Sulindac, Tamoxifen, Tetradecanoylphorbol Acetate, Thioctic Acid, Trichloroethylene, trichostatin A, Vancomycin, Zidovudine, Zinc, hsa-miR-92b-3p, hsa-miR-32-5p, hsa-miR-92a-3p, hsa-miR-25-3p, hsa-miR-363-3p, hsa-miR-367-3p, hsa-miR-130a-5p, hsa-miR-23c, hsa-miR-23b-3p, hsa-miR-23a-3p, hsa-miR-365b-3p, hsa-miR-365a-3p, hsa-miR-455-3p.1, hsa-miR-101-3p.2, hsa-miR-23b-3p, hsa-miR-23c, hsa-miR-130a-5p, hsa-miR-23a-3p, hsa-miR-140-3p.2, hsa-miR-137, hsa-miR-199b-5p, hsa-miR-199a-5p, hsa-miR-30d-5p, hsa-miR-30a-5p, hsa-miR-30b-5p, hsa-miR-30c-5p, hsa-miR-30e-5p, hsa-miR-203a-3p.1, hsa-miR-152-3p, hsa-miR-148b-3p, hsa-miR-148a-3p, hsa-miR-101-3p.1, hsa-miR-5195-3p, hsa-miR-145-5p, hsa-miR-141-3p, hsa-miR-200a-3p, hsa-miR-142-3p.2, hsa-miR-6088, hsa-miR-4770, hsa-miR-143-3p, hsa-miR-140-5p, hsa-miR-7-5p, hsa-miR-613, hsa-miR-206, hsa-miR-1-3p, hsa-miR-302c-3p.2, hsa-miR-520f-3p, hsa-miR-181a-5p, hsa-miR-181b-5p, hsa-miR-181c-5p, hsa-miR-181d-5p, hsa-miR-4262, hsa-miR-200b-3p, hsa-miR-429, hsa-miR-200c-3p, and combinations thereof.

Examples of SLC38A4 modulator include, but are not limited to, miR-221, miR-222, Sebacic acid, GW8510, Pyruvate, Imatinib, Tetrachlorodibenzodioxin, Valproic Acid, Benzo(a)pyrene, Cyclosporine, Estradiol, potassium chromate(VI), trichostatin A, 4-(5-benzo(1,3)dioxol-5-yl-4-pyridin-2-yl-1H-imidazol-2-yl)benzamide, (6-(4-(2-piperidin-1-ylethoxy)phenyl))-3-pyridin-4-ylpyrazolo(1,5-a)pyrimidine, belinostat, Endosulfan, (+)-JQ1 compound, N-Methyl-3,4-methylenedioxyamphetamine, Nickel, perfluorooctanoic acid, Testosterone, 3,4,3',4'-tetrachlorobiphenyl, 4,4'-diaminodiphenylmethane, Acetaminophen, Aldehydes, Ammonium Chloride, beta-Naphthoflavone, bisphenol A, Chloroprene, Ciguatoxins, decabromobiphenyl ether, Diethylnitrosamine, Diethylstilbestrol, 9,10-Dimethyl-1,2-benzanthracene, EMD 53998, epigallocatechin gallate, Flavonoids, glycidol, kojic acid, Methotrexate, Nanotubes Carbon, Oxycodone, Ozone, pentanal, perfluoro-n-undecanoic acid, perfluorooctane sulfonic acid, Phenobarbital, pirinixic acid, Progesterone, Propylthiouracil, Quercetin, Simvastatin, sodium arsenate, Surface-Active Agents, testosterone enanthate, tetrabromobisphenol A, Trichloroethylene, trimellitic anhydride, tris(1,3-dichloro-2-propyl) phosphate, Vanadates, vinclozolin, Zidovudine, hsa-miR-182-5p, hsa-miR-183-5p.2, hsa-miR-1271-5p, hsa-miR-96-5p, hsa-miR-142-3p.1, hsa-miR-27b-3p, hsa-miR-27a-3p, hsa-miR-3681-3p, hsa-miR-216a-3p, hsa-miR-128-3p, hsa-miR-200c-3p, hsa-miR-200b-3p, hsa-miR-429, hsa-miR-7-5p, and combinations thereof.

Examples of SLC38A9 modulator include, but are not limited to, antagonists listed in WO2015173398A1, miR-122, estradiol, miR-205, miR-140, hsa-miR-146a-5p, hsa-miR-7153-5p, hsa-miR-338-3p, hsa-miR-6504-5p, hsa-miR-3064-5p, hsa-miR-203a-3p.1, hsa-miR-140-3p.2, hsa-miR-200a-3p, hsa-miR-141-3p, hsa-miR-125a-5p, hsa-miR-125b-5p, hsa-miR-4319, hsa-miR-4458, hsa-let-7i-5p, hsa-miR-4500, hsa-let-7d-5p, hsa-let-7g-5p, hsa-let-7e-5p, hsa-let-7a-5p, hsa-miR-98-5p, hsa-let-7b-5p, hsa-let-7f-5p, hsa-let-7c-5p, hsa-miR-140-3p.1, hsa-miR-148a-3p, hsa-miR-152-3p, hsa-miR-148b-3p, hsa-miR-429, hsa-miR-200b-3p, hsa-miR-200c-3p, hsa-miR-4770, hsa-miR-143-3p, hsa-miR-6088, hsa-miR-520f-3p, hsa-miR-302c-3p.2, hsa-let-7i-5p, Vitamin D, bisphenol A, Nanotubes, Carbon, potassium chromate(VI), Tetrachlorodibenzodioxin, Valproic Acid, 2,2',3',4,4',5-hexachlorobiphenyl, 2,4,4'-trichlorobiphenyl, 2,4,5,2',4',5'-hexachlorobiphenyl, 2,4,5,2',5'-pentachlorobiphenyl, 2,5,2',5'-tetrachlorobiphenyl, Acetaminophen, Atrazine, benzo(b)fluoranthene, Estradiol, Copper Sulfate, epigallocatechin gallate, Ethyl Methanesulfonate, Ionomycin, Lipopolysaccharides, Methyl Methanesulfonate, PCB 180, Phenobarbital, pirinixic acid, Quercetin, salinomycin, Tetradecanoylphorbol Acetate, Vanadates, MeAIB, and combinations thereof.

Examples of SLC6A1 modulator include, but are not limited to, (R/S)-EF-1502, LU32-176B, Tiagabine hydrochloride, (S)-SNAP 5114, CI 966 hydrochloride, NNC 05-2090 hydrochloride, NNC 711, Potassium Chloride, Fluoxetine, Estradiol, Bis(2-chloroethoxy)methane, manganese chloride, Iron, Valproic Acid, gamma-Aminobutyric Acid, Ethinyl Estradiol, Morphine, NNC 711, Pilocarpine, 2,2',4,4'-tetrabromodiphenyl ether, Ammonium Chloride, Antirheumatic Agents, Estradiol, bisphenol A, Cyclosporine, Dronabinol, Dexamethasone, entinostat, estradiol 3-benzoate, furan, glyphosate, L 742694, Lipopolysaccharides, Niflumic Acid, Progesterone, Surface-Active Agents, Tacrine, tiagabine, troglitazone, hsa-miR-218, hsa-miR-27a, hsa-miR-27b, hsa-miR-376a, hsa-miR-376b, hsa-miR-590-3p, hsa-miR-133a, hsa-miR-133b, hsa-miR-200b, hsa-miR-200c, hsa-miR-429, hsa-miR-425, hsa-miR-217, hsa-miR-132, hsa-miR-212, hsa-miR-210, hsa-miR-873, hsa-miR-23a, hsa-miR-23b, hsa-miR-340, hsa-miR-365, hsa-miR-128, hsa-miR-539, hsa-miR-377, hsa-miR-876-5p, hsa-miR-449a, hsa-miR-449b, hsa-miR-34a, hsa-miR-22, hsa-miR-708, hsa-miR-25, hsa-miR-92a, hsa-miR-92b, hsa-miR-32, hsa-miR-28-5p, hsa-miR-363, hsa-miR-34c-5p, hsa-miR-367, hsa-miR-320a, hsa-miR-320b, hsa-miR-320c, hsa-miR-320d, hsa-miR-182, hsa-miR-137, hsa-miR-342-3p, hsa-miR-455-5p, hsa-miR-128, hsa-miR-132, hsa-miR-133a, hsa-miR-133b, hsa-miR-137, hsa-miR-182, hsa-miR-200b, hsa-miR-200c, hsa-miR-210, hsa-miR-212, hsa-miR-217, hsa-miR-218, hsa-miR-22, hsa-miR-23a, hsa-miR-23b, hsa-miR-25, hsa-miR-27a, hsa-miR-27b, hsa-miR-28-5p, hsa-miR-32, hsa-miR-320a, hsa-miR-320b, hsa-miR-320c, hsa-miR-320d, hsa-miR-340, hsa-miR-342-3p, hsa-miR-34a, hsa-miR-34c-5p, hsa-miR-363, hsa-miR-365, hsa-miR-367, hsa-miR-376a, hsa-miR-376b, hsa-miR-377, hsa-miR-425, hsa-miR-429, hsa-miR-449a, hsa-miR-449b, hsa-miR-455-5p, hsa-miR-539, hsa-miR-590-3p, hsa-miR-708, hsa-miR-873, hsa-miR-876-5p, hsa-miR-92a, hsa-miR-92b, hsa-let-7a-5p, hsa-let-7b-5p, hsa-let-7c-5p, hsa-let-7d-5p, hsa-let-7e-5p, hsa-let-7f-5p, hsa-let-7g-5p, hsa-let-7i-5p, hsa-miR-128-3p, hsa-miR-128-3p, hsa-miR-128-3p, hsa-miR-128-3p, hsa-miR-132-3p, hsa-miR-132-3p, hsa-miR-133a-3p.1, hsa-miR-133a-3p.2, hsa-miR-133b, hsa-miR-137, hsa-miR-138-5p, hsa-miR-200b-3p, hsa-miR-200c-3p, hsa-miR-212-3p, hsa-miR-212-3p, hsa-miR-216a-3p, hsa-miR-216a-3p, hsa-miR-216a-3p, hsa-miR-216a-3p, hsa-miR-217, hsa-miR-218-5p, hsa-miR-218-5p, hsa-miR-218-5p, hsa-miR-22-3p, hsa-miR-25-3p, hsa-miR-25-3p, hsa-miR-27a-3p, hsa-miR-27a-3p, hsa-miR-27a-3p, hsa-miR-27b-3p, hsa-miR-27b-3p, hsa-miR-27b-3p, hsa-miR-32-5p, hsa-miR-32-5p, hsa-miR-34a-5p, hsa-miR-34c-5p, hsa-miR-363-3p, hsa-miR-363-3p, hsa-miR-365a-3p, hsa-miR-365b-3p, hsa-miR-367-3p, hsa-miR-367-3p, hsa-miR-3681-3p, hsa-miR-3681-3p, hsa-miR-3681-3p, hsa-miR-3681-3p, hsa-miR-425-5p, hsa-miR-429, hsa-miR-4458, hsa-miR-449a, hsa-miR-449b-5p, hsa-miR-4500, hsa-miR-503-5p, hsa-miR-6807-3p, hsa-miR-92a-3p, hsa-miR-92a-3p, hsa-miR-92b-3p, hsa-miR-92b-3p, hsa-miR-98-5p, and combinations thereof.

Examples of SLC6A13 modulator include, but are not limited to, Guvacine hydrochloride, (±)-Nipecotic acid, Riluzole hydrochloride, Guvacine, (S)-SNAP 5114, CI 966 hydrochloride, NNC 05-2090 hydrochloride, NNC 711, Tiagabine hydrochloride, SRPIN803, Interleukin-22, Androgen deprivation, Potassium chloride, Tetrachlorodibenzodioxin, Benzo(a)pyrene, bisphenol A, Cisplatin, jinfukang, Magnetite Nanoparticles, Methamphetamine, potassium chromate(VI), SCH 23390, Succimer, Valproic Acid, 1,2-dithiol-3-thione, 2,4-dinitro 2,6-dinitro 3,4,5,3',4'-pentachlorobiphenyl, Acetaminophen, alachlor, gamma-Aminobutyric Acid, Ammonium Chloride, Atrazine, Clofibrate, Clofibric Acid, coumarin, Diethylnitrosamine, Dioxins, epigallocatechin gallate, Ethinyl Estradiol, Ethyl Methanesulfonate, Flavonoids, Fluconazole, Flutamide, furan, GW 4064, Hydralazine, leflunomide, Methyl Methanesulfonate, muraglitazar, PCI 5002, Phenobarbital, pirinixic acid, Pregnenolone Carbonitrile, Propylthiouracil, rosiglitazone, systhane, tesaglitazar, titanium dioxide, Tretinoin, triadimefon, trichostatin A, trimellitic anhydride, troglitazone, Zinc, hsa-miR-206, hsa-miR-1-3p, hsa-miR-613, and combinations thereof.

Examples of SLC6A11 modulator include, but are not limited to, (S)-SNAP 5114, CI 966 hydrochloride, NNC 05-2090 hydrochloride, NNC 711, Tiagabine hydrochloride, Clobazam, Guvacine, microRNA-128, Creatine, miR-221, pioglitazone, Vitamin D, gamma-Aminobutyric Acid, Chlorides, Sodium, bisphenol A, Phenylmercuric Acetate, Progesterone, Tetrachlorodibenzodioxin, Valproic Acid, 2,2',4,4'-tetrabromodiphenyl ether, 4-(5-benzo(1,3)dioxol-5-yl-4-pyridin-2-yl-1H-imidazol-2-yl)benzamide, (6-(4-(2-piperidin-1-ylethoxy)phenyl))-3-pyridin-4-ylpyrazolo(1,5-a)pyrimidine, Ammonium Chloride, Benzo(a)pyrene, Estradiol, Diazepam, Diethylnitrosamine, Flufenamic Acid, JP8 aviation fuel, lead acetate, Lipopolysaccharides, Niflumic Acid, Ozone, Paraquat, phenobarbital quinidine, Pilocarpine, Potassium Dichromate, prochloraz, Propylthiouracil, Quercetin, trichostatin A, Zidovudine, hsa-miR-205-5p, hsa-miR-338-3p, hsa-miR-6504-5p, hsa-miR-3064-5p, hsa-miR-22-3p, hsa-miR-138, hsa-miR-205-5p, hsa-miR-338-3p, hsa-miR-6504-5p, hsa-miR-3064-5p, hsa-miR-22-3p, hsa-miR-3064-5p, hsa-miR-6504-5p, hsa-miR-142-3p.1, hsa-miR-142-3p.2, hsa-miR-15b-5p, hsa-miR-15a-5p, hsa-miR-6838-5p, hsa-miR-16-5p, hsa-miR-195-5p, hsa-miR-497-5p, hsa-miR-424-5p, hsa-miR-101-3p.1, hsa-miR-503-5p, hsa-miR-19b-3p, hsa-miR-19a-3p, hsa-miR-200c-3p, hsa-miR-200b-3p, hsa-miR-429, hsa-miR-15a-5p, hsa-miR-497-5p, hsa-miR-424-5p, hsa-miR-6838-5p, hsa-miR-15b-5p, hsa-miR-16-5p, hsa-miR-195-5p, and combinations thereof.

Examples of SLC6A12 modulator include, but are not limited to, betaine, Aspirin, Guvacine, (R/S) EF-1500, (R)-EF-1520, (S)-EF-1520, (S)-SNAP 5114, CI 966 hydrochloride, NNC 05-2090 hydrochloride, NNC 711, (R/S)-EF-1502, LU32-176B, NNC052090, Tiagabine hydrochloride, (+/−)-Nipecotic acid, IL-13, Ribavirin, pregnenolone 16alpha-carbonitrile, High phosphate diet, Benzo(a)pyrene, Sodium Chloride, pirinixic acid, Cisplatin, Lipopolysaccharides, gamma-Aminobutyric Acid, Estradiol, Cyclosporine, Diethylhexyl Phthalate, jinfukang, Magnetite Nanoparticles, Pilocarpine, Succimer, Tetrachlorodibenzodioxin, 4,4'-diaminodiphenylmethane, Acetaminophen, Aminooxyacetic Acid, Ammonium Chloride, arsenic trioxide, Aspirin, AZM551248, Betaine, bisphenol A, Bleomycin, Chlorine, Clofibrate, Copper Sulfate, Diazepam, Dieldrin, Flavonoids, Flutamide, fumonisin B1, furan, gallium nitrate, Genistein, hydrazine, lonomycin, myxothiazol, Nanotubes, Carbon, nefazodone, Ozone, Paraquat, perfluorooctane sulfonic acid, phenobarbital quinidine, Quercetin, Rotenone, Tetradecanoylphorbol Acetate, valdecoxib, Valproic Acid, Zidovudine, hsa-miR-193b-3p, hsa-miR-193a-3p and combinations thereof.

Examples of SLC6A5 modulator include, but are not limited to, Glycine, Haloperidol, Amoxapine, ALX 1393, ALX 1405, Org 25543, Sarcosine, LY 2365109 hydrochloride, NFPS, Org 24598 lithium salt, Org 25543 hydrochloride, Bitopertin, N-Arachidonylglycine, Dopaminergic transcription factors Ascl1, Lmx1a, Nurr1, low-dose cadmium, Sonic hedgehog homolog, transcription factors and signaling proteins, Creatine, ethanol, microRNA-140, Interleukin-22, bisphenol A, Benzo(a)pyrene, Copper, 4-benzyloxy-3,5-dimethoxy-N-(1-(dimethylaminocyclopently)methyl) benzamide, Ammonium Chloride, Amoxapine, arsenic trioxide, arsenite, Ethanol, furan, Ionomycin, Propylthiouracil, Sodium Selenite, testosterone undecanoate, Tetradecanoylphorbol Acetate, hsa-miR-103 145, hsa-miR-107 hsa-miR-203a-3p.1, hsa-miR-142-5p, hsa-miR-5590-3p, hsa-miR-33b-5p, hsa-miR-33a-5p, hsa-miR-200a-3p, hsa-miR-141-3p, hsa-miR-519d-3p, hsa-miR-20b-5p, hsa-miR-93-5p, hsa-miR-17-5p, hsa-miR-106a-5p, hsa-miR-106b-5p, hsa-miR-20a-5p, hsa-miR-526b-3p, hsa-miR-9-5p, hsa-miR-135b-5p, hsa-miR-135a-5p, hsa-miR-10b-5p, hsa-miR-10a-5p, hsa-miR-124-3p.1, hsa-miR-124-3p.2, hsa-miR-506-3p, hsa-miR-135b-5p, hsa-miR-135a-5p, hsa-miR-93-5p, hsa-miR-106a-5p, hsa-miR-17-5p, hsa-miR-20b-5p, hsa-miR-519d-3p, hsa-miR-106b-5p, hsa-miR-526b-3p, hsa-miR-20a-5p, hsa-miR-4458, hsa-miR-4500, hsa-let-7d-5p, hsa-et-7c-5p, hsa-miR-98-5p, hsa-let-7e-5p, hsa-let-7b-5p, hsa-let-7f-5p, hsa-let-7a-5p, hsa-et-7i-5p, hsa-let-7g-5p, and combinations thereof.

Examples of SLC6A14 modulator include, but are not limited to, α-methyl-dl-tryptophan, L-Proline, Valaciclovir, Valganciclovir, D-serine, Alternaria, Pterygium, Interleukin-13, Interleukin-22, Estradiol, bisphenol A, Coumestrol, Tetrachlorodibenzodioxin, Benzo(a)pyrene, Genistein, methylmercury cysteine, Nanotubes Carbon, 1,2,5,6-dibenzanthracene, 2,3-bis(3'-hydroxybenzyl)butyrolactone, Acetaminophen, Ampicillin, 7,8-Dihydro-7,8-dihydroxybenzo(a)pyrene 9,10-oxide, 8-Bromo Cyclic Adenosine Monophosphate, tert-Butylhydroperoxide, Cyclosporine, cyfluthrin, Dexamethasone, Diethylstilbestrol, Ethinyl Estradiol, Hydrogen Peroxide, 1-Methyl-3-isobutylxanthine, pirinixic acid, Polychlorinated Biphenyls, resveratrol, Vitamin K3, Zeranol, hsa-miR-130a-5p, hsa-miR-23b-3p, hsa-miR-23a-3p, hsa-miR-23c, hsa-miR-29a-3p, hsa-miR-29b-3p, hsa-miR-29c-3p, hsa-miR-130a-5p, hsa-miR-23a-3p, hsa-miR-23c, hsa-miR-23b-3p, and combinations thereof.

Examples of SLC6A15 modulator include, but are not limited to, Loratadine and analogs, antihistamines, Potassium chloride, NSC319726, Rosiglitazone, Sleep and ethanol, resveratrol, miR-221/222, Valproic Acid, 4-(5-benzo(1,3)dioxol-5-yl-4-pyridin-2-yl-1H-imidazol-2-yl)benzamide, (6-(4-(2-piperidin-1-ylethoxy)phenyl))-3-pyridin-4-ylpyrazolo(1,5-a)pyrimidine, bisphenol A, Cisplatin, PD 0325901, Phenylmercuric Acetate, Piroxicam, vorinostat, 3-(4'-hydroxy-3'-adamantylbiphenyl-4-yl)acrylic acid, (4-amino-1,4-dihydro-3-(2-pyridyl)-5-thioxo-1,2,4-triazole)copper(II), Acetaminophen, adrenocorticotropin zinc, Aldehydes, Ammonium Chloride, Benzo(a)pyrene, butyraldehyde, Catechin, Chlorine, Chloroprene, Copper Sulfate, Cuprizone, Cyclosporine, Dronabinol, Grape Seed Proanthocyanidins, hydrazine, Indomethacin, (+)-JQ1 compound, ormosil, Ozone, pentabromodiphenyl ether, pentanal, Polyethylene Glycols, potassium chromate(VI), propionaldehyde, Silver, 2,4,5-Trichlorophenoxyacetic Acid, tesaglitazar, Tetrachlorodibenzodioxin, Tretinoin, trichostatin A, hsa-miR-10a-5p, hsa-miR-10b-5p, hsa-miR-155-5p, hsa-miR-203a-3p.1, hsa-miR-153-3p, hsa-miR-30d-5p, hsa-miR-30a-5p, hsa-miR-30e-5p, hsa-miR-30c-5p, hsa-miR-30b-5p, hsa-miR-137, hsa-let-7f-5p, hsa-let-7i-5p, hsa-miR-4500, hsa-et-7d-5p, hsa-let-7g-5p, hsa-let-7e-5p, hsa-let-7a-5p, hsa-let-7c-5p, hsa-miR-98-5p, hsa-let-7b-5p, hsa-miR-4458, and combinations thereof.

Examples of SLC6A18 modulator include, but are not limited to, miRNAs, pioglitazone, mir-221, 2,3,7,8-tetrachlorodibenzo-p-dioxin, 2,2',4,4'-tetrabromodiphenyl ether, 3-iodothyronamine, Acetaminophen, Amiodarone, Ammonium Chloride, Benzo(a)pyrene, bisphenol A, Chlorpromazine, Ciguatoxins, Clofibrate, Cyclosporine, Cisplatin, Ethinyl Estradiol, Fonofos, fullerene C60, Gentamicins, Morphine, muraglitazar, ochratoxin A, Paraquat, Parathion, pirinixic acid, ptaquiloside, rosiglitazone, terbufos, tesaglitazar, Tetracycline, Thioacetamide, troglitazone, Valproic Acid, hsa-miR-138-5p, and combinations thereof.

Examples of SLC6A19 modulator include, but are not limited to, Nimesulide, NS-398, Berberine HCL, verapamil, omeprazole, desipramine HCL, quercetine, cloramphenicol, coumaric acid, hsa-miR-377-3p, hsa-miR-10b-5p, hsa-miR-10a-5p, bupivacaine, lidocaine, tetracycline, scopolamine, quinidine, sulpiride, Benztropine, PKB/Ak, Creatine, miR-124, microRNA-140, Lipopolysaccharides, Triiodothyronine, Berberine, Tetrachlorodibenzodioxin, 2,3,4,5-tetrachlorophenate, Acetaminophen, benzo(k)fluoranthene, bisphenol A, Cysteine, Dioxins, Methionine, Methylcholanthrene, pentabromodiphenyl ether, Pentachlorophenol, perfluorooctane sulfonic acid, Selenomethionine, selenomethylselenocysteine, Vancomycin, and combinations thereof.

As used herein, "a solute carrier (SLC) modulator that increases or decreases proline levels" means any drug or other composition that increases or decreases the plasma proline levels in a subject. Such SLC modulators may be administered to a subject in partly or fully deuterated forms, or containing other stable, medically appropriate isotopes such as, e.g., $^{13}C$. Non-limiting examples of SLC modulators that increase proline levels include LX-6171, Benztropine, LP-403812, valproic acid (VPA, 2-propylpentanoic acid), divalproex sodium, valproate (2-propylpentanoate), sodium valproate, magnesium valproate, lactic acid, miR-23b, miR-23a/b, (L or D)-proline, (L or D)-arginine, (L or D)-glutamine, (L or D)-ornithine, (L or D)-glutamic acid, (L or D)-glutamate, poly(L or D)-proline, poly(L or D)-glutamine, poly(L or D)-ornithine, poly(L or D)-glutamate, poly(L or D)-arginine, analogs of any of the foregoing, and combinations thereof, including mixed polypeptides of (L or D)-proline, (L or D)-glutamine, (L or D)-ornithine, (L or D)-arginine, (L or D)-glutamic acid, or (L or D)-glutamate. As used herein, an "analog" of an SLC modulator means a chemical compound that is structurally and functionally similar to the SLC modulator. In the present invention, combinations of such SLC modulator and/or their analogs are also contemplated.

Non-limiting examples of SLC modulators that decrease proline levels include, e.g., activators of PRODH or activators of peroxisomal proliferator-activated receptor gamma (PPARy). As used herein, "activators" when used with respect to PRODH or PPARy, means a drug or other composition that can increase the function or expression of PRODH or PPARy. In the present invention, an SLC modulator that decreases proline levels in a subject includes, e.g., vitamin $D_1$, vitamin $D_2$, vitamin $D_3$, vitamin $D_4$, vitamin $D_5$, Calcitriol, curcumin, one or more thiazolidinedione compounds, colchicine, Etanercept (Amgen/Pfizer), S26948 (Sigma-Aldrich), INT131 (InteKrin), phentoin, analogs of any of the foregoing, and combinations thereof.

In the present invention, a "solute carrier (SLC) modulator" also includes any molecule, enzyme, or treatment that affects circulating proline levels. For example, Table S1 (provided at the end of this application) identifies molecules that up- or down-regulate expression of genes regulating proline synthesis, transport, or metabolism. All such molecules are "SLC modulators" of the present invention. The products of these genes influence circulating proline levels. These genes may also be targeted using known gene editing tools including, for example, CRISPR/Cas9 based systems, TALENs, etc., and thus are also considered "proline modulators" of the present invention. Table 1 contains a list of genes that are up- or down-regulated by valproate compounds, including VPA, valproate sodium salt and divalproate salt. These genes may provide targets for new treatments to modulate proline.

In the present invention, each embodiment optionally includes determining a proline level in the subject. Based on the determined proline level, if appropriate, the subject's treatment protocol may be adjusted. For example, by modifying the course of treatment, if necessary, including administering a different SLC modulator to the subject, or stopping or omitting treatment with an SLC modulator.

TABLE 1

Genes regulated by VPA, valproate sodium salt or divalproate sodium salt

| Up-regulated genes | | | | | |
|---|---|---|---|---|---|
| ABAT | FOS | EHHADH | EGR1 | Acot1 | THRSP |
| Cyp4a14 | DBP | PDK4 | CA3 | TUBB2B | CYP1A1 |
| NR1D2 | DPP8 | AKR1D1 | ANGPTL4 | ELOVL4 | AIG1 |
| KIF5C | RETSAT | ELOVL6 | FZD5 | PEX11A | TIMP3 |
| CPT1A | RRAGD | CKB | VNN1 | SPP1 | SAP30 |
| DLX5 | SLC22A8 | LYZ | GCFC2 | MAPT | HSD17B2 |
| ZFP37 | CLIC6 | FMO2 | PPAP2C | CTSH | CYP51A1 |
| SLC34A2 | CD36 | RGN | TUBB2A | H1F0 | GRPR |
| CYP4A11 | UBR2 | AKR1C3 | Plscr2 | EGLN3 | NGFRAP1 |
| PFN2 | GPC3 | PENK | USP2 | ARMCX2 | CEP104 |
| BCL6 | LRP11 | GABRB1 | IL1B | TNRC18 | HLA-DQB1 |
| ABAT | FOS | EHHADH | EGR1 | Acot1 | THRSP |
| SERPINE1 | MT2A | PGM2L1 | HMGCS1 | ATP8B3 | EDNRA |
| GUCY1B3 | Prl2c2 | TNFRSF9 | FAM5C | GJB5 | KRT23 |
| L1TD1 | RSPO4 | LOC284379 | S100A8 | PODXL | Retnla |
| AKR1C3 | FETUB | CYP2S1 | UGT2B10 | BCMO1 | SERPINB2 |
| PRR15L | DIO2 | CEACAM19 | GJB3 | GPX2 | PPBP |
| SLC17A6 | GATA4 | MGARP | FAM163A | UPP1 | MMP10 |
| CD7 | EPGN | ACPP | LRRC2 | ATP13A4 | BST1 |
| TMPRSS11BNL | GPR115 | WFDC12 | MUC5B | HDC | KRT8 |
| C4orf26 | GRIK2 | KRT18 | DPPA4 | QRFPR | KCNA3 |
| LOC643037 | CRYAA | FGB | | | |
| Down-regulated genes | | | | | |
| FAM111A | CDK1 | ALAS2 | ARNTL | TOLLIP | CCNA2 |
| DCXR | MX1 | SLC16A1 | C1orf210 | GPR37 | INMT |
| IGFBP3 | IL6 | NPAS2 | MFAP4 | CDKN1A | RRM2 |
| CHKA | ENPP2 | LOC100912446 | FBXW5 | CCNB2 | IRF7 |
| CDH17 | RBM8A | PC | ADAMTSL3 | MFAP4 | ITGA11 |
| C1QTNF3 | ASPN | DLK1 | PAPPA2 | CSPG4 | THBS4 |
| EGFL6 | COL8A1 | TSPAN18 | POSTN | Tlr13 | LYZ |
| FMOD | SOX10 | AFF3 | ITGBL1 | TNMD | NGFR |
| AW551984 | ELN | OGN | PTGDS | EPHA3 | NKD2 |
| COL14A1 | LPAR4 | PODN | LDB2 | TRIM66 | FAM180A |
| ADRA1B | Ccl9 | HR | MDGA1 | LPPR4 | SLC6A17 |
| PCSK9 | MSR1 | EDIL3 | SEMA3D | LAMA2 | LCP1 |
| CTSS | PTN | EMR1 | CHRDL1 | RSPO2 | |

As used herein, an "analog" of vitamin D means a chemical compound that is structurally and functionally similar to vitamin D, or (1,25-dihydroxyvitamin D3 [1,25 (OH)$_2$D3]). Non-limiting examples of vitamin D and analogs thereof include ergocalciferol, cholecalciferol, 22-oxacalcitriol, paricalcitol, doxercalciferol, alfacalcidol, dihydrotachystero, pharmaceutically acceptable salts thereof, and combinations thereof.

As used herein, an "analog" of curcumin means a chemical compound that is structurally and functionally similar to curcumin, and curcuminoid species. Non-limiting examples of curcumin and analogs thereof include curcumin, curcuma oil, turmerone, demethoxycurcumin, bisdemethoxycurcumin, pharmaceutically acceptable salts thereof, and combinations thereof.

Non-limiting examples of thiazolidinedione compounds include troglitazone, rosiglitazone, roglitazone, ciglitazone, darglitazone, englitazone, hydroxypioglitazone, ketopioglitazone, pioglitazone, pioglitazone hydrochloride, ragaglitazar, naveglitazar, aleglitazar, rivoglitazone, netoglitazone, pharmaceutically acceptable salts thereof, analogs of any of the foregoing, and combinations thereof.

Non-limiting examples of pharmaceutically acceptable salts include, for example, acid salts formed from inorganic or organic acids. Such acid salts are non-toxic and include those derived from inorganic acids such as hydrochloric, hydrobromic, sulfuric, sulfamic, phosphoric, and nitric acid; and the salts prepared from organic acids such as acetic, propionic, succinic, glycolic, stearic, lactic, malic, tartaric, citric, ascorbic, palmoic, maleic, hydroxymaleic, phenylacetic, glutamic, mesylate, benzoic, salicylic, sulfanilic, 2-acetoxybenzoic, fumaric, toluenesulfonic, methanesulfonic, ethane disulfonic, oxalic, and isethionic acid. Non-limiting examples of pharmaceutically acceptable base salts include, for example, ammonium, calcium, copper, ferric, ferrous, lithium, magnesium, manganic, manganous, potassium, sodium, and zinc salts.

In some preferred embodiments, a pharmaceutically acceptable salt of valproate is sodium valproate. In other preferred embodiments, a pharmaceutically acceptable salt of valproate is magnesium valproate.

The terms "administering", "administration" and variants thereof (particularly "administering" an agent or modulator) as used herein means introducing an agent, e.g., SLC modulator into the body of a subject, such as a human, in need of such treatment. In the present invention, however, administration of such an SLC modulator or agent is "appropriate" only if such administration will reduce, alleviate, or eradicate at least one negative symptom as defined herein. In the present invention, based on the result of the COMT genotype analysis and/or a subject's proline levels, it may be that no treatment should be administered, that a prior treatment with an SLC modulator should be reduced or discontinued, or that a different SLC modulator be administered. The appropriateness of a particular treatment option is readily determined by a medical professional based on the COMT genotype analysis and/or proline determination as disclosed herein.

In the present invention, an "effective amount" or a "therapeutically effective amount" of an SLC modulator, an agent, a compound, or a composition disclosed herein is an amount of such material that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of any active agent disclosed herein or a composition containing the same will be that amount of the active agent or composition, which is the lowest dose effective to produce the desired effect.

A suitable, non-limiting example of a dosage of an SLC modulator according to the present invention may be from about 1 ng/kg to about 5000 mg/kg. In general, however, doses employed for adult human treatment typically may be in the range of 0.0001 mg/kg/day to 0.0010 mg/kg/day, 0.0010 mg/kg/day to 0.010 mg/kg/day, 0.010 mg/kg/day to 0.10 mg/kg/day, 0.10 mg/kg/day to 1.0 mg/kg/day, 1.00 mg/kg/day to about 200 mg/kg/day, 200 mg/kg/day to about 5000 mg/kg/day. For example, the dosage may be about 1 mg/kg/day to about 100 mg/kg/day, such as, e.g., 2-10 mg/kg/day, 10-50 mg/kg/day, or 50-100 mg/kg/day. The dosage of the proline modulator also may be about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1 100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, 2300 mg/kg, 2400 mg/kg, 2500 mg/kg, 2600 mg/kg, 2700 mg/kg, 2800 mg/kg, 2900 mg/kg, 3000 mg/kg, 3500 mg/kg, 4000 mg/kg, 5000 mg/kg.

With respect to SLC modulators that are vitamin D and its analogs, the dosage of the proline modulator also may be denominated in International Units (IU) per day (IU/Day) and about 100 IU/day, 200 IU/day, 300 IU/day, 400 IU/day, 500 IU/day, 600 IU/day, 700 IU/day, 800 IU/day, 900 IU/day, 1000 IU/day, 1 100 IU/day, 1200 IU/day, 1300 IU/day, 1400 IU/day, 1500 IU/day, 1600 IU/day, 1700 IU/day, 1800 IU/day, 1900 IU/day, 2000 IU/day, 2100 IU/day, 2200 IU/day, 2300 IU/day, 2400 IU/day, 2500 IU/day, 2600 IU/day, 2700 IU/day, 2800 IU/day, 2900 IU/day, 3000 IU/day, 3100 IU/day, 3200 IU/day, 3300 IU/day, 3400 IU/day, 3500 IU/day, 3600 IU/day, 3700 IU/day, 3800 IU/day, 3900 IU/day, 4000 IU/day, 4500 IU/day, 5000 IU/day, 5500 IU/day, 6000 IU/day, 6500 IU/day, 7000 IU/day, 7500 IU/day, 8000 IU/day, 9000 IU/day, 10,000 IU/day, 20,000 IU/day, 30,000 IU/day, 40,000 IU/day, 50,000 IU/day, 60,000 IU/day, 70,000 IU/day, 90,000 IU/day, 100,000 IU/day, 200,000 IU/day, 300,000 IU/day, 400,000 IU/day, 500,000 IU/day, 600,000 IU/day, 700,000 IU/day, 800,000 IU/day, 900,000 IU/day, 1,000,000 IU/day, 1,100,000 IU/day, 1,200,000 IU/day, 1,300,000 IU/day, 1,400,000 IU/day, or 1,500,000 IU/day. Preferably, the dosage of the vitamin D species and analogs range between about 1,000-1,500,000 IU administered on a periodic basis of dosing per day or per week or per month.

The effective dose of the SLC modulator may be administered as two, three, four, five, six or more sub-doses, administered separately at appropriate intervals throughout the day.

The SLC modulators, agents and compositions of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, the SLC modulators, agents and compositions of the present invention may be administered in conjunction with other treatments. Each SLC modulator, agent and composition of the present invention may be encapsulated or otherwise protected against gastric or other secretions, if desired.

Another embodiment of the present invention is a method for monitoring the treatment of a subject in need thereof, the method comprising:
  a) obtaining a biological sample from the subject,
  b) determining the genotype for the allele(s) of the COMT gene at codon 158 (and/or codon 108 for S-COMT) in the biological sample;
  c) determining the subject's proline level; and
  d) modifying the course of treatment, if necessary, including administering a solute carrier (SLC) modulator to the subject, or stopping or omitting treatment with a proline modulator, or administering a different SLC modulator to the subject, based upon the presence or absence of a $Val^{158/108}Met$ polymorphism in the COMT gene, and/or an increase or decrease in the subject's proline level.

Assays for determining a subject's genotype for the allele(s) of the COMT gene have been disclosed previously herein. Assays for determining a subject's proline level are well-known in the art. See, e.g., Wu, 1993; Inoue et al., 1996; Le Boucher et al., 1997; and Grainger et al., 2004; Liang et al., 2015. Non-limiting examples of assays of proline and/or other molecules including D and/or L forms of: glycine, gamma-aminobutyric acid (GABA), serine, glutamate include high throughput (HTP) proline assay, liquid chromatography/mass spectrometry (LC-MS/MS), and automated ion-exchange chromatography. In addition, commercial services for such assays are also available from vendors such as ARUP Laboratories (Salt Lake City, Utah), or the Nathan Kline Institute Analytical Psychopharmacology laboratory. Other methods include but are not limited to enzyme-linked immunosorbent assays.

As used herein, "modifying the course of treatment" refers to any change in the subject's treatment type and/or dosage, including administering a different SLC modulator to the subject, stopping or omitting treatment with a SLC modulator, adding an additional SLC modulator to the treatment, and increasing or decreasing the dosage of an SLC modulator. For subjects homozygous for Val, when it is determined that a subject's proline levels are not optimal, a target overnight fasting proline range after treatment onset of greater than about 158 µM is desired. Other target proline ranges of the invention include, for example, between 150 µM to 700 µM or 150 µM to 550 µM. For subjects with at least one Met allele, when it is determined that a subject's proline levels are not optimal, a target overnight fasting proline range after treatment onset below about 258 µM, such as below 170 µM, is desired. Other target proline ranges of the invention include, for example, between 80 µM to 318 µM.

Another embodiment of the present invention is a diagnostic system for identifying a subject with a disorder who will benefit from a solute carrier (SLC) modulator that increases or decreases proline levels, comprising:
 a) obtaining a biological sample from the subject;
 b) determining the identity of alleles of the $Val^{158/108}Met$ locus associated with the COMT gene in the sample; wherein the presence of Val/Val at codon 158 (and/or codon 108 for S-COMT) is indicative of a subject who will benefit from an SLC modulator that increases proline levels and wherein the presence of at least one Met allele at codon 158 (and/or codon 108 for S-COMT) is indicative of a subject who will benefit from an SLC modulator that decreases proline levels.

In one aspect of the present invention, the diagnostic system may be used to assess prodromal subjects prior to onset of, e.g., psychotic symptoms, and to determine possible treatment protocols based on COMT and/or proline status.

One aspect of this embodiment may further comprise c) administering, to the subject who will benefit from an SLC modulator that increases proline levels, a composition that is selected from the group consisting of LX-6171, Benztropine, LP-403812, valproic acid (VPA), divalproex sodium, valproate, sodium valproate, magnesium valproate, lactic acid, miR-23b, miR-23a/b, (L or D)-proline, (L or D)-arginine, (L or D)-glutamine, (L or D)-ornithine, (L or D)-glutamic acid, (L or D)-glutamate, poly(L or D)-proline, poly(L or D)-glutamine, poly(L or D)-ornithine, poly(L or D)-glutamate, poly(L or D)-arginine, analogs of any of the foregoing, and combinations thereof, including mixed polypeptides of (L or D)-proline, (L or D)-glutamine, (L or D)-ornithine, (L or D)-arginine, (L or D)-glutamic acid, or (L or D)-glutamate. Alternatively, another aspect of this embodiment may further comprise c) administering, to the subject who will benefit from an SLC modulator that decreases proline levels, a composition that is selected from the group consisting of vitamin $D_1$, vitamin $D_2$, vitamin $D_3$, vitamin $D_4$, vitamin $D_5$, Calcitriol, curcumin, one or more thiazolidinedione compounds, colchicine, Etanercept, S26948, INT131, phentoin, analogs of any of the foregoing, and combinations thereof. In this embodiment, the obtaining and determining steps are previously disclosed herein.

Another embodiment of the present invention is a kit comprising any of the diagnostic systems disclosed herein. Such kits are packaged together with instructions for its use. Such a kit may include, for example, one or more reagents for determination/identification of a COMT genotype or $Val^{158/108}Met$ polymorphism, a collection device, and one or more containers. The kit may be used in determining how to regulate proline levels in a subject to effect reduction or eradication of one or more negative symptoms of the subject. Exemplary reagents include, but are not limited to, primers, probes, antibodies, enzymes, oligonucleotides, and immunoassays.

Another embodiment of the present invention is a method for predicting the clinical response of a subject with a disorder to a solute carrier (SLC) modulator comprising:
 a) determining the identity of the allele(s) of the $Val^{158/108}Met$ locus associated with the COMT gene using a biological sample of the subject;
 wherein the presence of Val/Val at the locus is indicative of a subject who will benefit from an SLC modulator that increases proline levels, and wherein the presence of at least one Met allele at the locus is indicative of a subject who will benefit from an SLC modulator that decreases proline levels; and
 b) administering, if appropriate based on the results of step (a), an effective amount of an SLC modulator to the subject to achieve a clinically appropriate response.

The determining and administering steps as well as the SLC modulators of this embodiment are as previously disclosed herein.

Another embodiment of the present invention is a method for monitoring the treatment of a subject with a disorder, the method comprising:
 a) determining the genotype for the allele(s) of the COMT gene at codon 158 (and/or codon 108 for S-COMT) in a biological sample of the subject;
 b) determining the proline level of the subject; and
 c) modifying the course of treatment of the subject, if necessary, including administering a solute carrier (SLC) modulator to the subject or stopping or omitting treatment with an SLC modulator, or administering a different SLC modulator to the subject, based upon the presence or absence of a $Val^{158/108}Met$ polymorphism in the COMT gene.

Another embodiment of the present invention is a diagnostic system for identifying a subject with a disorder who will benefit from treatment with a solute carrier (SLC) modulator that increases or decreases proline levels comprising:
 determining the identity of the allele(s) of the $Val^{158/108}Met$ locus associated with the COMT gene using a biological sample from the subject;
 wherein the presence of Val/Val at the locus is indicative of a subject who will benefit from an SLC modulator that increases proline levels and wherein the presence of at least one Met allele at the locus is indicative of a subject who will benefit from an SLC modulator that decreases proline levels.

In the last two embodiments, the determining and modifying steps, if present, and the proline modulators, are as disclosed previously herein.

Another embodiment of the present invention is a method for treating or ameliorating the effects of a disorder in a subject in need thereof. The method includes:
 a) obtaining a biological sample from the subject;
 b) determining, in the biological sample, the presence or absence of a $Val^{158/108}Met$ polymorphism in the COMT gene; and
 ci) administering to the subject, if appropriate based on the results of step (b), an effective amount of a solute carrier (SLC) modulator that increases proline levels if the subject is determined from step (b) to have a Val/Val genotype at codon 158 (and/or codon 108 for S-COMT); or
 cii) administering to the subject, if appropriate based on the results of step (b), an effective amount of an SLC modulator that decreases proline levels if the subject is determined from step (b) to have a Val/Met or Met/Met genotype at codon 158 (and/or codon 108 for S-COMT).

In this embodiment, the obtaining, determining, and administering steps have been disclosed previously herein. As used herein, the terms "ameliorate", "ameliorating" and grammatical variations thereof mean to decrease the severity of the symptoms, particularly negative symptoms, of a disease in a subject, preferably a human. The polymorphism, disorders, biological samples, and agents for increasing or decreasing proline levels in this embodiment are as disclosed previously herein.

In one aspect of this embodiment, carrying out the method results in reducing or eradicating negative symptoms associated with the disorder. Examples of such negative symptoms include, but are not limited to, flat or blunted affect, social withdrawal, apathy, diminished emotional expression, avolition, alogia, autonomic dysfunction, impairment of executive performances, inattention, and behavioral problems. Preferred examples of negative symptoms according to the present invention include diminished emotional expression, avolition, impaired social functioning, alogia, anhedonia, or combinations thereof.

In another aspect of this embodiment, numerous ways to assess negative symptoms in a subject are provided, including, e.g., a Scale for Negative Symptoms (SANS) score, a Brief Psychiatric Rating Scale (BPRS) negative symptom sub-scale score, a Positive and Negative Syndrome Scale (PANSS) negative symptom sub-scale score, a Brief Negative Symptom Scale (BNSS) score, clinical assessment interview for negative symptoms, negative assessment, or other measures of negative symptoms in the subject. Other methods for detecting negative symptoms known in the art may also be used. Such additional methods include, e.g., tests and assessments for physical, physiological, or behavioral markers, including neuroimaging, electroencephalogram (EEG), and neurophysiological tests such as mismatched negativity (MMN), P3a, P50, and P100 indices, pre-pulse inhibition (PPI), startle habituation, and antisaccade. In the present invention, however, the preferred method for assessing negative symptoms is the SANS score as disclosed in more detail in the Examples and Figures.

Another embodiment of the present invention is a method for treating or ameliorating the effects of a disorder in a subject in need thereof comprising:
 a) determining, using a biological sample of the subject, the presence or absence of a Val$^{158/108}$Met polymorphism in the COMT gene of the subject; and
  bi) administering to the subject, if clinically appropriate, an effective amount of a solute carrier (SLC) modulator that increases proline levels if the subject is determined from step a) to have a Val/Val genotype at codon 158 (and/or codon 108 for S-COMT); or
  bii) administering to the subject, if clinically appropriate, an effective amount of an SLC modulator that decreases proline levels if the subject is determined from step a) to have a Val/Met or Met/Met genotype at codon 158 (and/or codon 108 for S-COMT).

In this embodiment, the determining and administering steps, and the SLC modulators, are as disclosed previously herein.

Yet another embodiment of the present invention is a method for eradicating or reducing a negative symptom experienced by a subject who suffers from a disorder comprising:
 a) obtaining a biological sample from the subject;
 b) determining, in the biological sample, the presence or absence of a Val$^{158/108}$Met polymorphism in the COMT gene; and
  ci) administering to the subject, if clinically appropriate, an effective amount of a solute carrier (SLC) modulator that increases proline levels if the subject is determined from step b) to have a Val/Val genotype at codon 158 (and/or codon 108 for S-COMT); or
  cii) administering to the subject, if clinically appropriate, an effective amount of an SLC modulator that decreases proline levels if the subject is determined from step b) to have at least one Met allele at codon 158 (and/or codon 108 for S-COMT).

In this embodiment, the negative symptoms are as described previously. Furthermore, the obtaining, determining, and, if appropriate, administering steps in this embodiment have been described previously.

Another embodiment of the present invention is a method for monitoring the treatment of a subject with a disorder, the method comprising:
 a) determining the genotype for the allele(s) of the COMT gene at codon 158 (and/or codon 108 for S-COMT) in a biological sample of the subject;
 b) determining the proline level of the subject;
 c) determining the level of one or more of glycine, serine, GABA, glutamate of the subject; and
 d) modifying the course of treatment of the subject, if necessary, including administering a solute carrier (SLC) modulator to the subject or stopping or omitting treatment with an SLC modulator, or administering a different SLC modulator to the subject, based upon the presence or absence of a Val$^{158/108}$Met polymorphism in the COMT gene.

Another embodiment of the present invention is a method for choosing and/or monitoring the treatment of a subject with a disorder, the method comprising:
 a) determining the genotype for the allele(s) of the COMT gene at codon 158 (and/or codon 108 for S-COMT) in a biological sample of the subject;
 b) determining the level of one or more of glycine, serine, GABA, glutamate of the subject; and
 c) modifying the course of treatment of the subject, if necessary, including administering a solute carrier (SLC) modulator to the subject or stopping or omitting treatment with an SLC modulator, or administering a different SLC modulator to the subject, based upon the presence or absence of a Val$^{158/108}$Met polymorphism in the COMT gene.

Below are a set of genes and variants which (individually and/or in various combinations and/or groups) may modify interaction(s) of proline and/or (glutamate, GABA, glycine, L- and/or D-serine, D-cycloserine, and molecules listed above) with COMT. They include proline and dopamine metabolism and transporter genes.

COMT genotypes and/or gene-associated variants according to the present invention include the Val$^{158/108}$Met polymorphism and/or rs6270 and/or rs6269 and/or rs4633 and/or rs4818 and/or rs6267 and/or rs5031015 and/or rs4986871 and/or rs4680 (including either allele and/or sequence alternative for COMT Uniprot variant Ids: VAR_013925 and/or VAR_013926 and/or VAR_020274 and/or VAR_020275 and/or VAR_005139 (both alleles (Val and/or Met)) and/or VSP_018778.

PRODH variants according to the present invention include the rs450046 and/or rs372055 and/or rs2904552 and/or rs137852934 and/or rs4819756 and/or rs193919334 and/or rs2008720 and/or rs2904551 and/or rs3970559 and/or rs1807467 and/or rs2870983 and/or rs3970555 and/or rs2238731 and/or rs2870984 and/or (including either allele alternative for PRODH Uniprot Variant ids: VAR_029566 and/or VAR_029568 and/or VAR_029569 and/or VAR_029570 and/or VAR_029571 and/or VAR_029572 and/or VAR_029573 and/or VAR_029575 and/or VAR_029577 and/or VAR_029567 and/or VAR_029569 and/or VAR_029571 and/or VAR_029574 and/or VAR_029575 and/or VAR_029577.

SLC6A7 variants and associated variants according to the present invention include rs1468564, and/or rs13153971 and/or rs3776083.

SLC6A20 variants and associated variants according to the present invention include rs17279437 and/or rs2271615 and/or rs6770261 and/or rs758386 and/or rs4327428.

SLC6A15 variants and associated variants according to the present invention include rs1545843 and/or rs12424429 and/or rs3782369 and/or rs1031681.

SLC6A18 variants and associated variants according to the present invention include rs34469326 and/or rs7728667 and/or rs7705355 and/or rs113861454 and/or rs4073918 and/or rs147278493 and/or rs12522796 and/or rs4975623 and/or rs4975625 and/or rs7447815 and/or rs7728646.

PEPD variants and associated variants according to the present invention include rs121917721 and/or rs121917724 and/or rs121917723 and/or rs17570 and/or rs121917722 and/or rs121917725 and/or rs267606944 and/or rs267606943 and/or rs757386104 and/or rs797045185 and/or rs794728007 and/or rs747700126 and/or rs794728008 and/or rs3786897 and/or rs4805885 and/or rs731839 and/or rs8182584 and/or rs889140 and/or (including either allele alternative for Prolidase PEPD Uniprot Variant ids: VAR_011614 and/or VAR_004404 and/or VAR_011615 and/or VAR_004405 and/or VAR_004406).

MAOA variants and associated variants according to the present invention include rs77698881 and/or rs587777457 and/or rs1799835 and/or rs1800466 and/or rs1137070 and/or rs1465107 and/or rs2072743 and/or rs2235186 and/or rs2283725 and/or rs3027400 and/or rs3027407 and/or rs3027409 and/or rs5906883 and/or rs5906957 and/or rs5953210 and/or rs6323 and/or rs6609257 and/or rs72554632 and/or rs796065311 and/or rs796065312 and/or rs909525 and/or rs979606 and/or (including either allele and/or sequence alternative for MAOA Uniprot Variant and associated variant ids VAR_036545 and/or id VSP_045173).

MAOB variants and associated variants according to the present invention include rs10521432 and/or rs1799836 and/or rs2283729 and/or rs3027415 and/or rs6651806 and/or (including either allele and/or sequence alternative for MAOB Uniprot Variant and associated variant ids VSP_057047 and/or VSP_057048 and/or VSP_057049).

GAD1 variants and associated variants according to the present invention include rs121918345 and/or rs45566933 and/or rs769403 and/or rs769402 and/or rs1049736 and/or rs11542313 and/or rs12185692 and/or rs2058725 and/or rs2241165 and/or rs3749034 and/or rs3762555 and/or rs3791850 and/or rs3791851 and/or rs3791878 and/or rs3828275 and/or rs769390 and/or rs769391 and/or rs769404 and/or rs769407.

GAD2 variants and associated variants according to the present invention include rs8190591 and/or rs8190600 and/or rs2839672 and/or rs2839673 and/or rs8190671 and/or rs2839678 and/or rs8190730 and/or rs1805398 and/or rs185649317 and/or rs2236418 and/or rs8190590 and/or rs8190748 and/or rs992990.

Additional Definitions

The term "amino acid" means naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. An "amino acid analog" means compounds that have the same basic chemical structure as a naturally occurring amino acid, e.g., a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Imino acids such as, e.g., proline, are also within the scope of "amino acid" as used here. An "amino acid mimetic" means a chemical compound that has a structure that is different from the general chemical structure of an amino acid, but that functions similarly to a naturally occurring amino acid.

As used herein, the terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymers.

"Nucleic acid" or "oligonucleotide" or "polynucleotide" used herein mean at least two nucleotides covalently linked together. Many variants of a nucleic acid may be used for the same purpose as a given nucleic acid. Thus, a nucleic acid also encompasses substantially identical nucleic acids and complements thereof.

Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be synthesized as a single stranded molecule or expressed in a cell (in vitro or in vivo) using a synthetic gene. Nucleic acids may be obtained by chemical synthesis methods or by recombinant methods.

The nucleic acid may also be a RNA such as a mRNA, tRNA, short hairpin RNA (shRNA), short interfering RNA (siRNA), double-stranded RNA (dsRNA), transcriptional gene silencing RNA (ptgsRNA), Piwi-interacting RNA, pri-miRNA, pre-miRNA, micro-RNA (miRNA), or anti-miRNA, as described, e.g., in U.S. patent application Ser. Nos. 11/429,720, 11/384,049, 11/418,870, and 11/429,720 and Published International Application Nos. WO 2005/116250 and WO 2006/126040.

The terminology used herein is for the purpose of describing particular embodiments only and is not intended to be limiting. As used in the specification and the appended claims, the singular forms "a," "an," and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

EXAMPLES

The following examples are provided to further illustrate certain aspects of the present invention. These examples are illustrative only and are not intended to limit the scope of the invention in any way.

Example 1

Materials and Methods

Participants:

Male and female, African American, Caucasian and Hispanic patients, aged 18-65, were recruited from Bellevue Hospital Center (BHC). A diagnosis of schizophrenia or bipolar disorder was confirmed using the Structured Clinical Interview for DSM IV Disorders (SCID). After description of the study to subjects, written informed consent was obtained in accordance with IRB regulations.

For schizophrenia inpatients, recruitment was cross-sectional and independent of their duration of hospitalization. Psychiatric symptoms were measured using the Scale for the Assessment of Negative Symptoms (SANS), the Scale for the Assessment of Positive Symptoms (SAPS), and the Brief Psychiatric Rating Scale (BPRS). Proline levels of a subset of the schizophrenia patients, those who did not receive treatment with VPA or divalproex, were reported previously (Clelland et al., 2011).

Bipolar patients were recruited upon presentation at the BHC Comprehensive Emergency Psychiatric Program. Psychiatric symptoms in bipolar disorder patients were measured at an admission visit (visit 1), using the BPRS. At a follow-up inpatient ward visit (visit 2), fasting bloods were collected plus a repeat BPRS assessment performed. Additionally, as shown in FIG. 1, an association with elevated proline in bipolar disorder patients was tested. It was found that patients did not have fasting proline levels different to controls, consistent with previous findings (Jacquet et al., 2005).

Determination of Fasting Plasma Levels:

Fasting morning blood draws were performed and proline measured in pmoles/liter as reported (Clelland et al., 2011).

Genotyping:

DNA was extracted from blood using the Puregene Blood Core Kit (Qiagen Inc) and the COMT fragment containing the Val$^{158/108}$Met polymorphism amplified using the 5'-3' primers: ACTGTGGCTACTCAGCTGTG (SEQ ID No: 4) and CCTTTTTCCAGGTCTGACAA (SEQ ID NO: 5). A step-down PCR was employed with an initial denaturation of 94° C.:15 minutes, then 12 cycles of 94° C.:30 seconds, 58° C.:45 seconds and 72° C.:30 seconds, followed by 31 cycles of 94° C.:30 seconds, 50° C.:45 seconds and 72° C.:30 seconds, with a final 72° C.:7 minute extension. Restriction enzyme NlaIII recognizes and cleaves the amplicon into Val (114 bp) or Met (96 bp) fragments, visualized following electrophoreses. To confirm genotyping accuracy, 25% of samples were repeat assayed.

Statistical Analysis:

Group differences were assessed using ANOVA, Kruskal-Wallis and Mann-Whitney tests (following skewness and kurtosis normality tests), $\chi^2$ or Fisher exact tests. Means±standard deviations (SD) were reported, plus Bonferroni adjusted p-values where appropriate. Genotype distributions were tested for Hardy-Weinberg equilibrium (HWE) using a $\chi^2$ or exact test.

Linear regression was employed to test for an interaction between fasting plasma proline and COMT on symptoms in schizophrenia, modelling the relationships of these variables on outcomes of total SANS, SAPS and BPRS scores. Based upon the schizophrenia sample result, the primary outcome for bipolar patients was assessed using the BPRS negative symptom subscale (Kane et al., 1988), and percent reduction in negative symptoms calculated. Positive symptom subscale of the BPRS (Id.) and total BPRS scores were also investigated. When outliers in the data or leverage points were identified, a robust regression procedure was employed using an MM estimator to minimize data-point effects (SASv9.3).

Significant models were investigated further: To assess utility in adjusting the dependent variable, demographic and clinical covariates were entered into a bivariate regression and terms found to have p-values of <0.10 carried forward to a multivariate model. Gender was a covariate in all models, to adjust for previously reported proline gender differences (Jacquet et al., 2005; Tomiya et al., 2007; Clelland et al., 2011). Model fit and selection was determined using the Wald test, testing the null hypothesis that non-significant (p>0.05) covariate parameters were simultaneously equal to zero in full and subsequent reduced models. Statistical analysis was performed in SASv9.3, Stata ICv12, with graphs plotted in GGplot2v1.0.1 in Rv3.1.2.

Example 2

Results

COMT Genotype Modifies the Relationship Between Proline and Negative Symptoms of Schizophrenia:

The schizophrenia sample consisted of 95 patients. Although recruitment was not targeted by COMT genotype, patients were well matched on demographic characteristics and medication use across genotypes (Table 2).

In the entire sample, fasting plasma proline was not significantly different across genotypes (range 87 µM to 502 µM). There were also no differences in BPRS total or negative symptoms (SANS total score), however positive symptoms were significantly different: Met/Met patients had lower SAPS scores than Val/Met (Mann-Whitney z=2.52, adjusted p=0.035) or Val/Val patients (z=2.92, adjusted p=0.001), as previously reported (Goghari & Sponheim, 2008). 100% accuracy was achieved from confirmatory re-genotyping and a sample of 90 control subjects were in HWE for COMT Val$^{158/108}$Met (p>0.05, data not shown). However, COMT distributions of the schizophrenia patients deviated from HWE ($\chi^2$=8.08, df=1, p<0.05). Although deviations for this polymorphism in schizophrenia have been reported (Joober et al., 2002), this finding may represent substructure due to mixed ethnicity: when stratified by ethnicity, all groups were in HWE (p>0.05).

TABLE 2

Demographic and Clinical Characteristics of Schizophrenic Patients (SZ), n = 95

| Characteristic | Met/Met n = 21 | Val/Met n = 32 | Val/Val n = 42 | Prob$^a$ |
|---|---|---|---|---|
| Gender, n (row %) | | | | 0.288 |
| Female | 11 (23.4) | 19 (40.4) | 17 (36.2) | |
| Males | 10 (20.8) | 13 (27.1) | 25 (52.1) | |

TABLE 2-continued

Demographic and Clinical Characteristics of Schizophrenic Patients (SZ), n = 95

| Characteristic | Met/Met n = 21 | Val/Met n = 32 | Val/Val n = 42 | Prob[a] |
|---|---|---|---|---|
| Ethnicity, n (row %) | | | | 0.096 |
| African American | 5 (13.5) | 10 (27.0) | 22 (59.5) | |
| Caucasian | 10 (35.7) | 10 (35.7) | 8 (28.6) | |
| Hispanic | 6 (20.0) | 12 (40.0) | 12 (40.0) | |
| Age (years), mean ± SD | 40.9 ± 10.9 | 39.1 ± 11.5 | 39.9 ± 11.6 | 0.820 |
| Smoking Status[b], n (row %) | | | | 0.389 |
| Current or Previous | 15 (24.6) | 24 (39.3) | 22 (36.1) | |
| Never Smoked | 6 (20.7) | 8 (27.6) | 15 (51.7) | |
| History of Alcoholism, n (%) | | | | 0.426 |
| Neither | 17 (23.6) | 27 (37.5) | 28 (38.9) | |
| Abuse | 1 (10.0) | 2 (20.0) | 7 (70.0) | |
| Dependence | 3 (23.1) | 3 (23.1) | 7 (53.8) | |
| Education[c] | 3.6 ± 1.9 | 3.1 ± 1.0 | 3.4 ± 1.5 | 0.859 |
| Age at First Hospitalization[d], mean ± SD | 23.5 ± 8.0 | 25 ± 6.5 | 23.7 ± 7.5 | 0.465 |
| Hospital Duration (days)[e], mean ± SD | 19.1 ± 17.1 | 21.9 ± 23.4 | 20.0 ± 9.6 | 0.998 |
| Fasting Plasma Proline, umol/L | 219.9 ± 91.6 | 240.5 ± 68.6 | 246.4 ± 91.1 | 0.391 |
| Symptoms | | | | |
| BPRS[f] Total Symptoms, mean ± SD | 32 ± 8.5 | 33.6 ± 7.1 | 33.6 ± 8.4 | 0.500 |
| SAPS[g] Total Symptoms, mean ± SD | 10.3 ± 8.3 | 15.8 ± 9.6 | 18.2 ± 10.1 | 0.006* |
| SANS[h] Total Symptoms, mean ± SD | 24 ± 16.8 | 21.8 ± 13.1 | 17.5 ± 13.9 | 0.127 |
| Neuroleptic Medications | | | | |
| Neuroleptic Type, n (row %) | | | | 0.348 |
| Typical only | 5 (27.8) | 3 (16.7) | 10 (55.6) | |
| Atypical only | 13 (22.4) | 19 (32.8) | 26 (44.8) | |
| Both | 3 (16.7) | 9 (50.0) | 6 (33.3) | |
| None | 0 | 1 (100) | 0 | |
| Daily CPZE dose[i], mean ± SD | 490.6 ± 234.0 | 571.1 ± 418.1 | 526.8 ± 281.0 | 0.981 |
| Mood Stabilizing Medications | | | | |
| Total Number Administered, n (row %) | | | | 0.786 |
| 0 | 15 (26.3) | 19 (33.3) | 23 (40.4) | |
| 1 | 6 (16.7) | 12 (33.3) | 18 (50.0) | |
| 2 | 0 | 1 (50) | 1 (50) | |
| VPA Treatment, n (row %) | | | | 0.327 |
| Yes | 4 (12.9) | 11 (35.5) | 16 (51.6) | |
| No | 17 (26.6) | 21 (32.8) | 26 (40.6) | |
| Other Medications | | | | |
| Benzodiazapines, yes: n (row %) | 4 (21.0) | 8 (42.1) | 7 (36.8) | 0.641 |
| Antidepressants, yes: n (row %) | 1 (9.1) | 5 (45.4) | 5 (45.4) | 0.596 |

[a]*= significant p-value when comparing characteristic across three COMT genotypes, calculated by one-way ANOVA, Kruskal-Wallis, or Fisher exact tests.
[b]n = 90, five subjects not reported.
[c]Recorded as a continuous variable from the SCID (range 2-8). n = 93, two subjects not reported.
[d]n = 60 for whom this characteristic could be obtained.
[e]Days in hospital prior to fasting blood draw.
[f]Brief Psychiatric Rating Scale.
[g]Schedule for Assessment of Positive Symptoms.
[h]Schedule for Assessment of Negative Symptoms.
[i]Chlorpromazine (CPZ) equivalent dose, n = 94 as one subject's NL had no CPZ equivalent.

Figure 2A:
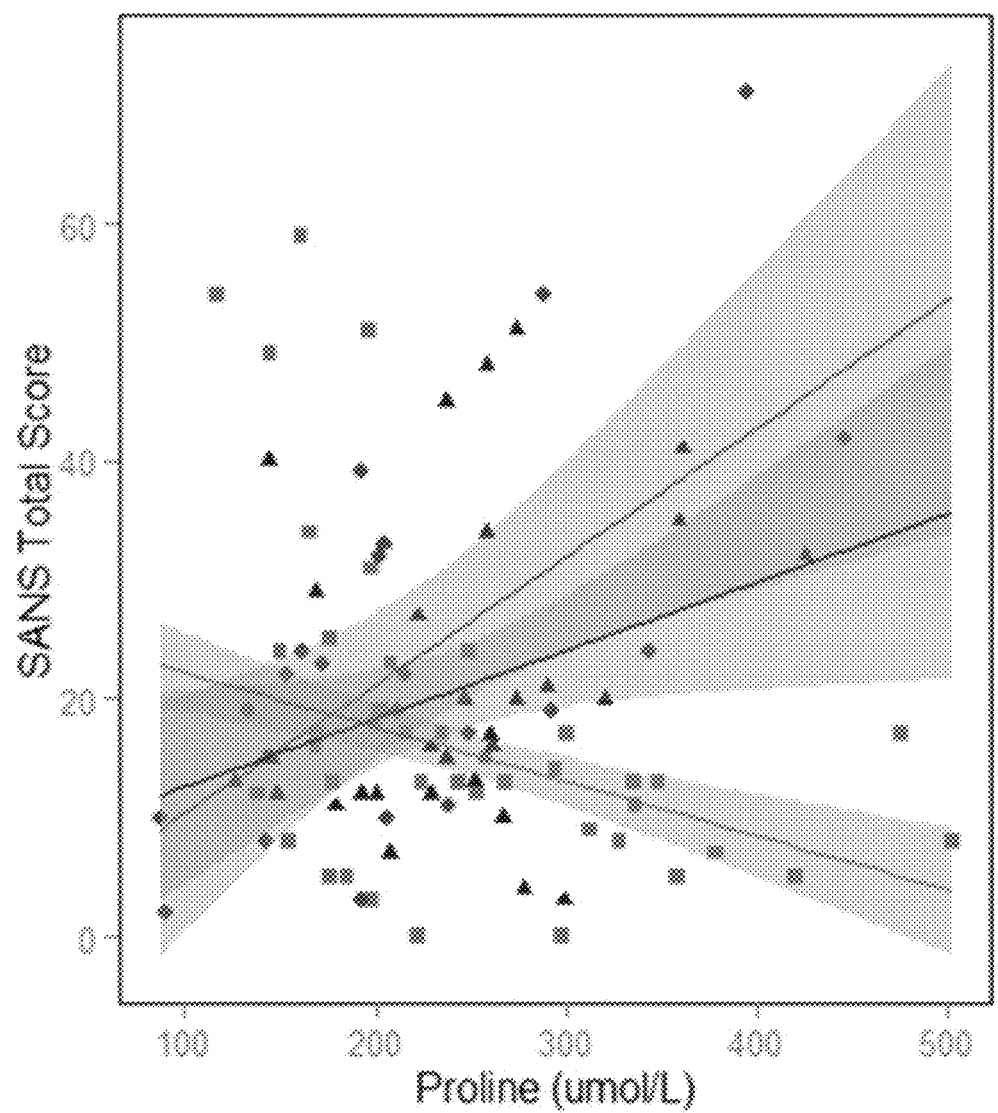
FIG. 2A shows a scatterplot graph of the relationship between proline and negative symptoms as measured using the Scale for the Assessment of Negative Symptoms (SANS), plotted for patients with the Met/Met (n=21, red diamonds), Val/Met (n=32, blue triangles) and Val/Val (n=42, green squares) COMT genotypes. Lines represent the predicted values from the regression model for each genotype, with 95% confidence intervals. There was a significant positive relationship between proline and SANS score in Met/Met and Val/Met patients, with high proline levels being associated with high SANS scores. Conversely there existed a significant negative relationship in Val/Val patients, with high proline associated with lower levels of negative symptoms.
Figure 2B:
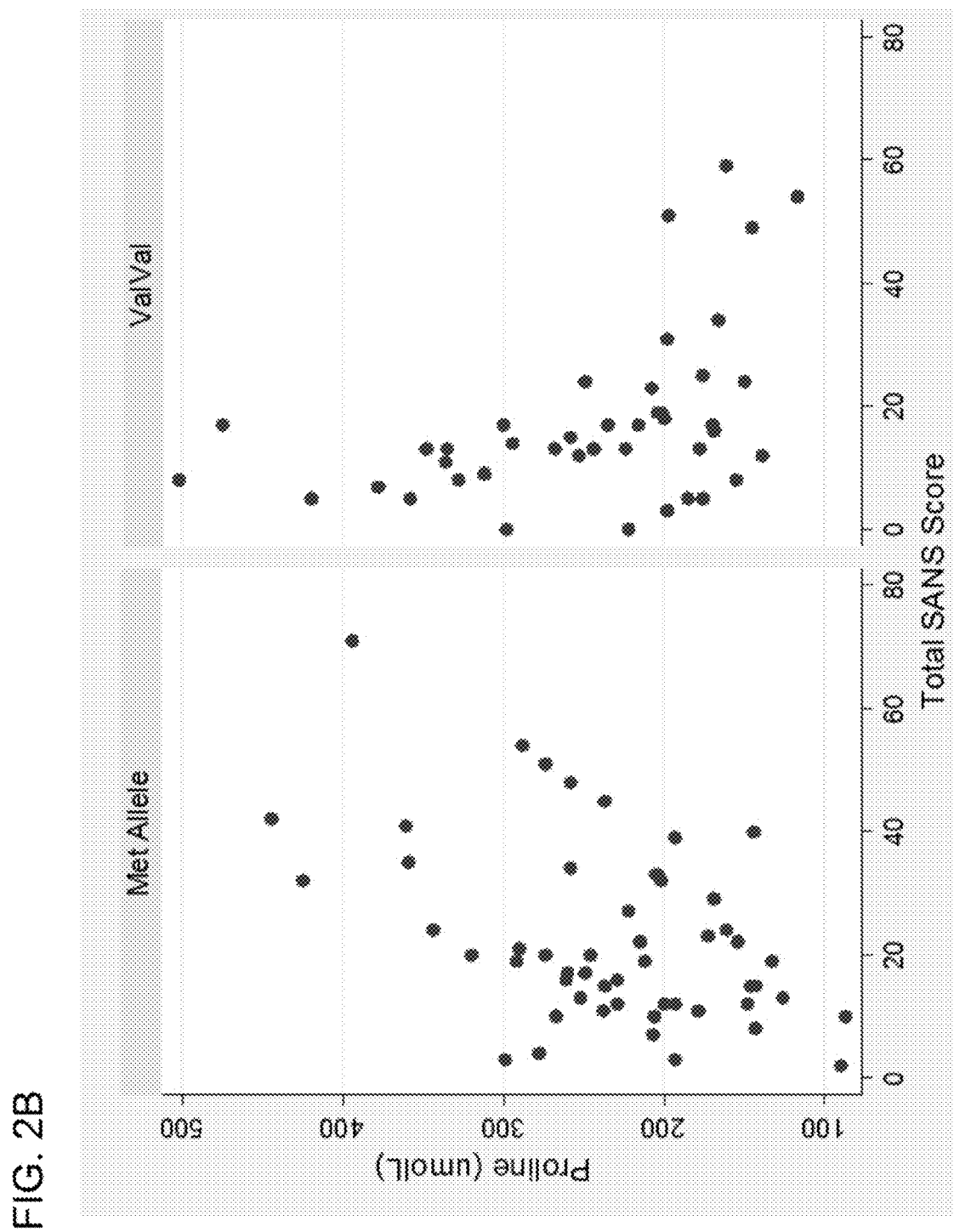
FIG. 2B shows scatterplot graphs of the relationship between proline and total negative symptoms, as assessed using the SANS, by COMT genotype (Met allele (left panel) or Val/Val (right panel)). There was a significant positive relationship between total SANS score and proline in schizophrenia patients with the Met allele (spearman's rho=0.36, p=0.009, n=53), while conversely there was a significant negative relationship between total SANS score and proline in Val/Val schizophrenia patients (spearman's rho=−0.47, p=0.0019, n=42).

Testing the primary hypothesis of effect modification, a significant interaction was observed between COMT genotype and proline on negative symptoms in schizophrenia patients (n=95, interaction β coefficient=0.082, p<0.0001). As shown in FIGS. 2A and 2B, for patients with both the Met/Met or Val/Met genotypes, high proline was associated with high SANS scores, while conversely high proline in Val/Val patients was associated with lower levels of negative symptoms. Stratifying by COMT (Met allele carrier or Val/Val), for Met carriers, every 100 μM increase in proline (approximately 1SD from the mean proline level) was associated with a SANS total score increase of over 8 points (β coefficient=0.084, p=0.001). Conversely, for Val/Val patients, every 100 μM increase in proline decreased SANS total scores by nearly 7 points (β=−0.067, p=0.003). Thus at proline levels only approximately 1 SD above the group means, Met carriers with a fasting plasma proline of 332 μM had a predicated SANS score of 30, while Val/Val patients with proline of 346 μM had a predicted score of only 10.

Possible confounds on this relationship were assessed (see Table 3). While there was no relationship between SANS score and either medication type, neuroleptic dose (summarized as daily chlorpromazine equivalents), or the number of days in hospital prior to blood draw and symptom assessment, covariate analysis showed that ethnicity and alcohol use were predictors of SANS score (p<0.1, Table 3), and along with gender were taken forward to a multivariate model (Table 4). Model fit was determined with the final model retaining genotype, proline, alcohol use, and the highly significant COMT-proline interaction (p<0.0001). The significant interaction also remained in a stratified analysis following removal of patients reporting alcohol abuse/dependence (p<0.001, n=72). Interestingly, there was no interaction of COMT genotype on the relationship between fasting peripheral proline and positive symptoms (interaction β=−0.005, p=0.64), or total symptoms (interaction β=−0.23, p=0.097), suggesting specificity of the relationship to negative symptoms.

TABLE 3

Bivariate Association Between Schizophrenia Patient Demographic and Clinical Characteristics, with Total SANS Score, n = 95

| Characteristic | β (95% CI) | Prob |
|---|---|---|
| Gender[a] | −1.697 (−7.609, 4.215) | 0.570 |
| Ethnicity[b] | | |
| African American v Caucasian | 6.059 (−1.026, 13.143) | 0.093* |
| African American v Hispanic | 7.028 (0.079, 13.977) | 0.047* |
| Age | 0.024 (−0.239, 0.287) | 0.857 |
| Education[c] | 0.389 (−1.660, 2.438) | 0.707 |
| Alcohol Dependence/abuse[b] | | |
| None v Abuse | −0.236 (−9.775, 9.303) | 0.961 |
| None v Dependence | −9.505 (−18.023, −0.987) | 0.029* |
| Smoking Status[d] | −0.882 (−4.112, 2.349) | 0.589 |
| Hospital Duration[e] | 0.026 (−0.121, 0.172) | 0.729 |
| Daily CPZE dose[f] | 0.004 (−0.005, 0.014) | 0.353 |
| Neuroleptic (NL) Type[b,g] | | |
| Atypical v Typical | 2.082 (−5.763, 9.930) | 0.599 |
| Atypical v both | −1.584 (−9.430, 6.261) | 0.689 |
| Total Number of NLs Administered[h] | −2.961 (−10.614, 4.692) | 0.444 |
| Total Number of Mood Stabilizers Administered[i] | 1.320 (−4.886, 7.526) | 0.674 |
| VPA Treatment[j] | −0.578 (−7.157, 6.001) | 0.862 |
| Benzodiazapines | −3.342 (−10.713, 4.028) | 0.370 |

[a]Binary variable: Male v female.
[b]For categorical analysis the reference category is the first level listed for each variable.
[c]Recorded as a continuous variable from the SCID (range 2-8)
[d]Binary variable: Never v current or previous smokers, n = 90 as four subjects did not report smoking status.
[e]Days in hospital prior to fasting blood draw and symptoms assessment.
[f]Chlorpromazine (CPZ) equivalent dose, n = 93 as one subject's NL had no CPZ equivalent, and one subjects did not receive a NL.
[g]n = 94, as one subject did not receive a NL.
[h]Binary variable: one v two, n = 92 (as one subject did not receive a NL, and only two subjects were administered > 2 different NLs).
[i]Binary variable: no versus yes, n = 92 (as three subjects had not received < 48 hours of VPA treatment).
[j]Binary variable: none versus one, n = 93 (as only two subjects were administered > 1 mood stabilizers).

TABLE 4

Prediction of Negative Symptoms from Proline Level and COMT in Psychiatric Patients

| | β Coefficient | SE | Test statistic[a] | Prob | Wald test |
|---|---|---|---|---|---|
| Schizophrenia Models (DV = Total SANS Score, n = 95) | | | | | |
| Full Model[b] | | | | | |
| Proline | −0.1050 | 0.0333 | 9.94 | 0.0016* | |
| COMT (ValVal, ValMet, MetMet) | −13.0179 | 4.2452 | 9.40 | 0.0022* | |
| Interaction (Proline × COMT) | 0.0744 | 0.0169 | 19.48 | <.0001* | |
| Alcohol Use | | | | | |
| Alcohol Abuse v None | −4.2178 | 4.2706 | 0.98 | 0.3233 | |
| Alcohol Dependence v None | −9.0807 | 3.5632 | 6.49 | 0.0108* | |
| Gender | −1.0466 | 2.3795 | 0.19 | 0.6600 | |
| Ethnicity | | | | | |
| African-American v Caucasian | 3.0258 | 3.0258 | 1.14 | 0.2866 | |
| African-American v Hispanic | 4.6703 | 2.8214 | 2.74 | 0.0979 | p = 0.517[c] |
| Full Model[b] | | | | | |
| Proline | −0.0804 | 0.0321 | 6.28 | 0.0122* | |
| COMT (ValVal, ValMet, MetMet) | −9.6576 | 4.0300 | 5.74 | 0.0166* | |
| Interaction (Proline × COMT) | 0.0651 | 0.0161 | 16.39 | <.0001* | |
| Alcohol Use | | | | | |
| Alcohol Abuse v None | −5.1234 | 3.9854 | 1.65 | 0.1986 | |
| Alcohol Dependence v None | −9.7478 | 3.3526 | 8.45 | 0.0036* | p = 0.020[d] |
| Bipolar Disorder Models (DV = % Change in BPRS Negative Symptoms Scale, n = 43) | | | | | |
| Full Model | | | | | |
| Proline | 0.0012 | 0.0006 | 2.09 | 0.044* | |
| COMT (Met/Met v ValVal) | 0.4281 | 0.1650 | 2.60 | 0.014* | |
| Interaction (Proline × COMT) | −0.0017 | 0.0007 | −2.42 | 0.022* | |
| Gender | 0.1960 | 0.0656 | 2.99 | 0.005* | |
| Ethnicity | | | | | |
| African-American v Caucasian | 0.0186 | 0.0839 | 0.22 | 0.826 | |
| African-American v Hispanic | −0.1528 | 0.1052 | −1.45 | 0.156 | |
| Duration (days) between Assessments | 0.0049 | 0.0070 | 0.69 | 0.492 | |
| Neuroleptic Type | | | | | |
| Atypical Neuroleptic v None | −0.0802 | 0.0818 | −0.98 | 0.334 | |
| Typical Neuroleptic v None | −0.1401 | 0.2087 | −0.67 | 0.507 | |
| Both v None | −0.1531 | 0.1184 | −1.29 | 0.206 | |
| Benzodiazepines | −0.0840 | 0.0714 | −1.18 | 0.249 | p = 0.056[e] |
| Final Model | | | | | |
| Proline | 0.0016 | 0.0006 | 2.55 | 0.015* | |
| COMT (Met/Met v ValVal) | 0.5029 | 0.1766 | 2.85 | 0.007* | |

TABLE 4-continued

Prediction of Negative Symptoms from Proline Level and COMT in Psychiatric Patients

| | β Coefficient | SE | Test statistic[a] | Prob | Wald test |
|---|---|---|---|---|---|
| Interaction (Proline × COMT) | −0.0021 | 0.0007 | −2.83 | 0.007* | |
| Gender | 0.1856 | 0.0656 | 2.83 | 0.007* | p = 0.0074[f] |

[a]$X^2$ (Schizophrenia models using Robust linear regression) or t (Bipolar models using linear regression)
[b]Robust regression, MM Estimation Method (28).
[c]Robust Wald tests canonical linear hypothesis that combined effect of non-significant covariates (Gender and Ethnicity) is zero.
[d]Robust Wald tests hypothesis that covariate effect (Alcohol use) is zero.
[e]Wald tests canonical linear hypothesis that combined effect of non-significant covariates (Ethnicity, Duration, Neuroleptic Type and use of Benzodiazepines) is zero.
[f]Wald tests hypothesis that covariate effect (Gender) is zero.

Example 3

Figure 3:
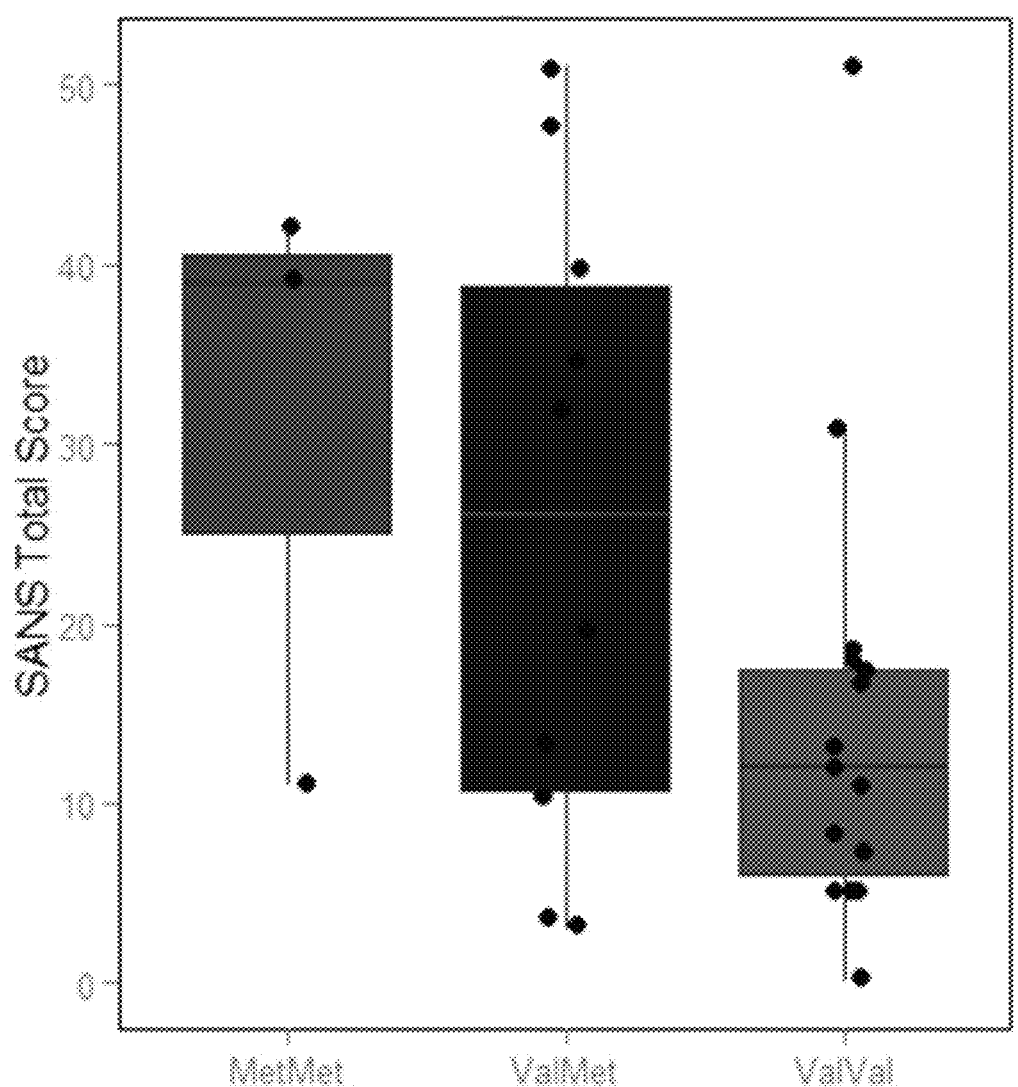
FIG. 3 shows a boxplot illustrating that negative symptoms, as assessed by the total SANS score, were significantly lower in VPA treated patients with the COMT Val/Val genotype (mean=14.6±12.67, n=15, green), as compared to pooled Met/Met (mean=30.67±17.1, n=3, red) and Val/Met (mean=25.6±17.93, n=10, blue) genotypes (F(1,26)=4.63, p=0.0408). Subjects were included if they had received 48 hours or more of VPA treatment, within 48 hours of the study visit (n=28, three subjects were dropped because they had less than 48 hours of VPA treatment). Black jittered points represent individual data. The horizontal line within each box represents the group median. The box indicates the IQR. The whiskers extend to the most extreme data point which is 1.5 times the IQR.

Valproate Treated COMT Val/Val Schizophrenia Patients have Significantly Lower Negative Symptoms than Met Allele Carriers:

An effect of VPA on plasma proline has been reported (Jacquet et al., 2005) and VPA-treated schizophrenia patients in the current study had significantly higher proline (mean=299.29±94.76, n=28) than those who did not receive VPA (mean=215.84±63, n=64) (z=−3.97, p=0.0001). Considering the finding of an interaction between COMT and proline on negative symptoms, the hypothesis was that VPA treated Val/Val patients would respond differently to the concomitant high levels of proline, with respect to their negative symptoms, as compared to Met carriers. As shown in FIG. 3, VPA-treated Val/Val schizophrenia patients had significantly lower SANS total scores, averaging twelve points lower than Val/Met and Met/Met patients (P=−12.17, p=0.041, n=28). This result remained significant after adjusting for the dose of VPA administered in the 48 hours prior to the blood draw (p=0.043).

Example 4

LX-6171 Treated COMT Val/Val Schizophrenia Patients are Expected to have Significantly Lower Negative Symptoms than Met Allele Carriers:

According to some embodiments, LX-6171-treated schizophrenia patients in the current study will have significantly higher proline than those who do not receive VPA (data not shown). Considering the finding of an interaction between COMT and proline on negative symptoms, the hypothesis is that LX-6171 treated Val/Val patients would respond differently to the concomitant high levels of proline, with respect to their negative symptoms, as compared to Met carriers. According to some embodiments, LX-6171-treated Val/Val schizophrenia patients had significantly lower SANS total scores, averaging, for example, twelve points lower than Val/Met and Met/Met patients (data not shown). This result is expected to remain significant after adjusting for the dose of LX-6171 administered in the 48 hours prior to the blood draw (data not shown).

Example 5

COMT Genotype Modifies the Relationship Between Proline and Negative Symptom Change in in Bipolar Disorder:

The hypothesis that COMT genotype modifies the relationship between proline and negative symptoms across psychiatric illnesses was explored, employing a second patient sample: 43 subjects with bipolar disorder who had completed a BPRS assessment upon admission to the psychiatric ER (visit 1) plus a second BPRS assessment and fasting blood draw during their follow-up visit (mean duration between assessments=9.5±4.6 days). Thus, for this sample the relationship between COMT and proline on the change in symptoms was calculated by the percent reduction in negative symptoms from admission to follow-up.

As for the schizophrenia cohort, recruitment of the bipolar sample was not targeted by COMT genotype, but subjects were matched on demographic characteristics (Table 5) and medication use at both study visits (Table 6). The distribution of COMT genotypes was in HWE ($\chi^2$=0.387, df=1, p>0.05). Due to the finding in schizophrenia that Met allele carriers have a similar response to high proline, and because of the smaller bipolar sample size, Met/Met and Val/Met bipolar groups were pooled for further analysis.

TABLE 5

Demographic and Clinical Characteristics of Bipolar Disorder Patients, n = 43

| Characteristic | Met/Met n = 5 | Val/Met n = 22 | Val/Val n = 16 | Prob[a] |
|---|---|---|---|---|
| Gender, n (row %) | | | | 0.328 |
| Female | 1 (6.2) | 11 (68.8) | 4 (25.0) | |
| Male | 4 (14.8) | 11 (40.7) | 12 (44.4) | |
| Ethnicity, n (row %) | | | | 0.450 |
| African American | 0 | 4 (57.1) | 3 (42.9) | |
| Asian | 0 | 0 | 1 (100) | |
| Caucasian | 3 (11.5) | 13 (50.0) | 10 (38.5) | |
| Hispanic | 2 (22.2) | 5 (55.6) | 2 (22.2) | |
| Age (years), mean ± SD | 34 ± 9.7 | 32.8 ± 8.4 | 33.2 ± 11.2 | 0.933 |
| Smoking Status[b], n (row %) | | | | 1.000 |
| Current or Previous | 4 (13.3) | 15 (50.0) | 11 (36.7) | |
| Never Smoked | 1 (8.3) | 6 (50.0) | 5 (41.7) | |
| History of Alcoholism, n (row %) | | | | 1.000 |

TABLE 5-continued

Demographic and Clinical Characteristics of Bipolar Disorder Patients, n = 43

| Characteristic | Met/Met n = 5 | Val/Met n = 22 | Val/Val n = 16 | Prob[a] |
|---|---|---|---|---|
| Abuse | 1 (7.1) | 8 (57.1) | 5 (35.7) | |
| Dependence | 1 (12.5) | 4 (50.0) | 3 (37.5) | |
| Neither | 3 (14.3) | 10 (47.6) | 8 (38.1) | |
| Education[c], mean ± SD | 4.2 ± 2.0 | 3.8 ± 1.6 | 4.2 ± 2.0 | 0.709 |
| Fasting Plasma Proline[d], umol/L | 213.6 ± 72.7 | 205.5 ± 63.2 | 245.8 ± 123.4 | 0.669 |
| Age at Onset, mean ± SD | 25.8 ± 2.8 | 26.4 ± 8.3 | 24.1 ± 7.8 | 0.207 |
| Age at First Hospitalization, mean ± SD[a] | 26 ± 3.2 | 26.8 ± 9.3 | 22.9 ± 7.4 | 0.112 |
| Days between Symptom Assessments, mean ± SD | 10.2 ± 6.2 | 9.4 ± 3.7 | 9.5 ± 5.1 | 0.382 |

[a]P-value values when comparing Met allele carriers to Val/Val patients, calculated by Satterthwaite t-test, Mann-Whitney, Chi-Square or Fisher exact test.
[b]n = 42, one subject not reported.
[c]Recorded as a continuous variable from the SCID (range 2-8).
[d]Sampled at visit 2.

TABLE 6

Clinical Characteristics of Bipolar Disorder Patients, n = 43

| | Admission (Visit 1) | | | | Follow-up (Visit 2) | | | |
|---|---|---|---|---|---|---|---|---|
| Characteristic | Met/Met n = 5 | Val/Met n = 22 | Val/Val n = 16 | Prob[a] | MetMet n = 5 | Val/Met n = 22 | ValVal n = 16 | Prob[a] |
| Brief Psychiatric Rating Scale[b] | | | | | | | | |
| Total Symptoms, mean ± SD | 42 ± 7.3 | 36.3 ± 5.9 | 36.4 ± 4.7 | 0.592 | 34.8 ± 8.8 | 25.9 ± 5.8 | 27.4 ± 5.2 | 0.772 |
| Negative Symptom[c], mean ± SD | 9.0 ± 5.1 | 6.3 ± 2.2 | 6.2 ± 1.7 | 0.872 | 6.0 ± 1.4 | 5.6 ± 0.9 | 5.6 ± 1.0 | 0.711 |
| Positive Symptoms[d], mean ± SD | 24.6 ± 5.0 | 18.7 ± 6.2 | 18.2 ± 6.2 | 0.457 | 18.4 ± 5.3 | 12.4 ± 4.8 | 13.7 ± 4.2 | 0.553 |
| Psychosis[e]: yes, n (row %) | 4 (13.3) | 14 (46.7) | 12 (40) | 0.735 | | | | |
| Neuroleptic (NL) Medications | | | | | | | | |
| NL Type, n (row %) | | | | 1.000 | | | | 0.745 |
| Typical only | 2 (22.2) | 4 (44.4) | 3 (33.3) | | 0 | 0 | 1 (100) | |
| Atypical only | 1 (12.5) | 4 (50.0) | 3 (37.5) | | 3 (9.7) | 17 (54.8) | 11 (35.5) | |
| Both | 0 | 3 (75) | 1 (25) | | 2 (40.0) | 1 (20.0) | 2 (40.0) | |
| None | 2 (9.1) | 11 (50.0) | 9 (40.9) | | 0 | 4 (66.7) | 2 (33.3) | |
| Daily CPZE dose[f], mean ± SD | 282.3 ± 202.1 | 284.1 + 109.7 | 239.3 + 81.5 | 0.403 | 566.7 + 372.1 | 344.4 + 162.6 | 362.3 + 202.6 | 0.863 |
| Total number of NLs, n (row %) | | | | 0.906 | | | | 0.731 |
| 0 | 2 (9.1) | 1 (50) | 9 (40.9) | | 0 | 4 (66.7) | 2 (33.3) | |
| 1 | 3 (17.6) | 8 (47.1) | 6 (35.3) | | 2 (7.1) | 16 (57.1) | 10 (35.7) | |
| 2 | 0 | 3 (75.0) | 1 (25.0) | | 3 (37.5) | 2 (25) | 3 (37.5) | |
| Mood Stabilizing Medications | | | | | | | | |
| Total number of mood stabilizers, n (row %) | | | | 0.282 | | | | 0.785 |
| 0 | 5 (12.5) | 19 (47.5) | 16 (40.0) | | 0 | 1 (100) | 0 | |
| 1 | 0 | 3(100) | 0 | | 3 (8.3) | 20 (55.6) | 13 (36.1) | |
| 2 | 0 | 0 | 0 | | 2 (33.3) | 1 (16.7) | 3 (50) | |
| VPA: yes, n (row %) | 0 | 1 (100) | 0 | 1.000 | 2 (9.5) | 11 (52.4) | 8 (38.1) | 1.000 |
| Other Medications | | | | | | | | |
| Benzodiazapines: yes, n (row %) | 3 (15.8) | 10 (52.6) | 6 (31.6) | 0.542 | 4 (22.2) | 4 (22.2) | 10 (55.6) | 0.055 |
| Antidepressants: yes, n (row %) | 0 | 2 (66.7) | 1 (33.3) | 1.000 | 1 (5.6) | 7 (38.9) | 10 (55.6) | 0.055 |

[a]P-value values when comparing M allele carriers to ValVal patients, calculated by Satterthwaite t-test, Mann-Whitney, Chi-Square or Fisher exact test.
[b]BPRS = Brief Psychiatric Rating Scale.
[c]Negative Symptoms (BPRS items 3 + 13 + 14 + 16 + 18)
[d]Positive Symptoms (BPRS items 4 + 7 + 8 + 10 + 11 + 12 + 15 + 17)
[e]Psychosis determined as current or previous psychotic illness at admission only.
[f]Chlorpromazine (CPZ) equivalent dose.

Figure 4:
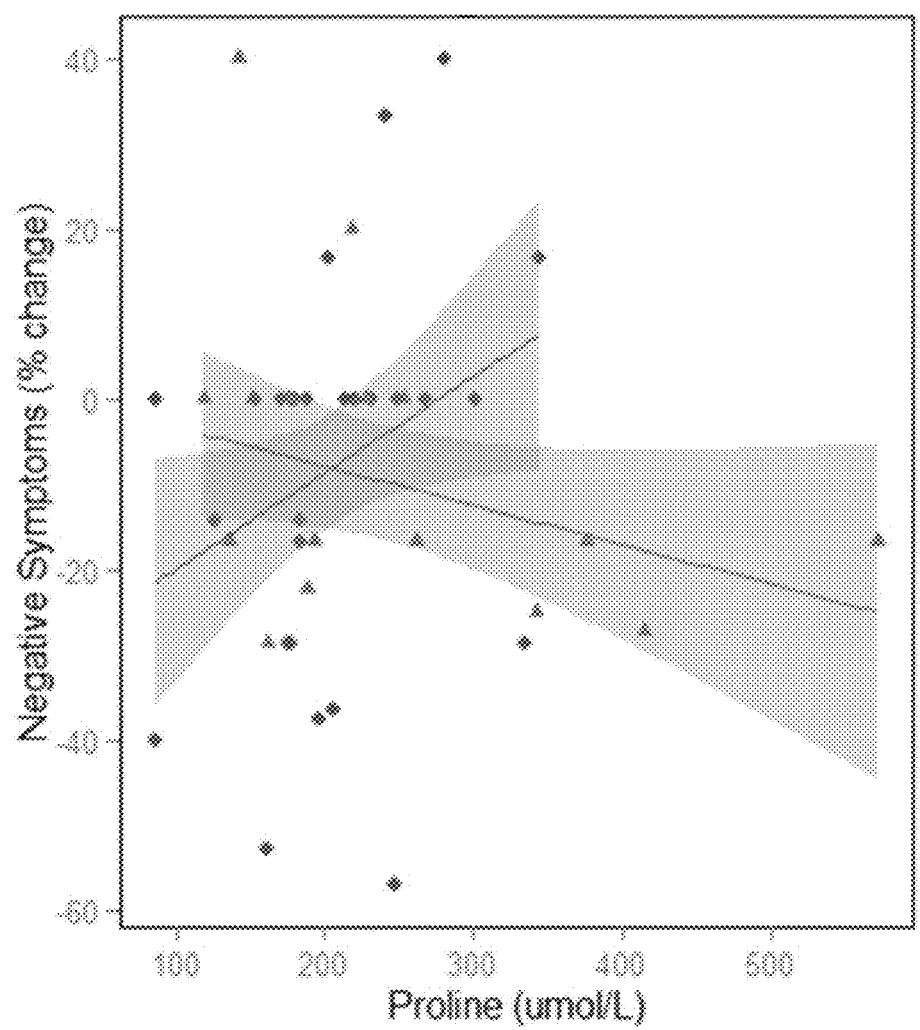
FIG. 4 is a graph showing the relationship between proline and percent change in negative symptoms, plotted for patients with the COMT Met allele (n=27, purple diamonds) and Val/Val genotype (n=16, green triangles). Lines represent the predicted values from the regression model. As proline rose, Val/Val patients exhibited a greater negative percent change in symptoms, thus their symptoms decreased. Conversely, there existed a positive relationship between change in symptoms and proline in Met allele carriers: those with high proline had less of a decrease of negative symptoms. Negative symptoms were evaluated using the following items from the Brief Rating Psychiatric Scale (BPRS): item 3 (emotional withdrawal), 13 (motor retardation), 14 (uncooperativeness), 16 (blunted affect) and 18 (disorientation). Percent change in symptoms was calculated using the following formula: ((negative symptoms at visit 2−negative symptoms at visit 1)/negative symptoms at visit 1)×100%.

A significant interaction was observed between COMT and fasting peripheral proline on the percent change in negative symptoms (n=43, interaction β coefficient=−0.0017, p=0.04). As shown in FIG. 4, high proline was associated with a greater reduction of negative symptoms for Val/Val bipolar patients but conversely, Met carrier patients with high proline levels had, in general, either no change or a positive change in negative symptoms, suggesting a worsening of symptoms over time. Again, possible confounds were assessed (Table 7). Regarding medication, while there was no relationship between the percent change in negative symptoms and mood stabilizer use or neuroleptic dose, covariate analysis indicated that neuroleptic type and benzodiazepine use, plus the duration between visits, were predictors of the change in negative symptoms, as were the demographic characteristics of ethnicity and gender (p<0.1, Table 7). These covariates were taken forward to multivariate models (Table 4). Sequential Wald Tests were performed, determining goodness-of-fit, with the proline-COMT interaction remaining significant after adjustment for gender in the final model (interaction β coefficient=−0.0021, p=0.0007).

Figure 5:
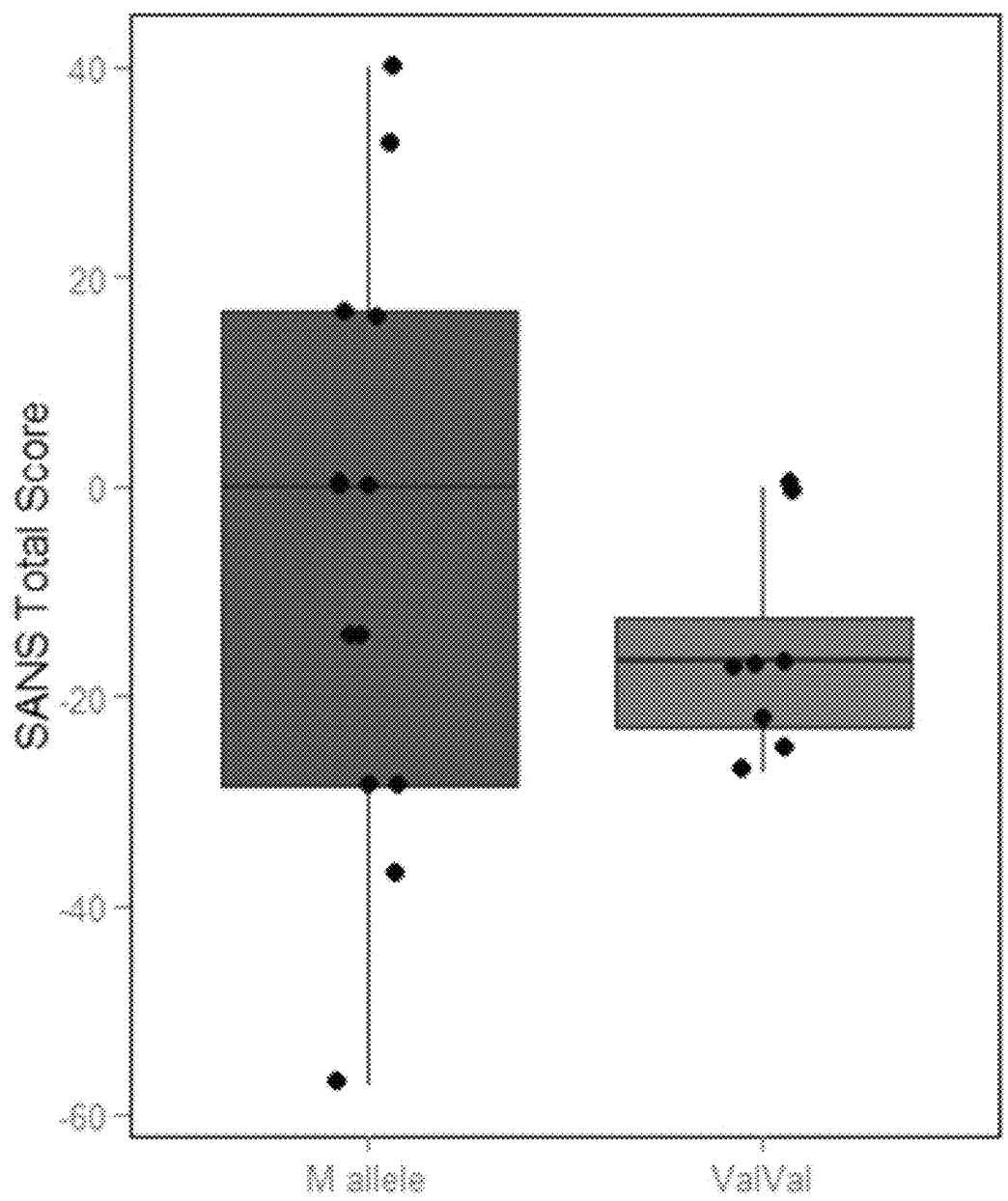
FIG. 5 is a graph showing the percent change in negative symptoms in bipolar disorder patients treated with VPA, by COMT genotype. Val/Val VPA treated bipolar patients had a greater overall percent reduction in negative symptoms (mean=−0.156±0.10, n=8) as compared to Met carrier patients (mean=−0.056±0.28, n=13). However, this result did not reach statistical significance (Mann-Whitney z=0.95, p=0.34), likely due to the variability observed in the Met patients as well as the small sample size. Black jittered points represent individual data. The horizontal line within each box represents the group median. The box indicates the IQR. The whiskers extend to the most extreme data point which is 1.5 times the IQR. The percent change in symptoms was calculated as: ((total negative symptoms subscale at visit 2−total negative subscale at visit 1)/(total negative subscale at visit 1))×100%.

As found with the schizophrenia sample, bipolar VPA-treated patients had significantly higher fasting plasma proline than those who did not receive VPA (FIG. 5). According to some embodiments, bipolar LX-6171-treated patients also have significantly higher fasting plasma proline than those who do not receive LX-6171 (data not shown). However, while Val/Val treated patients had a greater overall reduction in negative symptoms compared to Met carriers, this result did not reach significance, possibly due to the variability observed and the small sample (FIG. 5). There was no significant effect modification of COMT on the relationship between proline and percent change in positive symptoms (interaction β=0.0005, p=0.950), or percent change in total BPRS scores (interaction β=−0.0009, p=0.153), again suggesting specificity of the relationship between COMT and proline to negative symptoms.

TABLE 7

Bivariate Association Between Bipolar Disorder Patient Demographic and Clinical Characteristics, with Percent Change in Negative Symptoms, n = 43

| Characteristic (at Visit 2) | β (95% CI) | Prob$^a$ |
|---|---|---|
| Gender$^b$ | 1.359 (0.003, 0.268) | 0.045* |
| Ethnicity$^c$ | | |
| African American v Caucasian$^d$ | −0.048 (−0.022, 0.121) | 0.566 |
| African American v Hispanic | −0.272 (−0.473, −0.071) | 0.009* |
| Age | 0.003 (−0.004, 0.010) | 0.369 |
| Education$^e$ | 0.013 (−0.026, 0.051) | 0.513 |
| Alcohol Dependence/abuse$^b$ | | |
| None v Abuse | −0.020 (−0.174, 0.133) | 0.790 |
| None v Dependence | −0.055 (−0.240, 0.130) | 0.554 |
| Smoking Status$^f$ | −0.104 (−0.045, 0.253) | 0.165 |
| Duration (days) between symptom assessments | 0.013 (−0.002, 0.028) | 0.082* |
| Daily CPZE dose$^g$ | −0.000 (−0.000, 0.000) | 0.607 |
| Neuroleptic (NL) Type$^b$ | | |
| None v Atypical | −0.091 (−0.285, 0.103) | 0.348 |
| None v Typical | −0.006 (−0.476, 0.465) | 0.981 |
| None v both | −0.230 (−0.494, 0.033) | 0.085* |
| Total Number of NLs Administered$^h$ | −0.074 (−0.192, 0.043) | 0.209 |
| Total Number of Mood Stabilizers Administered$^i$ | −0.050 (−0.154, 0.054) | 0.338 |
| VPA Treatment | −0.013 (−0.148, 0.122) | 0.845 |
| Benzodiazepines | −0.120 (−0.251, 0.011) | 0.072* |
| Antidepressants | 0.004 (−0.133, 0.140) | 0.958 |

$^a$*Taken forward into multivariate model.
$^b$Binary variable: Male v female.
cFor categorical analysis the reference category is the first level listed for each variable.
$^d$Includes n = 1 Asian subject. Parameter estimates did not change following the removal of this subject, and so they were included in all final models.
$^e$Recorded as a continuous variable from the SCID (range 2-8).
$^f$Binary variable: Never v current or previous smokers, n = 42 (as one subject did not report smoking status).
$^g$Chlorpromazine (CPZ) equivalent dose, n = 37 (as six subjects did not receive a NL).
$^h$Continuous variable with three levels (none, one or two), n = 42 (as only subject was administered >two NLs).
$^i$Binary variable: one v two, n = 42 (as one subject did not receive a mood stabilizer).

Example 6

Discussion

The data presented herein demonstrate that fasting peripheral proline and COMT Val$^{158/108}$Met genotype predict negative symptom severity across psychiatric diagnoses. Specifically, evidence is presented that in schizophrenia patients with the Val/Val genotype (encoding the high activity COMT enzyme), high proline was associated with lower levels of negative symptoms. As proline rose across the Val/Val patient sample, negative symptoms decreased. Conversely, Met allele carriers displayed the opposite relationship, exhibiting significantly more negative symptoms as proline levels rose. Over the range of fasting proline in the schizophrenia sample (87-502 μM), this represents a significant and clinically relevant difference in negative symptoms between COMT genotype groups.

VPA upregulates circulating proline (Jacquet et al., 2005) and VPA-treated schizophrenia Val/Val patients had significantly less negative symptoms than VPA-treated Met allele patients, likely due to the impact of VPA on proline level. Similarly, LX-6171 also upregulates circulating proline and LX-6171-treated schizophrenia Val/Val patients have significantly less negative symptoms than LX-6171-treated Met allele patients, accordingly, likely due to the impact of LX-6171 on proline level. Interestingly, the relationship between proline, COMT and negative symptoms was consistent across the entire schizophrenia sample, whether subjects received VPA or not, suggesting that the source of circulating proline is less important than the actual level in predicting symptoms. This data has implications for treatment decisions, because proline-modulating medications such as VPA, which is very commonly used to treat bipolar disorder and also schizophrenia, may have differential benefits on negative symptoms and conversely, detrimental effects, based upon the Val$^{158/108}$Met genotype.

In a second sample, the interaction between COMT and proline on negative symptom change was explored in patients with bipolar disorder (using the BPRS negative symptom subscale). Supporting the earlier schizophrenia finding, a significant interaction was observed between proline and COMT: high proline was associated with improvement of negative symptoms in homozygous Val/Val bipolar patients, while high proline in Met allele carriers was associated with less improvement or an increase in negative symptom severity. This finding was not confounded by medication use, the duration of time between assessments, or demographic characteristics of the bipolar sample. Interestingly, the bipolar patients did not have proline levels significantly higher than controls, suggesting that proline may impact negative symptoms and their severity, but not bipolar disorder risk.

The present disclosure is believed to be the first to document that proline and COMT interact to predict negative symptom outcomes in psychiatric and other disorders. The finding of a detrimental effect of high proline in combination with the COMT Met allele on schizophrenia and bipolar disorder negative symptoms, is in part supported by studies of 22q11DS patients, who have an increased risk of psychosis (albeit exhibiting positive symptoms (Raux et al., 2007)) plus a neurophysiological visual sensory deficit (Vorstman et al., 2009), when carrying the Met allele in the presence of high proline.

This finding that high proline is protective in Val/Val patients with schizophrenia and bipolar disorder is novel and significant. Intriguingly, Zarchi et al. (2013), reported the protective effect of a PRODH variant (the Tryptophan (Trp) allele of the Arg$^{185}$Trp polymorphism) on a neurophysiological measure (MMN) in COMT Val 22q11DS patients. Since the Trp allele exhibits decreased POX activity in vitro (Bender et al., 2005), Zarchi et al., discussed either an opposite effect of this allele in vivo, or alternatively that the Arg$^{185}$Trp polymorphism is in linkage disequilibrium with another functional SNP; in each circumstance likely resulting in increased POX activity and low peripheral proline. The data disclosed herein suggests the opposite to that interpretation: that high proline is actually protective in hemizygous 22q11DS patients with the Val genotype, with regards to MMN.

Putative CNS roles of proline have been described both in terms of its potential as a neurotransmitter, suggested by its uptake into and direct synthesis within synaptosomes and its release at the synapse after K+ induced depolarization (Phang et al., 2001; Nickolson, 1982; Yoneda and Roberts, 1982; Nadler, 1987), as well as a neuromodulator of neurotransmitter systems, suggested by the presence of high-affinity proline transporters in glutamatergic neurons (Phang et al., 2001; Renick et al., 1999; Cohen and Nadler, 1997a; Cohen and Nadler, 1997b), and the enhancements of glutamatergic and prefrontal DA transmission in the presence of Prodh deficiency and elevated proline (Paterlini et al., 2005). Although the mechanism by which proline elevation may impact neurotransmission requires further investigation, it is apparent from the Prodh null model (Gogos et al., 1999; Paterlini et al., 2005) and the human hyperprolinemias (Phang et al., 2001) that elevated proline can be detrimental in the CNS. In schizophrenia and bipolar disorder, carrying the Met allele may further accentuate proline's toxicity. In this model, enhanced DA-transmission in the PFC as a result of excess proline is exacerbated by low COMT activity and concomitant higher prefrontal DA availability, ultimately resulting in a frontal hyperdopaminergic state that mimics that of the Prodh null mouse (Paterlini et al., 2005; and as reviewed in Drew et al., 2011).

A hyperdopaminergic model influencing negative symptom severity is somewhat counterintuitive, given that negative symptoms are generally considered to arise from deficient mesocortical DA stimulation. However, COMT is involved in maintaining PFC cognitive stability (Bilder et al., 2004; Turnbridge et al., 2006), and in situations of high cortical DA concentrations and $D_1$ receptor stimulation (likely present in Met/Met and to a lesser degree Val/Met psychiatric patients), enhanced cognitive stability of neuronal network activation has been theorized by Bilder et al. (2004) to result in a cognitive rigidity that may increase the likelihood of negative symptoms. Thus, the Met allele may be less effective in alleviating the increased dopaminergic tone in schizophrenia and bipolar disorder patients with elevated proline, significantly impacting negative symptoms or at least the persistence of negative symptoms and their improvement after treatment.

Conversely, as disclosed herein, proline elevation beneficially influences negative symptom severity in Val/Val patients. In a COMT Val homozygous state, high enzymatic activity in the PFC would likely reduce prefrontal DA, limiting $D_1$ receptor-mediated excitation (Bilder et al., 2004; Turnbridge et al., 2006). Speculatively, proline elevation may increase prefrontal DA signaling, through interference with glutamatergic pathways (Paterlini et al., 2005), reducing vulnerability to a prefrontal hypodopaminergic state in Val/Val patients (Bilder et al., 2004). Taken together these models suggest that negative symptoms are significantly impacted in conditions of both hyper- or hypo-DA activity.

Interestingly, no relationship was found between COMT and proline on positive symptoms. Positive symptoms are considered to arise from hyperactive subcortical mesolimbic projections, and the current finding is consistent with the action of proline in murine cortical but not striatal DA potentiation (Paterlini et al., 2005). Additionally, DA transporters are relatively sparse in the PFC (Lewis et al., 2001), and the removal of DA there may be more impacted by COMT activity and the interaction with proline, as compared to subcortical regions.

Some study limitations exist: in the schizophrenia sample, proline was measured and symptoms assessed cross-sectionally. Thus the findings may be confounded by enrollment differences across genotypes. However, negative symptoms were not significantly different between genotypes, there was no significant main effect of COMT on negative symptoms, and the length of hospitalization prior to symptom assessment had no relationship with negative symptoms, suggesting that the cross-sectional nature of the study did not confound the results. Additionally, while the bipolar study allowed investigation of symptom change, the bipolar sample size was smaller and negative symptoms assessed using only a subscale of the BPRS. Further research would therefore benefit from a longitudinal approach, investigating the interaction between proline and COMT on the change in negative symptoms assessed via the SANS, in a large sample of both schizophrenia and bipolar disorder patients.

Nonetheless, there are currently no medications approved for the treatment of negative symptoms in psychiatric illness, which are associated with poor functional outcomes and quality of life, are highly persistent, and are a great burden for caregivers (Blanchard et al., 2011). The finding of a beneficial effect on negative symptoms of high proline in Val/Val patients suggests that personalization of treatments based upon a patient's COMT genotype, for the purpose of up- or down-regulating proline level, holds promise as a pharmacogenomics approach to intervene and target this unaddressed symptom domain.

Example 7

Figure 6:
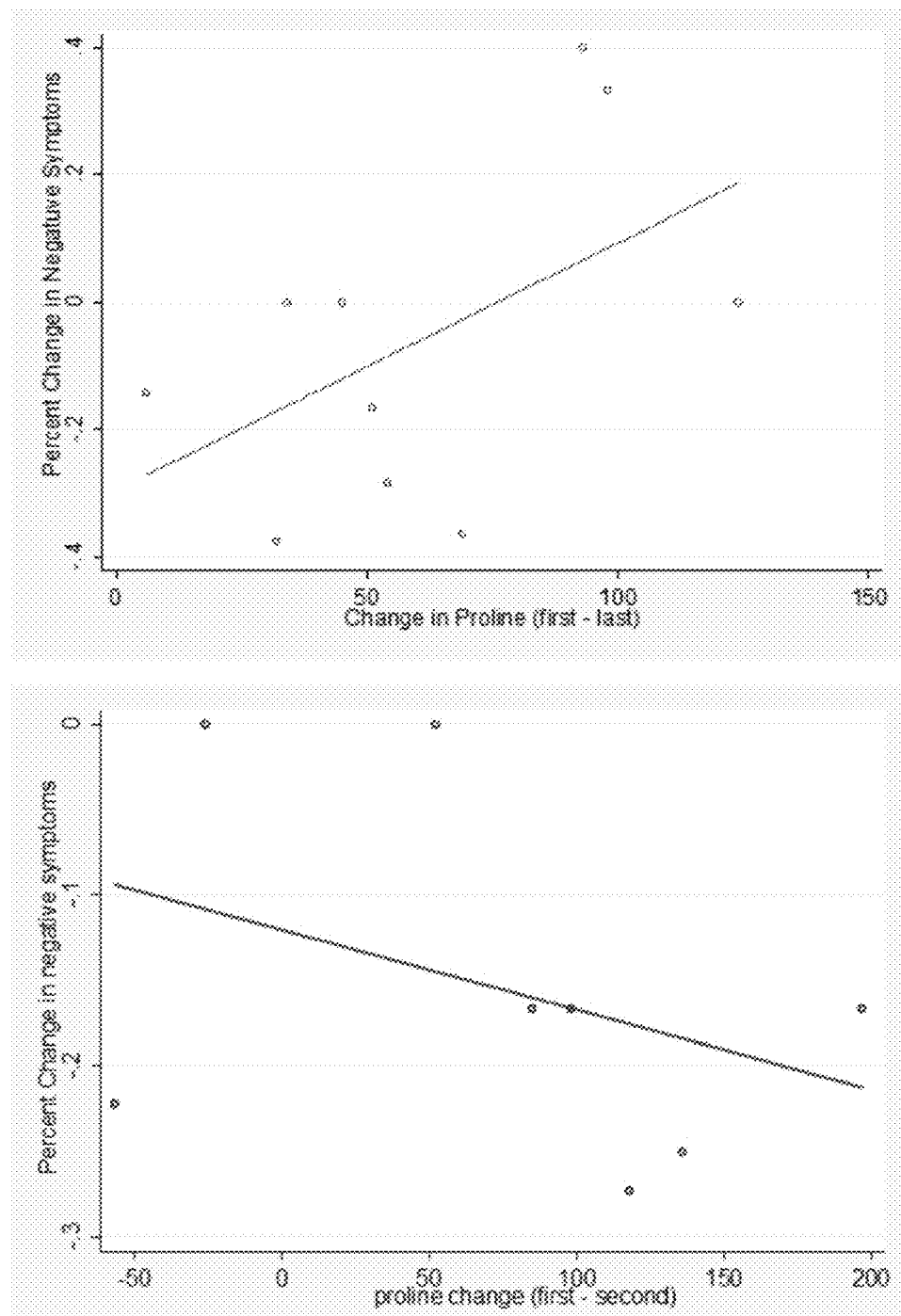
FIG. 6 shows scatterplot graphs of the direct relationship between the change in proline level (pre- to post-medication) and the change in negative symptoms. The top panel shows ten bipolar disorder Met allele carriers (Met/Met or Val/Met) that had a strong positive relationship between the change in proline and the percent change in negative symptoms: as proline increased, a positive change was observed in negative symptoms, suggesting a worsening of symptoms over time, although this result did not reach significance (p=0.19), likely due to the small sample size. The bottom panel shows that Val/Val patients treated with valproate (n=8) had a negative relationship between the change in proline and symptoms (spearman's rho=−0.4), although this result again did not reach significance likely due to the small sample size (p=0.3).

Relationship Between Change in Proline and Negative Symptoms:

Preliminary data also suggests that a change in proline level is directly related to change in negative symptoms. Specifically, twelve bipolar disorder patients had a pre- and post-medication fasting blood draw (with proline measured), plus pre- and post-assessment. Of these, ten were Met allele carriers (Met/Met or Val/Met). Findings suggest that high proline is associated with no improvement or a worsening of symptoms in the presence of high proline. Thus, it was expected that for these subjects, an increase in proline would be related to a worsening of symptoms. Testing this hypothesis, a strong positive relationship was found between the change in proline and the percent change in negative symptoms (see FIG. 6). As proline increased (change in proline was calculated as the post medication proline level—pre-medication proline level, and for all ten subjects proline increased), a positive change was observed in negative symptoms, suggesting a worsening of symptoms over time (spearman's rho=0.45), although this result did not reach significance (p=0.19), likely due to the small sample size.

Only two subjects were Val/Val homozygotes with both pre- and post-medication values. Interestingly, one subject whose proline went down (from 167 µM to 119 µM) had no change in negative symptoms. However, the other subject, whose proline went up (from 206 µM to 332 µM), had a corresponding decrease in negative symptoms (from a score of 8 to 6). Again, this supports the hypothesis that high proline is good for Val/Val homozygotes.

However, valproate increases peripheral proline, so it can be assumed that all Val/Val patients treated with Valproate (n=8) had an increase in peripheral proline between blood draws (regardless of whether the blood draw at visit one was fasting). Therefore, using this subsample, there was seen a negative relationship between the change in proline and symptoms (spearman's rho=−0.4), although this result again did not reach significance likely due to the small sample size (p=0.3).

Example 8

Proline and COMT in Other Disorders:

Pomara et al. (1992) showed elevated cerebrospinal fluid (CSF) proline level in Alzheimers disease (AD). Patients with AD are also known to display negative symptoms. Treatment to modulate proline levels based upon COMT Val$^{158/108}$Met genotype would be beneficial to control those symptoms in AD.

Ethanol increases circulating proline levels, and comorbid alcohol use disorder is the most common comorbidity in schizophrenia (Drake and Mueser, 2002), and is also common in bipolar disorder (Sonne and Brady, 2002). Up- or down-regulation of proline level may exacerbate negative symptoms or conversely improve them, depending on COMT genotype. Alcohol use may be a form of self-medication that could be replaced by other proline modulation methods/treatments. Recently, differential effects were found of alcohol abuse or dependence frequency based on genotype (COMT Val/Val subjects were 2.4 times more likely to report alcohol abuse and/or dependence than Met allele patients, p=0.09, unpublished).

Susceptibility to alcohol abuse and/or dependence may be related to differential effects on mood and/or pleasure-ability based upon proline level and COMT genotype. Treatments to alter proline level based on COMT genotype may be useful for the treatment of alcohol use disorders and potentially for gambling disorders (Guillot et al., 2015).

Example 9

Figure 7:
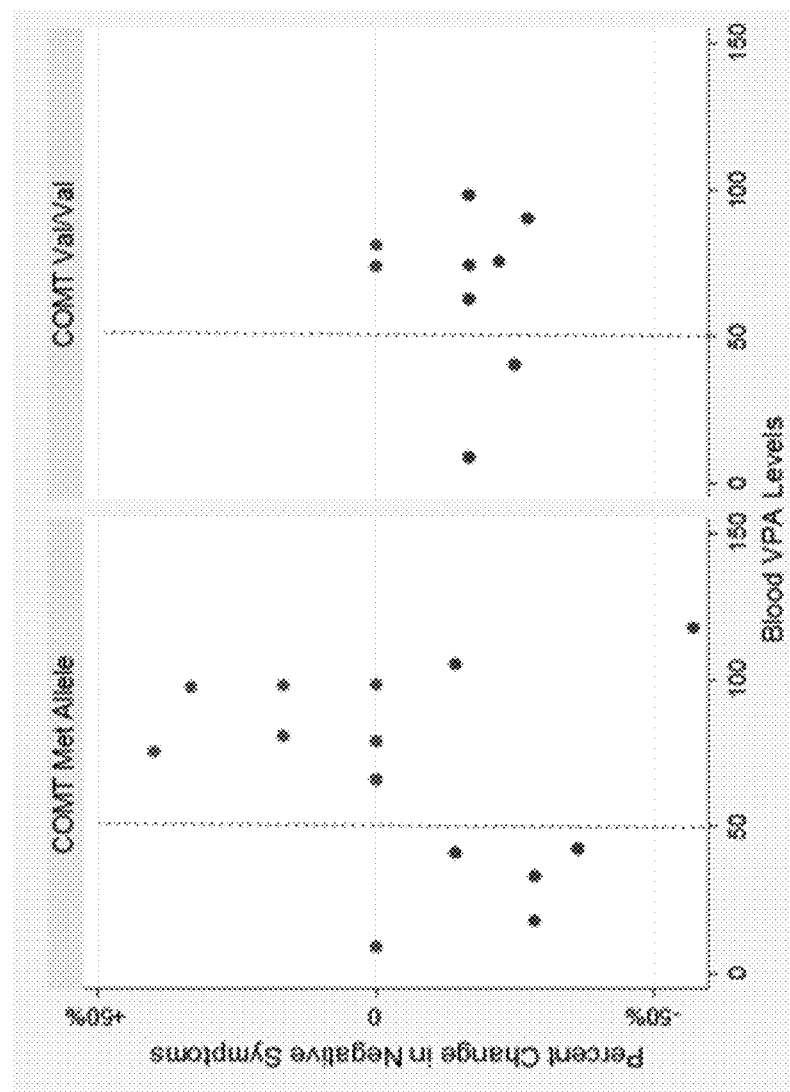
FIG. 7 is a scatterplot graph showing the relationship between blood VPA level (in μg/ml) and percent change in negative symptoms. The left panel shows nine Met allele carriers, only two of whom showed improvement in negative symptoms after treatment onset. The right panel shows seven Val/Val patients, five of whom improved after VPA treatment. The difference between genotypes did not reach significance (p=0.07), likely due to the small sample size.

Relationship Between Negative Symptoms and VPA Level:

The relationship between blood levels of VPA and negative symptoms was investigated by COMT genotype. It was hypothesized that those with the Met allele and high levels of blood VPA would have a lower % negative symptom change, i.e. a positive % change, indicating increased negative symptoms, due to exacerbation by increased proline level. Conversely, Val/Val patients would be expected to have a greater % decrease in negative symptoms as levels of VPA rose. As hypothesized, and as shown in FIG. 7, negative symptoms generally either increased or did not change after treatment onset (red points) for Met allele carriers as VPA levels rose, as compared to Val/Val patients. A blood level of 50 µg/ml of VPA is considered the lower end of the therapeutic range: of the Met allele carriers within this range, only 2 out of 9 showed improvement in negative symptoms, as opposed to 5 out of 7 Val/Val patients (p=0.07).

Example 10

Relationship Between Negative Symptoms and LX-6171 Level:

The relationship between blood levels of LX-6171 and negative symptoms will be investigated by COMT genotype. It is hypothesized that those with the Met allele and high levels of blood LX-6171 may have a lower % negative symptom change, i.e. a positive % change, indicating increased negative symptoms, due to exacerbation by increased proline level. Conversely, Val/Val patients are expected to have a greater % decrease in negative symptoms as levels of VPA rose. According to some embodiments, negative symptoms generally either increase or do not change after treatment onset for Met allele carriers as LX-6171 levels rise, as compared to Val/Val patients. A blood level of 50 µg/ml of LX-6171 is considered the lower end of the therapeutic range: of the Met allele carriers within this range, fewer may show improvement in negative symptoms, compared to Val/Val patients (data not shown).

Example 11

Proline may function as a neuromodulator via stimulation or alteration of neuronal glutamate and/or GABA signaling, which may underlie its effect on negative and other neuropsychiatric symptoms (Clelland et al., 2016; Crabtree et al., 2016). Molecules that can modulate neuronal glutamate signaling including NMDA receptor and/or glutamatergic signaling functions, and have been considered and/or tested in clinical trials in psychiatric disorders include glycine, D-serine, D-cycloserine and bitopterin (Roche RG1678; RO-4917838), sarcosine, SSR103800, Org 25935 and betaine. These are thought to alter glutamate receptor activity or function either directly or indirectly via modulation of the concentration of glycine and/or function of the glycine binding site.

Considering that clinical studies of molecules also thought to influence glutamate signaling have had mixed results, an initial exploratory analysis was performed of fasting plasma glycine and I-serine and an interaction with COMT genotype on negative symptoms of schizophrenia. Plasma glycine concentrations reflect CNS levels (Jiménez-Jiménez et al., 1998; Scholl-Bürgi et al., 2008; Luykx et al., 2013) and CSF D-serine, which is derived from L-serine via serine racemase, is significantly correlated with plasma L-serine (Luykx et al., 2013; Hashimoto et al., 2003).

In a sample of schizophrenia patients (n=95), fasting plasma glycine and I-serine significantly predicted increased negative symptoms in those subjects with the COMT Val/Met or Met/Met genotypes (glycine r=0.48, p=0.0003, n=53; I-serine r=0.32, p=0.02, n=53), but not in Val/Val carriers (glycine r=−0.05, p=0.78, n=42; I-serine r=−0.12, p=0.46, n=42). Following on from this, in regression analysis any significant effect of glycine was tested for after adjusting for the potential confounding effect of proline. A significant effect of glycine on negative symptoms remained (p=0.013) with medium effect size (partial eta$^2$=0.116). As for proline, as glycine increased, so did negative symptoms in Met allele carrier patients.

In addition, analysis of valproate versus non-valproate-treated subjects indicated that valproate significantly upregulates fasting glycine levels (268 uM no valp n=64, 361 uM valp n=31, p=0.0007) and L-serine levels (103 uM no valp n=64, 117 uM valp n=31, p=0.004).

Given these findings of glycine and serine interactions with COMT, the interaction of COMT Val$^{158/108}$Met genotype with glycine on negative symptoms therefore also likely occurs when glycine modulators, including those listed above, are used in psychiatric and neuropsychiatric disorders.

As some of the molecules listed above have been extensively tested in clinical trials, reanalysis of the trial data and/or new trials accounting for COMT genotype when determining efficacy, may lead to evidence of therapeutic efficacy that has been previously undetected.

Trials of the molecules listed above for the treatment of psychiatric, neuropsychiatric, psychotic, mood and personality disorders, and symptoms thereof such as negative symptoms, should therefore be analyzed to account for the interaction of individuals' COMT Val$^{158/108}$Met genotype with glycine and (L- and/or D-) serine levels (and/or with potentially glutamate and/or GABA), with the expectation that COMT Val/Val genotype individuals will respond differently from Met allele carriers, and the failure of clinical trials to achieve efficacy may be due to patients not being chosen based on their COMT genotype (and thus whether they would benefit or be harmed by such treatment).

A further embodiment of the invention is that for patients treated with an SLC modulator, for example, LX-6171, inhibition of glutamic acid decarboxylase (GAD) activity will be decreased via decreased transport of synaptic proline across the pre- and/or post-synaptic membrane and relaxation of proline-mediated GAD inhibition, thus increasing gabaergic signaling (Crabtree et al. 2016). This may lead to increased inhibition of dopamine signaling to the prefrontal cortex and worsened negative symptoms for COMT Val/Val carriers. Conversely, for COMT Met allele carriers, LX-6171 may alleviate negative symptoms.

Proline concentration is also influenced by (one or more of) the genes and/or gene variants, and/or gene RNA and protein products of the following genes: PTPRE, AC089984.3, RAB21, DGCR2, MYL7, TBC1D7, KCNQ5, STK32A, NCAM1, LINC01288, DGCR5, DGCR6, DGCR9, FAM230F, AC007326.4, PRODH, ASPG (Rhee et al. 2013; Imaizumi et al. 2019). One or more of the above may interact for patients treated with one or more SLC modulator, for example LX-6171, inhibition of glutamic acid decarboxylase (GAD) activity will be decreased via decreased transport of synaptic proline across the pre- and/or post-synaptic membrane and relaxation of proline-mediated GAD inhibition, thus increasing gabaergic signaling (Crabtree et al. 2016). This may lead to increased inhibition of dopamine signaling and worsened symptoms (e.g., Negative symptoms) for COMT Val/Val carriers. Conversely, for COMT Met allele carriers, LX-6171 may alleviate negative symptoms.

Proline modulating molecules, e.g., upregulators including valproate, ethanol etc. and/or downregulators, e.g., Vitamin D and/or thiazolidinediones including, e.g., rosiglitazone and/or pioglitazone will interact with (one or more of) the above genes and/or gene variants, and/or gene RNA and protein products, and/or along with SLC genes, and/or gene variants, and/or gene RNA and protein products and/or SLC modulators (e.g., LX-6171), to regulate pre-synaptic and/or synaptic and/or post-synaptic proline, and its concomitant effects on neurotransmission and/or neuromodulation. These effects and/or interactions may cause proline upregulation and/or downregulation to have differential effects on symptoms, dependent upon COMT genotype, and may be associated with increased symptom severity or decreased symptom severity for COMT rs4680 V/V and/or V/M and/or M/M carriers, dependent upon optimal or ideal or beneficial proline level for individuals.

TABLE S1

| Molecules that regulate genes or gene products relevant to proline transport and metabolism. | | |
| --- | --- | --- |
| A1. Molecules that upregulate PRODH: | | |
| gefitinib | harman | Dimethylformamide |
| Pyrilamine | Fluocinolone Acetonide | cephalonium |
| Phenacetin | Methylnitrosourea | Ketoconazole |
| dexibuprofen | Cortisone | Ceftriaxone |
| aristolochic acid I | Mycophenolic Acid | GW 501516 |
| Betamethasone | Rifabutin | Caffeine |
| Methotrexate | Fluphenazine | dihydroquinghaosu |
| piperaquine | Isotretinoin | Naproxen |
| leflunomide | bromodichloromethane | Itraconazole |
| Roxarsone | Dicumarol | fluvastatin |
| Hydrocortisone | diindolylmethane | cyclonite |
| Gliclazide | cerivastatin | Digoxin |
| Doxorubicin | Hexachlorophene | Ifosfamide |
| meloxicam | Melatonin | Malathion |
| Triiodothyronine | Sulfacetamide | Tacrolimus |
| Fluoxetine | Desoxycorticosterone | chloroxylenol |
| genipin | Trenbolone Acetate, (17beta)-isomer | phenacemide |
| erlotinib | Chlorpropamide | arsenic trioxide |
| decitabine | Terfenadine | Paraquat |
| Dantrolene | Cymarine | quelamycin |
| Maprotiline | 2,2-bis(bromomethyl)-1,3-propanediol | Ethamsylate |
| Dexamethasone | AICA ribonucleotide | methyl salicylate |
| Doxazosin | Methylprednisolone | loxoprofen |
| pipenzolate | Epirubicin | monobenzone |
| Valproic Acid | fluticasone | naphthalene |
| Ofloxacin | enrofloxacin | Hemicholinium 3 |
| Acrolein | 4-dichlorobenzene | 4,4'-diaminodiphenylmethane |
| depudecin | 1,3-dichlorobenzene | riddelliine |
| halofuginone | Ethyl Methanesulfonate | Clioquinol |
| p-Aminohippuric Acid | Antipyrine | N-benzyladenine |
| Oxprenolol | Diflunisal | Cyclosporine |
| Bithionol | loracarbef | ebastine |
| Chlorpyrifos | oxiconazole | Sulindac |
| Amoxapine | Oxyquinoline | Thioguanine |
| Pyrethrins | phenethyl isothiocyanate | Ultraviolet Rays |
| gefitinib | harman | Dimethylformamide |
| amprenavir | Cisapride | Bromisovalum |
| oxcarbazepine | Thioctic Acid | blebbistatin |
| trichlorofluoromethane | Methyldopa | Clemastine |

TABLE S1-continued

Molecules that regulate genes or gene products relevant to proline transport and metabolism.

| | | |
|---|---|---|
| Altretamine | Gold | Hydrochloric Acid |
| 9-(2-hydroxy-3-nonyl)adenine | torsemide | Etidronic Acid |
| Bisacodyl | Sulfisoxazole | Clobetasol |
| Erythromycin Ethylsuccinate | 1-Methyl-4-phenyl-1,2,3,6-tetrahydropyridine | Pimozide |
| Betahistine | Iproniazid | sodium arsenite |
| valdecoxib | oxybutynin | Promazine |
| letrozole | 4'-N-benzoylstaurosporine | Trichloroethylene |
| 4-octylphenol | naringin | Hydralazine |
| dibenzazepine | Gallamine Triethiodide | Flavoxate |
| Xylazine | Terazosin | Chlorpromazine |
| acetylleucine | Meclofenoxate | N-Methyl-3,4-methylenedioxyamphetamine |
| Acetazolamide | Calcium | Cephalexin |
| Saquinavir | Etoposide | Sulpiride |
| nabumetone | Luteolin | Metyrapone |
| Glipizide | Trimetazidine | Foscarnet |
| hexachlorobutadiene | adiphenine | lapatinib |
| n-hexanal | Trichlormethiazide | lamotrigine |
| benoxinate | 8-Bromo Cyclic Adenosine Monophosphate | Nitrazepam |
| Moxisylyte | N-(2-cyclohexyloxy-4-nitrophenyl)methanesulfonamide | fipexide |
| Y 27632 | Interleukins | Mianserin |
| Amiloride | Sulfadimethoxine | Amikacin |
| 1,1,1-trichloroethane | Lactic Acid | Rolipram |
| Tobramycin | oxaliplatin | Buspirone |
| Lithium Chloride | carbinoxamine | Cisplatin |
| gabapentin | Choline | Naphazoline |
| Cefuroxime | Flurbiprofen | anisindione |
| oxaprozin | Cholecalciferol | Dexfenfluramine |
| rescinnamine | Pivampicillin | Plicamycin |
| Dicyclomine | laudanosine | Antibodies, Monoclonal |
| trichostatin A | Daunorubicin | vesamicol |
| Ketoprofen | oxolamine | Captopril |
| Atovaquone | Fluorouracil | Furosemide |
| gefitinib | harman | Dimethylformamide |
| 2-amino-1-methyl-6-phenylimidazo(4,5-b)pyridine | Neomycin | carbetapentane |
| Isoflurophate | Prochlorperazine | Alprenolol |
| olanzapine | Oxymetazoline | Acarbose |
| Metaraminol | Levamisole | Trifluridine |
| oltipraz | arsenic acid | candesartan |
| Sulfamethoxazole | vorinostat | Metoclopramide |
| Prazosin | Dizocilpine Maleate | 2-(4-morpholinyl)-8-phenyl-4H-1-benzopyran-4-one |
| Metoprolol | Angiotensin-Converting Enzyme Inhibitors | imatinib |
| Phenelzine | Risperidone | Terbutaline |
| Harmaline | Fluspirilene | chelidonine |
| irinotecan | 6-thioguanosine | Imipramine |
| Vincristine | Atenolol | Haloperidol |
| 2,2'-Dipyridyl | Puromycin Aminonucleoside | Domperidone |
| Fenoprofen | Dobutamine | Norfloxacin |
| 3,3',4',5-tetrachlorosalicylanilide | Hydroxyurea | Diltiazem |
| Dichlorvos | Felodipine | N-Methylaspartate |
| Dyphylline | Zidovudine | sodium selenate |
| Clarithromycin | Nystatin | Azacitidine |
| Trihexyphenidyl | ONO 2235 | Aspirin |
| Busulfan | Nocodazole | Amlodipine |
| Nimodipine | 1-Methyl-3-isobutylxanthine | dasatinib |
| Nortriptyline | Losartan | Verapamil |
| Mebendazole | Loratadine | Baclofen |
| Piroxicam | Ionomycin | Zalcitabine |
| Flunarizine | Guanethidine | Deoxyglucose |
| Levodopa | 8-((4-chlorophenyl)thio)cyclic-3',5'-AMP | triptolide |
| Lorazepam | Sarin | Cyclophosphamide |
| Chlorambucil | Methyl Methanesulfonate | Ascorbic Acid |

| A2. Molecules that downregulate PRODH: | | |
|---|---|---|
| Aminosalicylic Acid | Ursodeoxycholic Acid | Miconazole |
| anastrozole | Clotrimazole | Nafenopin |
| Thioacetamide | Tinidazole | Salicylates |
| Spironolactone | rabeprazole | Hexachlorobenzene |
| Aminosalicylic Acid | Ursodeoxycholic Acid | Miconazole |
| Carbon Tetrachloride | bromfenac | Fenofibrate |

TABLE S1-continued

Molecules that regulate genes or gene products relevant to proline transport and metabolism.

| | | |
|---|---|---|
| Lovastatin | Praziquantel | Bezafibrate |
| pirinixic acid | Methapyrilene | Ethylestrenol |
| Fluconazole | Theobromine | Indomethacin |
| 7,8-Dihydro-7,8-dihydroxybenzo(a)pyrene 9,10-oxide | Isoniazid | Dipyrone |
| celecoxib | Stavudine | geraniol |
| Dimethylnitrosamine | Ketorolac | Simvastatin |
| Aminoglutethimide | pantoprazole | ferulic acid |
| Cyproterone Acetate | Stanozolol | Econazole |
| N-nitrosomorpholine | vinylidene chloride | Chloroform |
| Diethylstilbestrol | Ecdysterone | Mestranol |
| Benzbromarone | naftopidil | beta-Naphthoflavone |
| temafloxacin | atorvastatin | Ticlopidine |
| Aphidicolin | Ticrynafen | Piperonyl Butoxide |
| rosiglitazone | TO-901317 | Estriol |
| Proglumide | Cyproterone | Ibuprofen |
| bromobenzene | artemisinine | Ethinyl Estradiol |
| Chlormezanone | Gemfibrozil | Ajmaline |
| benziodarone | Diethylhexyl Phthalate | Diethylnitrosamine |
| Clonazepam | Clofibrate | beta-cyclodextrin-benzaldehyde |
| Pravastatin | Chloramphenicol | Phenobarbital |
| tranilast | Dehydroepiandrosterone | piclamilast |
| Bupropion | Pentobarbital | Fendiline |
| cetraxate | terbinafine | Danazol |
| Clonidine | Vinblastine | Ethylnitrosourea |
| carvedilol | pioglitazone | abacavir |
| Clofibric Acid | Cefixime | Shiga Toxin |
| Disulfiram | 2-Acetylaminofluorene | Carisoprodol |
| ipriflavone | Spectinomycin | irbesartan |
| perfluorooctanoic acid | Flutamide | methylformamide |
| lornoxicam | Mifepristone | bendazolic acid |
| ciprofibrate | Finasteride | Neostigmine |
| Methylcholanthrene | nimesulide | zileuton |
| Vitamin K 3 | 2-nitrofluorene | Metronidazole |
| amitraz | closantel | 4-nonylphenol |
| Oxytetracycline | penciclovir | Secobarbital |
| Cinnarizine | Ethambutol | Colchicine |
| salicylamide | zopiclone | desloratadine |
| Aminosalicylic Acid | Ursodeoxycholic Acid | Miconazole |
| Methyltestosterone | Tetrachlorodibenzodioxin | Granisetron |
| Safrole | trovafloxacin | 2-dichlorobenzene |
| Doxepin | Gonadotropins | eperisone |
| Carbamazepine | Roflumilast | N-methylolacrylamide |
| Azathioprine | hydrazine | Parathion |
| Ondansetron | Monocrotaline | Pyrogallol |
| Estradiol | balsalazide | Carmustine |
| phenothiazine | sparfloxacin | triadimefon |
| Clofazimine | 1-hydroxycholecalciferol | pristane |
| bortezomib | Mefloquine | Fonofos |
| Clomipramine | Tretinoin | systhane |
| coumarin | amineptin | naphthalenediimide |
| Acetaminophen | Enoxacin | Omeprazole |
| telmisartan | 4-(5-benzo(1,3)dioxol-5-yl-4-pyridin-2-yl-1H-imidazol-2-yl)benzamide | Zimeldine |
| Isoproterenol | Benzalkonium Compounds | Dimercaprol |
| Bicuculline | tenofovir | tenidap |
| hydroxytamoxifen | norethindrone acetate | sulfathiazole |
| Erythromycin | Tolazamide | Galantamine |
| Minoxidil | Sertraline | Trimethadione |
| Dactinomycin | perfluorooctane sulfonic acid | Ethionine |
| Progesterone | Vanadates | venlafaxine |
| Tetracycline | rofecoxib | graveoline |
| tazobactam | lactacystin | Glycerol |
| Amitriptyline | Diclofenac | Griseofulvin |
| Naloxone | Caerulein | benoxaprofen |
| urapidil | Benzethonium | Megestrol |
| Floxuridine | quintozene | shikonin |
| Buthionine Sulfoximine | Prednisone | Lamivudine |
| Propylthiouracil | ranolazine | Protoveratrines |
| oxfendazole | Cefotetan | Aflatoxin B1 |
| Amantadine | Capsaicin | Megestrol Acetate |
| Todralazine | Amiodarone | ibufenac |
| sunitinib | Nifedipine | Norethindrone |
| meropenem | 1,10-phenanthroline | Ethionamide |
| Phenylephrine | compactin | Lasalocid |
| oxalylglycine | esmolol | lansoprazole |
| homatropine | Penicillamine | Lead |
| Nitroprusside | bambuterol | Bleomycin |

TABLE S1-continued

Molecules that regulate genes or gene products relevant to proline transport and metabolism.

| | | |
|---|---|---|
| Aminosalicylic Acid | Ursodeoxycholic Acid | Miconazole |
| Diphenhydramine | etofylline | Benzo(a)pyrene |
| Lomustine | methylparaben | Ouabain |
| etiracetam | idebenone | cilostazol |
| ochratoxin A | isoconazole | guanadrel |
| Nickel | 1-ethyl-2-benzimidazolinone | Rifampin |
| Raloxifene | Thiabendazole | Benzydamine |
| indole-3-carbinol | Hydroxyzine | Astemizole |
| Diazepam | Vitamin B 12 | Chitosan |
| Nisoldipine | Alprazolam | Aconitine |
| 4-hydroxytamoxifen | Oxazepam | Bacitracin |
| Dipyridamole | Citalopram | Atropine |
| efavirenz | Sotalol | Genistein |
| dironyl | Soman | U 0126 |
| deferiprone | pralidoxime | Propranolol |
| Camptothecin | Tolazoline | HI 6 |
| resveratrol | Cytarabine | Allopurinol |
| Quercetin | Clozapine | sildenafil |
| Labetalol | Albendazole | valsartan |
| Famotidine | Ciprofloxacin | Gentamicins |
| Tacrine | Amphetamine | Nadolol |
| Chlorpheniramine | Mitomycin | MRK 003 |
| Netilmicin | Paroxetine | Pregnenolone Carbonitrile |
| 6-bromoindirubin-3'-oxime | doxofylline | Azauridine |
| Paclitaxel | benzyloxycarbonylleucyl-leucyl-leucine aldehyde | NG-Nitroarginine Methyl Ester |
| N,N'-diphenyl-4-phenylenediamine | Calcitriol | Enalapril |
| SB 203580 | bisphenol A | Inosine Monophosphate |
| Perhexiline | cyanoginosin LR | gemcitabine |
| Kainic Acid | Pentylenetetrazole | 6-Mercaptopurine |
| Promethazine | | |

B1. Molecules that upregulate COMT:

| | | |
|---|---|---|
| Sulbactam | 6-methoxy-2-naphthylacetic acid | Cefuroxime |
| Diazoxide | Stanozolol | Lead |
| 2,4-Dinitrophenol | tenidap | Norfloxacin |
| Cephalexin | rosiglitazone | pirinixic acid |
| Vanadates | Levobunolol | lorglumide |
| Metoprolol | Trimetazidine | oltipraz |
| Omeprazole | Methylcholanthrene | Quinpirole |
| Sulbactam | 6-methoxy-2-naphthylacetic acid | Cefuroxime |
| chloroxylenol | Pyridoxine | tropisetron |
| Noscapine | Inosine Monophosphate | Nitroprusside |
| beta-Naphthoflavone | Clomipramine | Netilmicin |
| Fluphenazine | Itraconazole | bromodichloromethane |
| 4-dichlorobenzene | Benserazide | nabumetone |
| apramycin | Altretamine | butenafine |
| tomatidine | Econazole | Pemoline |
| NG-Nitroarginine Methyl Ester | Epirubicin | tazobactam |
| Diethylnitrosamine | etofenamate | Mitoxantrone |
| graveoline | betulinic acid | arsenic trioxide |
| Cortisone | Sotalol | Promethazine |
| temsirolimus | Dimethylformamide | Progesterone |
| sulfathiazole | beta-cyclodextrin-benzaldehyde | Galantamine |
| oxaliplatin | Trichloroethylene | vinorelbine |
| pentachlorobenzene | riddelliine | Ethacrynic Acid |
| Neomycin | Ethionine | valsartan |
| gefitinib | Terazosin | Mifepristone |
| Acarbose | bestatin | 1-Methyl-4-phenyl-1,2,3,6-tetrahydropyridine |
| Iproniazid | 3,3',4',5-tetrachlorosalicylanilide | Warfarin |
| Benzethonium | Chloroquine | Citalopram |
| Vitamin K 2 | gabapentin | Sulindac |
| Roxithromycin | oxfendazole | letrozole |
| Chitosan | N-Methyl-3,4-methylenedioxyamphetamine | Azithromycin |
| Clindamycin | Cytochalasin B | Sulfinpyrazone |
| pristane | Simazine | Cholecalciferol |
| Doxapram | erlotinib | Tetracycline |
| marimastat | Atropine | fenbufen |
| Tetrachlorodibenzodioxin | Flunarizine | Niacin |
| PK 11195 | Polychlorinated Biphenyls | Clonidine |
| homosalate | spiradoline | Phentolamine |
| Ethamsylate | Scopolamine Hydrobromide | Chlorambucil |
| 1,1,1-trichloroethane | asperflavin | zomepirac |
| Selenomethionine | N-(2-aminophenyl)-4-(N-(pyridin-3-ylmethoxycarbonyl)aminomethyl)benzamide | Benzo(a)pyrene |

TABLE S1-continued

Molecules that regulate genes or gene products relevant to proline transport and metabolism.

| | | |
|---|---|---|
| clebopride | Concanavalin A | Lovastatin |
| mebeverine | Doxorubicin | Lorazepam |
| Sulbactam | 6-methoxy-2-naphthylacetic acid | Cefuroxime |
| Simvastatin | 6-bromoindirubin-3'-oxime | sorafenib |
| rofecoxib | U 0126 | celecoxib |
| SU 5402 | sildenafil | imatinib |
| anastrozole | 2-(4-morpholinyl)-8-phenyl-4H-1-benzopyran-4-one | adiphenine |
| methantheline | clemizole | olanzapine |
| fluvastatin | chelidonine | lansoprazole |
| ebastine | cyanoginosin LR | clopidogrel |
| bromfenac | alfuzosin | carvedilol |
| dihydroquinghaosu | idebenone | vitexin |
| fragment C, human serum albumin | closantel | cobaltous chloride |
| bromopride | ceforanide | ascorbate-2-phosphate |
| ciclopirox | 2,4-diaminotoluene | 9-(2-hydroxy-3-nonyl)adenine |
| cineole | tolfenamic acid | 6-thioguanosine |
| hexylcaine | pimethixene | 5-fluorouridine |
| triptolide | Cardiotoxins | Dichlororibofuranosylbenzimidazole |
| Antibodies, Monoclonal | Caerulein | Ionomycin |
| Streptomycin | Bleomycin | Chorionic Gonadotropin |
| Beclomethasone | Cyproterone Acetate | Chlormadinone Acetate |
| Finasteride | Colistin | Alpha-Amanitin |
| Rifampin | Amoxapine | Mianserin |
| Clozapine | Dactinomycin | Enoxacin |
| Ciprofloxacin | 1-Methyl-3-isobutylxanthine | Acyclovir |
| 8-Bromo Cyclic Adenosine Monophosphate | Allopurinol | Melatonin |
| Cytochalasin D | gamma-Tocopherol | alpha-Tocopherol |
| Vitamin E | Acenocoumarol | Astemizole |
| Diltiazem | Nitrazepam | Diazepam |
| Apazone | Cotinine | Kainic Acid |
| Fluorouracil | Risperidone | Zidovudine |
| Stavudine | Cytarabine | Chlorpheniramine |
| Nevirapine | Nicardipine | Trazodone |
| Amiodarone | Fluconazole | Clotrimazole |
| Nicotine | Pilocarpine | Lobeline |
| Reserpine | Vinblastine | Quinidine |
| Papaverine | Apomorphine | Dacarbazine |
| Acetazolamide | Thiethylperazine | Bithionol |
| Isoflurophate | Auranofin | Ethylnitrosourea |
| Dimethylnitrosamine | Erythromycin | Haloperidol |
| Sulbactam | 6-methoxy-2-naphthylacetic acid | Cefuroxime |
| Ifosfamide | Cyclophosphamide | Chloroform |
| 7,8-Dihydro-7,8-dihydroxybenzo(a)pyrene 9,10-oxide | Naproxen | Demeclocycline |
| Loratadine | Amitriptyline | Losartan |
| Ketamine | Isoniazid | Ketoprofen |
| Ibuprofen | Fenoprofen | Diflunisal |
| Mefenamic Acid | Diethylcarbamazine | Aminocaproic Acids |
| Gemfibrozil | Clofibric Acid | Azoxymethane |
| Azauridine | Methapyrilene | Dobutamine |
| Amrinone | Guanethidine | Amoxicillin |
| Cefotaxime | Dibucaine | Sulpiride |
| Busulfan | Isoxsuprine | Bismuth |
| Calcium | | |

| B2. Molecules that downregulate COMT: | | |
|---|---|---|
| Tin Fluorides | Tobramycin | Phenacetin |
| dexibuprofen | bendazolic acid | 3-hydroxyacetanilide |
| Cyclosporine | flubendazole | Acrolein |
| cephalonium | Fluoxetine | valdecoxib |
| Hesperidin | nimetazepam | Niacinamide |
| Diethylstilbestrol | ajmalicine | Trichlorfon |
| 2-nitrofluorene | clinafloxacin | Ethinyl Estradiol |
| methiazole | Gentamicins | Cyproheptadine |
| Chlorpropamide | lornoxicam | Bezafibrate |
| Methoxsalen | 4-hydroxyestradiol-17 beta | Suprofen |
| Piperonyl Butoxide | norethindrone acetate | Clomiphene |
| Nizatidine | 4-acetylaminofluorene | DDT |
| Meptazinol | Trioxsalen | Carmustine |
| acidocin CH5, *Lactobacillus acidophilus* | Cymarine | Acetylmuramyl-Alanyl-Isoglutamine |
| Tiletamine | atorvastatin | salicylamide |
| cilostazol | vinylidene chloride | ferulic acid |
| Cyclizine | ifenprodil | hydroquinone |
| Dyphylline | Procarbazine | Ampicillin |

TABLE S1-continued

Molecules that regulate genes or gene products relevant to proline transport and metabolism.

| | | |
|---|---|---|
| Estriol | Propylthiouracil | Fursultiamin |
| Cloxacillin | fipronil | Theophylline |
| apicidin | Coumaphos | ONO 2235 |
| meloxicam | lomefloxacin | phosphonoacetamide |
| oxiconazole | fulvestrant | Podophyllotoxin |
| Tin Fluorides | Tobramycin | Phenacetin |
| Acetaminophen | cinchonine | Aspirin |
| Atractyloside | penciclovir | Cinnarizine |
| Terfenadine | Ketorolac | Raloxifene |
| trichostatin A | Tretinoin | Natamycin |
| Mestranol | Estradiol | Nystatin |
| 2-chloropyrazine | Azathioprine | Flufenamic Acid |
| picrotoxinin | Aminosalicylic Acid | asiaticoside |
| daidzein | Tiapamil Hydrochloride | Valproic Acid |
| Diquat | Carboplatin | Tacrolimus |
| ranolazine | piperacetazine | Curcumin |
| pramoxine | Idoxuridine | Ethylestrenol |
| Todralazine | boldine | sparfloxacin |
| Cetylpyridinium | Nafenopin | abamectin |
| Canrenoate Potassium | Dantrolene | Cisapride |
| bisphenol A | Dihydroergocristine | Calcitriol |
| decitabine | Diethylhexyl Phthalate | Budesonide |
| 2-dichlorobenzene | Okadaic Acid | eperisone |
| Carbimazole | Genistein | Hymecromone |
| biphenylylacetic acid | Ampyrone | canadine |
| U 54494A | syrosingopine | tetrahydrotriamcinolone |
| blebbistatin | phenacemide | Hydralazine |
| Propranolol | Oxazepam | terbinafine |
| Pyrantel | Leucovorin | Mustard Gas |
| nimesulide | Acetohexamide | Propanil |
| pioglitazone | benfluorex | Pregnenolone |
| 1,2-dithiol-3-thione | Dinoprostone | Phenobarbital |
| Thioctic Acid | Propantheline | Protriptyline |
| Clofibrate | Cytokines | bis(tri-n-butyltin)oxide |
| Sulfaphenazole | Piribedil | hydrazine |
| Aztreonam | tosufloxacin | Oxymetazoline |
| 4-biphenylamine | Lomustine | 1-hydroxycholecalciferol |
| ubiquinol | Doxylamine | Levamisole |
| scriptaid | phenylhydrazine | hydroxyhydroquinone |
| Betamethasone | Pheniramine | Tolnaftate |
| 4-(5-benzo(1,3)dioxol-5-yl-4-pyridin-2-yl-1H-imidazol-2-yl)benzamide | direct black 3 | Dipyridamole |
| repaglinide | naphthalenediimide | rimexolone |
| Thiostrepton | Sulfamethazine | Timolol |
| Tacrine | acetovanillone | Trichloroepoxypropane |
| Tin Fluorides | Tobramycin | Phenacetin |
| eticlopride | 8-aminohexylamino cAMP | Streptozocin |
| HC toxin | vorinostat | genipin |
| dibenzazepine | 4-methyl-N-(3-(4-methylimidazol-1-yl)-5-(trifluoromethyl)phenyl)-3-((4-pyridin-3-ylpyrimidin-2-yl)amino)benzamide | LBH589 |
| lapatinib | dasatinib | bevacizumab |
| CPG-oligonucleotide | bortezomib | 17-(allylamino)-17-demethoxygeldanamycin |
| Y 27632 | 1-ethyl-2-benzimidazolinone | azacyclonol |
| tenofovir | benzyloxycarbonylvalyl-alanyl-aspartyl fluoromethyl ketone | bexarotene |
| daboiatoxin | piclamilast | cerivastatin |
| telmisartan | irbesartan | colforsin |
| benzyloxycarbonylleucyl-leucyl-leucine aldehyde | zardaverine | zileuton |
| 2,3-dioxo-6-nitro-7-sulfamoylbenzo(f)quinoxaline | dorzolamide | resveratrol |
| 1,2-dilinolenoyl-3-(4-aminobutyryl)propane-1,2,3-triol | gemcitabine | aceclofenac |
| levocabastine | buparvaquone | leflunomide |
| vanoxerine | 1,3-dichlorobenzene | oxalylglycine |
| monorden | ozagrel | artemether |
| lysophosphatidic acid | bromobenzene | beta-glycerophosphoric acid |
| artemisinine | doxofylline | sulmazole |
| dexamisole | ochratoxin A | perfluorooctanoic acid |
| 2-methoxyestradiol | 4-O-methyl-12-O-tetradecanoylphorbol 13-acetate | ciprofibrate |
| sodium arsenite | 4-hydroxytamoxifen | 8-((4-chlorophenyl)thio)cyclic-3',5'-AMP |
| lycorine | dipivefrin | amitraz |
| tranilast | compactin | benoxaprofen |

TABLE S1-continued

Molecules that regulate genes or gene products relevant to proline transport and metabolism.

| | | |
|---|---|---|
| acadesine | halofuginone | diphenylpyraline |
| wortmannin | 4,4'-diaminodiphenylmethane | alginic acid |
| naringin | isoascorbic acid | benzothiazide |
| geldanamycin | Shiga Toxin | Cholera Toxin |
| BCG Vaccine | Ribavirin | Phytohemagglutinins |
| Antigen-Antibody Complex | Enalapril | Captopril |
| Phenylalanine | Palmitic Acid | Alprostadil |
| Tin Fluorides | Tobramycin | Phenacetin |
| Deoxyglucose | Clobetasol | Dexamethasone |
| Danazol | Vecuronium Bromide | Dihydrotestosterone |
| Androsterone | Viomycin | Bacitracin |
| Clofazimine | Carbamazepine | Quinacrine |
| Oxolinic Acid | Clioquinol | Oxyquinoline |
| Amodiaquine | Thioguanine | Bucladesine |
| Vidarabine | Methotrexate | Saquinavir |
| Indomethacin | Dicumarol | Rotenone |
| Quercetin | Luteolin | Aflatoxin B1 |
| Nocodazole | Atrazine | Rolipram |
| Clemastine | Triprolidine | 2,2'-Dipyridyl |
| Nifedipine | Trihexyphenidyl | Aminoglutethimide |
| Cycloheximide | Paroxetine | Domperidone |
| Ketoconazole | Betazole | Miconazole |
| Pentylenetetrazole | Caffeine | Dextromethorphan |
| Vincristine | Ajmaline | Harmaline |
| Dihydroergotamine | Pergolide | Colchicine |
| Camptothecin | Fusaric Acid | Hydroxyurea |
| Allantoin | Dimethyl Sulfoxide | Hydrochlorothiazide |
| 6-Mercaptopurine | Triflupromazine | Thioridazine |
| Promazine | Perphenazine | Mesoridazine |
| Chlorpromazine | Acetylcysteine | Mitomycin |
| Diazinon | Dichlorvos | Pregnenolone Carbonitrile |
| Clarithromycin | Brefeldin A | Melphalan |
| Carbon Tetrachloride | Pravastatin | Vitamin K 3 |
| Plicamycin | Daunorubicin | Aclarubicin |
| Meclizine | Thapsigargin | Paclitaxel |
| Amantadine | Methyl Methanesulfonate | Phenelzine |
| Doxepin | Diclofenac | Dicyclomine |
| Puromycin | Ascorbic Acid | Dextropropoxyphene |
| Disulfiram | Mycophenolic Acid | Butyric Acid |
| Vigabatrin | Baclofen | Azacitidine |
| Ipratropium | Granisetron | Edrophonium |
| Gallamine Triethiodide | Benzalkonium Compounds | Aminophylline |
| Fluvoxamine | Verapamil | Mephentermine |
| Methamphetamine | Amphetamine | Methyldopa |
| Levodopa | Bromhexine | Furosemide |
| Ceftazidime | Cephaloridine | Cephalothin |
| Cefazolin | 2-Acetylaminofluorene | Nadolol |
| Tin Fluorides | Tobramycin | Phenacetin |
| Metaproterenol | Midodrine | Isoproterenol |
| Epinephrine | Clenbuterol | Choline |
| Cisplatin | Lithium Carbonate | |

C1. Molecules that upregulate PYCR1:

| | | |
|---|---|---|
| Ethionamide | halofuginone | coumarin |
| Asbestos | Hyaluronic Acid | methylformamide |
| Teriparatide | Phenylephrine | Carbon Tetrachloride |
| Mannitol | Ethambutol | 1,3-dichloro-2-propanol |
| artemisinine | clebopride | 4-(4-fluorophenyl)-2-(4-hydroxyphenyl)-5-(4-pyridyl)imidazole |
| Methimazole | Hypericum extract LI 160 | Carbimazole |
| Riluzole | bromobenzene | 6-bromoindirubin-3'-oxime |
| Methapyrilene | Chlormezanone | U 0126 |
| Trimethadione | Chloroform | Tunicamycin |
| Nafcillin | Cloxacillin | hydrazine |
| crotamiton | Ticlopidine | Procyclidine |
| ceforanide | estradiol 3-benzoate | 4-methyl-N-(3-(4-methylimidazol-1-yl)-5-(trifluoromethyl)phenyl)-3-((4-pyridin-3-ylpyrimidin-2-yl)amino)benzamide |
| Okadaic Acid | ascorbate-2-phosphate | GW 3965 |
| Azoxymethane | Estriol | Propylthiouracil |
| Trenbolone Acetate, (17beta)-isomer | 4-dichlorobenzene | Estradiol |
| Cymarine | 3-nitropropionic acid | Molindone |
| Tryptophan | Trichlormethiazide | Propoxycaine |
| graveoline | Glycocholic Acid | Mestranol |

TABLE S1-continued

Molecules that regulate genes or gene products relevant to proline transport and metabolism.

| | | |
|---|---|---|
| 4,5-dianilinophthalimide | N-(2-aminophenyl)-4-(N-(pyridin-3-ylmethoxycarbonyl)aminomethyl)benzamide | Thioctic Acid |
| Thiabendazole | Insulin | Clodronic Acid |
| 2-dichlorobenzene | Disulfiram | Cephapirin |
| Doxycycline | Carbamazepine | anastrozole |
| Acetaminophen | Cephalexin | Cyproterone Acetate |
| shogaol | Stavudine | 2,4-Dinitrophenol |
| Dihydrotestosterone | Carcinogens | Bromocriptine |
| iodoform | Thapsigargin | Danazol |
| Dimethylformamide | arcaine | vanoxerine |
| Ethionamide | halofuginone | coumarin |
| fosfosal | Thioacetamide | Canavanine |
| Piromidic Acid | pantoprazole | KCB-1 protein, recombinant |
| epidermal growth factor (1-45) | oltipraz | Omeprazole |
| diisopropyl methylphosphonate | Hydrogen Peroxide | Clonazepam |
| acetylleucine | Reserpine | Dapsone |
| Fluconazole | Ethinyl Estradiol | Sulfadimethoxine |
| Nalidixic Acid | Estrogens | Azacitidine |
| etofenamate | Erythromycin | Sulindac |
| epoxomicin | sulconazole | Methylene Chloride |
| Pipemidic Acid | Cefazolin | Bleomycin |
| Trimipramine | Ultraviolet Rays | tolfenamic acid |
| Spiperone | Todralazine | Phenobarbital |
| Allopurinol | Isoniazid | 1,2-dithiol-3-thione |
| oxaliplatin | Equilin | Orphenadrine |
| Amphotericin B | N-(2-cyclohexyloxy-4-nitrophenyl)methanesulfonamide | zaprinast |
| apicidin | BCG Vaccine | closantel |
| Roxithromycin | kavain | dironyl |
| tracazolate | Methyltestosterone | Ionomycin |
| Amanitins | Lasalocid | withaferin A |
| Pentolinium Tartrate | pristane | Hexachlorobenzene |
| oxolamine | Hydroflumethiazide | Hydroxyzine |
| Stanozolol | sodium nitrate | Triflupromazine |
| Oxyquinoline | Roflumilast | Thiethylperazine |
| Gossypol | phenothiazine | Fursultiamin |
| Muromonab-CD3 | Ibuprofen | Trimethoprim |
| cerivastatin | N-benzyladenine | Tetrachlorodibenzodioxin |
| X-Rays | Diazepam | Phenazopyridine |
| Cyproheptadine | Selegiline | salmeterol |
| bromperidol | Clioquinol | Pizotyline |
| Ketorolac | acetorphan | Cefaclor |
| verteporfin | Phenelzine | Khellin |
| (melle-4)cyclosporin | Nifedipine | Isoproterenol |
| Diethylstilbestrol | Vitamin E | Diquat |
| Prenylamine | Deoxyglucose | gibberellic acid |
| Cinnarizine | Azathioprine | Acetazolamide |
| Carmustine | butoconazole | Diclofenac |
| Domperidone | abamectin | Benzocaine |
| famprofazone | Particulate Matter | Progesterone |
| Ethionamide | halofuginone | coumarin |
| Gentamicins | Desoxycorticosterone | Monensin |
| Remoxipride | sodium arsenite | Benzethonium |
| Genistein | hydrastinine | Phenylalanine |
| Felodipine | Glycerol | Captopril |
| fulvestrant | Acetohexamide | nifuroxazide |
| hydroxyachillin | Tobramycin | bisphenol A |
| Astemizole | rituximab | Folic Acid |
| methylbenzethonium | enterotoxin B, staphylococcal | Hydrogel |
| Cyclosporine | Caerulein | Mesalamine |
| Naproxen | bicalutamide | fragment C, human serum albumin |
| tibolone | Antibodies, Monoclonal | LBH589 |
| phorbolol myristate acetate | Soman | Niclosamide |
| Tiapamil Hydrochloride | Clotrimazole | SC 514 |
| Mitomycin | Dactinomycin | Quercetin |
| Flecainide | Ketoconazole | N-nitrosomorpholine |
| sunitinib | Aminoglutethimide | irinotecan |
| Apomorphine | thymoglobulin | HC toxin |
| methyleugenol | Anti-Retroviral Agents | Dipyridamole |
| Berberine | mometasone furoate | Promethazine |
| ethotoin | 4-hydroxytamoxifen | HI 6 |
| Diazinon | Flutamide | 8-Bromo Cyclic Adenosine Monophosphate |
| beta-Naphthoflavone | Cardiotoxins | Piracetam |
| Dantrolene | Lithium | arsenic trioxide |
| Itraconazole | Ozone | scriptaid |
| N-Methylaspartate | methylatropine | Econazole |

TABLE S1-continued

Molecules that regulate genes or gene products relevant to proline transport and metabolism.

| | | |
|---|---|---|
| nimesulide | Diphenhydramine | acadesine |
| mono-(2-ethylhexyl)phthalate | vorinostat | Selenomethionine |
| Mebendazole | Choline | Iproniazid |
| Indomethacin | Dichlororibofuranosylbenzimidazole | Furosemide |
| Altretamine | bortezomib | Enoxacin |
| Citalopram | Sotalol | atorvastatin |
| Pregnenolone Carbonitrile | Aspirin | valdecoxib |
| olanzapine | meloxicam | Clozapine |
| Risperidone | Perphenazine | Chlorpromazine |
| Amitriptyline | | |

C2. Molecules that down regulate PYCR1:

| | | |
|---|---|---|
| 1-(5-Isoquinolinesulfonyl)-2-Methylpiperazine | Aphidicolin | Methylnitrosourea |
| monastrol | Aclarubicin | geldanamycin |
| mafosfamide | blebbistatin | Ornidazole |
| N-methylpyrrolidone | 4-(N-methyl-N-nitrosamino)-1-(3-pyridyl)-1-butanone | Dimethyl Sulfoxide |
| Disopyramide | Metaproterenol | gefitinib |
| sesamin | Immunoglobulin M | Lithium Carbonate |
| Mycophenolic Acid | Clofibric Acid | benziodarone |
| Idarubicin | enzastaurin | 2-(1H-indazol-4-yl)-6-(4-methanesulfonylpiperazin-1-ylmethyl)-4-morpholin-4-ylthieno(3,2-d)pyrimidine |
| edelfosine | Doxorubicin | Puromycin Aminonucleoside |
| bendazolic acid | Daunorubicin | Mycotoxins |
| Camptothecin | imatinib | MRK 003 |
| nickel sulfate | Synephrine | Etoposide |
| naringenin | Clofibrate | Coumaphos |
| Cycloheximide | Sirolimus | ethaverine |
| Gemfibrozil | trichostatin A | Idoxuridine |
| imiquimod | Cisplatin | Vincristine |
| Protriptyline | CEP 14083 | Paroxetine |
| decitabine | Benzbromarone | Potassium Dichromate |
| hydrastine | tetrahydrozoline | 17-(allylamino)-17-demethoxygeldanamycin |
| Diethylhexyl Phthalate | Fonofos | Dexamethasone |
| Minocycline | Streptozocin | pronethalol |
| Dihydroergotamine | bamipine | perfluorooctane sulfonic acid |
| Dilazep | Ethyl Methanesulfonate | eticlopride |
| levocabastine | Santonin | CD 437 |
| Ceftriaxone | Sulfapyridine | Gonadotropins |
| cidofovir | 4-acetylaminofluorene | wortmannin |
| troglitazone | Hemin | 1-Methyl-3-isobutylxanthine |
| zardaverine | Simvastatin | Vinblastine |
| Prazosin | sulforafan | Fenofibrate |
| Mafenide | 2-(4-morpholinyl)-8-phenyl-4H-1-benzopyran-4-one | Curcumin |
| clinafloxacin | Benzo(a)pyrene | buparvaquone |
| cyanopindolol | Caffeine | Zimeldine |
| Fenoterol | everolimus | 2-Acetylaminofluorene |
| 1-(5-Isoquinolinesulfonyl)-2-Methylpiperazine | Aphidicolin | Methylnitrosourea |
| minaprine | pioglitazone | 1-ethyl-2-benzimidazolinone |
| Dichlorphenamide | methiazole | TO-901317 |
| 8-((4-chlorophenyl)thio)cyclic-3',5'-AMP | Chitosan | 4-(5-benzo(1,3)dioxol-5-yl-4-pyridin-2-yl-1H-imidazol-2-yl)benzamide |
| Doxepin | alpha-Amino-3-hydroxy-5-methyl-4-isoxazolepropionic Acid | Tretinoin |
| Bezafibrate | colforsin | Phalloidine |
| Diltiazem | Deferoxamine | flubendazole |
| biphenylylacetic acid | Oxolinic Acid | SB 203580 |
| 3,3',5-triiodothyroacetic acid | carcinine | Luteinizing Hormone |
| Plicamycin | Phenylbutazone | lapatinib |
| 15-deoxy-delta(12,14)-prostaglandin J2 | Enalapril | Allantoin |
| diloxanide furoate | Etidronic Acid | Metribolone |
| chelidonine | marimastat | Chorionic Gonadotropin |
| fenspiride | Valproic Acid | Clonidine |
| dibenzazepine | gabazine | Corticosterone |
| vinylidene chloride | Thioguanine | Ethionine |
| Isoetharine | Vidarabine | LPS 9 |
| letrozole | salsolidine | Betazole |
| Oxymetazoline | Ethylnitrosourea | Dextran Sulfate |
| linalool | NG-Nitroarginine Methyl Ester | Pyrantel |
| Zinc Oxide | Fusaric Acid | Tetradecanoylphorbol Acetate |

TABLE S1-continued

Molecules that regulate genes or gene products relevant to proline transport and metabolism.

| | | |
|---|---|---|
| Ranitidine | Dexfenfluramine | canadine |
| mycophenolate mofetil | rosiglitazone | AICA ribonucleotide |
| Metolazone | Tolazoline | Alprostadil |
| Oxazepam | Colchicine | Mefenamic Acid |
| dexchlorpheniramine | alginic acid | Sulpiride |
| Dinoprost | Acetylcysteine | systhane |
| Finasteride | vinorelbine | Fluphenazine |
| gemcitabine | erlotinib | Raloxifene |
| 1,2-dilinolenoyl-3-(4-aminobutyryl)propane-1,2,3-triol | bis(tri-n-butyltin)oxide | Pergolide |
| Ascorbic Acid | Monocrotaline | Papaverine |
| Imipramine | Trifluoperazine | Phenol |
| Metformin | benzyloxycarbonylleucyl-leucyl-leucine aldehyde | triadimefon |
| Rifampin | leflunomide | nimetazepam |
| 1-(5-Isoquinolinesulfonyl)-2-Methylpiperazine | Aphidicolin | Methylnitrosourea |
| Methyl Methanesulfonate | Dimethylnitrosamine | Ajmaline |
| Tetracycline | Cefuroxime | monorden |
| cobaltous chloride | Paraquat | Chlorambucil |
| naphthalan | Chlorpheniramine | Emetine |
| terbinafine | lansoprazole | Methotrexate |
| Nicotine | Cyclophosphamide | Diethylnitrosamine |
| Prochlorperazine | Haloperidol | Quinidine |
| Digoxin | Losartan | fluvastatin |
| Puromycin | Cytarabine | Paclitaxel |
| pirinixic acid | Tranylcypromine | dasatinib |
| resveratrol | carvedilol | Ribavirin |
| Calcitriol | Ofloxacin | Rolipram |
| Amiodarone | Thioridazine | Lovastatin |
| Fluoxetine | | |

D1. Molecules that upregulate ALDH18A1:

| | | |
|---|---|---|
| halofuginone | bestatin | Tunicamycin |
| Ecdysterone | beta-cyclodextrin-benzaldehyde | Methapyrilene |
| Vanadates | Captopril | Dimethylnitrosamine |
| ONO 2235 | Azathioprine | Thapsigargin |
| Loratadine | acodazole | Biperiden |
| Stanozolol | 3-nitropropionic acid | Clodronic Acid |
| Naloxone | enterotoxin B, staphylococcal | rifapentine |
| 1,3-dichloro-2-propanol | sildenafil | Glycocholic Acid |
| Hypericum extract LI 160 | irbesartan | sulconazole |
| apicidin | Paroxetine | Lomustine |
| balsalazide | Cyclosporine | U 0126 |
| cetraxate | amineptin | Ethambutol |
| ascorbate-2-phosphate | Levodopa | Capsaicin |
| Calcium | 4,4'-diaminodiphenylmethane | Etodolac |
| Cardiotoxins | Carmustine | Allopurinol |
| Acetaminophen | Indinavir | SB 203580 |
| Piracetam | valdecoxib | Niridazole |
| Altretamine | lornoxicam | Ethylnitrosourea |
| Ethionamide | Diflunisal | 6-Mercaptopurine |
| Hyaluronic Acid | Busulfan | Doxepin |
| Fluphenazine | cyanoginosin LR | Salicylic Acid |
| Isoproterenol | Promazine | Clomipramine |
| halofuginone | bestatin | Tunicamycin |
| Rifampin | Thioacetamide | tetrandrine |
| amprenavir | LG 268 | Ketoconazole |
| pristane | Ampicillin | Albendazole |
| Itraconazole | Triiodothyronine | Muromonab-CD3 |
| fulvestrant | nimesulide | meloxicam |
| telmisartan | Raloxifene | Bromisovalum |
| Terbutaline | Nitrofurazone | tracazolate |
| 6-bromoindirubin-3'-oxime | Bleomycin | vinylidene chloride |
| valsartan | geraniol | Progesterone |
| lacidipine | tropisetron | 4-(4-fluorophenyl)-2-(4-hydroxyphenyl)-5-(4-pyridyl)imidazole |
| Sulindac | enterotoxin I, staphylococcal | eperisone |
| Stavudine | estradiol 3-benzoate | testosterone 17 beta-cypionate |
| Thiorphan | Podophyllotoxin | Doxapram |
| ferulic acid | Ethinyl Estradiol | ovalicin |
| Pentobarbital | Ethionine | Tetracycline |
| Cyproterone Acetate | desloratadine | Vinblastine |
| olanzapine | lead acetate | Chloroform |
| Isotretinoin | artemisinine | pirenperone |
| Aspirin | Diethylstilbestrol | Diclofenac |

TABLE S1-continued

| Molecules that regulate genes or gene products relevant to proline transport and metabolism. | | |
|---|---|---|
| N-(2-aminophenyl)-4-(N-(pyridin-3-ylmethoxycarbonyl)aminomethyl)benzamide | Estradiol | Mebendazole |
| Valproic Acid | pantoprazole | Ticrynafen |
| Isoflurophate | Lithium Carbonate | Labetalol |
| lansoprazole | Carbon Tetrachloride | Particulate Matter |
| 1-amino-2,4-dibromoanthraquinone | clorsulon | Pentylenetetrazole |
| Lead | tris(2,3-dibromopropyl)phosphate | Pregnenolone Carbonitrile |
| alginic acid | ciclopirox | Phenylephrine |
| Teriparatide | Glipizide | thymoglobulin |
| Folic Acid | Ozone | linezolid |
| Oxyquinoline | Clotrimazole | fazarabine |
| 8-Bromo Cyclic Adenosine Monophosphate | Serotonin | Caerulein |
| Neostigmine | Lithium | Proglumide |
| Morantel | Saquinavir | CpG ODN 2216 |
| Dipyrone | Tinidazole | Cisapride |
| Glycerol | Mannitol | Chlormadinone Acetate |
| Memantine | Minoxidil | Tetracaine |
| 1,5-naphthalenediamine | Monensin | nateglinide |
| halofuginone | bestatin | Tunicamycin |
| bromodichloromethane | Phytohemagglutinins | Insulin |
| erlotinib | Trifluridine | zomepirac |
| Aminosalicylic Acid | Amitriptyline | Hydrogen Peroxide |
| 2,4-diaminotoluene | Triacetin | Mestranol |
| Ethanol | 4'-N-benzoylstaurosporine | ferric nitrilotriacetate |
| Nortriptyline | Thiamphenicol | Metformin |
| benzyloxycarbonylleucyl-leucyl-leucine aldehyde | Risperidone | Calcitriol |
| Pyrethrins | Melphalan | BCG Vaccine |
| R 848 | 4-acetylaminofluorene | bortezomib |
| Diphenhydramine | procyanidin | Soman |
| Tranexamic Acid | Atovaquone | Cyclophosphamide |
| Pempidine | Luteolin | Metaraminol |
| Indomethacin | HI 6 | Citric Acid |
| Omeprazole | anastrozole | Diethylnitrosamine |
| N-acetylsphingosine | Imipramine | Curcumin |
| Ritonavir | Lobeline | Ipratropium |
| Digitoxin | temsirolimus | Ionomycin |
| Metoprolol | flavopiridol | 1-Methyl-4-phenyl-1,2,3,6-tetrahydropyridine |
| Promethazine | Lamivudine | Streptomycin |
| Tubocurarine | Vitamin E | Nitrendipine |
| Riluzole | Glycine | 2,2'-Dipyridyl |
| Enalapril | Doxazosin | Aphidicolin |
| Amlodipine | Ketoprofen | benazepril |
| Hydrochlorothiazide | Vincristine | dexchlorpheniramine |
| Nisoldipine | Lisinopril | Alpha-Amanitin |
| doxofylline | Piroxicam | Dimenhydrinate |
| Amphetamine | Cimetidine | Naproxen |
| Ketorolac | Citalopram | tenidap |
| efavirenz | Sulpiride | 4-(5-benzo(1,3)dioxol-5-yl-4-pyridin-2-yl-1H-imidazol-2-yl)benzamide |
| candesartan | gemcitabine | ochratoxin A |
| Ribavirin | Deoxyglucose | Chitosan |
| Nevirapine | Miconazole | Nicotine |
| Hydroxyurea | Ticlopidine | Sarin |
| Nafenopin | Atropine | |

| D2. Molecules that downregulate ALDH18A1: | | |
|---|---|---|
| neuropeptide Y (18-36) | Platelet Activating Factor | Chloroquine |
| sodium chromate(VI) | GW 501516 | Methylnitronitrosoguanidine |
| troglitazone | Natriuretic Peptide, C-Type | scriptaid |
| 1-hydroxycholecalciferol | amitraz | Perhexiline |
| Terfenadine | Amiodarone | hexachloroethane |
| Prostaglandins E | Gentian Violet | Rolipram |
| Zalcitabine | Vecuronium Bromide | HC toxin |
| Ethylestrenol | vinorelbine | AICA ribonucleotide |
| torsemide | sodium selenate | Mephentermine |
| 8-aminohexylamino cAMP | artemether | Idarubicin |
| Fluocinolone Acetonide | Thioguanine | Humic Substances |
| monastrol | trovafloxacin | insulin-like growth factor I (57-70) |
| Hexachlorophene | benoxaprofen | rofecoxib |
| rosiglitazone | Chlorpyrifos | Shiga Toxin |
| Methylnitrosourea | Fluoxetine | Cyclandelate |
| Etoposide | methyl salicylate | Tolazoline |
| Acrolein | Benzocaine | zardaverine |
| Roflumilast | parbendazole | Methyl Methanesulfonate |

TABLE S1-continued

Molecules that regulate genes or gene products relevant to proline transport and metabolism.

| | | |
|---|---|---|
| CPG-oligonucleotide | zopiclone | ibufenac |
| carvedilol | Methylcholanthrene | benzyloxycarbonylvalyl-alanyl-aspartyl fluoromethyl ketone |
| quintozene | 4-dichlorobenzene | Sulfadiazine |
| Clofibrate | Puromycin Aminonucleoside | hydrastine |
| Metronidazole | Menthol | beta-Naphthoflavone |
| Sirolimus | Dexfenfluramine | sodium arsenite |
| Cisplatin | Daunorubicin | 2-Acetylaminofluorene |
| Phenobarbital | Simvastatin | Camptothecin |
| Niacin | Tacrine | Sotalol |
| Nifedipine | nitrosobenzylmethylamine | Alprazolam |
| fenspiride | Immunoglobulin M | mafosfamide |
| Doxorubicin | Dichlorvos | Dihydrostreptomycin Sulfate |
| Clofazimine | Ceftazidime | Niacinamide |
| Emodin | naphthalan | clinafloxacin |
| naphthalenediimide | rabeprazole | Diazinon |
| Propantheline | Pergolide | 6-methoxy-2-naphthylacetic acid |
| Digoxin | Probenecid | Pimozide |
| Carboplatin | benfluorex | terbinafine |
| Tetrachlorodibenzodioxin | Ampyrone | Mafenide |
| tetrahydrozoline | Lindane | phosphonoacetamide |
| neuropeptide Y (18-36) | Platelet Activating Factor | Chloroquine |
| Maprotiline | Neomycin | infliximab |
| 2-methoxyestradiol | Finasteride | Dexamethasone |
| Methylene Chloride | Cycloheximide | 1-(5-Isoquinolinesulfonyl)-2-Methylpiperazine |
| Flavoxate | Hydralazine | Etidronic Acid |
| Poly I-C | Mercuric Chloride | zileuton |
| trichostatin A | DDT | Methotrexate |
| atorvastatin | Bismuth | oxcarbazepine |
| tosufloxacin | piclamilast | Vidarabine |
| Anti-Retroviral Agents | Benzo(a)pyrene | cerivastatin |
| cobaltous chloride | Propylthiouracil | Erythromycin |
| Hydrocortisone | Bepridil | Caffeine |
| Benserazide | LBH589 | Amikacin |
| Trifluoperazine | Harmaline | Fenofibrate |
| tranilast | chromium hexavalent ion | Aflatoxin B1 |
| gabapentin | lomefloxacin | fomepizole |
| Metoclopramide | Chlorpropamide | Phenol |
| Histidinol | Chlorpromazine | chelidonine |
| myricetin | Bezafibrate | letrozole |
| phenacemide | everolimus | edelfosine |
| Clonidine | imatinib | celecoxib |
| Pravastatin | Prochlorperazine | nifenazone |
| Granisetron | oxiconazole | Isoniazid |
| phorbolol myristate acetate | Suloctidil | Albuterol |
| Acetazolamide | Diethylhexyl Phthalate | Ethosuximide |
| Halothane | tenofovir | 1,2,3-trichloropropane |
| Metaproterenol | N-(2-cyclohexyloxy-4-nitrophenyl)methanesulfonamide | Fusaric Acid |
| beta-1,3-glucan | ipriflavone | Fluconazole |
| 2-(1H-indazol-4-yl)-6-(4-methanesulfonylpiperazin-1-ylmethyl)-4-morpholin-4-ylthieno(3,2-d)pyrimidine | Inosine Monophosphate | hydrazine |
| Betamethasone | isoconazole | Cyproheptadine |
| Gonadotropins | Sumatriptan | Dihydroergotamine |
| Furosemide | Fluspirilene | Ciprofloxacin |
| Azaguanine | Mifepristone | Clarithromycin |
| Gentamicins | arsenic trioxide | Dihydroergocristine |
| decitabine | Ultraviolet Rays | Genistein |
| neuropeptide Y (18-36) | Platelet Activating Factor | Chloroquine |
| Sertraline | Ethylene Glycol | Zinc Oxide |
| Sulfaphenazole | Rifabutin | 4-octylphenol |
| hydroquinone | Paclitaxel | Foscarnet |
| lingzhi | tazobactam | Bithionol |
| Furazolidone | calycanthine | Thioridazine |
| 2-(4-morpholinyl)-8-phenyl-4H-1-benzopyran-4-one | Iproniazid | Flutamide |
| diphenylpyraline | Chorionic Gonadotropin | 2-dichlorobenzene |
| 15-deoxy-delta(12,14)-prostaglandin J2 | Dinoprost | hexachlorobutadiene |
| Clozapine | CEP 14083 | pioglitazone |
| betulinic acid | Fludrocortisone | Lovastatin |
| Pyridoxine | Sulfadoxine | Acetylcysteine |
| glycidol | isocorydine | blebbistatin |
| 1,3-dichlorobenzene | Clofibric Acid | X-Rays |
| 1-ethyl-2-benzimidazolinone | Troleandomycin | boldine |

TABLE S1-continued

Molecules that regulate genes or gene products relevant to proline transport and metabolism.

| | | |
|---|---|---|
| Tretinoin | Amoxapine | Pregnenolone |
| Tolazamide | Ethacrynic Acid | Coumaphos |
| 5-episisomicin | oxaliplatin | Cefadroxil |
| pyrvinium | Monocrotaline | Tramadol |
| harmol | Phenelzine | fluvastatin |
| ethotoin | Puromycin | Ergocalciferols |
| oltipraz | Penicillamine | acemetacin |
| dexibuprofen | Piperonyl Butoxide | Topotecan |
| Choline | PI103 | dorzolamide |
| Dantrolene | Norethindrone | Bromocriptine |
| Gossypol | bisphenol A | Alprostadil |
| Carbachol | repaglinide | Melatonin |
| Clonazepam | Quinacrine | Moxalactam |
| Domperidone | Bisacodyl | Prednisolone |
| phenethyl isothiocyanate | Butyric Acid | ebastine |
| Malathion | Azacitidine | Lorazepam |
| Ethyl Methanesulfonate | Nitric Oxide | 1-Methyl-3-isobutylxanthine |
| geldanamycin | Nimodipine | Colchicine |
| Fluvoxamine | Nystatin | monorden |
| Mitomycin | Atenolol | vorinostat |
| Chlorambucil | NG-Nitroarginine Methyl Ester | Metergoline |
| irinotecan | Netilmicin | gefitinib |
| 3-deazaneplanocin | Benperidol | Deferoxamine |
| neuropeptide Y (18-36) | Platelet Activating Factor | Chloroquine |
| Y 27632 | canadine | Losartan |
| Dizocilpine Maleate | Cytarabine | Haloperidol |
| Clemastine | resveratrol | dibenzazepine |
| Enoxacin | Rotenone | Amiloride |
| Prazosin | Terazosin | Quercetin |
| 17-(allylamino)-17-demethoxygeldanamycin | mono-(2-ethylhexyl)phthalate | Gemfibrozil |
| SU 5402 | Emetine | Flunarizine |
| Plicamycin | Vitamin K 3 | 4-hydroxy-2-nonenal |
| Nocodazole | Fenoprofen | Zidovudine |
| Ranitidine | Dicyclomine | Mycophenolic Acid |
| compactin | dasatinib | leflunomide |
| Econazole | Galantamine | Diazepam |
| lysophosphatidic acid | 8-((4-chlorophenyl)thio)cyclic-3',5'-AMP | Dactinomycin |
| Ofloxacin | Fluorouracil | Oxymetazoline |
| Papaverine | Ifosfamide | Amantadine |
| Disulfiram | Methyldopa | |

| E1. Molecules that upregulate OAT: | | |
|---|---|---|
| Forskolin | LBH589 | fipronil |
| sorafenib | riddelliine | Sirolimus |
| trichostatin A | decitabine | tetra(4-N-methylpyridyl)porphine |
| testosterone 17 beta-cypionate | Sodium Benzoate | Aphidicolin |
| Diquat | bevacizumab | ellipticine |
| Amitrole | benzimidazole | Ecdysterone |
| marimastat | Copper Sulfate | dasatinib |
| Sulpiride | Cantharidin | erlotinib |
| Meptazinol | 4,4'-diaminodiphenylmethane | Aclarubicin |
| Idoxuridine | Diethylhexyl Phthalate | Tolnaftate |
| sulforafan | 2-nitrofluorene | thermozymocidin |
| fludarabine | Theophylline | suxibuzone |
| Valproic Acid | beta-Naphthoflavone | HC toxin |
| Methylnitrosourea | 1-ethyl-2-benzimidazolinone | vorinostat |
| Molindone | Triiodothyronine | cidofovir |
| Pyrethrins | Fenoterol | Aflatoxins |
| butamben | diisopropyl methylphosphonate | Paraquat |
| Thapsigargin | Mannitol | geldanamycin |
| monastrol | Hycanthone | Pregnenolone Carbonitrile |
| Forskolin | LBH589 | fipronil |
| Ofloxacin | Thiostrepton | bafilomycin A |
| tripterine | tenidap | 4-cyclododecyl-2,6-dimethylmorpholine acetate |
| senecionine | Vincristine | Benzalkonium Compounds |
| Methyldopa | zardaverine | Phenylmercuric Acetate |
| Papaverine | Isoniazid | Fenofibrate |
| sanguinarine | Haloperidol | Pregnenolone |
| Metribolone | 2-methoxyestradiol | phenethyl isothiocyanate |
| imatinib | Camptothecin | Ozone |
| blebbistatin | Gabexate | 4-nonylphenol |
| Amphetamine | Clodronic Acid | Methylprednisolone |
| VX | Cytokines | Dihydrotestosterone |
| Tretinoin | doxofylline | Thioctic Acid |

TABLE S1-continued

Molecules that regulate genes or gene products relevant to proline transport and metabolism.

| | | |
|---|---|---|
| Fenoprofen | oxaprozin | cerivastatin |
| Yellow Fever Vaccine | Hemin | N-methylpyrrolidone |
| Zidovudine | Etidronic Acid | tenofovir |
| Diflunisal | isoconazole | trilinolein |
| Methanol | Folic Acid | Clofibrate |
| nimesulide | Fluphenazine | Quercetin |
| Botulinum Toxins, Type A | Prostaglandins E | Acrolein |
| Cefuroxime | Chlorpheniramine | Tetanus Toxin |
| Ribavirin | bis(tri-n-butyltin)oxide | Methylcholanthrene |
| heliotrine | triptolide | ciclopirox |
| Bupropion | Clenbuterol | Dicyclomine |
| Strophanthidin | gefitinib | Hydrogen Peroxide |
| gedunin | Caffeine | Trenbolone Acetate, (17beta)-isomer |
| atorvastatin | romidepsin | Hydroxyurea |
| Flurbiprofen | Nevirapine | Moxisylyte |
| Cytochalasin B | pristane | bicalutamide |
| Cholera Toxin | Zalcitabine | gamma-Tocopherol |
| 8-Bromo Cyclic Adenosine Monophosphate | Anti-Retroviral Agents | Phenylbutazone |
| 8-((4-chlorophenyl)thio)cyclic-3',5'-AMP | 1-(5-Isoquinolinesulfonyl)-2-Methylpiperazine | Corticosterone |
| thymoglobulin | Insulin | cathelicidin antimicrobial peptide |
| everolimus | BCG Vaccine | X-Rays |
| letrozole | Mycophenolic Acid | Doxepin |
| Enalapril | NG-Nitroarginine Methyl Ester | Dimethyl Sulfoxide |
| Metoprolol | Methotrexate | Furosemide |
| Forskolin | LBH589 | fipronil |
| Enoxacin | alpha-Tocopherol | Cyclosporine |
| Phenylephrine | 4-methyl-N-(3-(4-methylimidazol-1-yl)-5-(trifluoromethyl)phenyl)-3-((4-pyridin-3-ylpyrimidin-2-yl)amino)benzamide | Deferoxamine |
| Rifampin | Vinblastine | Amitriptyline |
| Quinidine | oxybutynin | Dactinomycin |
| lysophosphatidic acid | Atropine | resveratrol |
| Terbutaline | Paroxetine | 17-(allylamino)-17-demethoxygeldanamycin |
| Losartan | Albendazole | Diphenhydramine |
| Fluoxetine | Fluorouracil | bisphenol A |
| acetopyrrothine | 1-Methyl-3-isobutylxanthine | Cytarabine |
| Vitamin K 3 | Paclitaxel | Benomyl |

E2. Molecules that downregulate OAT:

| | | |
|---|---|---|
| Thioacetamide | Ticlopidine | bendazolic acid |
| Dimethylnitrosamine | Hexachlorobenzene | methylformamide |
| Chlormezanone | coumarin | bromobenzene |
| Flutamide | Ethambutol | lornoxicam |
| Piperonyl Butoxide | Clonazepam | nitrosobenzylmethylamine |
| N-nitrosomorpholine | Propylthiouracil | Diethylnitrosamine |
| 1,3-dichloro-2-propanol | pantoprazole | Methimazole |
| Aminoglutethimide | Hexamethonium | Carbamazepine |
| artemisinine | 1,2-dithiol-3-thione | oltipraz |
| Chloroform | Monocrotaline | 4-dichlorobenzene |
| Ethionamide | Stavudine | Asbestos |
| hydroxytamoxifen | Carbimazole | Phenobarbital |
| ochratoxin A | Pyrogallol | Disopyramide |
| Gemfibrozil | alachlor | Carbon Tetrachloride |
| 2-dichlorobenzene | Acetaminophen | Cinnarizine |
| Chloramphenicol | 2-Acetylaminofluorene | terbinafine |
| Naproxen | Colchicine | Lorazepam |
| gentamicin C | salicylamide | Econazole |
| estradiol 3-benzoate | Omeprazole | bambuterol |
| Phenacetin | garcinol | Gentian Violet |
| Okadaic Acid | Phenytoin | Clotrimazole |
| Testosterone | iodoform | Trimethadione |
| Citrinin | Hydroxyzine | nimetazepam |
| Thioacetamide | Ticlopidine | bendazolic acid |
| Polychlorinated Biphenyls | crotamiton | benziodarone |
| iturelix | Dehydroepiandrosterone | Mestranol |
| Methyltestosterone | Etodolac | Miconazole |
| Dantrolene | PI103 | Safrole |
| Estriol | Niclosamide | Ibuprofen |
| Malathion | Penicillamine | Calcium Chloride |
| Carmustine | Methapyrilene | lead tetraacetate |
| vanadyl sulfate | Benperidol | dexamisole |
| Procarbazine | hexachlorobutadiene | Benzbromarone |
| Methylene Chloride | Cymarine | ranolazine |

TABLE S1-continued

Molecules that regulate genes or gene products relevant to proline transport and metabolism.

| | | |
|---|---|---|
| Azathioprine | Chromium | Famotidine |
| Tryptophan | Lead | Ketanserin |
| Atovaquone | Phleomycins | Trypsin Inhibitor, Bowman-Birk Soybean |
| Amanitins | meloxicam | Sulfasalazine |
| Mifepristone | Salicylates | Dinoprostone |
| Sulindac | 5'-methylthioadenosine | Patulin |
| Danazol | Doxorubicin | Metolazone |
| pioglitazone | zileuton | Canavanine |
| Dizocilpine Maleate | Urethane | Tacrine |
| sodium chromate(VI) | Estradiol | Disulfiram |
| fosfosal | 4-(5-benzo(1,3)dioxol-5-yl-4-pyridin-2-yl-1H-imidazol-2-yl)benzamide | fenamiphos |
| Vancomycin | Dimethylformamide | Lomustine |
| Luteolin | Lasalocid | naphthalene |
| Diazepam | perfluorooctanoic acid | 2,4-Dinitrophenol |
| phenothiazine | Nitrazepam | acetovanillone |
| acadesine | Gentamicins | Diltiazem |
| Ketorolac | shikonin | Edrophonium |
| Isotretinoin | rabeprazole | Fursultiamin |
| Lidocaine | Fluocinolone Acetonide | Genistein |
| Minocycline | syrosingopine | GW 3965 |
| Thiabendazole | Ethinyl Estradiol | Itraconazole |
| Fluorometholone | 3-deazaneplanocin | Fluconazole |
| Diethylstilbestrol | Cyproterone Acetate | Promethazine |
| rosiglitazone | aristolochic acid I | Cisplatin |
| scriptaid | Ganciclovir | Emetine |
| Diclofenac | lingzhi | ferric nitrilotriacetate |
| Ethionine | Khellin | hydrazine |
| Thioacetamide | Ticlopidine | bendazolic acid |
| Canrenoate Potassium | Nystatin | 9-(2-hydroxy-3-nonyl)adenine |
| Tunicamycin | systhane | Caerulein |
| Phenylalanine | Calcium | Clofibric Acid |
| arsenic trioxide | Hemicholinium 3 | Ethylnitrosourea |
| sodium arsenite | Remoxipride | Oxazepam |
| Dexamethasone | Hydrocortisone | dirithromycin |
| homatropine | U 0126 | Clobetasol |
| triadimefon | Melphalan | Zimeldine |
| Antigen-Antibody Complex | Nitrofurazone | Ethanol |
| cephaelin | apratoxin A | Aspirin |
| arsenic acid | Betamethasone | furaltadon |
| flunixin | 1,3-dichlorobenzene | anastrozole |
| nifuroxazide | Lovastatin | Pivampicillin |
| Nifedipine | Tolazoline | Nocodazole |
| tropisetron | Orotic Acid | Simvastatin |
| Carcinogens | CpG ODN 2216 | isoxicam |
| naftopidil | leflunomide | Nicotine |
| Dihydroergotamine | acidocin CH5, Lactobacillus acidophilus | Bezafibrate |
| Serotonin | Allopurinol | Spironolactone |
| Piribedil | Glyburide | Clomiphene |
| temozolomide | Nordefrin | Niacinamide |
| Primidone | Lobeline | Ethylestrenol |
| Tetrachlorodibenzodioxin | Carnitine | 4-(4-fluorophenyl)-2-(4-hydroxyphenyl)-5-(4-pyridyl)imidazole |
| Trichloroethylene | Clonidine | sevoflurane |
| Immunoglobulin M | motexafin gadolinium | Pilocarpine |
| Deoxycholic Acid | dihydroquinghaosu | piperaquine |
| Amiodarone | Ajmaline | Amantadine |
| picrotoxinin | versipelostatin | Mephentermine |
| Calcitriol | tracazolate | gatifloxacin |
| nilutamide | securinine | Azaguanine |
| Ampicillin | Epitestosterone | Y 27632 |
| Nicergoline | Isoproterenol | 16-ketoestradiol |
| mycophenolate mofetil | Aminocaproic Acids | Epirubicin |
| fulvestrant | Immunoglobulins, Intravenous | Amphotericin B |
| Shiga Toxin | Pemoline | balsalazide |
| Chlortetracycline | Inosine Monophosphate | Pimozide |
| Thioacetamide | Ticlopidine | bendazolic acid |
| Betaxolol | MF59 oil emulsion | Nimodipine |
| enterotoxin B, staphylococcal | Nitrofurantoin | pirinixic acid |
| carvedilol | Methazolamide | Azacitidine |
| Indomethacin | Rotenone | Rolipram |
| Propranolol | Albuterol | Dichlorvos |
| Sotalol | enzastaurin | Nitric Oxide |
| N-Ac-CHAVC-NH2 | Tranylcypromine | Cyclophosphamide |
| Puromycin | mono-(2-ethylhexyl)phthalate | Neomycin |

TABLE S1-continued

Molecules that regulate genes or gene products relevant to proline transport and metabolism.

| | | |
|---|---|---|
| Plicamycin | phosphonoacetamide | Ascorbic Acid |
| bortezomib | rofecoxib | Mitomycin |
| Chlorpromazine | fluvastatin | Clindamycin |
| Palmitic Acid | Deoxyglucose | Kainic Acid |
| Alpha-Amanitin | Pergolide | Oxymetazoline |
| Vitamin E | Mebendazole | Ketoconazole |
| Ciprofloxacin | Clomipramine | isoascorbic acid |
| Ionomycin | Thioguanine | Cycloheximide |
| Methyl Methanesulfonate | | |

F1. Molecules that upregulate ALDH4A1:

| | | |
|---|---|---|
| Cyclopenthiazide | Sulfadimethoxine | Mephenesin |
| Tiletamine | Methotrimeprazine | Trimethoprim |
| tomatidine | Pilocarpine | citiolone |
| Bisoprolol | butacaine | Glycopyrrolate |
| Bufexamac | chloropyramine | pipenzolate |
| Meclizine | Zimeldine | acetylleucine |
| Albuterol | amylocaine | Methoxamine |
| bacampicillin | Etanidazole | Riluzole |
| Propranolol | zaprinast | telenzepine |
| Azathioprine | Cefixime | Buspirone |
| Bemegride | 4-acetylaminofluorene | Sulfisoxazole |
| ajmalicine | pelargonic acid | trimethobenzamide |
| naringin | sulfanilamide | Oxyquinoline |
| Dihydrostreptomycin Sulfate | triadimefon | Hydralazine |
| oxaliplatin | Norethindrone | Chlorpheniramine |
| Procaine | Aclarubicin | diflorasone diacetate |
| Felodipine | Tolmetin | Sulfacetamide |
| Amiloride | Bromocriptine | harman |
| Propidium | TO-901317 | benzothiazide |
| Propylthiouracil | Remoxipride | efavirenz |
| Cyclopenthiazide | Sulfadimethoxine | Mephenesin |
| Cefazolin | tridihexethyl | Aristolochic Acids |
| Dipyrone | Moricizine | Dihydrotestosterone |
| 1-(2-cyano-3,12-dioxooleana-1,9-dien-28-oyl) imidazole | Etoposide | Pargyline |
| triptolide | diisopropyl methylphosphonate | Ethylnitrosourea |
| Hymecromone | Josamycin | Methylnitrosourea |
| clopidogrel | Heptaminol | Orphenadrine |
| Tobramycin | 4-(N-methyl-N-nitrosamino)-1-(3-pyridyl)-1-butanone | Nalidixic Acid |
| eperisone | Moxisylyte | Ondansetron |
| arcaine | Spironolactone | trichostatin A |
| fenhexamid | Doxorubicin | monastrol |
| Cyclopentolate | clidinium | Hydrocortisone |
| artemisinine | lorglumide | Forskolin |
| troglitazone | 8-(3-Chlorostyryl)-1,3,7-trimethylxanthine | geldanamycin |
| Cromolyn Sodium | Selenomethionine | 2-nitrofluorene |
| 4,4'-diaminodiphenylmethane | Glutamic Acid | Vecuronium Bromide |
| Guanfacine | vorinostat | Streptozocin |
| Ethambutol | Diethylnitrosamine | Mephenytoin |
| Azaperone | diperodon | Allantoin |
| fomepizole | Lamivudine | Etilefrine |
| Sulfasalazine | VX | oxolamine |
| 1-Methyl-3-isobutylxanthine | Enalapril | carbinoxamine |
| Hydroxyzine | Dilazep | Cisplatin |
| Glycocholic Acid | Sulfameter | clemizole |
| apicidin | ethotoin | decitabine |
| Levodopa | isopyrin | Aminopyrine |
| Ticlopidine | salicylamide | enzastaurin |
| chloroacetaldehyde | butenafine | fenspiride |
| gefitinib | Acetaminophen | 2-Acetylaminofluorene |
| Kinetin | Clarithromycin | Practolol |
| Cortisone | Thiabendazole | Nisoldipine |
| Aflatoxin B1 | HC toxin | discretamine |
| Thiethylperazine | Ketanserin | 3-nitropropionic acid |
| tris(2,3-dibromopropyl)phosphate | Mianserin | Megestrol Acetate |
| Aflatoxins | Ultraviolet Rays | vinorelbine |
| pyrithyldione | pirenperone | Daunorubicin |
| LBH589 | lapatinib | asiaticoside |
| Cyclopenthiazide | Sulfadimethoxine | Mephenesin |
| Methacholine Chloride | oxcarbazepine | Ipratropium |
| 8-((4-chlorophenyl)thio)cyclic-3',5'-AMP | Etidronic Acid | Tin Fluorides |
| Sulfamethazine | rosiglitazone | 3,3',4',5-tetrachlorosalicylanilide |
| amitraz | romidepsin | ascorbate-2-phosphate |

TABLE S1-continued

Molecules that regulate genes or gene products relevant to proline transport and metabolism.

| | | |
|---|---|---|
| Corticosterone | Pyrazinamide | vinpocetine |
| Ethamsylate | Minocycline | Ketamine |
| Rolipram | Ronidazole | Curcumin |
| Pinacidil | Trichlormethiazide | Mitomycin |
| Luteolin | lomefloxacin | Dexamethasone |
| piclamilast | 1,3-dichlorobenzene | tranilast |
| Carboplatin | Glafenine | diphemanil methylsulfate |
| Sulfadiazine | Testosterone | Verapamil |
| velnacrine | Phorbol Esters | Zalcitabine |
| Zidovudine | butamben | Atrazine |
| Ciprofloxacin | Sumatriptan | Tacrine |
| fazarabine | Cytochalasin B | Carbimazole |
| Botulinum Toxins, Type A | Mustard Gas | Carbamazepine |
| Amphotericin B | Dipyridamole | Furosemide |
| lead tetraacetate | Mannitol | cefepime |
| Sorbitol | letrozole | Serotonin |
| Tolbutamide | Androsterone | abacavir |
| blebbistatin | Cisapride | Flunarizine |
| Ritodrine | Pentoxifylline | scriptaid |
| Camptothecin | Bupropion | picrotoxinin |
| delsoline | Hydroxyurea | 4-hydroxy-2-nonenal |
| Valproic Acid | Amoxapine | Metaraminol |
| Oxazepam | Theophylline | marimastat |
| Citric Acid | Podophyllotoxin | Altretamine |
| Mycophenolic Acid | candesartan | Paclitaxel |
| Fenoprofen | Gentamicins | Vincristine |
| versipelostatin | erlotinib | Nitric Oxide |
| Phenoxybenzamine | Prochlorperazine | 8-Bromo Cyclic Adenosine Monophosphate |
| Enoxacin | Chlortetracycline | Choline |
| Pregnenolone Carbonitrile | Phenobarbital | Chloramphenicol |
| Vitamin E | Clofibrate | Busulfan |
| sodium selenate | Methotrexate | Trifluoperazine |
| Physostigmine | Dimethyl Sulfoxide | benazepril |
| Cyclopenthiazide | Sulfadimethoxine | Mephenesin |
| imatinib | Galantamine | Azauridine |
| Diflunisal | Fluorouracil | 4-(5-benzo(1,3)dioxol-5-yl-4-pyridin-2-yl-1H-imidazol-2-yl)benzamide |
| Phenylephrine | sodium arsenite | Aspirin |
| Neomycin | Iproniazid | Saquinavir |
| Melphalan | 1-Methyl-4-phenyl-1,2,3,6-tetrahydropyridine | dasatinib |
| Ascorbic Acid | Nocodazole | Soman |
| U 0126 | HI 6 | Captopril |
| Ionomycin | Chitosan | Digoxin |
| Dactinomycin | Cycloheximide | Amitrole |
| Nicotine | Chlorpyrifos | Dichlorvos |
| Cyclophosphamide | Azacitidine | |

| F2. Molecules that downregulate ALDH4A1: | | |
|---|---|---|
| spiradoline | alfuzosin | Buthionine Sulfoximine |
| hydroxytamoxifen | Oxolinic Acid | Nialamide |
| tianeptine | amineptin | homosalate |
| 9-(2-hydroxy-3-nonyl)adenine | Vinblastine | Lidoflazine |
| Gliclazide | althiazide | Isosorbide |
| Isotretinoin | sunitinib | enrofloxacin |
| telmisartan | Cefuroxime | doxofylline |
| Estradiol | Quinidine | Ursodeoxycholic Acid |
| piretanide | ubiquinol | daidzein |
| Aminosalicylic Acid | Colchicine | Genistein |
| fulvestrant | Imipramine | Probenecid |
| Amantadine | desloratadine | Pheniramine |
| Fluoxetine | Disopyramide | Ecdysterone |
| Simvastatin | Methylergonovine | ebselen |
| betulinic acid | repaglinide | Anti-Retroviral Agents |
| naringenin | Reserpine | nickel chloride |
| Lithocholic Acid | N-acetylsphingosine | bisphenol A |
| vinylidene chloride | valdecoxib | Tetracycline |
| beta-Naphthoflavone | Cinoxacin | bendazolic acid |
| Diclofenac | Cytochalasin D | Ethinyl Estradiol |
| venlafaxine | Lovastatin | Mestranol |
| moroxydine | Cephapirin | alachlor |
| Chloroquine | norethindrone acetate | Erythromycin |
| Sparteine | Labetalol | 2-dichlorobenzene |
| spiradoline | alfuzosin | Buthionine Sulfoximine |
| Clonidine | lacidipine | Indomethacin |
| Gold | Sulindac | Etodolac |

TABLE S1-continued

Molecules that regulate genes or gene products relevant to proline transport and metabolism.

| | | |
|---|---|---|
| Clemastine | 4-hydroxytamoxifen | Diethylstilbestrol |
| Ranitidine | Oxytetracycline | Zinc Sulfate |
| Natamycin | etofylline | isopropamide iodide |
| olanzapine | Estriol | triflusal |
| Canrenoate Potassium | Methapyrilene | Lobeline |
| Alprazolam | Pergolide | pioglitazone |
| Ethionamide | hydrastinine | Clozapine |
| Pravastatin | calycanthine | N-(2-cyclohexyloxy-4-nitrophenyl)methanesulfonamide |
| Sertraline | Naproxen | Digitoxin |
| Carbon Tetrachloride | estradiol 3-benzoate | bicalutamide |
| Roflumilast | suxibuzone | acetorphan |
| Viomycin | Dichlorphenamide | aluminum sulfate |
| Acetohexamide | carvedilol | Vincamine |
| Thioacetamide | Metoprolol | Raloxifene |
| Doxepin | Promethazine | geraniol |
| Niridazole | Nafenopin | Antigen-Antibody Complex |
| dexchlorpheniramine | Nitrendipine | Isoflurophate |
| Amitriptyline | Miconazole | Biotin |
| Betamethasone | Glycine | Phenelzine |
| Sotalol | Trihexyphenidyl | Tacrolimus |
| famciclovir | Isoniazid | 4-dichlorobenzene |
| Cimetidine | Bumetanide | Dinitrophenols |
| benziodarone | Paroxetine | Fluocinolone Acetonide |
| Dimethylformamide | sulfathiazole | Danazol |
| Rifampin | Phenindione | boldine |
| Pirenzepine | Fluphenazine | Naloxone |
| Ethionine | sorafenib | Pemoline |
| Amiodarone | Capsaicin | Disulfiram |
| motexafin gadolinium | Hydrogel | oxfendazole |
| Antimycin A | prochloraz | sildenafil |
| ipriflavone | Deoxycholic Acid | N-Methylscopolamine |
| gabapentin | dexibuprofen | Cyclosporine |
| Brefeldin A | Secobarbital | anastrozole |
| rabeprazole | Meclofenamic Acid | Diphenhydramine |
| oxybutynin | Phenytoin | atorvastatin |
| canadine | biphenylylacetic acid | Dobutamine |
| spiradoline | alfuzosin | Buthionine Sulfoximine |
| pantoprazole | Diltiazem | Risperidone |
| Astemizole | Methylcholanthrene | aceclofenac |
| genipin | Rotenone | idebenone |
| cobaltous chloride | Diazinon | titanium dioxide |
| Estrogens | deferiprone | alpha-Amino-3-hydroxy-5-methyl-4-isoxazolepropionic Acid |
| Sirolimus | Ifosfamide | 1,1,1-trichloroethane |
| halofuginone | pristane | Chloroform |
| sulforafan | Flutamide | phenylhydrazine |
| 5'-methylthioadenosine | lysophosphatidic acid | Ecdysone |
| quetiapine | Acyclovir | Finasteride |
| epoxomicin | Indapamide | Nalbuphine |
| Gemfibrozil | Azlocillin | beta-cyclodextrin-benzaldehyde |
| modafinil | rifapentine | 4-octylphenol |
| Nortriptyline | Ofloxacin | Dantrolene |
| efalizumab | Diethylhexyl Phthalate | Poly I-C |
| tazobactam | sparfloxacin | nimesulide |
| Citalopram | Phentolamine | 4-nonylphenol |
| Bacitracin | Tiapamil Hydrochloride | Nimodipine |
| Bezafibrate | Chlorpromazine | Metyrapone |
| benfluorex | Chlormadinone Acetate | Coumaphos |
| Potassium Dichromate | 6-Mercaptopurine | Clomipramine |
| leflunomide | Thioridazine | Chlorambucil |
| cyanoginosin LR | Thapsigargin | 2-(4-morpholinyl)-8-phenyl-4H-1-benzopyran-4-one |
| Clonazepam | meloxicam | 2-methoxyestradiol |
| cilostazol | Quinacrine | Ibuprofen |
| fluvastatin | phenethyl isothiocyanate | chlorcyclizine |
| Vanadates | lactacystin | Ketoconazole |
| Itraconazole | Econazole | Isoproterenol |
| Tocainide | benzamil | Floxuridine |
| Thioguanine | Tranexamic Acid | temsirolimus |
| Concanavalin A | Aminoglutethimide | Deoxyglucose |
| Clotrimazole | Terazosin | resveratrol |
| SB 203580 | Nadolol | cerivastatin |
| Fluconazole | Tinidazole | Promazine |
| Allopurinol | lansoprazole | Perhexiline |
| linezolid | Pentylenetetrazole | ONO 2235 |
| Deferoxamine | Loratadine | bortezomib |
| spiradoline | alfuzosin | Buthionine Sulfoximine |

TABLE S1-continued

| Molecules that regulate genes or gene products relevant to proline transport and metabolism. | | |
|---|---|---|
| ferulic acid | Sulpiride | Tropicamide |
| Cytarabine | Baclofen | Nifedipine |
| acadesine | Fluvoxamine | Melatonin |
| Haloperidol | Methazolamide | Streptomycin |
| Omeprazole | Clindamycin | terbinafine |
| Terfenadine | Diazepam | Ramipril |
| Caffeine | Cinnarizine | Calcitriol |
| Quercetin | Granisetron | Phenylalanine |
| valsartan | Dicyclomine | Ketorolac |
| Lisinopril | Cyproheptadine | Nevirapine |
| Pyrogallol | Piroxicam | Stavudine |
| rofecoxib | benzyloxycarbonylleucyl-leucyl-leucine aldehyde | zileuton |
| gemcitabine | irinotecan | pirinixic acid |
| isoascorbic acid | Oxymetazoline | Papaverine |
| Acetazolamide | Hydrochlorothiazide | Lomustine |
| Carmustine | Clofibric Acid | Amphetamine |

| G1. Molecules that upregulate SLC36A1: | | |
|---|---|---|
| pridinol | Talampicillin | N(1)-methyl-2-lysergic acid diethylamide |
| Piperacillin | sertaconazole | Theobromine |
| isopyrin | Sulfaquinoxaline | adrenosterone |
| iturelix | troglitazone | Salicylates |
| CpG ODN 2216 | Grape Seed Proanthocyanidins | pioglitazone |
| 4-hydroxy-2-nonenal | Insulin | tripterine |
| lenalidomide | Erythromycin Ethylsuccinate | Pentolinium Tartrate |
| Aclarubicin | SC 514 | cryptoxanthin |
| tridihexethyl | Cromolyn Sodium | Mycotoxins |
| Endotoxins | Glafenine | SB 203580 |
| Yellow Fever Vaccine | Vitamin E | withaferin A |
| Botulinum Toxins, Type A | lorglumide | flumequine |
| Propanil | rosiglitazone | Albuterol |
| CD 437 | Fluorometholone | 1,3-dichlorobenzene |
| MF59 oil emulsion | Inosine Monophosphate | Trimethoprim |
| Methoxamine | romidepsin | Didanosine |
| diphemanil methylsulfate | sodium chlorate | 15-deoxy-delta(12,14)-prostaglandin J2 |
| gefitinib | Trimeprazine | fazarabine |
| pridinol | Talampicillin | N(1)-methyl-2-lysergic acid diethylamide |
| Valproic Acid | Tetrachloroethylene | 1,5-naphthalenediamine |
| decitabine | procyanidin | monobenzone |
| indole-3-carbinol | Mexiletine | direct black 3 |
| Biotin | Metribolone | mefexamide |
| trichostatin A | Quercetin | GW 3965 |
| 2-dichlorobenzene | 4-dichlorobenzene | alginic acid |
| Roxarsone | rilmenidine | Nefopam |
| Fludrocortisone | lapatinib | Dexamethasone |
| midecamycin | Hycanthone | Monocrotaline |
| caffeic acid | zaprinast | Dihydrotestosterone |
| blebbistatin | monastrol | enzastaurin |
| Calcitriol | pristane | vesamicol |
| geldanamycin | Pempidine | cyanopindolol |
| Trifluoperazine | Cytochalasin B | Lincomycin |
| fragment C, human serum albumin | LPS 9 | Thioridazine |
| Dimethylnitrosamine | Epirizole | Cefuroxime |
| Perhexiline | N-nitrosomorpholine | Octopamine |
| Dichlororibofuranosylbenzimidazole | Paclitaxel | Metoclopramide |
| Bleomycin | Acetylcysteine | Vincristine |
| ajmalicine | Gonadotropins | Simazine |
| Pipemidic Acid | homatropine | daboiatoxin |
| lomefloxacin | Rifabutin | Amiloride |
| Heparin | Chlorpromazine | celecoxib |
| homochlorocyclizine | quintozene | Lynestrenol |
| Carcinogens | Ascorbic Acid | Immunoglobulin M |
| Carbachol | Oxyquinoline | Doxepin |
| Malathion | vorinostat | Rolipram |
| kavain | Vitamin K 3 | 16-ketoestradiol |
| 4-amino-6-hydrazino-7-beta-D-ribofuranosyl-7H-pyrrolo(2,3-d)-pyrimidine-5-carboxamide | Apomorphine | Phenoxybenzamine |
| imatinib | Dinoprost | sapphyrin |
| benzyloxycarbonylleucyl-leucyl-leucine aldehyde | Doxorubicin | Disulfiram |
| sulfathiazole | triadimefon | LBH589 |
| Diltiazem | Hydroxyzine | Aztreonam |

TABLE S1-continued

Molecules that regulate genes or gene products relevant to proline transport and metabolism.

| | | |
|---|---|---|
| adalimumab | Benzo(a)pyrene | heliotrine |
| resveratrol | Methylnitrosourea | rituximab |
| pridinol | Talampicillin | N(1)-methyl-2-lysergic acid diethylamide |
| Ethacrynic Acid | Propylthiouracil | Diazinon |
| fluticasone | Tetradecanoylphorbol Acetate | Methotrexate |
| Sulfasalazine | Clomipramine | fulvestrant |
| copolymer 1 | Piperonyl Butoxide | Levonorgestrel |
| 4-hydroxytamoxifen | bromodichloromethane | dasatinib |
| Acetaminophen | Tretinoin | Azathioprine |
| Hemin | Chorionic Gonadotropin | Labetalol |
| Fluoxetine | Nifedipine | Iproniazid |
| Aflatoxin B1 | Phenacetin | testosterone 17 beta-cypionate |
| Ergocalciferols | HI 6 | Topotecan |
| irinotecan | Mycophenolic Acid | Methyl Methanesulfonate |
| colforsin | bortezomib | Hydrogen Peroxide |
| 4-(5-benzo(1,3)dioxol-5-yl-4-pyridin-2-yl-1H-imidazol-2-yl)benzamide | methylatropine | Nitric Oxide |
| pantoprazole | Pregnenolone Carbonitrile | Immunotoxins |
| sulforafan | Ethosuximide | Promazine |
| Methylene Chloride | Colchicine | Nortriptyline |
| Particulate Matter | Medroxyprogesterone Acetate | torsemide |
| rabeprazole | Risperidone | Nocodazole |
| Puromycin | ochratoxin A | Tacrine |
| Penicillamine | Enalapril | Atropine |
| Caffeine | Indomethacin | Camptothecin |
| fluvastatin | sodium arsenite | Diazepam |
| Fluorouracil | Clotrimazole | Amitriptyline |
| Azacitidine | | |

| G2. Molecules that downregulate SLC36A1: | | |
|---|---|---|
| carbetapentane | Methoxsalen | lonidamine |
| Alpha-Amanitin | genipin | quinethazone |
| Betaxolol | clemizole | Bisoprolol |
| verteporfin | Prenylamine | Nafronyl |
| fenspiride | ciclopirox | ascorbate-2-phosphate |
| Indapamide | GW 501516 | Cholera Toxin |
| Dihydroergotamine | Methamphetamine | parbendazole |
| harmol | Trioxsalen | BCG Vaccine |
| Eugenol | Benserazide | Apigenin |
| moxonidine | Immunoglobulin G | naphthalene |
| enterotoxin I, staphylococcal | Bethanechol | Curcumin |
| carbetapentane | Methoxsalen | lonidamine |
| Mesalamine | Famotidine | Growth Hormone |
| Santonin | mebhydroline | Cisapride |
| Coumarins | Platelet Activating Factor | Mannitol |
| Tetrachlorodibenzodioxin | 2-nitrofluorene | Ambroxol |
| Aflatoxins | Ganciclovir | hydroxachillin |
| Ethambutol | MK 0591 | Tolmetin |
| flunixin | Acetohexamide | phthalylsulfathiazole |
| Thapsigargin | Tunicamycin | Sulfadimethoxine |
| rauwolscine-OHPC | lobelanidine | acidocin CH5, *Lactobacillus acidophilus* |
| infliximab | Glipizide | Concanavalin A |
| chelidonine | Clorgyline | Antigen-Antibody Complex |
| 2,2'-(hydroxynitrosohydrazono)bis-ethanamine | Practolol | Azoxymethane |
| Oxytocin | skimmianine | Ethisterone |
| shikonin | Minocycline | 1-Methyl-3-isobutylxanthine |
| Flutamide | Primaquine | Mafenide |
| Diethylhexyl Phthalate | Acepromazine | Cyclophosphamide |
| Harmine | Protoveratrines | solasodine |
| Dinoprostone | 17-(allylamino)-17-demethoxygeldanamycin | Prednisolone |
| Corticosterone | Ceftazidime | CPG-oligonucleotide |
| Palmitic Acid | Selenomethionine | Cholecalciferol |
| halofuginone | Beclomethasone | beta-cyclodextrin-benzaldehyde |
| amlexanox | trilinolein | amylocaine |
| Staurosporine | Deoxycholic Acid | Gemfibrozil |
| Atrazine | Isoniazid | sangivamycin |
| triptolide | Enterotoxins | Rifampin |
| titanium dioxide | ellipticine | AICA ribonucleotide |
| nifuroxazide | Estriol | Paroxetine |
| Dextran Sulfate | Pyrazinamide | Procainamide |
| Dilazep | Imipramine | TO-901317 |
| Clonidine | salsolidine | Estradiol |
| 6-azathymine | 4-acetylaminofluorene | Chlorprothixene |

TABLE S1-continued

Molecules that regulate genes or gene products relevant to proline transport and metabolism.

| | | |
|---|---|---|
| Niclosamide | Methyltestosterone | Ethanol |
| 8-Bromo Cyclic Adenosine Monophosphate | Propofol | Poly I-C |
| Immunoglobulins, Intravenous | Hydralazine | sanguinarine |
| Dextromethorphan | Piracetam | Acrolein |
| carbetapentane | Methoxsalen | lonidamine |
| Cyclosporine | Vincamine | Lovastatin |
| Cycloheximide | ciprofibrate | Luteinizing Hormone |
| Penicillin G | vinclozolin | emtricitabine |
| bis (tri-n-butyltin)oxide | Benzbromarone | Folic Acid |
| bicalutamide | Pyrogens | Bicuculline |
| Doxazosin | Deoxyglucose | docetaxel |
| R 848 | Phenobarbital | tenofovir |
| arsenic trioxide | Luteolin | Pentylenetetrazole |
| Mitoxantrone | Norfloxacin | poly ICLC |
| lead acetate | Diethylstilbestrol | cobaltous chloride |
| Hydroxyurea | fasudil | piclamilast |
| dibenzazepine | Sirolimus | X-Rays |
| 2-(4-morpholinyl)-8-phenyl-4H-1-benzopyran-4-one | enterotoxin B, staphylococcal | trovafloxacin |
| Cisplatin | Cytokines | Dinitrofluorobenzene |
| Cephalothin | quelamycin | Epitestosterone |
| Albendazole | Anti-Retroviral Agents | salicylamide |
| Niacinamide | Chlormadinone Acetate | Guanethidine |
| Amoxicillin | versipelostatin | lonomycin |
| Metformin | Papaverine | mycophenolate mofetil |
| pirinixic acid | balsalazide | Bezafibrate |
| Trimethadione | Sulpiride | Haloperidol |
| Forskolin | Ticlopidine | Ultraviolet Rays |
| Tacrolimus | Methapyrilene | Chloroform |
| Nicotine | Procarbazine | Dactinomycin |
| Phytohemagglutinins | bisphenol A | erlotinib |
| nimesulide | Cytarabine | Carmustine |
| Naproxen | Diclofenac | Aspirin |
| Clofibrate | | |

| H1. Molecules that upregulate SLC36A2: | | |
|---|---|---|
| Ascorbic Acid | Teriparatide | aluminum sulfate |
| Gonadotropins | Bismuth | Salicylates |
| acodazole | Enterotoxins | rosiglitazone |
| beta-Naphthoflavone | Tretinoin | Chorionic Gonadotropin |
| Azacitidine | Hyaluronic Acid | 4-(5-benzo(1,3)dioxol-5-yl-4-pyridin-2-yl-1H-imidazol-2-yl)benzamide |
| Cycloheximide | Metronidazole | bisphenol A |
| Heparin | MF59 oil emulsion | pioglitazone |
| Ascorbic Acid | Teriparatide | aluminum sulfate |
| Tetracycline | Phenobarbital | blebbistatin |
| Niacinamide | CPG-oligonucleotide | Trenbolone Acetate, (17beta)-isomer |
| 4-hydroxytamoxifen | Dimethylnitrosamine | Hemin |
| Insulin | Azoxymethane | imatinib |
| Quercetin | Doxorubicin | Immunotoxins |
| Clomipramine | Dinoprostone | Sulindac |
| gefitinib | Tetrachlorodibenzodioxin | Genistein |
| Indomethacin | Dactinomycin | bortezomib |
| Diethylstilbestrol | Methotrexate | Sirolimus |

| H2. Molecules that downregulate SLC36A2: | | |
|---|---|---|
| ubiquinol | BRL 37344 | Bleomycin |
| Trichloroepoxypropane | ranolazine | Nandrolone |
| chlorinated dibenzofurans | pristane | withaferin A |
| Berberine | lysophosphatidic acid | Ouabain |
| Melphalan | 1,5-naphthalenediamine | vanadium pentoxide |
| Ozone | quintozene | resveratrol |
| Chitosan | R 848 | Dinitrofluorobenzene |
| Anti-Retroviral Agents | Estradiol | dexibuprofen |
| sulforafan | Cytokines | enterotoxin B, staphylococcal |
| Megestrol Acetate | Isoproterenol | acidocin CH5, *Lactobacillus acidophilus* |
| Hydralazine | Antigen-Antibody Complex | Betamethasone |
| Growth Hormone | Vitamin E | Dexamethasone |
| Methylene Chloride | Fluoxetine | Estriol |
| Cyclophosphamide | Phenytoin | Captopril |
| Progesterone | Kainic Acid | Tetradecanoylphorbol Acetate |
| Calcitriol | Colchicine | Valproic Acid |
| Bezafibrate | Cisplatin | |

TABLE S1-continued

Molecules that regulate genes or gene products relevant to proline transport and metabolism.

I1. Molecules that upregulate SLC36A4:

| | | |
|---|---|---|
| Glutamic Acid | Phytohemagglutinins | Cymarine |
| daidzein | Brefeldin A | Caffeine |
| 2,2-bis(bromomethyl)-1,3-propanediol | Ergocalciferols | Patulin |
| Deferoxamine | Cefuroxime | 1-ethyl-2-benzimidazolinone |
| Dihydrotestosterone | Methylnitrosourea | Tretinoin |
| 8-Bromo Cyclic Adenosine Monophosphate | 25-hydroxycholesterol | Lithium |
| Glutamic Acid | Phytohemagglutinins | Cymarine |
| Ecdysone | bisphenol A | Eugenol |
| Medroxyprogesterone Acetate | R 848 | fragment C, human serum albumin |
| Genistein | Malathion | alpha-Tocopherol |
| Potassium Dichromate | N-Methylaspartate | infliximab |
| bafilomycin A | 6-bromoindirubin-3'-oxime | Estradiol |
| 4-biphenylamine | tenofovir | Dinoprostone |
| 2,2'-(hydroxynitrosohydrazono)bis-ethanamine | DDT | Enterotoxins |
| Diethylstilbestrol | benzyloxycarbonylleucyl-leucyl-leucine aldehyde | interferon alfa-2b |
| gamma-Tocopherol | cyanoginosin LR | Glycerol |
| Folic Acid | Azacitidine | vorinostat |
| sorafenib | procyanidin | Progesterone |
| Tunicamycin | Pregnenolone Carbonitrile | Cardiotoxins |
| Dexamethasone | Calcitriol | Nifedipine |
| Captopril | Piperonyl Butoxide | Plicamycin |
| Acetaminophen | indole-3-carbinol | Levonorgestrel |
| Vincristine | Cholecalciferol | Thapsigargin |
| Ranitidine | pristane | quintozene |
| Theophylline | triadimefon | Doxepin |
| Choline | 2-(4-morpholinyl)-8-phenyl-4H-1-benzopyran-4-one | Azoxymethane |
| Y 27632 | rosiglitazone | letrozole |
| Enalapril | Dactinomycin | Acetylcysteine |
| Cisplatin | Phosphorylcholine | cobaltous chloride |
| Aflatoxin B1 | Propylthiouracil | colforsin |
| Cadmium | Insulin | Ecdysterone |
| lead acetate | 4-hydroxytamoxifen | Paclitaxel |
| Promethazine | Chlorpromazine | Camptothecin |
| Ionomycin | Amitrole | Ethanol |
| Isoniazid | sodium arsenite | Pyrazinamide |
| Chlorambucil | Ultraviolet Rays | 4-(5-benzo(1,3)dioxol-5-yl-4-pyridin-2-yl-1H-imidazol-2-yl)benzamide |
| bortezomib | imatinib | gefitinib |
| Ethinyl Estradiol | Vitamin K 3 | Hydroxyurea |

I2. Molecules that downregulate SLC36A4:

| | | |
|---|---|---|
| chromium hexavalent ion | 3-deazaneplanocin | 1-(2-cyano-3,12-dioxooleana-1,9-dien-28-oyl) imidazole |
| chromium hexavalent ion | 3-deazaneplanocin | 1-(2-cyano-3,12-dioxooleana-1,9-dien-28-oyl) imidazole |
| Metformin | Inosine Monophosphate | Am 580 |
| cryptoxanthin | lapatinib | 1-(5-Isoquinolinesulfonyl)-2-Methylpiperazine |
| SC 514 | 4-cyclododecyl-2,6-dimethylmorpholine acetate | 4-dichlorobenzene |
| Histidinol | Aphidicolin | N-(2-aminophenyl)-4-(N-(pyridin-3-ylmethoxycarbonyl)aminomethyl) benzamide |
| trichostatin A | Hemin | blebbistatin |
| Sirolimus | Quercetin | N-nitrosomorpholine |
| Azithromycin | decitabine | Methylene Chloride |
| Cycloheximide | TO-901317 | Poly I-C |
| lactacystin | Polychlorinated Biphenyls | Benzo(a)pyrene |
| fulvestrant | romidepsin | Diethylhexyl Phthalate |
| bicalutamide | Dinitrofluorobenzene | enzastaurin |
| monastrol | fluticasone | salmeterol |
| Doxycycline | Bucladesine | 2-dichlorobenzene |
| Calcium | 2-(1H-indazol-4-yl)-6-(4-methanesulfonylpiperazin-1-ylmethyl)-4-morpholin-4-ylthieno(3,2-d)pyrimidine | Calcium Chloride |
| halofuginone | 4-acetylaminofluorene | CPG-oligonucleotide |
| geldanamycin | Cyproterone Acetate | Phenobarbital |
| withaferin A | Hydrogen Peroxide | Raloxifene |
| bexarotene | Dimethyl Sulfoxide | Curcumin |

TABLE S1-continued

Molecules that regulate genes or gene products relevant to proline transport and metabolism.

| | | |
|---|---|---|
| atorvastatin | Doxorubicin | erlotinib |
| dihydroquinghaosu | piperaquine | fasudil |
| sapphyrin | BCG Vaccine | acidocin CH5, *Lactobacillus acidophilus* |
| Antigen-Antibody Complex | Lactic Acid | Vitamin E |
| bromobenzene | troglitazone | Zinc Oxide |
| Tacrine | phorbolol myristate acetate | pioglitazone |
| Ribavirin | Papaverine | Bleomycin |
| LBH589 | X-Rays | Ascorbic Acid |
| Cyclosporine | Daunorubicin | bevacizumab |
| Pyrogens | beta-Naphthoflavone | Ozone |
| 1-Methyl-3-isobutylxanthine | gatifloxacin | Methimazole |
| 2-Acetylaminofluorene | peginterferon alfa-2a | Tetradecanoylphorbol Acetate |
| chromium hexavalent ion | 3-deazaneplanocin | 1-(2-cyano-3,12-dioxooleana-1,9-dien-28-oyl) imidazole |
| Etoposide | docetaxel | beta-glycerophosphoric acid |
| leflunomide | Indomethacin | Diclofenac |
| Formaldehyde | Cyclophosphamide | Methotrexate |
| Valproic Acid | | |

J1. Molecules that upregulate SLC6A20:

| | | |
|---|---|---|
| Sulfamerazine | sodium selenate | gefitinib |
| dibenzazepine | Hemin | N,N-dimethylarginine |
| aluminum sulfate | fingolimod | 7-aminocephalosporanic acid |
| 1-Methyl-4-phenyl-1,2,3,6-tetrahydropyridine | MRK 003 | everolimus |
| acodazole | SB 203580 | carbinoxamine |
| Curcumin | Pizotyline | Cephalexin |
| picrotoxinin | trichlorofluoromethane | Chlorhexidine |
| bis(tri-n-butyltin)oxide | Perhexiline | picotamide |
| Tetradecanoylphorbol Acetate | Particulate Matter | naphthalan |
| thioperamide | Fursultiamin | levocabastine |
| erlotinib | isocorydine | ochratoxin A |
| Cyclopenthiazide | SEW2871 | esculetin |
| Atractyloside | Dihydrostreptomycin Sulfate | lobelanidine |
| acetorphan | Vehicle Emissions | Naltrexone |
| Loxapine | medrysone | Pancuronium |
| Ultraviolet Rays | cyanoginosin LR | Dichlororibofuranosylbenzimidazole |
| N-(2-cyclohexyloxy-4-nitrophenyl)methanesulfonamide | Pentetic Acid | iodoform |
| Pheniramine | Indapamide | Meptazinol |
| Flutamide | Acebutolol | Edrophonium |
| Spiramycin | Etiocholanolone | Alprostadil |
| boldine | asiaticoside | Loperamide |
| Sulfamethazine | gibberellic acid | citiolone |
| vanoxerine | Cefotaxime | Bicuculline |
| pyrvinium | hesperetin | Isradipine |
| Tiapamil Hydrochloride | Suloctidil | Ganciclovir |
| Paraquat | Selegiline | Mesalamine |
| diphenidol | Clodronic Acid | decitabine |
| Dilazep | Bleomycin | Hexetidine |
| Meclofenoxate | clemizole | Paclitaxel |
| bicalutamide | Gabexate | Enterotoxins |
| Sulfamerazine | sodium selenate | gefitinib |
| Heparin | Amiloride | triptolide |
| Cytokines | Metribolone | enzastaurin |
| Tranylcypromine | Am 580 | enterotoxin B, staphylococcal |
| flunisolide | Carboplatin | Zinc Oxide |
| Methylnitrosourea | trichostatin A | pramoxine |
| Sirolimus | Phenelzine | Hydrogen Peroxide |
| Reserpine | Genistein | phosphonoacetamide |
| Primaquine | Dihydrotestosterone | Flurbiprofen |
| Clonidine | glimepiride | Carbimazole |
| Fenoprofen | Fluorouracil | Chlorambucil |
| Naproxen | Roxithromycin | Valproic Acid |
| Chloroquine | Probenecid | geldanamycin |
| Ergocalciferols | Cortisone | Phenobarbital |
| Acyclovir | Nitrofurantoin | Pyrogens |
| Calcium | Neomycin | Ifosfamide |
| R 848 | X-Rays | imatinib |
| gatifloxacin | resveratrol | Cyclosporine |
| Quercetin | Nifedipine | Ranitidine |
| Azithromycin | Benzo(a)pyrene | Doxorubicin |
| Diethylstilbestrol | Tretinoin | Methyl Methanesulfonate |
| Lactic Acid | Azacitidine | Methapyrilene |
| Acetaminophen | Cisplatin | |

TABLE S1-continued

Molecules that regulate genes or gene products relevant to proline transport and metabolism.

J2. Molecules that downregulate SLC6A20:

| | | |
|---|---|---|
| Go 6976 | Progesterone | Parathion |
| testosterone 17 beta-cypionate | Apomorphine | Fonofos |
| Alpha-Amanitin | Shiga Toxin | Grape Seed Proanthocyanidins |
| shikonin | Malathion | sulfanilamide |
| Fusaric Acid | polidocanol | Teriparatide |
| Doxylamine | tibolone | Ethylene Oxide |
| mefexamide | infliximab | quintozene |
| Arecoline | Dextran Sulfate | caffeic acid |
| Gonadotropins | Estradiol | acyline |
| gabapentin | Puromycin | chlorcyclizine |
| sodium arsenite | 3-deazaneplanocin | Hydrochloric Acid |
| estradiol 3-benzoate | Isoniazid | Folic Acid |
| nilutamide | Eugenol | imiquimod |
| Levodopa | Rifampin | Diethylhexyl Phthalate |
| Chorionic Gonadotropin | Epitestosterone | Deoxyglucose |
| Go 6976 | Progesterone | Parathion |
| Luteinizing Hormone | Cocaine | Zinc |
| rosiglitazone | Anti-Retroviral Agents | bromodichloromethane |
| Captopril | Azoxymethane | bisphenol A |
| Choline | Methylene Chloride | Tetrachlorodibenzodioxin |
| efavirenz | Deferoxamine | Cholecalciferol |
| bortezomib | vorinostat | Dexamethasone |
| Clomipramine | Lamivudine | Etoposide |
| Diclofenac | Fluoxetine | Metformin |

K1. Molecules that upregulate SLC6A13:

| | | |
|---|---|---|
| sapphyrin | 1-(5-Isoquinolinesulfonyl)-2-Methylpiperazine | Furosemide |
| Diethylhexyl Phthalate | Chitosan | triptolide |
| Clofibrate | Ethyl Methanesulfonate | monastrol |
| Digitoxin | Isoflurane | Carteolol |
| phosphonoacetamide | Zinc Oxide | fosfosal |
| topiramate | Mexiletine | Carbarson |
| 2-nitrofluorene | flunisolide | tiaprofenic acid |
| sildenafil | Estradiol | Sulfameter |
| Proglumide | Cytokines | butenafine |
| deferiprone | hexachloroethane | Ethylene Glycol |
| Lidoflazine | sulforafan | cefepime |
| carcinine | Amiodarone | tenoxicam |
| prednicarbate | Meclofenamic Acid | Acetaminophen |
| lead tetraacetate | midecamycin | myricetin |
| Clarithromycin | Lithium Chloride | trovafloxacin |
| Propranolol | Amprolium | Simvastatin |
| shikonin | glycidol | ochratoxin A |
| scriptaid | sodium chlorate | Puromycin Aminonucleoside |
| VX | sulfathiazole | Talampicillin |
| Isoflurophate | Diclofenac | Auranofin |
| torsemide | bendazolic acid | Hymecromone |
| Busulfan | Deoxycholic Acid | sparfloxacin |
| phenylhydrazine | Vidarabine | Ibuprofen |
| Dichlororibofuranosylbenzimidazole | Lomustine | Clofibric Acid |
| Mianserin | troglitazone | picotamide |
| Pantothenic Acid | Quercetin | Penicillamine |
| Polychlorinated Biphenyls | Niacinamide | sodium nitrate |
| ponasterone A | Valproic Acid | Indomethacin |
| sapphyrin | 1-(5-Isoquinolinesulfonyl)-2-Methylpiperazine | Furosemide |
| Fenofibrate | oltipraz | Meclofenoxate |
| benoxaprofen | Dexamethasone | erlotinib |
| Xylazine | Minoxidil | Finasteride |
| Sulfachlorpyridazine | Aspirin | diindolylmethane |
| amitraz | Chlorzoxazone | tropisetron |
| Doxorubicin | Captopril | Meptazinol |
| vinylidene chloride | benphothiamine | Azaguanine |
| Perhexiline | compactin | phenethyl isothiocyanate |
| Diquat | Mitomycin | Neomycin |
| zaleplon | trichostatin A | Testosterone |
| balsalazide | alitretinoin | hesperetin |
| Kinetin | Cycloheximide | rofecoxib |
| chloroxylenol | Lindane | Dimethylformamide |
| sesamin | Ciprofloxacin | Staurosporine |
| Vincristine | Cefixime | fluvastatin |
| aplidine | Oxyquinoline | Ticrynafen |
| Azacitidine | Spironolactone | venlafaxine |
| Sulfadoxine | Tocainide | Pregnenolone |

TABLE S1-continued

Molecules that regulate genes or gene products relevant to proline transport and metabolism.

| | | |
|---|---|---|
| ibufenac | graveoline | 1-hydroxycholecalciferol |
| Amlodipine | Carmustine | phenothiazine |
| Prednisolone | romidepsin | bromfenac |
| Procarbazine | Thiabendazole | CPG-oligonucleotide |
| tranilast | sodium selenate | Methyl Methanesulfonate |
| Aristolochic Acids | terbinafine | carbinoxamine |
| Digoxin | Gliclazide | Pivampicillin |
| leflunomide | oxcarbazepine | Gentamicins |
| Fenbendazole | rosiglitazone | decitabine |
| Methylcholanthrene | lead acetate | Megestrol Acetate |
| Chlorambucil | Pravastatin | homatropine |
| dioxybenzone | Betamethasone | 6-methoxy-2-naphthylacetic acid |
| Promethazine | Ritonavir | modafinil |
| dexibuprofen | Lovastatin | Kanamycin |
| Naproxen | Nevirapine | hydrastinine |
| Etoposide | Thioguanine | Triamterene |
| Cyproterone Acetate | Ofloxacin | 4-dichlorobenzene |
| Deferoxamine | nabumetone | sodium arsenite |
| R 848 | bisphenol A | sangivamycin |
| Epirubicin | Benzocaine | wortmannin |
| sapphyrin | 1-(5-Isoquinolinesulfonyl)-2-Methylpiperazine | Furosemide |
| Netilmicin | Nitrofurantoin | 1,2,3-trichloropropane |
| Raloxifene | Cisplatin | BCG Vaccine |
| Canavanine | lamotrigine | hydroxyachillin |
| Antibodies, Monoclonal | Nitrofurazone | famciclovir |
| Mercuric Chloride | Triiodothyronine | Droperidol |
| irinotecan | Acetazolamide | Maprotiline |
| Tacrine | Thiostrepton | Lithium |
| cerivastatin | Tretinoin | Dibucaine |
| Domperidone | Rifabutin | Benzethonium |
| Camptothecin | Azoxymethane | Imipramine |
| Disopyramide | Pregnenolone Carbonitrile | Losartan |
| Ketoprofen | Methotrexate | Baclofen |
| SU 5402 | Vitamin K 3 | Diflunisal |
| alpha-Tocopherol | vorinostat | Sulpiride |
| Luteolin | Cyclosporine | valsartan |
| Genistein | phenacemide | 1-Methyl-3-isobutylxanthine |
| Ascorbic Acid | N,N'-diphenyl-4-phenylenediamine | 2-(4-morpholinyl)-8-phenyl-4H-1-benzopyran-4-one |
| Reserpine | Erythromycin | Pergolide |
| Streptomycin | Nitric Oxide | Lorazepam |
| Chlorpyrifos | lapatinib | Melphalan |
| efavirenz | atorvastatin | bortezomib |
| Enalapril | Dactinomycin | Fluorouracil |
| Lamivudine | Hydroxyurea | Isoproterenol |

K2. Molecules that downregulate SLC6A13:

| | | |
|---|---|---|
| Aroclors | ferric nitrilotriacetate | Ethionine |
| Aminosalicylic Acid | Methapyrilene | amineptin |
| tianeptine | carvedilol | Labetalol |
| Paclitaxel | Itraconazole | Yohimbine |
| desloratadine | sulconazole | Sotalol |
| Methiocarb | Amantadine | coumarin |
| Chloroquine | Colchicine | cyanoginosin LR |
| TO-901317 | Hexachlorobenzene | Doxepin |
| Omeprazole | tenidap | Methylcellulose |
| piperidolate | Monocrotaline | Estriol |
| beta-Naphthoflavone | Ethinyl Estradiol | Safrole |
| norethindrone acetate | Chloroform | lansoprazole |
| Aroclors | ferric nitrilotriacetate | Ethionine |
| Bacitracin | Tinidazole | Fluoxetine |
| Zidovudine | Ketoconazole | Tacrolimus |
| Clomipramine | Isotretinoin | gibberellic acid |
| Etodolac | Sulfisoxazole | Granisetron |
| lobelanidine | Loratadine | Dicumarol |
| Citalopram | Cyproterone | Hypericum extract LI 160 |
| methylparaben | N-nitrosomorpholine | Nortriptyline |
| Clozapine | Trimethadione | Metronidazole |
| KCB-1 protein, recombinant | epidermal growth factor (1-45) | Ethisterone |
| meloxicam | 2-Acetylaminofluorene | sunitinib |
| Tetracycline | Fursultiamin | Carbenoxolone |
| Desipramine | Carbon Tetrachloride | N-acetylsphingosine |
| Miconazole | Naloxone | gefitinib |
| Amphetamine | Secobarbital | bromobenzene |
| valdecoxib | Bretylium Tosylate | Chlorpromazine |
| Atropine | nimesulide | Amitriptyline |

TABLE S1-continued

Molecules that regulate genes or gene products relevant to proline transport and metabolism.

| | | |
|---|---|---|
| Doxapram | Ifosfamide | Lithium Carbonate |
| Acebutolol | Khellin | Cinnarizine |
| Thioctic Acid | Diethylstilbestrol | piperacetazine |
| mebeverine | pralidoxime | Ethambutol |
| Mestranol | Clotrimazole | flubendazole |
| Methyltestosterone | Sarin | eticlopride |
| aristolochic acid | Diethylnitrosamine | Fonofos |
| Mycotoxins | Fluphenazine | Guanfacine |
| oxolamine | Metformin | Stavudine |
| Teriparatide | apicidin | Stanozolol |
| Mephentermine | pantoprazole | Isoniazid |
| Deoxyglucose | naringin | Diazepam |
| Rifampin | 6-Mercaptopurine | crotamiton |
| norflurane | 4-octylphenol | Sirolimus |
| Sulbactam | Cytarabine | Ramipril |
| Bicuculline | Vinblastine | Nifedipine |
| Paroxetine | Chlortetracycline | sulfabenzamide |
| Allopurinol | Cortisone | 1,2-dithiol-3-thione |
| HC toxin | rabeprazole | Sertraline |
| harman | acetovanillone | Mebendazole |
| Melatonin | Danazol | Hexamethonium |
| letrozole | Choline | marimastat |
| Aflatoxin B1 | Cetylpyridinium | pristane |
| Aroclors | ferric nitrilotriacetate | Ethionine |
| Chlormezanone | Carbamazepine | 2,3-dioxo-6-nitro-7-sulfamoylbenzo(f)quinoxaline |
| Mifepristone | Tamoxifen | Roxithromycin |
| 4-nonylphenol | DDT | dexamisole |
| Ajmaline | Promazine | Folic Acid |
| cineole | pioglitazone | Propylthiouracil |
| Phenobarbital | Bezafibrate | testosterone 17 beta-cypionate |
| Abscisic Acid | olanzapine | 4-biphenylamine |
| salicylamide | Phalloidine | Azithromycin |
| beta-cyclodextrin-benzaldehyde | Ethionamide | Clonazepam |
| Vancomycin | ferulic acid | Tolazamide |
| tetrahydrotriamcinolone | Cytochalasin B | Benzo(a)pyrene |
| Cyclophosphamide | Azauridine | amlexanox |
| Fluocinolone Acetonide | Haloperidol | temozolomide |
| Minocycline | nimetazepam | Norethindrone |
| sorafenib | nateglinide | Dihydrotestosterone |
| 2-dichlorobenzene | Tetrachlorodibenzodioxin | Fluconazole |
| Alpha-Amanitin | idebenone | Amoxicillin |
| Vitamin E | Gemfibrozil | Bromisovalum |
| ascorbate-2-phosphate | Catechin | tosufloxacin |
| Ampicillin | Nafenopin | Nitrazepam |
| Chlormadinone Acetate | anastrozole | Spectinomycin |
| Glipizide | Econazole | Clomiphene |
| Sulindac | Azathioprine | quetiapine |
| Dinitrofluorobenzene | Dimenhydrinate | Clonidine |
| Amrinone | Thioacetamide | Levobunolol |
| Cephaloridine | Vanadates | Neostigmine |
| quintozene | Enoxacin | bromodichloromethane |
| diflorasone diacetate | Altretamine | Phenacetin |
| Phenelzine | Amoxapine | Streptozocin |
| Procainamide | artemisinine | lomefloxacin |
| enterotoxin B, staphylococcal | direct black 3 | Oxazepam |
| Lead | estradiol 3-benzoate | alginic acid |
| Levonorgestrel | Phenol | Phenformin |
| mono-(2-ethylhexyl)phthalate | Chlorpheniramine | LBH589 |
| Methylnitrosourea | pirinixic acid | Ethacrynic Acid |
| Chloramphenicol | Saquinavir | versipelostatin |
| Calcitriol | imatinib | 6-bromoindirubin-3'-oxime |
| doxofylline | Bupropion | perfluorooctanoic acid |
| Aroclors | ferric nitrilotriacetate | Ethionine |
| Diltiazem | Caffeine | Disulfiram |
| Zalcitabine | Nicotine | Hydroxyzine |
| celecoxib | Theophylline | tenofovir |
| Perphenazine | Shiga Toxin | Rolipram |
| Ticlopidine | | |

L1. Molecules that upregulate SLC6A14:

| | | |
|---|---|---|
| infliximab | moroxydine | Diethylhexyl Phthalate |
| Progesterone | N-methylolacrylamide | quintozene |
| Calcium | Trichloroepoxypropane | naphthalenediimide |
| bisphenol A | Lithium Carbonate | naphthalan |
| 8-Bromo Cyclic Adenosine Monophosphate | Vincamine | Vitamin K 2 |

TABLE S1-continued

Molecules that regulate genes or gene products relevant to proline transport and metabolism.

| | | |
|---|---|---|
| Methylene Chloride | cidofovir | Pyrogens |
| Dimethylnitrosamine | pipenzolate | Bismuth |
| Practolol | dipropizine | Penicillin G |
| Ticlopidine | 4-hydroxyestradiol-17 beta | 8-(3-Chlorostyryl)-1,3,7-trimethylxanthine |
| Pivampicillin | Quinidine | Ethinyl Estradiol |
| Idoxuridine | Terbutaline | BW B70C |
| 4,5-dianilinophthalimide | Enterotoxins | Netilmicin |
| CD 437 | 1-Methyl-3-isobutylxanthine | Amrinone |
| Cefotetan | 4'-N-benzoylstaurosporine | N-Methylscopolamine |
| vanadium pentoxide | Pregnenolone | Poly I-C |
| Hydrochloric Acid | picrotoxinin | Ethynodiol Diacetate |
| fenbufen | Hymecromone | Tetracycline |
| Pyocyanine | Spectinomycin | Pentamidine |
| Ultraviolet Rays | Dibucaine | Cyclopenthiazide |
| Tetradecanoylphorbol Acetate | Bleomycin | irinotecan |
| mycophenolate mofetil | lobelanidine | Proscillaridin |
| letrozole | canadine | Metronidazole |
| benfluorex | Clobetasol | daidzein |
| Cytochalasin B | Antimycin A | vinclozolin |
| Lactic Acid | Estrogens | 4-methyl-N-(3-(4-methylimidazol-1-yl)-5-(trifluoromethyl)phenyl)-3-((4-pyridin-3-ylpyrimidin-2-yl)amino)benzamide |
| wortmannin | Flecainide | Dexamethasone |
| Minoxidil | decitabine | Folic Acid |
| infliximab | moroxydine | Diethylhexyl Phthalate |
| Vehicle Emissions | Piperonyl Butoxide | Podophyllotoxin |
| Dantrolene | Zalcitabine | Dichlororibofuranosylbenzimidazole |
| blebbistatin | Ascorbic Acid | Phosgene |
| Bupropion | Finasteride | Insulin |
| U 0126 | Disopyramide | 4-nonylphenol |
| docetaxel | Epitestosterone | celecoxib |
| Particulate Matter | colforsin | acidocin CH5, *Lactobacillus acidophilus* |
| Tetrachlorodibenzodioxin | pralidoxime | quelamycin |
| 4-(5-benzo(1,3)dioxol-5-yl-4-pyridin-2-yl-1H-imidazol-2-yl)benzamide | Methapyrilene | Ribavirin |
| Dactinomycin | Carboplatin | |

| L2. Molecules that downregulate SLC6A14: | | |
|---|---|---|
| 1-amino-2,4-dibromoanthraquinone | fulvestrant | trimethobenzamide |
| Fluocinonide | gefitinib | tetrafluoroethylene |
| 4-amino-6-hydrazino-7-beta-D-ribofuranosyl-7H-pyrrolo(2,3-d)-pyrimidine-5-carboxamide | iodoform | Norethynodrel |
| Dihydroergotamine | solasodine | Benzo(a)pyrene |
| Milrinone | Thyroxine | 4-acetylaminofluorene |
| Estradiol | Levonorgestrel | Dilazep |
| Curcumin | Genistein | tris(2,3-dibromopropyl)phosphate |
| Thiostrepton | verteporfin | 15-deoxy-delta(12,14)-prostaglandin J2 |
| Corticosterone | withaferin A | Diethylstilbestrol |
| Azoxymethane | Reserpine | 2-methoxyestradiol |
| phthalylsulfathiazole | Oxytocin | Apigenin |
| Scopolamine Hydrobromide | medrysone | 4-biphenylamine |
| meropenem | Carbachol | Niridazole |
| Chloroquine | 4-hydroxytamoxifen | diindolylmethane |
| Diazinon | Ethisterone | Isradipine |
| Alcuronium | chlorinated dibenzofurans | Trimipramine |
| tribenoside | Oxyphenbutazone | tyrphostin AG 1478 |
| Luteolin | Furazolidone | Atovaquone |
| Halcinonide | salmeterol | ergocryptine |
| Bromocriptine | ebselen | Clioquinol |
| Sulfisoxazole | Promegestone | Am 580 |
| polidocanol | chloropyramine | Trimethoprim |
| 1-amino-2,4-dibromoanthraquinone | fulvestrant | trimethobenzamide |
| fluticasone | Phenoxybenzamine | rottlerin |
| piperlonguminine | lansoprazole | mometasone furoate |
| hydrastine | flunisolide | Zimeldine |
| Amoxicillin | Equilin | Cotinine |
| everolimus | skimmianine | 17-(dimethylaminoethylamino)-17-demethoxygeldanamycin |
| harpagoside | bromperidol | Isosorbide |
| prednicarbate | rosiglitazone | Theobromine |
| Etidronic Acid | Flavoxate | Clofazimine |
| sapphyrin | LBH589 | Fludrocortisone |

TABLE S1-continued

Molecules that regulate genes or gene products relevant to proline transport and metabolism.

| | | |
|---|---|---|
| Gossypol | resveratrol | cephaelin |
| Felodipine | Malathion | Imipenem |
| 1-(5-Isoquinolinesulfonyl)-2-Methylpiperazine | Natamycin | imatinib |
| epitiostanol | zardaverine | Catechin |
| phenethyl isothiocyanate | Atenolol | securinine |
| 17-(allylamino)-17-demethoxygeldanamycin | 6-thioguanosine | Prenylamine |
| sanguinarine | Propidium | discretamine |
| Androsterone | Lindane | ciclopirox |
| Methylergonovine | dironyl | Betahistine |
| Budesonide | famprofazone | Ethacrynic Acid |
| Clonidine | tripterine | Metaraminol |
| acacetin | Dextran Sulfate | Quercetin |
| nifuroxazide | Astemizole | oltipraz |
| Dinitrofluorobenzene | Sulfamerazine | methylbenzethonium |
| Vancomycin | triptolide | Vitamin K 3 |
| Tolbutamide | buparvaquone | Cadmium |
| sulconazole | enzastaurin | Bucladesine |
| Betaxolol | Griseofulvin | Bepridil |
| cinchonine | geldanamycin | Azathioprine |
| Vitamin E | Sulfamethoxazole | sulforafan |
| Trifluoperazine | Paclitaxel | vanoxerine |
| monorden | Diclofenac | Doxorubicin |
| Tretinoin | parthenolide | Mefloquine |
| Tunicamycin | torsemide | Thapsigargin |
| Lithium | Promazine | monastrol |
| GW 3965 | Selenomethionine | Aflatoxin B1 |
| Primaquine | Hydrocortisone | Raloxifene |
| 1-amino-2,4-dibromoanthraquinone | fulvestrant | trimethobenzamide |
| Mexiletine | dibenzazepine | Dipyrone |
| Dipyridamole | Freund's Adjuvant | Papaverine |
| 2-(4-morpholinyl)-8-phenyl-4H-1-benzopyran-4-one | Cyclosporine | Hydrogen Peroxide |
| trichostatin A | Valproic Acid | Triiodothyronine |
| 1-Methyl-4-phenyl-1,2,3,6-tetrahydropyridine | enterotoxin B, staphylococcal | Puromycin |
| Isotretinoin | Pyrazinamide | Cycloheximide |
| benzyloxycarbonylleucyl-leucyl-leucine aldehyde | Estriol | vorinostat |
| erlotinib | Testosterone | Nifedipine |
| Carbamazepine | dasatinib | Chlorpromazine |
| Amiodarone | Hemin | Ketoconazole |
| Fluphenazine | Vincristine | Omeprazole |
| Sirolimus | Cyclophosphamide | Simvastatin |
| Lovastatin | Tamoxifen | Acetaminophen |
| Thioacetamide | Ethanol | Cisplatin |

M1. Molecules that upregulate SLC6A15:

| | | |
|---|---|---|
| flavanone | PI103 | alginic acid |
| Ethylene Dibromide | Oxymetholone | Hydroxyzine |
| Azacitidine | Cefixime | Cymarine |
| 4-octylphenol | Dimethadione | Doxycycline |
| Megestrol Acetate | Alprazolam | nimesulide |
| Diflunisal | nifenazone | versipelostatin |
| Finasteride | Diethylstilbestrol | Miconazole |
| Calcium | temsirolimus | Idarubicin |
| Ethisterone | Mephenytoin | Valproic Acid |
| Chorionic Gonadotropin | edelfosine | Carboplatin |
| Diethylhexyl Phthalate | vanadyl sulfate | Bromisovalum |
| Hydrochloric Acid | Norethindrone | X-Rays |
| Econazole | Chlorambucil | leflunomide |
| Simvastatin | Trichloroepoxypropane | Chlorpromazine |
| Ascorbic Acid | cefepime | Plicamycin |
| 2-(1H-indazol-4-yl)-6-(4-methanesulfonylpiperazin-1-ylmethyl)-4-morpholin-4-ylthieno(3,2-d)pyrimidine | LBH589 | Ibuprofen |
| Caerulein | Ethamsylate | Deoxyglucose |
| flavanone | PI103 | alginic acid |
| quintozene | pioglitazone | Pargyline |
| flumequine | Clopenthixol | gefitinib |
| Lactic Acid | amprenavir | N-methylolacrylamide |
| Rifampin | Enterotoxins | clemizole |
| Ivermectin | Acetylmuramyl-Alanyl-Isoglutamine | Nadolol |
| Cytokines | Clotrimazole | oxaliplatin |
| picotamide | Carbon Tetrachloride | Secobarbital |

TABLE S1-continued

Molecules that regulate genes or gene products relevant to proline transport and metabolism.

| | | |
|---|---|---|
| bromfenac | beta-cyclodextrin-benzaldehyde | Chloroquine |
| Rolitetracycline | Niacinamide | MRK 003 |
| Cytarabine | Equilin | Glycocholic Acid |
| Cyclopenthiazide | suxibuzone | tranilast |
| Metformin | Isocarboxazid | Hydrocortisone |
| ovalicin | vinclozolin | Ethylene Glycol |
| Sulindac | dexamisole | Hexestrol |
| Aztreonam | Epirizole | Practolol |
| tetrahydrotriamcinolone | furaltadon | Carbamazepine |
| Nafronyl | 3-hydroxyacetanilide | Butyric Acid |
| vorinostat | naftopidil | flunisolide |
| Sirolimus | Clofibrate | bromobenzene |
| Ultraviolet Rays | Acetylcysteine | Methylene Chloride |
| atorvastatin | 2-methoxyestradiol | Zidovudine |
| Cholecalciferol | Guanfacine | gatifloxacin |
| bortezomib | Puromycin | repaglinide |
| 6-Mercaptopurine | phthalylsulfathiazole | Mifepristone |
| Spectinomycin | candesartan | olanzapine |
| beta-glycerophosphoric acid | Ondansetron | Dimenhydrinate |
| Kainic Acid | Acepromazine | N-nitrosomorpholine |
| Bezafibrate | Tunicamycin | Carbachol |
| Deoxycholic Acid | rimexolone | Tobramycin |
| Mesalamine | Acetohexamide | Ethosuximide |
| Fluorometholone | Piroxicam | Diazepam |
| Cyclosporine | Heparin | Naloxone |
| Propafenone | Aphidicolin | Bacitracin |
| isoascorbic acid | Glyburide | cyclonite |
| Baclofen | Methyl Methanesulfonate | Amoxapine |
| Gliclazide | Dicumarol | Hydralazine |
| Cromolyn Sodium | Clomipramine | Amphetamine |
| naphthalan | vinorelbine | sodium arsenite |
| Amikacin | Formaldehyde | oxcarbazepine |
| flavanone | PI103 | alginic acid |
| Insulin | Levonorgestrel | Amiloride |
| Follicle Stimulating Hormone | Nitrendipine | Phenacetin |
| Asbestos | scriptaid | Particulate Matter |
| cerivastatin | 4-methyl-N-(3-(4-methylimidazol-1-yl)-5-(trifluoromethyl)phenyl)-3-((4-pyridin-3-ylpyrimidin-2-yl)amino)benzamide | sulconazole |
| quetiapine | celecoxib | Thalidomide |
| Trenbolone Acetate, (17beta)-isomer | Alpha-Amanitin | Perhexiline |
| Sulfisoxazole | 2-Acetylaminofluorene | Camptothecin |
| Zalcitabine | Ergocalciferols | Methylcholanthrene |
| Dantrolene | Nortriptyline | Fenofibrate |
| Griseofulvin | Amiodarone | Sparteine |
| Iproniazid | fomepizole | Ethinyl Estradiol |
| torsemide | Luteinizing Hormone | Citalopram |
| Lithium | Indomethacin | Methyldopa |
| Hydrochlorothiazide | Clofibric Acid | Lovastatin |
| Progesterone | zomepirac | Fluorouracil |
| Oxymetazoline | Bupropion | meloxicam |
| pralidoxime | Danazol | Calcitriol |
| Clozapine | Dactinomycin | Ketoconazole |
| Colchicine | Hydroxyurea | Ticlopidine |
| Azathioprine | Chlorpropamide | Bithionol |
| Tacrolimus | Azithromycin | Tetradecanoylphorbol Acetate |
| Vitamin K 3 | Isoniazid | Gemfibrozil |
| Atropine | Methapyrilene | Dimethylformamide |
| Terbutaline | Isoproterenol | |

M2. Molecules that downregulate SLC6A15:

| | | |
|---|---|---|
| tianeptine | Rotenone | polidocanol |
| Enalapril | 3-deazaneplanocin | Hydrogel |
| Ranitidine | geldanamycin | Botulinum Toxins |
| Antimycin A | 1-ethyl-2-benzimidazolinone | epoxomicin |
| Mitomycin | Corticosterone | Estriol |
| lactacystin | Tretinoin | U 0126 |
| Vitamin A | 4-(4-fluorophenyl)-2-(4-hydroxyphenyl)-5-(4-pyridyl)imidazole | Gonadotropins |
| Amphotericin B | Thioguanine | Fluoxetine |
| tianeptine | Rotenone | polidocanol |
| fasudil | decitabine | Gentamicins |
| trichostatin A | Estradiol | 1-amino-2,4-dibromoanthraquinone |
| temozolomide | Pyrazinamide | Cadmium |
| Promegestone | Chlorpyrifos | clopidogrel |

TABLE S1-continued

Molecules that regulate genes or gene products relevant to proline transport and metabolism.

| | | |
|---|---|---|
| Ouabain | mycophenolate mofetil | Diethylnitrosamine |
| Timolol | bisphenol A | Ceftriaxone |
| 25-hydroxycholesterol | Genistein | Tubocurarine |
| alpha-Amino-3-hydroxy-5-methyl-4-isoxazolepropionic Acid | Doxorubicin | Etoposide |
| Ifosfamide | Poly I-C | Sumatriptan |
| 4-(5-benzo(1,3)dioxol-5-yl-4-pyridin-2-yl-1H-imidazol-2-yl)benzamide | cyanopindolol | bafilomycin A |
| Ketamine | Paclitaxel | Sarin |
| Sotalol | Procarbazine | Atrazine |
| harman | Procainamide | Dexamethasone |
| lacidipine | n-hexanal | SB 203580 |
| Phenylephrine | Chitosan | Quercetin |
| 17-(allylamino)-17-demethoxygeldanamycin | Propranolol | lead tetraacetate |
| 2-(4-morpholinyl)-8-phenyl-4H-1-benzopyran-4-one | Streptomycin | Cisplatin |
| efavirenz | Lidocaine | cidofovir |
| Carbimazole | sildenafil | Acrolein |
| Acyclovir | enterotoxin B, staphylococcal | Y 27632 |
| Losartan | Lead | Loratadine |
| blebbistatin | Bleomycin | 4-hydroxytamoxifen |
| Dimethyl Sulfoxide | sulforafan | ciprofibrate |
| Vecuronium Bromide | N-Methyl-3,4-methylenedioxyamphetamine | linalool |
| fulvestrant | Immunotoxins | Lamivudine |
| Oxazepam | sodium selenate | 1-Methyl-3-isobutylxanthine |
| famciclovir | Folic Acid | Pyrogens |
| Anti-Retroviral Agents | Diphenhydramine | triptolide |
| Deferoxamine | Metribolone | sanguinarine |
| Triiodothyronine | Monocrotaline | gabapentin |
| Phenobarbital | Tranylcypromine | erlotinib |
| Captopril | Phenytoin | Ozone |
| Daunorubicin | Ethanol | Penicillamine |
| docetaxel | Tetrachlorodibenzodioxin | imatinib |
| tianeptine | Rotenone | polidocanol |
| Cyclophosphamide | Benzo(a)pyrene | Thapsigargin |
| cobaltous chloride | infliximab | rituximab |
| rosiglitazone | Dihydrotestosterone | Methotrexate |
| Nicotine | Forskolin | Epirubicin |
| Levodopa | Choline | |

N1. Molecules that upregulate SLC6A17:

| | | |
|---|---|---|
| alpha-Amino-3-hydroxy-5-methyl-4-isoxazolepropionic Acid | Deoxycholic Acid | alpha-Tocopherol |
| gamma-Tocopherol | 2-tert-butylhydroquinone | Enterotoxins |
| Dactinomycin | Tretinoin | Polychlorinated Biphenyls |
| trichostatin A | BCG Vaccine | LBH589 |
| Dichlororibofuranosylbenzimidazole | Hydrocortisone | 8-aminohexylamino CAMP |
| cobaltous chloride | Oxazepam | buparvaquone |
| Bicuculline | vinclozolin | SEW2871 |
| Epitestosterone | Lithium Chloride | AICA ribonucleotide |
| Cholecalciferol | enzastaurin | Bupropion |
| SU 5402 | Immunoglobulins, Intravenous | Diethylhexyl Phthalate |
| pirinixic acid | Plicamycin | Bucladesine |
| Insulin | Vincristine | 1-Methyl-3-isobutylxanthine |
| Methylene Chloride | Ethanol | Hydroxyurea |
| Oxyquinoline | Cycloheximide | Fluoxetine |
| Hydrogen Peroxide | decitabine | Growth Hormone |
| Cyclosporine | R 848 | Deferoxamine |
| vorinostat | Methimazole | Quercetin |
| Nifedipine | Cisplatin | Testosterone |
| Acetaminophen | Doxorubicin | Hemin |
| Phenobarbital | | |

N2. Molecules that downregulate SLC6A17:

| | | |
|---|---|---|
| Tranylcypromine | fasudil | Ouabain |
| 4-hydroxy-2-nonenal | Phorbol Esters | Forskolin |
| Pyrazinamide | Ethambutol | Tetrahydrocannabinol |
| Rifampin | imiquimod | Lithium |
| Staurosporine | Isoniazid | Zinc |
| monastrol | HC toxin | lactacystin |
| N-Methylaspartate | Dimethyl Sulfoxide | Pentachlorophenol |
| Coumaphos | Clodronic Acid | 4-biphenylamine |
| Tranylcypromine | fasudil | Ouabain |

TABLE S1-continued

Molecules that regulate genes or gene products relevant to proline transport and metabolism.

| | | |
|---|---|---|
| SB 203580 | Levodopa | 1-(5-Isoquinolinesulfonyl)-2-Methylpiperazine |
| Methamphetamine | Hydroxyzine | blebbistatin |
| Bleomycin | quintozene | bis (tri-n-butyltin)oxide |
| 1,2-dilinolenoyl-3-(4-aminobutyryl)propane-1,2,3-triol phosphonoacetamide | Camptothecin | scriptaid |
| | Cefuroxime | Glycerol |
| Y 27632 | apicidin | Luteinizing Hormone |
| bromodichloromethane | Freund's Adjuvant | Niacinamide |
| naphthalene | Ultraviolet Rays | Immunotoxins |
| Mycophenolic Acid | Estradiol | resveratrol |
| Phytohemagglutinins | Fluorouracil | troglitazone |
| Captopril | Azoxymethane | Ozone |
| Estriol | Dexamethasone | Rotenone |
| gefitinib | CPG-oligonucleotide | quelamycin |
| pioglitazone | bisphenol A | rosiglitazone |
| Benzo(a)pyrene | Alpha-Amanitin | Methotrexate |
| Tamoxifen | Amiodarone | Cyclophosphamide |
| Etoposide | Paclitaxel | Tunicamycin |
| bortezomib | erlotinib | X-Rays |
| Tetradecanoylphorbol Acetate | Diethylstilbestrol | Carbon Tetrachloride |
| Progesterone | Valproic Acid | |

O1. Molecules that upregulate SLC6A19:

| | | |
|---|---|---|
| 4-hydroxy-2-nonenal | imatinib | pelargonic acid |
| neuropeptide Y (18-36) | Paclitaxel | Fenretinide |
| Carboplatin | Testosterone | lysophosphatidic acid |
| Tetrachlorodibenzodioxin | Platelet Activating Factor | Inosine Monophosphate |
| Nicotine | TO-901317 | 4'-N-benzoylstaurosporine |
| 5'-methylthioadenosine | fulvestrant | gefitinib |
| dihydroquinghaosu | piperaquine | Oxyquinoline |
| Doxorubicin | monastrol | sulforafan |
| 2-methoxyestradiol | SU 5402 | sangivamycin |
| Sodium Dodecyl Sulfate | decitabine | Nitric Oxide |
| Perhexiline | SC 514 | imiquimod |
| Immunoglobulin G | dibenzazepine | enzastaurin |
| Reserpine | Cisplatin | bicalutamide |
| testosterone 17 beta-cypionate | Cefuroxime | Dactinomycin |
| blebbistatin | Methylnitrosourea | vorinostat |
| 4-hydroxy-2-nonenal | imatinib | pelargonic acid |
| Azacitidine | Estradiol | efavirenz |
| Alpha-Amanitin | Enterotoxins | geldanamycin |
| Mannitol | Ethanol | Tolbutamide |
| Vitamin E | 1-Methyl-3-isobutylxanthine | Metformin |
| Hydrogen Peroxide | Theophylline | trichostatin A |
| Lamivudine | Amphotericin B | 2-Acetylaminofluorene |
| BCG Vaccine | beta-glycerophosphoric acid | Dexamethasone |
| Phenobarbital | Diethylnitrosamine | Cyclosporine |
| Methapyrilene | Indomethacin | Colchicine |
| Benzo(a)pyrene | nimesulide | Gentamicins |
| Sirolimus | Fluorouracil | Doxycycline |
| X-Rays | Tretinoin | Acetaminophen |

O2. Molecules that downregulate SLC6A19:

| | | |
|---|---|---|
| Fonofos | beta-cyclodextrin-benzaldehyde | Parathion |
| cyclonite | motexafin gadolinium | 8-aminohexylamino CAMP |
| phorbolol myristate acetate | R 848 | Beclomethasone |
| Concanavalin A | alpha-Amino-3-hydroxy-5-methyl-4-isoxazolepropionic Acid | Folic Acid |
| Ionomycin | alitretinoin | Choline |
| Epitestosterone | Cholecalciferol | Ascorbic Acid |
| Tetradecanoylphorbol Acetate | shikonin | direct black 3 |
| Am 580 | Anti-Retroviral Agents | Deoxyglucose |
| sodium arsenite | Freund's Adjuvant | Brefeldin A |
| Palmitic Acid | aluminum sulfate | Poly I-C |
| Bicuculline | infliximab | Chloroquine |
| Dinitrofluorobenzene | pioglitazone | Cycloheximide |
| Phytohemagglutinins | Kainic Acid | CPG-oligonucleotide |
| Tamoxifen | Captopril | bisphenol A |
| Insulin | rituximab | Dihydrotestosterone |
| Methotrexate | Ribavirin | Carbon Tetrachloride |

TABLE S1-continued

Molecules that regulate genes or gene products relevant to proline transport and metabolism.

P1. Molecules that upregulate SLC38A2:

| | | |
|---|---|---|
| 2-tert-butyl-9-fluoro-3,6-dihydro-7H-benz(h)imidazo(4,5-f)isoquinoline-7-one | apratoxin A | 1-hydroxycholecalciferol |
| Niacin | 2-Acetylaminofluorene | Zalcitabine |
| pyrvinium | eseroline | Clomipramine |
| Ethionamide | N,N'-diphenyl-4-phenylenediamine | Tranylcypromine |
| 2-tert-butyl-9-fluoro-3,6-dihydro-7H-benz(h)imidazo(4,5-f)isoquinoline-7-one | apratoxin A | 1-hydroxycholecalciferol |
| motexafin gadolinium | Dichlorvos | closantel |
| Phenacetin | Aspirin | methylparaben |
| Sotalol | phenylhydrazine | methyl salicylate |
| ferulic acid | salicylamide | Clarithromycin |
| Chlorpromazine | Caffeine | compactin |
| lactacystin | Niclosamide | Nitrofurantoin |
| ibufenac | trovafloxacin | Bromhexine |
| temafloxacin | Praziquantel | Rolipram |
| Shiga Toxin | Methazolamide | Fenbendazole |
| Cinnarizine | Thioridazine | Mianserin |
| Ergocalciferols | Carbamazepine | Theophylline |
| Baclofen | Monensin | Cholecalciferol |
| Foscarnet | chloropyramine | Gentian Violet |
| Norepinephrine | vinylidene chloride | coumarin |
| ipriflavone | Trimeprazine | Buthionine Sulfoximine |
| Ticrynafen | zaleplon | Fluphenazine |
| Chloramphenicol | Acetaminophen | butenafine |
| Chlorhexidine | Doxepin | Aflatoxin B1 |
| piclamilast | tranilast | dimethisoquin |
| Megestrol | balsalazide | romidepsin |
| Yellow Fever Vaccine | Methanol | nateglinide |
| Sulindac | Digoxin | Methotrimeprazine |
| glimepiride | Nitrazepam | Prednisolone |
| Phosgene | bendazolic acid | Methocarbamol |
| Bisacodyl | cyanoginosin LR | Dimapri |
| Disulfiram | Glutamic Acid | PI103 |
| Dimethylformamide | Cephalothin | methylbenzethonium |
| hydrazine | Strophanthidin | zileuton |
| Mefenamic Acid | alclometasone dipropionate | Methyltestosterone |
| profenamine | Vecuronium Bromide | troglitazone |
| Halcinonide | GW 3965 | Metronidazole |
| oxfendazole | wortmannin | Dequalinium |
| Lindane | Pemoline | Lasalocid |
| ONO 2235 | Cymarine | 1,3-dichloro-2-propanol |
| Stanozolol | Amantadine | Thioacetamide |
| amitraz | Morphine | Gossypol |
| cloperastine | Chlorambucil | Budesonide |
| 2-tert-butyl-9-fluoro-3,6-dihydro-7H-benz(h)imidazo(4,5-f)isoquinoline-7-one | apratoxin A | 1-hydroxycholecalciferol |
| Verapamil | Safrole | Fluocinolone Acetonide |
| Chloroform | Capsaicin | Amiodarone |
| Isoniazid | beta-cyclodextrin-benzaldehyde | bromfenac |
| Lithocholic Acid | Cyclophosphamide | Pizotyline |
| Clofibric Acid | methixene | Colchicine |
| Domperidone | Albendazole | Fluocinonide |
| U 54494A | lysophosphatidic acid | Zinc Oxide |
| benzamil | amlexanox | Bupropion |
| Trimipramine | CEP 14083 | Digitoxigenin |
| homochlorocyclizine | Diquat | Dicyclomine |
| Tolazamide | thioperamide | Estradiol |
| Methyl Methanesulfonate | Dimethylnitrosamine | Chlormadinone Acetate |
| Fludrocortisone | Amphetamine | Inosine Monophosphate |
| Proglumide | Altretamine | Methiothepin |
| systhane | Aldosterone | Chloroquine |
| Niacinamide | Naproxen | Desipramine |
| Proadifen | rimexolone | Lidoflazine |
| Pyrilamine | cetraxate | cerivastatin |
| Ibuprofen | Gentamicins | Deoxycholic Acid |
| Pyrazinamide | Minocycline | Azaperone |
| Methapyrilene | Tunicamycin | Amlodipine |
| CPG-oligonucleotide | Clomiphene | nebivolol |
| phenothiazine | Amoxicillin | hydroquinidine |
| estradiol 3-benzoate | Propafenone | Albuterol |
| aminneptin | Folic Acid | Cyclosporine |
| Estriol | 2-(4-morpholinoanilino)-6-cyclohexylaminopurine | Tacrine |

TABLE S1-continued

Molecules that regulate genes or gene products relevant to proline transport and metabolism.

| | | |
|---|---|---|
| olanzapine | tetrandrine | Epirubicin |
| Enalapril | Dexamethasone | Neostigmine |
| Histidinol | Trihexyphenidyl | triadimefon |
| Pregnenolone | eperisone | irinotecan |
| piperacetazine | Indomethacin | Isoflurophate |
| Prenylamine | Spironolactone | Diethylnitrosamine |
| Fluvoxamine | Sirolimus | 3-hydroxyacetanilide |
| Mustard Gas | alpha-Amino-3-hydroxy-5-methyl-4-isoxazolepropionic Acid | MF59 oil emulsion |
| bisphenol A | Rifabutin | Fluspirilene |
| 2-tert-butyl-9-fluoro-3,6-dihydro-7H-benz(h)imidazo(4,5-f)isoquinoline-7-one | apratoxin A | 1-hydroxycholecalciferol |
| meloxicam | anastrozole | Proscillaridin |
| Berberine | N-acetylsphingosine | leflunomide |
| Roflumilast | Bepridil | Benzo(a)pyrene |
| Mesoridazine | Oxprenolol | letrozole |
| hydroquinone | halofuginone | flunisolide |
| ubiquinol | Aflatoxins | piperlonguminine |
| halofantrine | Ethyl Methanesulfonate | lanatoside C |
| Ethambutol | Protriptyline | bromobenzene |
| calmidazolium | Monocrotaline | Etodolac |
| Thiorphan | nimesulide | Triprolidine |
| acemetacin | Spiperone | Triiodothyronine |
| Prednisone | tenidap | Prochlorperazine |
| Melatonin | Methyldopa | cobaltous chloride |
| direct black 3 | Alprazolam | monobenzone |
| KCB-1 protein, recombinant | epidermal growth factor (1-45) | Ciprofloxacin |
| 2-dichlorobenzene | gefitinib | Triamterene |
| Trifluoperazine | Zidovudine | diflorasone diacetate |
| Choline | chlorcyclizine | Carmustine |
| Hydralazine | Finasteride | Thapsigargin |
| valsartan | medrysone | Beclomethasone |
| geraniol | Tetradecanoylphorbol Acetate | Itraconazole |
| Erythromycin | Imipramine | Fendiline |
| Lovastatin | Astemizole | Dihydrotestosterone |
| 4-acetylaminofluorene | Methylprednisolone | mometasone furoate |
| Puromycin Aminonucleoside | Ceftriaxone | venlafaxine |
| nickel chloride | Chlorprothixene | pantoprazole |
| TO-901317 | Proguanil | Phenylbutazone |
| Tranexamic Acid | Clemastine | pramoxine |
| Danazol | R 848 | Cisapride |
| Diclofenac | parbendazole | oxidized-L-alpha-1-palmitoyl-2-arachidonoyl-sn-glycero-3-phosphorylcholine |
| Pyrogens | Vanadates | lansoprazole |
| Azathioprine | Mycophenolic Acid | Ethylene Glycol |
| Nefopam | Norethynodrel | clemizole |
| tripterine | nisoxetine | Tamoxifen |
| Chlormezanone | Nitrofurazone | Mefloquine |
| 2-tert-butyl-9-fluoro-3,6-dihydro-7H-benz(h)imidazo(4,5-f)isoquinoline-7-one | apratoxin A | 1-hydroxycholecalciferol |
| eticlopride | Tetracycline | Omeprazole |
| vanoxerine | Thiethylperazine | marimastat |
| dibenzazepine | lingzhi | prednicarbate |
| Desoxycorticosterone | Oxyquinoline | Cyproheptadine |
| tetrahydrotriamcinolone | Hexetidine | 4-hydroxy-2-nonenal |
| bortezomib | Captopril | Promethazine |
| Diazinon | Iproniazid | pimethixene |
| Propranolol | Vinblastine | doxofylline |
| Brefeldin A | Hydroxyzine | asperflavin |
| ursolic acid | Enoxacin | Acetazolamide |
| Nocodazole | 1-Methyl-4-phenyl-1,2,3,6-tetrahydropyridine | Saquinavir |
| Ouabain | Metergoline | Sumatriptan |
| boldine | Stavudine | N-(2-cyclohexyloxy-4-nitrophenyl)methanesulfonamide |
| Pravastatin | Nystatin | chelidonine |
| Diazepam | N,N-dimethylarginine | Perphenazine |
| dasatinib | Pergolide | Podophyllotoxin |
| Orphenadrine | Haloperidol | Ketorolac |
| Palmitic Acid | Promazine | Dizocilpine Maleate |
| Tinidazole | sodium arsenite | Furosemide |
| Diphenhydramine | Loxapine | bafilomycin A |
| Maprotiline | Propylthiouracil | Isoproterenol |
| Clopenthixol | Methamphetamine | Perhexiline |

TABLE S1-continued

Molecules that regulate genes or gene products relevant to proline transport and metabolism.

| | | |
|---|---|---|
| 4-(5-benzo(1,3)dioxol-5-yl-4-pyridin-2-yl-1H-imidazol-2-yl)benzamide | rabeprazole | Oxymetazoline |
| Pimozide | 2-methoxyestradiol | Nafenopin |
| Thioguanine | 2-(4-morpholinyl)-8-phenyl-4H-1-benzopyran-4-one | Penicillamine |
| 6-Mercaptopurine | phenacemide | Labetalol |
| Loratadine | Nordihydroguaiaretic Acid | Ethacrynic Acid |
| Nicotine | Lobeline | Phenoxybenzamine |
| Mephentermine | candesartan | fluvastatin |
| acadesine | idebenone | 6-methoxy-2-naphthylacetic acid |
| Chitosan | Fluconazole | Meclizine |
| Citalopram | Ifosfamide | Acetylcysteine |
| desloratadine | Nevirapine | Nitric Oxide |
| 2-tert-butyl-9-fluoro-3,6-dihydro-7H-benz(h)imidazo(4,5-f)isoquinoline-7-one | apratoxin A | 1-hydroxycholecalciferol |
| fragment C, human serum albumin | Risperidone | resveratrol |
| Amiloride | Soman | benzyloxycarbonylleucyl-leucyl-leucine aldehyde |
| Chlorpyrifos | Puromycin | Quinidine |
| HI 6 | alpha-Tocopherol | Streptomycin |
| 2-(1H-indazol-4-yl)-6-(4-methanesulfonylpiperazin-1-ylmethyl)-4-morpholin-4-ylthieno(3,2-d)pyrimidine | Rifampin | carvedilol |
| Staurosporine | 1-Methyl-3-isobutylxanthine | Moxisylyte |
| lamotrigine | Ketoprofen | perfluorooctanoic acid |
| MRK 003 | Vitamin K 3 | Nifedipine |
| erlotinib | Aminoglutethimide | Phytohemagglutinins |
| Methotrexate | Fluorouracil | Diltiazem |
| Ribavirin | Clozapine | |

P2. Molecules that downregulate SLC38A2:

| | | |
|---|---|---|
| ellipticine | Mitoxantrone | 4'-epidaunomycin |
| N(1)-methyl-2-lysergic acid diethylamide | midecamycin | triptolide |
| Echinomycin | Paraoxon | quelamycin |
| Busulfan | Dactinomycin | sapphyrin |
| Buformin | Deoxyglucose | Chlortetracycline |
| Phenformin | Papaverine | Alpha-Amanitin |
| Econazole | cephaelin | versipelostatin |
| Coumarins | perfosfamide | Aclarubicin |
| Polychlorinated Biphenyls | Diamide | Adenosine-5'-(N-ethylcarboxamide) |
| sesamin | Metformin | Terfenadine |
| Antazoline | Cyproterone Acetate | CpG ODN 2216 |
| iodoform | Butyric Acid | Deferoxamine |
| Nisoldipine | Cortisone | Cyclandelate |
| oltipraz | Emetine | tenofovir |
| flavopiridol | insulin-like growth factor I (57-70) | 8-aminohexylamino cAMP |
| Ketoconazole | Hycanthone | verteporfin |
| neuropeptide Y (18-36) | amprenavir | 1-(2-cyano-3,12-dioxoooleana-1,9-dien-28-oyl) imidazole |
| Guanethidine | apicidin | Ultraviolet Rays |
| ellipticine | Mitoxantrone | 4'-epidaunomycin |
| Methylcholanthrene | Dinoprostone | Sulpiride |
| Atovaquone | Ceftazidime | aluminum sulfate |
| Zinc Sulfate | dihydroquinghaosu | piperaquine |
| beta-Naphthoflavone | Methylnitronitrosoguanidine | Bezafibrate |
| Ganciclovir | Fenofibrate | Testosterone |
| tropisetron | pirinixic acid | Paclitaxel |
| trichostatin A | Triacetin | Secobarbital |
| vanadium pentoxide | Doxorubicin | Cantharidin |
| Apigenin | Mifepristone | rosiglitazone |
| Phenobarbital | anisindione | hydrastine |
| gatifloxacin | isoconazole | Lorazepam |
| Amoxapine | acidocin CH5, *Lactobacillus acidophilus* | Hemin |
| Tretinoin | Carotenoids | Grape Seed Proanthocyanidins |
| fasudil | Dimenhydrinate | fipexide |
| Immunoglobulin M | grepafloxacin | Oxazepam |
| Mebendazole | Trimethadione | blebbistatin |
| daboiatoxin | X-Rays | 3-nitropropionic acid |
| N-Methyl-3,4-methylenedioxyamphetamine | edelfosine | Metribolone |
| Piperonyl Butoxide | trilinolein | Flurbiprofen |
| Cycloheximide | cineole | Y 27632 |
| Camptothecin | Luteolin | gabapentin |

TABLE S1-continued

Molecules that regulate genes or gene products relevant to proline transport and metabolism.

| | | |
|---|---|---|
| Pentobarbital | Rotenone | Lidocaine |
| Hydrogen Peroxide | Natriuretic Peptide, C-Type | Azithromycin |
| Insulin | Nadolol | Ipratropium |
| rofecoxib | pioglitazone | 7,8-Dihydro-7,8-dihydroxybenzo(a)pyrene 9,10-oxide |
| senecionine | Paroxetine | Ethionine |
| Clonazepam | Ethisterone | Poly I-C |
| Miconazole | shikonin | Dehydrocholic Acid |
| Flunarizine | Tacrolimus | imatinib |
| Valproic Acid | naphthalene | Benzalkonium Compounds |
| Azacitidine | valdecoxib | atorvastatin |
| Clofibrate | bis(tri-n-butyltin)oxide | Genistein |
| calycanthine | ethaverine | lacidipine |
| alginic acid | Doxapram | 4-nonylphenol |
| decitabine | Platelet Activating Factor | Timolol |
| Chlordiazepoxide | Glyburide | Ranitidine |
| ellipticine | Mitoxantrone | 4'-epidaunomycin |
| vorinostat | 2,2'-(hydroxynitrosohydrazono)bis-ethanamine | Dichlororibofuranosylbenzimidazole |
| 4-(4-fluorophenyl)-2-(4-hydroxyphenyl)-5-(4-pyridyl) imidazole | Clotrimazole | Dobutamine |
| Benserazide | 4-methyl-N-(3-(4-methylimidazol-1-yl)-5-(trifluoromethyl)phenyl)-3-((4-pyridin-3-ylpyrimidin-2-yl)amino)benzamide | Amitriptyline |
| Dimethyl Sulfoxide | Nitroarginine | Malathion |
| Metaproterenol | Dacarbazine | Sarin |
| Acepromazine | acacetin | Tiapamil Hydrochloride |
| discretamine | Concanavalin A | Droperidol |
| 3-deazaneplanocin | Benperidol | Quinacrine |
| Digitoxin | Neomycin | LBH589 |
| procyanidin | Zimeldine | 8-Bromo Cyclic Adenosine Monophosphate |
| Quercetin | Atropine | U 0126 |
| dexchlorpheniramine | 2,2'-Dipyridyl | Simvastatin |
| Plicamycin | Ticlopidine | HC toxin |
| sildenafil | 1-(5-Isoquinolinesulfonyl)-2-Methylpiperazine | Famotidine |
| ochratoxin A | Vitamin E | Calcitriol |
| Phenylephrine | oxybutynin | Mitomycin |
| Lomustine | Terazosin | Ethylnitrosourea |
| Azauridine | Cytarabine | salmeterol |
| efavirenz | scriptaid | Clonidine |
| Gemfibrozil | Ascorbic Acid | SU 5402 |
| 17-(allylamino)-17-demethoxygeldanamycin | SB 203580 | Vincristine |
| Clindamycin | Pregnenolone Carbonitrile | Anisomycin |
| Losartan | Lamivudine | Ionomycin |
| Ramipril | Ofloxacin | Kainic Acid |
| NG-Nitroarginine Methyl Ester | Atenolol | gemcitabine |
| Hydroxyurea | geldanamycin | Terbutaline |
| Levodopa | sorafenib | Probucol |
| Melphalan | Tocainide | |

| Q1. Molecules that upregulate SLC38A4: | | |
|---|---|---|
| 2-methoxyestradiol | 4-acetylaminofluorene | Captopril |
| N-(2-cyclohexyloxy-4-nitrophenyl)methanesulfonamide | Hydrocortisone | Sulfaguanidine |
| ascorbate-2-phosphate | Isoniazid | 6-bromoindirubin-3'-oxime |
| Ascorbic Acid | Rifampin | Ethylene Glycol |
| Trichloroepoxypropane | SEW2871 | sparfloxacin |
| Mitomycin | troglitazone | N-Methylaspartate |
| Penicillamine | Clarithromycin | 8-aminohexylamino cAMP |
| vinclozolin | Dihydrotestosterone | Ozone |
| Nitrendipine | lapatinib | Sulfisoxazole |
| Ergocalciferols | Zalcitabine | Sirolimus |
| Dexamethasone | Calcium | Cetylpyridinium |
| Mannitol | Dextran Sulfate | Aflatoxin B1 |
| Ibuprofen | Benzethonium | Theophylline |
| 4-nonylphenol | aluminum sulfate | ibufenac |
| benoxaprofen | Rifabutin | Ciprofloxacin |
| meloxicam | Nimodipine | temsirolimus |
| methyl salicylate | Azoxymethane | cidofovir |
| cryptoxanthin | U 0126 | hydrazine |
| lead tetraacetate | torsemide | Gentian Violet |
| Lomustine | Tryptophan | Valproic Acid |

TABLE S1-continued

Molecules that regulate genes or gene products relevant to proline transport and metabolism.

| | | |
|---|---|---|
| boldine | trovafloxacin | Probenecid |
| Aspirin | flavopiridol | Dimethylnitrosamine |
| Doxorubicin | 4'-N-benzoylstaurosporine | Procarbazine |
| amprenavir | pristane | tosufloxacin |
| butenafine | 5-fluorouridine | Fluocinolone Acetonide |
| arsenic acid | Busulfan | Amphotericin B |
| rofecoxib | Hydralazine | phenethyl isothiocyanate |
| Atenolol | 2-tert-butylhydroquinone | Diethylhexyl Phthalate |
| Ethylestrenol | Niacin | Choline |
| cilostazol | vinorelbine | Epirubicin |
| chloroxylenol | Thioguanine | Chlorambucil |
| Chorionic Gonadotropin | ferric nitrilotriacetate | Physostigmine |
| Diethylnitrosamine | Indomethacin | Bithionol |
| Camptothecin | Caffeine | Nafenopin |
| Tiapamil Hydrochloride | Sparteine | Citalopram |
| Forskolin | diphenidol | Gentamicins |
| pramoxine | Oxyquinoline | Roxithromycin |
| Didanosine | Fenofibrate | Betamethasone |
| Octopamine | valsartan | Phenacetin |
| 2-methoxyestradiol | 4-acetylaminofluorene | Captopril |
| 1-Methyl-3-isobutylxanthine | LPS 9 | gefitinib |
| diloxanide furoate | estradiol 3-benzoate | Daunorubicin |
| sildenafil | Itraconazole | Acetazolamide |
| arsenic trioxide | Nortriptyline | Digitoxin |
| efavirenz | Clofibrate | 3,3',4',5-tetrachlorosalicylanilide |
| Chlorpromazine | Felodipine | ebastine |
| Gonadotropins | Mexiletine | ifenprodil |
| Phosgene | Carbimazole | Zidovudine |
| Sulfadiazine | Monocrotaline | Diethylstilbestrol |
| Etomidate | coumarin | Clomiphene |
| Methylcholanthrene | Ouabain | Bezafibrate |
| harmol | Dexfenfluramine | Rolipram |
| sorafenib | Tolazamide | Meclofenoxate |
| Heparin | Promazine | lomefloxacin |
| Acyclovir | Amoxicillin | wortmannin |
| 4-octylphenol | Dimethylformamide | Chloramphenicol |
| Mercuric Chloride | Methyldopa | Lamivudine |
| fluvastatin | Vitamin K 3 | Levonorgestrel |
| Ketoconazole | zileuton | glimepiride |
| phenothiazine | Vincristine | methyleugenol |
| Thalidomide | Fluoxetine | Simvastatin |
| zomepirac | Cefuroxime | flubendazole |
| N-nitrosomorpholine | Progesterone | Melatonin |
| Altretamine | dihydroquinghaosu | piperaquine |
| Phenytoin | 1,2,3-trichloropropane | Lithocholic Acid |
| Levodopa | Mefenamic Acid | nabumetone |
| tranilast | idebenone | Etoposide |
| Aclarubicin | Neomycin | Methotrexate |
| 1-(5-Isoquinolinesulfonyl)-2-Methylpiperazine | Chlormezanone | buflomedil |
| Moxisylyte | artemether | Cocaine |
| Bupropion | SU 5402 | monastrol |
| Sotalol | Pyrazinamide | Methyl Methanesulfonate |
| Dicyclomine | Clomipramine | Trimethadione |
| Doxycycline | acidocin CH5, *Lactobacillus acidophilus* | Dichlorvos |
| acemetacin | Nystatin | dexibuprofen |
| Dinitrofluorobenzene | Nevirapine | Stanozolol |
| 2-Acetylaminofluorene | Ethambutol | Dactinomycin |
| 2-methoxyestradiol | 4-acetylaminofluorene | Captopril |
| Naproxen | Terbutaline | Naloxone |
| Fluconazole | Fluorouracil | Amoxapine |
| Ultraviolet Rays | Sulfadoxine | Tocainide |
| Lactic Acid | 6-Mercaptopurine | Stavudine |
| Ribavirin | erlotinib | Deoxyglucose |
| Spironolactone | R 848 | Norethindrone |
| olanzapine | Atropine | |

| Q2. Molecules that downregulate SLC38A4: | | |
|---|---|---|
| bicalutamide | apicidin | Tolbutamide |
| 1-amino-2,4-dibromoanthraquinone | scriptaid | 17-(allylamino)-17-demethoxygeldanamycin |
| Go 6976 | LBH589 | cobaltous chloride |
| vorinostat | Chitosan | Cycloheximide |
| Clonidine | Tetanus Toxin | HC toxin |
| Cholera Toxin | DDT | 2,4-diaminotoluene |

TABLE S1-continued

Molecules that regulate genes or gene products relevant to proline transport and metabolism.

| | | |
|---|---|---|
| Diazinon | Colchicine | 8-Bromo Cyclic Adenosine Monophosphate |
| infliximab | senecionine | triadimefon |
| Risperidone | Hexachlorobenzene | Okadaic Acid |
| Sulindac | Omeprazole | Tubocurarine |
| Lindane | GW 501516 | Simazine |
| trichostatin A | Ethylnitrosourea | Cyclosporine |
| Coumaphos | Thapsigargin | Danazol |
| Tretinoin | pioglitazone | trilinolein |
| quintozene | Insulin | cetraxate |
| rabeprazole | 25-hydroxycholesterol | 4'-epidaunomycin |
| Sulpiride | Cyclophosphamide | Carmustine |
| Propylthiouracil | Nisoldipine | Glycerol |
| Noscapine | Lead | Tetradecanoylphorbol Acetate |
| Cardiotoxins | ovalicin | Medroxyprogesterone Acetate |
| testosterone 17 beta-cypionate | Norepinephrine | Tinidazole |
| Azathioprine | hexachlorobutadiene | mono-(2-ethylhexyl)phthalate |
| Plicamycin | Disopyramide | Ranitidine |
| Labetalol | Perhexiline | ranolazine |
| Eugenol | Alpha-Amanitin | Benzbromarone |
| famciclovir | beta-Naphthoflavone | Bromocriptine |
| Benzo(a)pyrene | cathelicidin antimicrobial peptide | rosiglitazone |
| Vecuronium Bromide | Hexachlorophene | Papaverine |
| bicalutamide | apicidin | Tolbutamide |
| trichlorofluoromethane | (melle-4)cyclosporin | Cisplatin |
| clopidogrel | ipriflavone | bendazolic acid |
| Beclomethasone | doxofylline | Diclofenac |
| Erythromycin | Flutamide | Nifedipine |
| cortisone acetate | Phenobarbital | atorvastatin |
| Bleomycin | Tunicamycin | geraniol |
| Pyrogens | Promethazine | Etidronic Acid |
| Tacrine | crotamiton | Caerulein |
| Dipyrone | celecoxib | Primidone |
| vanadium pentoxide | sodium selenate | sodium arsenite |
| Cyproterone Acetate | Ethionine | Terazosin |
| Bromhexine | Acetaminophen | Sulbactam |
| Miconazole | Malathion | Ticlopidine |
| Phenol | Tetrachlorodibenzodioxin | Cadmium |
| nitrosobenzylmethylamine | Carbamazepine | Estradiol |
| terbinafine | Paclitaxel | Haloperidol |
| Aminoglutethimide | Mestranol | Vinblastine |
| Methyltestosterone | Palmitic Acid | Carbon Tetrachloride |
| Ketorolac | Fenbendazole | Aminosalicylic Acid |
| ciprofibrate | Lovastatin | Chlormadinone Acetate |
| Cholecalciferol | Tetracaine | genipin |
| lead acetate | sulforafan | Nitrofurantoin |
| Dantrolene | ferulic acid | Methapyrilene |
| Tamoxifen | sulconazole | Clotrimazole |
| quetiapine | Isoproterenol | Idarubicin |
| Hydroxyzine | Ethinyl Estradiol | Dimenhydrinate |
| Azacitidine | Nizatidine | Clonazepam |
| Procaine | bromfenac | Pyocyanine |
| artemisinine | anastrozole | nimesulide |
| Isotretinoin | Tetracycline | Particulate Matter |
| decitabine | heliotrine | Furosemide |
| Cyproheptadine | MF59 oil emulsion | Bacitracin |
| Finasteride | Vitamin E | Salicylic Acid |
| Ethanol | Fluphenazine | Acrolein |
| Loratadine | Netilmicin | AICA ribonucleotide |
| acadesine | lansoprazole | Hydrogen Peroxide |
| Gemfibrozil | Cytarabine | Melphalan |
| Mitoxantrone | Streptomycin | compactin |
| Diazepam | Y 27632 | pantoprazole |
| bicalutamide | apicidin | Tolbutamide |
| Quercetin | Lithium | Chlorzoxazone |
| Mifepristone | carvedilol | Deoxycholic Acid |
| SB 203580 | 1,2-dilinolenoyl-3-(4-aminobutyryl)propane-1,2,3-triol | bromobenzene |
| Acarbose | fulvestrant | Doxapram |
| Metformin | Piperonyl Butoxide | leflunomide |
| Sulfadimethoxine | Poly I-C | irinotecan |
| 3-hydroxyacetanilide | acyline | bisphenol A |
| Ticrynafen | Dobutamine | Kainic Acid |
| 2-(4-morpholinyl)-8-phenyl-4H-1-benzopyran-4-one | Nitrofurazone | Imipramine |
| Minoxidil | norethindrone acetate | Calcitriol |
| Tranylcypromine | Chloroform | NG-Nitroarginine Methyl Ester |
| Lorazepam | Methimazole | Amiodarone |

TABLE S1-continued

Molecules that regulate genes or gene products relevant to proline transport and metabolism.

| | | |
|---|---|---|
| Chloroquine | Diltiazem | Doxepin |
| Sertraline | Amlodipine | Dinoprostone |
| Estriol | Ifosfamide | Amantadine |
| benzyloxycarbonylleucyl-leucyl-leucine aldehyde | 2-dichlorobenzene | Genistein |
| Carboplatin | pralidoxime | imatinib |
| Thioacetamide | Enalapril | Amitriptyline |

R1. Molecules that upregulate SLC6A7:

| | | |
|---|---|---|
| Canavanine | Lithium | sodium arsenite |
| Theobromine | amprenavir | aceclofenac |
| Digitoxin | Nomifensine | diindolylmethane |
| Ribostamycin | telenzepine | nabumetone |
| Nitrendipine | N-Methyl-3,4-methylenedioxyamphetamine | Hydroxyzine |
| valsartan | Dimethylformamide | tetrahydrotriamcinolone |
| Sulindac | Glycopyrrolate | Clopamide |
| Capsaicin | Trichloroacetic Acid | Secobarbital |
| Pentobarbital | Nadolol | Aminophylline |
| Mitomycin | Aminopyrine | sildenafil |
| triptolide | Ketoprofen | trovafloxacin |
| 4-octylphenol | alverine | Simvastatin |
| Diflunisa | Cefmetazole | Ouabain |
| Chlorambucil | Hesperidin | Bisacodyl |
| phenethyl isothiocyanate | cephalonium | lead acetate |
| Canavanine | Lithium | sodium arsenite |
| Clofibrate | Salicylates | moxonidine |
| Ticrynafen | Ibuprofen | Dyphylline |
| tranilast | Erythromycin Ethylsuccinate | Bithionol |
| Progesterone | Digoxin | Sparteine |
| buflomedil | Methacycline | esculetin |
| olanzapine | Amantadine | 4-(N-methyl-N-nitrosamino)-1-(3-pyridyl)-1-butanone |
| Lovastatin | Clarithromycin | carcinine |
| oxybutynin | benazepril | Mexiletine |
| benoxaprofen | Probucol | Azathioprine |
| Gliclazide | Foscarnet | Rifabutin |
| Metoprolol | Methyldopa | Finasteride |
| Norethindrone | amylocaine | Hydrocortisone |
| Hydrochlorothiazide | Econazole | Megestrol Acetate |
| Diethylstilbestrol | leflunomide | Sulfadoxine |
| Ethamsylate | nimesulide | bromperidol |
| Clomiphene | Podophyllotoxin | Chlordiazepoxide |
| Citric Acid | Mifepristone | Didanosine |
| Canrenoate Potassium | Chlorpromazine | Clonidine |
| 4-methyl-N-(3-(4-methylimidazol-1-yl)-5-(trifluoromethyl)phenyl)-3-((4-pyridin-3-ylpyrimidin-2-yl)amino)benzamide | Flurbiprofen | Stavudine |
| gabapentin | temafloxacin | Ethisterone |
| tenidap | compactin | Procainamide |
| Chloroquine | Ranitidine | Aconitine |
| Fluconazole | famciclovir | Sulfameter |
| ibufenac | Amlodipine | Tetracaine |
| diphenidol | vinylidene chloride | Ethanol |
| Valproic Acid | flunisolide | clinafloxacin |
| Theophylline | Pantothenic Acid | sulforafan |
| Fursultiamin | Cisapride | tracazolate |
| 2-chloropyrazine | Meptazinol | verteporfin |
| 4'-N-benzoylstaurosporine | eperisone | atorvastatin |
| estradiol 3-benzoate | Acetaminophen | tropisetron |
| gibberellic acid | oxolamine | Etoposide |
| Propidium | phenothiazine | Tropicamide |
| Nafenopin | Carbon Tetrachloride | Nimodipine |
| Noscapine | Amitriptyline | pramoxine |
| Canavanine | Lithium | sodium arsenite |
| Clomipramine | Roxarsone | pantoprazole |
| Tetracycline | Thiamphenicol | Ondansetron |
| Dicyclomine | anastrozole | oltipraz |
| Tetanus Toxin | Tiapamil Hydrochloride | Miconazole |
| Fluocinolone Acetonide | acacetin | heliotrine |
| oxfendazole | Hydroxyurea | wortmannin |
| Paroxetine | bisphenol A | dexibuprofen |
| Etidronic Acid | Nortriptyline | Droperidol |
| Ergocalciferols | pioglitazone | Lamivudine |
| Metolazone | Physostigmine | Betaxolol |
| Metoclopramide | Raloxifene | mycophenolate mofetil |

TABLE S1-continued

Molecules that regulate genes or gene products relevant to proline transport and metabolism.

| | | |
|---|---|---|
| marimastat | Cyclosporine | Cholera Toxin |
| Dexfenfluramine | Cisplatin | candesartan |
| Y 27632 | Flupenthixol | Chlorpheniramine |
| Phenobarbital | Doxazosin | TO-901317 |
| Immunoglobulin M | Chlortetracycline | Kainic Acid |
| Sulpiride | Estradiol | phenacemide |
| Minoxidil | ochratoxin A | Luteolin |
| Cimetidine | Cholecalciferol | Netilmicin |
| Lithium Chloride | Methimazole | Trifluoperazine |
| Bacitracin | Amiloride | Prazosin |
| Fluphenazine | Saquinavir | Colchicine |
| gefitinib | Itraconazole | Flavoxate |
| Vincamine | vanoxerine | Triacetin |
| Pemoline | N,N'-diphenyl-4-phenylenediamine | Gentamicins |
| oxcarbazepine | Losartan | rabeprazole |
| Azithromycin | Clobetasol | Clonazepam |
| Thioacetamide | nateglinide | Asbestos |
| Warfarin | Amiodarone | valdecoxib |
| Altretamine | Ramipril | N-nitrosomorpholine |
| lamotrigine | rituximab | zomepirac |
| Furosemide | Hydralazine | Puromycin |
| pirinixic acid | Paclitaxel | bromfenac |
| Diethylhexyl Phthalate | Aflatoxin B1 | Dexamethasone |
| Ketoconazole | Vinblastine | Thioguanine |
| Methylprednisolone | U 0126 | Calcitriol |
| bromobenzene | Ethinyl Estradiol | irinotecan |
| Haloperidol | Alpha-Amanitin | Dactinomycin |
| Vincristine | Cycloheximide | isoascorbic acid |
| Canavanine | Lithium | sodium arsenite |
| fluvastatin | Tetradecanoylphorbol Acetate | |

R2. Molecules that downregulate SLC6A7:

| | | |
|---|---|---|
| Nisoldipine | Ethylene Glycol | Nevirapine |
| Promethazine | Benzocaine | PK 11195 |
| solasodine | Hexachlorophene | Penicillin G Benzathine |
| Alprazolam | Atenolol | graveoline |
| Ciprofloxacin | lomefloxacin | Mebendazole |
| Nitrofurantoin | Cyproterone | Sulfinpyrazone |
| Cefaclor | flubendazole | Melatonin |
| Urethane | N-Methylaspartate | 3,3',4',5-tetrachlorosalicylanilide |
| Ifosfamide | zopiclone | Aminoglutethimide |
| lead tetraacetate | Glipizide | Oxymetazoline |
| Clofibric Acid | sparfloxacin | Chromium |
| balsalazide | Gentian Violet | Etiocholanolone |
| minaprine | Mesna | Penicillamine |
| Thioctic Acid | Trimethadione | Promazine |
| Omeprazole | citiolone | Hexetidine |
| Indomethacin | ipriflavone | alpha-Amino-3-hydroxy-5-methyl-4-isoxazolepropionic Acid |
| Aspirin | methyl salicylate | fenbufen |
| Vecuronium Bromide | Benzethonium | levocabastine |
| Acetazolamide | closantel | glimepiride |
| chlorinated dibenzofurans | Succinylcholine | Busulfan |
| Niacin | Sulfamethoxazole | Clotrimazole |
| Carmustine | Fonofos | Procarbazine |
| Cefotaxime | Propylthiouracil | Primaquine |
| modafinil | Tramadol | Isoproterenol |
| sodium selenate | rofecoxib | resveratrol |
| Neomycin | Enterotoxins | artemether |
| Clofazimine | Acyclovir | Rifampin |
| Griseofulvin | Methyltestosterone | salicylamide |
| chloroxylenol | Pempidine | letrozole |
| celecoxib | 6-methoxy-2-naphthylacetic acid | Diethylnitrosamine |
| Ticlopidine | Bromisovalum | Atropine |
| Isoflurophate | torsemide | Isoniazid |
| dexchlorpheniramine | Loratadine | Carboplatin |
| Cromolyn Sodium | Ritonavir | Mannitol |
| Lomustine | Vitamin E | Sulfaphenazole |
| Nisoldipine | Ethylene Glycol | Nevirapine |
| Tocainide | Iproniazid | Tetrachlorodibenzodioxin |
| Phenacetin | tazobactam | Cyclophosphamide |
| Terazosin | norethindrone acetate | 2-methoxyestradiol |
| abamectin | Azacitidine | meloxicam |
| geraniol | 2,3-dioxo-6-nitro-7-sulfamoylbenzo(f)quinoxaline | Soman |
| Debrisoquin | Verapamil | Methocarbamol |
| acemetacin | Amikacin | ubiquinol |

TABLE S1-continued

Molecules that regulate genes or gene products relevant to proline transport and metabolism.

| | | |
|---|---|---|
| Beclomethasone | oxiconazole | Biperiden |
| Doxorubicin | troglitazone | Kanamycin |
| Mefenamic Acid | ozagrel | enrofloxacin |
| 7-aminocephalosporanic acid | Fenofibrate | HI 6 |
| Chloroform | Aminosalicylic Acid | Cytarabine |
| SC 514 | Tubocurarine | nifuroxazide |
| Zidovudine | ONO 2235 | Praziquantel |
| Chlorzoxazone | Astemizole | Safrole |
| valacyclovir | Fluoxetine | Dipyridamole |
| Bezafibrate | 4-nonylphenol | Oxytetracycline |
| clopidogrel | lansoprazole | Bleomycin |
| venlafaxine | telmisartan | methylatropine |
| idebenone | Citalopram | Gossypol |
| Erythromycin | 1,5-naphthalenediamine | meropenem |
| Cinnarizine | diphemanil methylsulfate | Albendazole |
| phthalylsulfathiazole | Tranexamic Acid | Estriol |
| Cortisone | artemisinine | 1-hydroxycholecalciferol |
| tianeptine | ethotoin | Piperonyl Butoxide |
| Norfloxacin | Oxazepam | Riluzole |
| bromodichloromethane | Aztreonam | Nystatin |
| Ethambutol | 2,2'-(hydroxynitrosohydrazono)bis-ethanamine | Spironolactone |
| 4,4'-diaminodiphenylmethane | Sertraline | Naproxen |
| Azlocillin | gatifloxacin | imiquimod |
| Metronidazole | Labetalol | Diazepam |
| zaleplon | Nicotine | Daunorubicin |
| Azoxymethane | Vancomycin | Tranylcypromine |
| enzastaurin | Fludrocortisone | lactacystin |
| Maprotiline | Pilocarpine | Tacrine |
| Mitoxantrone | Cyproterone Acetate | parthenolide |
| Hydrogen Peroxide | Methylcholanthrene | Sirolimus |
| Nisoldipine | Ethylene Glycol | Nevirapine |
| quelamycin | Pyrazinamide | Pyrogallol |
| Freund's Adjuvant | Poly I-C | Doxepin |
| Tamoxifen | Prochlorperazine | Piroxicam |
| Diphenhydramine | fomepizole | Mestranol |
| Tolbutamide | Tolazamide | Roxithromycin |
| Genistein | Triamterene | imatinib |
| Prednisone | Carbimazole | pralidoxime |
| Fluorouracil | Forskolin | 17-(allylamino)-17-demethoxygeldanamycin |
| Tretinoin | Thioridazine | Levodopa |
| Bupropion | CPG-oligonucleotide | Streptozocin |
| Imipramine | Ultraviolet Rays | Melphalan |
| rosiglitazone | beta-Naphthoflavone | quintozene |
| Methotrexate | Caffeine | Epirubicin |
| 4-(5-benzo(1,3)dioxol-5-yl-4-pyridin-2-yl-1H-imidazol-2-yl)benzamide | Diclofenac | |

| S1. Molecules that upregulate DTNBP1: | | |
|---|---|---|
| SC 514 | PK 11195 | Paraoxon |
| Go 6976 | decitabine | X-Rays |
| Emetine | Prostaglandins E | Azacitidine |
| Paclitaxel | Dinoprostone | norflurane |
| benzyloxycarbonylleucyl-leucyl-leucine aldehyde | emtricitabine | tetrafluoroethylene |
| shogaol | procyanidin | Promegestone |
| Cytochalasin D | temsirolimus | Moxisylyte |
| Mianserin | iodoform | Ethanol |
| Levodopa | Carcinogens | Immunoglobulin M |
| (melle-4)cyclosporin | gatifloxacin | tenofovir |
| Staurosporine | Antibodies, Monoclonal | sapphyrin |
| Ethionine | bortezomib | enrofloxacin |
| Ecdysterone | lenalidomide | Sodium Dodecyl Sulfate |
| 2-(1H-indazol-4-yl)-6-(4-methanesulfonylpiperazin-1-ylmethyl)-4-morpholin-4-ylthieno(3,2-d)pyrimidine | epoxomicin | Estradiol |
| Hemin | Azithromycin | Buspirone |
| Carboplatin | motexafin gadolinium | BCG Vaccine |
| monastrol | Isoproterenol | Disopyramide |
| SC 514 | PK 11195 | Paraoxon |
| Inosine Monophosphate | Cytochalasin B | Antimycin A |
| Ajmaline | Sulpiride | Amitriptyline |
| 1,3-dichlorobenzene | systhane | ascorbate-2-phosphate |
| vorinostat | 8-((4-chlorophenyl)thio)cyclic-3',5'-AMP | Ethionamide |

TABLE S1-continued

Molecules that regulate genes or gene products relevant to proline transport and metabolism.

| | | |
|---|---|---|
| Spironolactone | Nifedipine | Tetrachlorodibenzodioxin |
| Poly I-C | Immunoglobulin G | Methamphetamine |
| mycophenolate mofetil | Daunorubicin | Tretinoin |
| Doxepin | Piperonyl Butoxide | dasatinib |
| acidocin CH5, *Lactobacillus acidophilus* | GW 3965 | 4-(5-benzo(1,3)dioxol-5-yl-4-pyridin-2-yl-1 H-imidazol-2-yl)benzamide |
| gefitinib | CPG-oligonucleotide | erlotinib |
| U 0126 | everolimus | peginterferon alfa-2a |
| rituximab | rosiglitazone | cerivastatin |
| letrozole | atorvastatin | benziodarone |
| troglitazone | gemcitabine | bicalutamide |
| norethindrone acetate | HI 6 | nimesulide |
| withaferin A | lead acetate | methylatropine |
| arsenic trioxide | geldanamycin | Enalapril |
| NG-Nitroarginine Methyl Ester | Bleomycin | Triiodothyronine |
| Chitosan | Cortisone | Methylprednisolone |
| Fluocinolone Acetonide | Danazol | Norethindrone |
| Cyclosporine | Imipramine | Carbamazepine |
| Methotrexate | Genistein | Quercetin |
| Aflatoxin B1 | Rolipram | Propylthiouracil |
| Phenobarbital | Tunicamycin | Hydralazine |
| Paroxetine | Flunarizine | Ranitidine |
| Benzbromarone | Clonidine | Reserpine |
| Quinidine | Tolbutamide | Chlorpropamide |
| Acetylcysteine | Pyrogallol | Sarin |
| Nitrofurantoin | Haloperidol | Ifosfamide |
| Minocycline | Doxycycline | Idarubicin |
| Sulindac | Thapsigargin | Amantadine |
| Isotretinoin | Diethylhexyl Phthalate | Ascorbic Acid |
| Azoxymethane | Methapyrilene | Metformin |
| Flutamide | Atenolol | Cadmium |

S2. Molecules that downregulate DTNBP1:

| | | |
|---|---|---|
| N (1)-methyl-2-lysergic acid diethylamide | lysophosphatidic acid | triptolide |
| Nickel | Diquat | Terbutaline |
| alpha-Amino-3-hydroxy-5-methyl-4-isoxazolepropionic Acid | Nerve Growth Factors | Propanil |
| ubiquinol | Melphalan | bis(tri-n-butyltin)oxide |
| Aphidicolin | 2-amino-1-methyl-6-phenylimidazo(4,5-b)pyridine | Acetylmuramyl-Alanyl-Isoglutamine |
| CEP 14083 | Topotecan | 4-acetylaminofluorene |
| Triazolam | coumarin | Ethambutol |
| Camptothecin | Ceftriaxone | Theophylline |
| R 848 | indole-3-carbinol | Platelet Activating Factor |
| 8-aminohexylamino CAMP | trichostatin A | Alpha-Amanitin |
| 4-hydroxytamoxifen | Pentachlorophenol | 7,8-Dihydro-7,8-dihydroxybenzo(a)pyrene 9,10-oxide |
| 1-(5-Isoquinolinesulfonyl)-2-Methylpiperazine | Cisplatin | Zinc Oxide |
| n-hexanal | Dihydrotestosterone | Ibuprofen |
| sangivamycin | Acrolein | Dactinomycin |
| sulforafan | naphthalan | Growth Hormone |
| Doxorubicin | 4-biphenylamine | cobaltous chloride |
| Cytokines | shikonin | Curcumin |
| Colchicine | cidofovir | Sirolimus |
| Tacrine | Estrogens | 8-Bromo Cyclic Adenosine Monophosphate |
| bevacizumab | Cholera Toxin | Acetaminophen |
| Phosphorylcholine | 3-deazaneplanocin | Phenacetin |
| Dichlororibofuranosylbenzimidazole | Potassium Dichromate | Plicamycin |
| quintozene | CpG ODN 2216 | 4-amino-6-hydrazino-7-beta-D-ribofuranosyl-7H-pyrrolo(2,3-d)-pyrimidine-5-carboxamide |
| fasudil | penciclovir | Benzo(a)pyrene |
| Dantrolene | Vincristine | ferric nitrilotriacetate |
| Chorionic Gonadotropin | Testosterone | phenethyl isothiocyanate |
| Hydrogel | Insulin | Acetazolamide |
| N-nitrosomorpholine | Pyrazinamide | Isoniazid |
| Caffeine | Ultraviolet Rays | Methyltestosterone |
| Cephapirin | SB 203580 | Lithium |
| Brefeldin A | N-methylpyrrolidone | Rifampin |
| N (1)-methyl-2-lysergic acid diethylamide | lysophosphatidic acid | triptolide |
| 1,2-dilinolenoyl-3-(4-aminobutyryl)propane-1,2,3-triol | Vehicle Emissions | Tetradecanoylphorbol Acetate |
| imatinib | Dexamethasone | Penicillamine |

TABLE S1-continued

Molecules that regulate genes or gene products relevant to proline transport and metabolism.

| | | |
|---|---|---|
| Vancomycin | Methylene Chloride | Deferoxamine |
| lapatinib | dibenzazepine | sunitinib |
| Roflumilast | 17-(allylamino)-17-demethoxygeldanamycin | infliximab |
| lactacystin | fluvastatin | phosphonoacetamide |
| 2,3-dioxo-6-nitro-7-sulfamoylbenzo(f)quinoxaline | pioglitazone | resveratrol |
| irinotecan | 4-nonylphenol | terbinafine |
| bromobenzene | enterotoxin B, staphylococcal | phenothiazine |
| beta-glycerophosphoric acid | AICA ribonucleotide | oxaliplatin |
| pralidoxime | ochratoxin A | bromodichloromethane |
| closantel | quelamycin | sodium arsenite |
| testosterone 17 beta-cypionate | bisphenol A | crotamiton |
| Pyrogens | Cardiotoxins | Anti-Retroviral Agents |
| Ribavirin | Immunoglobulins, Intravenous | Antigen-Antibody Complex |
| N-Methylaspartate | Ionomycin | Dinoprost |
| Medroxyprogesterone Acetate | Progesterone | Prednisolone |
| Cyproterone Acetate | Chlormadinone Acetate | Ergocalciferols |
| Ciprofloxacin | Oxyquinoline | Indomethacin |
| Luteolin | beta-Naphthoflavone | Diazepam |
| Cycloheximide | Hydroxyzine | Fluconazole |
| Miconazole | Econazole | Monocrotaline |
| Azathioprine | Chlormezanone | Omeprazole |
| Fluphenazine | Chlorpromazine | Mitomycin |
| Bithionol | Diethylnitrosamine | Cyclophosphamide |
| Chlorambucil | Chloroform | Carbon Tetrachloride |
| Vitamin K 3 | Tetracycline | Epirubicin |
| Raloxifene | Tamoxifen | Diethylstilbestrol |
| Lactic Acid | Diclofenac | Puromycin Aminonucleoside |
| Aspirin | Valproic Acid | Disulfiram |
| Mycophenolic Acid | Fenofibrate | Clofibrate |
| Bezafibrate | Atropine | Tranylcypromine |
| Methyldopa | Guanethidine | Sulfisoxazole |
| Thioacetamide | 2-Acetylaminofluorene | Formaldehyde |
| Glycerol | Lead | Hydrogen Peroxide |

T1. Molecules that upregulate NDN:

| | | |
|---|---|---|
| neuropeptide Y (18-36) | perfosfamide | decitabine |
| naphthalene | norflurane | dibenzazepine |
| trichostatin A | Papaverine | Cytochalasin D |
| tyloxapol | Methionine Sulfoximine | mycophenolate mofetil |
| Okadaic Acid | Parathyroid Hormone | beta-cyclodextrin-benzaldehyde |
| Pivampicillin | pelargonic acid | Nocodazole |
| Clodronic Acid | lonidamine | Tryptophan |
| trichlorofluoromethane | Botulinum Toxins, Type A | fazarabine |
| Edrophonium | acodazole | Tranylcypromine |
| Dibucaine | Riboflavin | Tetanus Toxin |
| Norepinephrine | Tretinoin | Ergocalciferols |
| velnacrine | diindolylmethane | tetrahydrozoline |
| Mianserin | 2,4-diaminotoluene | amylocaine |
| 1-(2-cyano-3,12-dioxooleana-1,9-dien-28-oyl) imidazole | tris(2,3-dibromopropyl)phosphate | tetrafluoroethylene |
| Puromycin Aminonucleoside | telenzepine | Isoproterenol |
| Betazole | midecamycin | Cholera Toxin |
| N-Methylscopolamine | Rolitetracycline | temsirolimus |
| Triprolidine | Fursultiamin | CPG-oligonucleotide |
| Talampicillin | Triflupromazine | LPS 9 |
| 1-amino-2,4-dibromoanthraquinone | Glycerol | dironyl |
| Isoxsuprine | Vitamin B 12 | hydrocotarnine |
| Estrone | Khellin | Dextran Sulfate |
| Cardiotoxins | solasodine | Doxorubicin |
| Sirolimus | oltipraz | iodoform |
| 2-methoxyestradiol | letrozole | Dimethyl Sulfoxide |
| dasatinib | Hydrogen Peroxide | Epirubicin |
| sertaconazole | Bupropion | gramine |
| Pregnenolone | Amitriptyline | 1-ethyl-2-benzimidazolinone |
| Cinnarizine | delsoline | Spiramycin |
| MF59 oil emulsion | Triamterene | Lynestrenol |
| ferric nitrilotriacetate | Cyclophosphamide | Bisoprolol |
| sulforafan | fenbufen | Tacrine |
| Propidium | efavirenz | sunitinib |
| phenethyl isothiocyanate | docetaxel | Roxarsone |
| 17-(dimethylaminoethylamino)-17-demethoxygeldanamycin | Vitamin E | Azacitidine |
| Albuterol | Calcitriol | Imipramine |
| neuropeptide Y (18-36) | perfosfamide | decitabine |
| Rifampin | aluminum sulfate | Heparin |

TABLE S1-continued

Molecules that regulate genes or gene products relevant to proline transport and metabolism.

| | | |
|---|---|---|
| Sulfamerazine | Bacitracin | resveratrol |
| acemetacin | bis(tri-n-butyltin)oxide | heliotrine |
| Ethambutol | cinchonine | acidocin CH5, *Lactobacillus acidophilus* |
| Diethylhexyl Phthalate | Atropine | Diazinon |
| N-methylpyrrolidone | Lamivudine | Allopurinol |
| Dapsone | Nicotine | fulvestrant |
| phosphonoacetamide | Cytokines | Paclitaxel |
| Amoxapine | Progesterone | Allantoin |
| Fenbendazole | GW 3965 | Mifepristone |
| Dimethylnitrosamine | Betahistine | Flavoxate |
| Fenoprofen | fluticasone | lapatinib |
| Androsterone | Cisplatin | Hydralazine |
| diflorasone diacetate | Alpha-Amanitin | Ethanol |
| Acetaminophen | Galantamine | N-nitrosomorpholine |
| gemcitabine | sulconazole | Pergolide |
| 2-(4-morpholinyl)-8-phenyl-4H-1-benzopyran-4-one | Propylthiouracil | Sulfadiazine |
| Pregnenolone Carbonitrile | Methimazole | Dactinomycin |
| Tetracycline | aristolochic acid I | Isotretinoin |
| Inosine Monophosphate | Doxycycline | Fluorouracil |
| Ultraviolet Rays | gefitinib | Dinoprostone |
| Norethindrone | Cytarabine | Carboplatin |
| Etoposide | Sulindac | Raloxifene |
| Tamoxifen | Metformin | |

| T2. Molecules that upregulate NDN: | | |
|---|---|---|
| scriptaid | apicidin | X-Rays |
| shikonin | Cefoperazone | Natriuretic Peptide, C-Type |
| quintozene | Methylene Chloride | monophosphoryl lipid A |
| Pindolol | 2,2'-Dipyridyl | 2,4-Dinitrophenol |
| Enterotoxins | Ethylene Oxide | naphthalan |
| vanadium pentoxide | Estrogens, Conjugated (USP) | vorinostat |
| ranolazine | Emodin | TO-901317 |
| 4,4'-diaminodiphenylmethane | Pyrazinamide | Etidronic Acid |
| Piperonyl Butoxide | N-Methylaspartate | Anti-Retroviral Agents |
| Cymarine | Fusidic Acid | Ozone |
| Ethylene Dibromide | enterotoxin B, staphylococcal | VX |
| scriptaid | apicidin | X-Rays |
| Butyric Acid | Fonofos | Deoxycholic Acid |
| testosterone 17 beta-cypionate | Rotenone | 1,2,3-trichloropropane |
| Thiethylperazine | Ampicillin | Shiga Toxin |
| Trichloroepoxypropane | 1-Methyl-3-isobutylxanthine | Parathion |
| chlorinated dibenzofurans | isoconazole | ceforanide |
| Phenobarbital | Immunoglobulins, Intravenous | Abscisic Acid |
| Fluocinolone Acetonide | alpha-Amino-3-hydroxy-5-methyl-4-isoxazolepropionic Acid | Methylnitrosourea |
| Phosgene | direct black 3 | perfluorooctane sulfonic acid |
| iturelix | Dexfenfluramine | Hydrocortisone |
| beta-glycerophosphoric acid | infliximab | lactacystin |
| valdecoxib | rosiglitazone | Creatine |
| Ranitidine | Risperidone | 1-Methyl-4-phenyl-1,2,3,6-tetrahydropyridine |
| Benzo(a)pyrene | benzyloxycarbonylleucyl-leucyl-leucine aldehyde | everolimus |
| Acrolein | Terfenadine | R 848 |
| ubiquinol | Thapsigargin | Insulin |
| Chitosan | Metolazone | temozolomide |
| Chorionic Gonadotropin | Azoxymethane | Phytohemagglutinins |
| Isoniazid | cyclobenzaprine | Cyproterone Acetate |
| 4-biphenylamine | Bleomycin | Y 27632 |
| 6-methoxy-2-naphthylacetic acid | Paroxetine | Calcium |
| Dexamethasone | Ascorbic Acid | 4-O-methyl-12-O-tetradecanoylphorbol 13-acetate |
| halofuginone | Testosterone | Hydrochloric Acid |
| Cyproheptadine | Enalapril | Ouabain |
| Urethane | Chlorpropamide | Gonadotropins |
| Moclobemide | Diethylstilbestrol | linezolid |
| Dinitrofluorobenzene | Vehicle Emissions | Corticosterone |
| LBH589 | dexchlorpheniramine | Valproic Acid |
| mono-(2-ethylhexyl)phthalate | imatinib | Lithium |
| Pyrogens | 4-dichlorobenzene | alginic acid |
| Medroxyprogesterone Acetate | Carbamazepine | Deoxyglucose |
| Benzethonium | Cefuroxime | Lactic Acid |
| 4-hydroxy-2-nonenal | Mitoxantrone | isoascorbic acid |
| Captopril | Propofol | Estradiol |
| Tolbutamide | Tetrachlorodibenzodioxin | U 0126 |

TABLE S1-continued

Molecules that regulate genes or gene products relevant to proline transport and metabolism.

| | | |
|---|---|---|
| Methylprednisolone | Phenacetin | Loratadine |
| scriptaid | apicidin | X-Rays |
| tenofovir | Dinoprost | Forskolin |
| Quercetin | Tetradecanoylphorbol Acetate | glimepiride |
| 4-(5-benzo(1,3)dioxol-5-yl-4-pyridin-2-yl-1H-imidazol-2-yl)benzamide | Vancomycin | Cycloheximide |
| Azauridine | Caffeine | Methyl Methanesulfonate |
| Tunicamycin | Monocrotaline | Fluoxetine |
| Chlormadinone Acetate | Metronidazole | Betamethasone |
| Ethinyl Estradiol | Methotrexate | Bucladesine |
| Ethionine | Folic Acid | atorvastatin |
| Amiodarone | sodium arsenite | hydrazine |
| Prednisolone | Genistein | Lovastatin |
| Trimethadione | gatifloxacin | Diazepam |
| bortezomib | Fenofibrate | Nitrofurantoin |
| Diethylnitrosamine | Neomycin | BCG Vaccine |
| Ethionamide | fluvastatin | pioglitazone |
| troglitazone | leflunomide | bisphenol A |
| Poly I-C | lonomycin | Epitestosterone |
| Cyclosporine | Indomethacin | Miconazole |
| Vincristine | Colchicine | Chlorpromazine |
| Azithromycin | Carbon Tetrachloride | Ibuprofen |
| Diclofenac | Gemfibrozil | Bezafibrate |
| Thioacetamide | | |

U1. Molecules that upregulate TP53:

| | | |
|---|---|---|
| sangivamycin | 4-amino-6-hydrazino-7-beta-D-ribofuranosyl-7H-pyrrolo(2,3-d)-pyrimidine-5-carboxamide | Curcumin |
| pirlindole | Paclitaxel | Piroxicam |
| Ethionine | Mannitol | versipelostatin |
| Caerulein | 2-Acetylaminofluorene | Ethylene Oxide |
| Dimethylnitrosamine | Acetylmuramyl-Alanyl-Isoglutamine | sapphyrin |
| Foscarnet | Sulfisoxazole | Dicloxacillin |
| 4-(N-methyl-N-nitrosamino)-1-(3-pyridyl)-1-butanone | Cefmetazole | Diclofenac |
| isoxicam | Go 6976 | thiocolchicoside |
| Oxytocin | Plicamycin | tranilast |
| alphaxalone | Moricizine | Fluorouracil |
| sangivamycin | 4-amino-6-hydrazino-7-beta-D-ribofuranosyl-7H-pyrrolo(2,3-d)-pyrimidine-5-carboxamide | Curcumin |
| 1-hydroxycholecalciferol | 1-Methyl-4-phenyl-1,2,3,6-tetrahydropyridine | Diethylhexyl Phthalate |
| Idoxuridine | Mitomycin | hexachlorobutadiene |
| Viomycin | phenoclor | Gentamicins |
| benoxaprofen | Zalcitabine | Isoniazid |
| Estradiol | lead tetraacetate | Midodrine |
| Pyrazinamide | naphthalene | Nickel |
| Spironolactone | Amiodarone | Emetine |
| Ethynodiol Diacetate | Phenobarbital | Oxyquinoline |
| Thioacetamide | bisphenol A | PI103 |
| flumequine | estradiol 3-benzoate | Methylene Chloride |
| Vecuronium Bromide | apratoxin A | Phytohemagglutinins |
| Benzo(a)pyrene | glycitein | lornoxicam |
| motexafin gadolinium | Benzethonium | Y 27632 |
| Yellow Fever Vaccine | fasudil | Netilmicin |
| flavanone | Nifedipine | Histidinol |
| (melle-4)cyclosporin | Ethambutol | Naproxen |
| Ketorolac | eseroline | testosterone 17 beta-cypionate |
| Megestrol Acetate | Acrolein | hydrastine |
| pipenzolate | Methylcholanthrene | Aristolochic Acids |
| Cyclosporine | Diethylnitrosamine | Furosemide |
| Methimazole | Nordefrin | aceclofenac |
| Oxytetracycline | Sulfaphenazole | phenacemide |
| Aconitine | Ethionamide | Methyldopa |
| Molsidomine | Botulinum Toxins | Orotic Acid |
| 1,3-dichlorobenzene | Malathion | phenothiazine |
| daidzein | Cephapirin | temafloxacin |
| artemisinine | Botulinum Toxins, Type A | Tunicamycin |
| piclamilast | Didanosine | Roflumilast |
| Epitestosterone | Soman | Metformin |
| Cefoxitin | Nomifensine | hexachloroethane |
| sulfathiazole | 4-octylphenol | Methotrexate |
| deferiprone | Mebendazole | quintozene |
| Nitrofurazone | Dihydrotestosterone | sodium arsenite |
| Sulfadoxine | Betamethasone | ethamivan |

TABLE S1-continued

Molecules that regulate genes or gene products relevant to proline transport and metabolism.

| | | |
|---|---|---|
| monophosphoryl lipid A | Lomustine | erlotinib |
| Enalapril | Ranitidine | Clotrimazole |
| sangivamycin | 4-amino-6-hydrazino-7-beta-D-ribofuranosyl-7H-pyrrolo(2,3-d)-pyrimidine-5-carboxamide | Curcumin |
| triptolide | Rifampin | Bupropion |
| Acetylcysteine | lactacystin | direct black 3 |
| HI 6 | nateglinide | 1,5-naphthalenediamine |
| tris (2,3-dibromopropyl)phosphate | Quinpirole | sildenafil |
| Captopril | Vitamin E | nimesulide |
| lead acetate | Ribostamycin | sodium selenate |
| Methapyrilene | Disulfiram | Tetradecanoylphorbol Acetate |
| Monocrotaline | Tryptophan | Forskolin |
| Mifepristone | Risperidone | Ganciclovir |
| polidocanol | Remoxipride | beta-cyclodextrin-benzaldehyde |
| N-Ac-CHAVC-NH2 | Abscisic Acid | isopyrin |
| Metribolone | 6-azathymine | Azacitidine |
| benazepril | Bethanechol | Famotidine |
| Vancomycin | diisopropyl methylphosphonate | Ethylene Dibromide |
| Fluspirilene | atorvastatin | iodoform |
| 7,8-Dihydro-7,8-dihydroxybenzo(a)pyrene 9,10-oxide | Oxyphenisatin Acetate | 1-amino-2,4-dibromoanthraquinone |
| lonidamine | Pinacidil | methylatropine |
| Estriol | Melphalan | cephaelin |
| Pirenzepine | Altretamine | beta-Naphthoflavone |
| alpha-Amino-3-hydroxy-5-methyl-4-isoxazolepropionic Acid | Cadmium | Mesna |
| Bithionol | Ibuprofen | Nafronyl |
| Tolazoline | Sotalol | Muromonab-CD3 |
| Calcitriol | amitraz | Amphotericin B |
| Cholecalciferol | Sulbactam | Insulin |
| Beclomethasone | Cardiotoxins | Azlocillin |
| SU 5416 | Selenomethionine | oxcarbazepine |
| Kanamycin | Lithium | Etodolac |
| 1,2,3-trichloropropane | Mephenytoin | Clarithromycin |
| Carboplatin | Chlorpromazine | Enoxacin |
| Azithromycin | modafinil | Cyproterone Acetate |
| hydroxytamoxifen | Moxalactam | Ciprofloxacin |
| Milrinone | Miconazole | rituximab |
| Ethinyl Estradiol | Aminosalicylic Acid | 6-Mercaptopurine |
| Freund's Adjuvant | CpG ODN 2216 | Methyltestosterone |
| Cyclophosphamide | Busulfan | nabumetone |
| sangivamycin | 4-amino-6-hydrazino-7-beta-D-ribofuranosyl-7H-pyrrolo(2,3-d)-pyrimidine-5-carboxamide | Curcumin |
| Harmaline | Diflunisal | Lincomycin |
| Azathioprine | Cyclopenthiazide | Stavudine |
| N,N'-diphenyl-4-phenylenediamine | Rolipram | Phenylalanine |
| ONO 2235 | celecoxib | 4-hydroxy-2-nonenal |
| Sulindac | lamotrigine | Ketoprofen |
| Indomethacin | Digoxin | Cytarabine |
| Baclofen | fluvastatin | cilostazol |
| Nordihydroguaiaretic Acid | Amphetamine | Penicillamine |
| Nystatin | temozolomide | dibenzazepine |
| linezolid | lacidipine | flavopiridol |
| acadesine | olanzapine | Hydroxyurea |
| Nevirapine | Chlorpyrifos | Acetazolamide |
| Streptomycin | Niacin | ciprofibrate |
| Flupenthixol | Econazole | Allopurinol |
| 17-(allylamino)-17-demethoxygeldanamycin | Amlodipine | 2,2'-Dipyridyl |
| Nicotine | Nitrendipine | Neomycin |
| edelfosine | Mycophenolic Acid | Fluphenazine |
| Sumatriptan | canadine | Edrophonium |
| acetovanillone | Doxazosin | Domperidone |
| Atropine | N-Methylaspartate | Fluconazole |
| Lovastatin | mono-(2-ethylhexyl)phthalate | U 0126 |
| Dexfenfluramine | alpha-Tocopherol | Methazolamide |
| Ketoconazole | desloratadine | Aphidicolin |
| Quercetin | Citalopram | Nadolol |
| Podophyllotoxin | Perhexiline | leflunomide |
| ferulic acid | lansoprazole | MRK 003 |
| pirinixic acid | Omeprazole | Papaverine |
| Vinblastine | Kainic Acid | Luteolin |
| 4-(5-benzo(1,3)dioxol-5-yl-4-pyridin-2-yl-1H-imidazol-2-yl)benzamide | Lisinopril | Staurosporine |
| Nimodipine | NG-Nitroarginine Methyl Ester | tenofovir |
| Finasteride | Levodopa | Paroxetine |

TABLE S1-continued

Molecules that regulate genes or gene products relevant to proline transport and metabolism.

| | | |
|---|---|---|
| carvedilol | Aminoglutethimide | Terbutaline |
| Imipramine | Clonazepam | Pregnenolone Carbonitrile |
| anastrozole | pralidoxime | |

U2. Molecules that downregulate TP53:

| | | |
|---|---|---|
| Cycloserine | monastrol | JM 3100 |
| nilutamide | Aclarubicin | 1-(5-Isoquinolinesulfonyl)-2-Methylpiperazine |
| blebbistatin | Vincristine | LBH589 |
| geldanamycin | N-benzyladenine | tridihexethyl |
| Dimethyl Sulfoxide | cyanoginosin LR | buflomedil |
| 4-acetylaminofluorene | trichostatin A | apicidin |
| Coumaphos | Cefotiam | PK 11195 |
| Prilocaine | HC toxin | Biotin |
| scriptaid | Butyric Acid | Deoxycholic Acid |
| Piracetam | 4,4'-diaminodiphenylmethane | Immunoglobulin M |
| Histamine | decitabine | Suppressor Factors, Immunologic |
| Doxycycline | Amikacin | Primaquine |
| bafilomycin A | Debrisoquin | 7-aminocephalosporanic acid |
| DDT | phenylhydrazine | Etiocholanolone |
| Simazine | 4-biphenylamine | Asbestos |
| Mycotoxins | 3-deazaneplanocin | 8-aminohexylamino CAMP |
| 9-(2-hydroxy-3-nonyl)adenine | Chlordiazepoxide | Theophylline |
| anisindione | Reserpine | geraniol |
| Bromhexine | Dobutamine | 2-(4-morpholinoanilino)-6-cyclohexylaminopurine |
| Piperonyl Butoxide | kavain | abamectin |
| pimethixene | bromodichloromethane | Sirolimus |
| halofuginone | Probucol | Clorgyline |
| Vitamin B 12 | Tetanus Toxin | ochratoxin A |
| Procainamide | diphenidol | cidofovir |
| compactin | Growth Hormone | Promegestone |
| Antibodies, Monoclonal | Bismuth | Ofloxacin |
| Eugenol | Ergocalciferols | Citric Acid |
| 1-ethyl-2-benzimidazolinone | N-Methyl-3,4-methylenedioxyamphetamine | Doxapram |
| Sparteine | adiphenine | Aflatoxin B1 |
| Valproic Acid | Sulfamonomethoxine | Cholera Toxin |
| Amoxapine | Cycloheximide | Acetaminophen |
| cineole | Phenol | Doxorubicin |
| Hydrocortisone | quelamycin | doxofylline |
| Sodium Dodecyl Sulfate | vinclozolin | Antimycin A |
| Lamivudine | Nitric Oxide | Fluoxetine |
| Ethacrynic Acid | Flavoxate | Guanethidine |
| Cycloserine | monastrol | JM 3100 |
| Dactinomycin | Lindane | vorinostat |
| Zinc Oxide | Triacetin | Methylnitrosourea |
| clinafloxacin | rifapentine | CPG-oligonucleotide |
| phensuximide | Disopyramide | benfluorex |
| Methoxsalen | Flufenamic Acid | Fusaric Acid |
| Carcinogens | irinotecan | 4-dichlorobenzene |
| Tacrine | Chlorpropamide | Tetracycline |
| Anti-Retroviral Agents | Azaperone | eburnamonine |
| methiazole | Camptothecin | Carbimazole |
| Buspirone | aluminum sulfate | Erythromycin |
| vinylidene chloride | Diltiazem | tosufloxacin |
| rauwolscine-OHPC | Buformin | pioglitazone |
| temsirolimus | Chloroquine | Colchicine |
| Ethyl Methanesulfonate | Lidocaine | Prochlorperazine |
| Nitrofurantoin | Etidronic Acid | Caffeine |
| Terazosin | Prednisolone | Dexamethasone |
| Moxisylyte | Amiloride | dexamisole |
| Alprazolam | Medroxyprogesterone | Daunorubicin |
| Fenbendazole | Deoxyglucose | methyl salicylate |
| Zidovudine | Ticlopidine | Fluocinolone Acetonide |
| enzastaurin | Procaine | Chlorambucil |
| oxybenzone | Lactic Acid | 1,1,1-trichloroethane |
| Diazinon | Flunarizine | Genistein |
| interferon alfa-2b | Pyrilamine | Clomipramine |
| romidepsin | oxiconazole | Clofibric Acid |
| 4-methyl-N-(3-(4-methylimidazol-1-yl)-5-(trifluoromethyl)phenyl)-3-((4-pyridin-3-ylpyrimidin-2-yl)amino)benzamide | meloxicam | Clemastine |
| Haloperidol | bis(tri-n-butyltin)oxide | Dothiepin |
| Metoprolol | shogaol | Aminocaproic Acids |

TABLE S1-continued

Molecules that regulate genes or gene products relevant to proline transport and metabolism.

| | | |
|---|---|---|
| 8-Bromo Cyclic Adenosine Monophosphate | n-hexanal | Clofibrate |
| Chlorpheniramine | Etoposide | hexylcaine |
| Dantrolene | Methylprednisolone | resveratrol |
| Alpha-Amanitin | epoxomicin | colforsin |
| Ascorbic Acid | Folic Acid | Safrole |
| loxoprofen | Dimethylformamide | securinine |
| letrozole | ranolazine | adalimumab |
| Cycloserine | monastrol | JM 3100 |
| X-Rays | Atenolol | Clonidine |
| naringin | Verapamil | Phenacetin |
| vinpocetine | gabapentin | Topotecan |
| Dipyridamole | Nifurtimox | Pergolide |
| Losartan | Alendronate | Gemfibrozil |
| Promazine | tianeptine | Hexachlorophene |
| Loratadine | bortezomib | 1,10-phenanthroline |
| Oxymetazoline | candesartan | Azaguanine |
| Inosine Monophosphate | pantoprazole | Granisetron |
| Pentolinium Tartrate | efavirenz | Ifosfamide |
| Methyl Methanesulfonate | sorafenib | Doxepin |
| cerivastatin | 2-(4-morpholinyl)-8-phenyl-4H-1-benzopyran-4-one | Phenylephrine |
| Propidium | Mesoridazine | ebselen |
| Aspirin | Dichlororibofuranosylbenzimidazole | Deferoxamine |
| VX | Gallamine Triethiodide | Isoflurophate |
| Clozapine | imatinib | Norepinephrine |
| Nocodazole | Metergoline | Rotenone |
| tropisetron | Simvastatin | Mianserin |
| ebastine | Sarin | Sulpiride |
| Propranolol | Gabexate | Thioridazine |
| Clindamycin | 3,3',4',5-tetrachlorosalicylanilide | Indinavir |
| Dimenhydrinate | 1-Methyl-3-isobutylxanthine | Ribavirin |
| Brefeldin A | Pravastatin | zaleplon |
| Dicumarol | valdecoxib | Terfenadine |
| Phenelzine | Timolol | Melatonin |
| Carmustine | fragment C, human serum albumin | Diazepam |
| Chloramphenicol | Nitrazepam | Shiga Toxin |
| Isoproterenol | 2-methoxyestradiol | Amitriptyline |
| Fluvoxamine | phosphonoacetamide | isoascorbic acid |
| clopidogrel | 2,3-dioxo-6-nitro-7-sulfamoylbenzo(f)quinoxaline | Albendazole |
| Labetalol | Maprotiline | Choline |
| Trihexyphenidyl | zileuton | Propylthiouracil |
| rofecoxib | venlafaxine | Ionomycin |
| SU 5402 | Tocainide | Ramipril |
| Bezafibrate | Flurbiprofen | oxybutynin |
| dasatinib | gemcitabine | gefitinib |
| Tranylcypromine | Sertraline | Thioguanine |
| Cycloserine | monastrol | JM 3100 |
| Vitamin K 3 | Promethazine | |

| V1. Molecules that upregulate PPAR-y: | | |
|---|---|---|
| rosiglitazone | 1,5-naphthalenediamine | 2-(4-morpholiny!)-8-phenyl-4H-1-benzopyran-4-one |
| N,N'-diphenyl-4-phenylenediamine | Dimaprit | Lithocholic Acid |
| Ethylestrenol | Tolazamide | benphothiamine |
| 1,3-dichlorobenzene | compactin | artemether |
| Spironolactone | Bromhexine | amineptin |
| eperisone | Halcinonide | 5-fluorouridine |
| Erythromycin | Chlorzoxazone | Cinnarizine |
| Mycotoxins | Tretinoin | Azaguanine |
| Clioquinol | acemetacin | artemisinine |
| geraniol | Carbamazepine | Am 580 |
| ONO 2235 | Tinidazole | Isosorbide |
| Praziquantel | nateglinide | Niacinamide |
| GW 3965 | SU 5416 | Dipyridamole |
| trimethylcolchicinic acid | 3,3',4',5-tetrachlorosalicylanilide | Staurosporine |
| Danazol | Stavudine | Pyrazinamide |
| Tropicamide | Curcumin | Raloxifene |
| 4-acetylaminofluorene | Pentolinium Tartrate | Colchicine |
| Dipyrone | zileuton | ipriflavone |
| Methyltestosterone | salicylamide | Thioridazine |
| Warfarin | diphenidol | Metoclopramide |
| 1-Methyl-3-isobutylxanthine | Hemin | Atractyloside |
| nabumetone | 9-(2-hydroxy-3-nonyl)adenine | Apomorphine |
| Monensin | Nisoldipine | Buthionine Sulfoximine |
| cetraxate | 4,5-dianilinophthalimide | Prochlorperazine |

TABLE S1-continued

Molecules that regulate genes or gene products relevant to proline transport and metabolism.

| | | |
|---|---|---|
| Hydralazine | Oxyquinoline | Loperamide |
| Propylthiouracil | N-acetylsphingosine | daboiatoxin |
| anisindione | ponasterone A | Citric Acid |
| Alprazolam | Estriol | pantoprazole |
| Phytohemagglutinins | diisopropyl methylphosphonate | Isocarboxazid |
| Clomipramine | dibenzazepine | Ticrynafen |
| norethindrone acetate | Granisetron | Lithium Carbonate |
| Sulfaphenazole | cyclazosin | Triacetin |
| Amoxapine | 3-nitropropionic acid | Mestranol |
| Ofloxacin | Bupropion | hydrazine |
| Penicillin G | Ifosfamide | Floxuridine |
| rosiglitazone | 1,5-naphthalenediamine | 2-(4-morpholinyl)-8-phenyl-4H-1-benzopyran-4-one |
| Tranexamic Acid | Bendroflumethiazide | idebenone |
| Mianserin | flavanone | Malathion |
| Neomycin | Aminosalicylic Acid | tosufloxacin |
| 4-(4-fluorophenyl)-2-(4-hydroxyphenyl)-5-(4-pyridyl)imidazole | Cyproterone Acetate | Ciprofloxacin |
| benoxaprofen | dexchlorpheniramine | Fludrocortisone |
| Methapyrilene | Guaifenesin | Flurandrenolone |
| Fluocinonide | trichlorofluoromethane | Terazosin |
| Histamine | 6-methoxy-2-naphthylacetic acid | Concanavalin A |
| Metformin | Ticlopidine | amitraz |
| Primidone | Idarubicin | lansoprazole |
| epigallocatechin gallate | desloratadine | Lasalocid |
| Flavoxate | doxifluridine | zopiclone |
| Sertraline | Clonazepam | Dimenhydrinate |
| Cyclosporine | Tacrolimus | Clotrimazole |
| Sulfisoxazole | bisphenol A | Cytochalasin D |
| mycophenolate mofetil | Albuterol | lactacystin |
| Triamterene | Nitrazepam | Glycine |
| Carboplatin | Vincamine | Omeprazole |
| Gossypol | Amlodipine | Nitrofurazone |
| 8-Bromo Cyclic Adenosine Monophosphate | 4-(5-benzo(1,3)dioxol-5-yl-4-pyridin-2-yl-1H-imidazol-2-yl)benzamide | romidepsin |
| Hexachlorophene | oxfendazole | gabapentin |
| Insulin | Promazine | Dinitrofluorobenzene |
| resveratrol | Acetazolamide | quetiapine |
| beta-1,3-glucan | Metribolone | Neostigmine |
| Merbromin | neuropeptide Y (18-36) | Chlorthalidone |
| Paraquat | Methimazole | Epinephrine |
| methyl salicylate | flunisolide | Bezafibrate |
| doxofylline | Aspirin | glimepiride |
| 2-Acetylaminofluorene | 1,1,1-trichloroethane | 2-(4-morpholinoanilino)-6-cyclohexylaminopurine |
| Milrinone | Ganciclovir | Gemfibrozil |
| Phenylephrine | phorbolol myristate acetate | Glipizide |
| Mefenamic Acid | Chlormezanone | leflunomide |
| Oxymetholone | abamectin | Metronidazole |
| Chlordiazepoxide | terbinafine | Triiodothyronine |
| rosiglitazone | 1,5-naphthalenediamine | 2-(4-morpholinyl)-8-phenyl-4H-1-benzopyran-4-one |
| Tamoxifen | 1-hydroxycholecalciferol | Immunotoxins |
| rabeprazole | Cadmium | cyanoginosin LR |
| Minoxidil | oxaliplatin | Budesonide |
| Fluoxetine | Safrole | lamotrigine |
| Nafcillin | Endotoxins | Epirubicin |
| Sotalol | Terfenadine | sodium arsenite |
| Trifluoperazine | Benzo(a)pyrene | MK 0591 |
| diflorasone diacetate | Diethylhexyl Phthalate | Oxymetazoline |
| Ritonavir | decitabine | Griseofulvin |
| clopidogrel | Bretylium Tosylate | 6-Mercaptopurine |
| loxoprofen | Etidronic Acid | Aflatoxins |
| CD 437 | 4-dichlorobenzene | Rifabutin |
| Nafenopin | vanoxerine | 4,4'-diaminodiphenylmethane |
| Bleomycin | Daunorubicin | Phenobarbital |
| 4-nonylphenol | Carbimazole | olmesartan |
| flubendazole | Losartan | sildenafil |
| salsolidine | blebbistatin | Methotrimeprazine |
| Calcitriol | ibufenac | Rolipram |
| iturelix | Folic Acid | Loratadine |
| Tiapamil Hydrochloride | candesartan | Desipramine |
| Norepinephrine | bromobenzene | Cholecalciferol |
| parbendazole | Ethionamide | venlafaxine |
| 8-((4-chlorophenyl)thio)cyclic-3',5'-AMP | Tolazoline | bromperidol |
| Cefoxitin | Aflatoxin B1 | Timolol |

TABLE S1-continued

Molecules that regulate genes or gene products relevant to proline transport and metabolism.

| | | |
|---|---|---|
| Anisomycin | Labetalol | Phalloidine |
| Ethacrynic Acid | trovafloxacin | Amantadine |
| Bromisovalum | bephenium hydroxynaphthoate | Protriptyline |
| Camptothecin | valdecoxib | Doxapram |
| Clemastine | Doxepin | Diethylnitrosamine |
| Procarbazine | tranilast | Gallamine Triethiodide |
| sulconazole | letrozole | diloxanide furoate |
| Phosphorylcholine | Phenacetin | marimastat |
| Clenbuterol | Lorazepam | Sulfachlorpyridazine |
| fomepizole | Amanitins | Streptozocin |
| Aminoglutethimide | Escin | Cromolyn Sodium |
| phenethyl isothiocyanate | Ketoprofen | Cefoperazone |
| Thioacetamide | Cobalt | trilinolein |
| rosiglitazone | 1,5-naphthalenediamine | 2-(4-morpholinyl)-8-phenyl-4H-1-benzopyran-4-one |
| 1-(5-Isoquinolinesulfonyl)-2-Methylpiperazine | Penicillamine | lapatinib |
| Isoniazid | rofecoxib | Quinacrine |
| bafilomycin A | Clonidine | Trihexyphenidyl |
| 4'-N-benzoylstaurosporine | Tetracycline | Triazolam |
| Quercetin | Flunarizine | Clozapine |
| Betazole | Fluspirilene | Sulpiride |
| Nordihydroguaiaretic Acid | oltipraz | celecoxib |
| Cyclophosphamide | Clofibric Acid | SB 203580 |
| Atenolol | Diazepam | Catechin |
| benzamil | Dihydroergotamine | Perhexiline |
| Propranolol | cephaelin | Y 27632 |
| Alprostadil | Deoxyglucose | Nizatidine |
| Cycloserine | Alprenolol | Metaproterenol |
| Captopril | Vincristine | wortmannin |
| Nortriptyline | imatinib | Clarithromycin |
| Choline | Famotidine | Rotenone |
| Carbachol | Vidarabine | Nocodazole |
| Phenelzine | Moxisylyte | gemcitabine |
| Paroxetine | Cocaine | Verapamil |
| Ionomycin | Deferoxamine | Haloperidol |
| olanzapine | Ramipril | Levodopa |
| Melatonin | Emetine | Podophyllotoxin |
| Maprotiline | Azacitidine | Amitriptyline |
| Nitric Oxide | Thapsigargin | Nevirapine |
| U 0126 | Dichlorvos | Allopurinol |
| Ascorbic Acid | triptolide | Atropine |
| Perphenazine | ochratoxin A | Ribavirin |
| Vitamin K 3 | Kainic Acid | Gentamicins |
| Chitosan | | |

| V2. Molecules that downregulate PPAR-Y: | | |
|---|---|---|
| troglitazone | pioglitazone | tomatidine |
| ebastine | N-Methylaspartate | Diphenhydramine |
| nifuroxazide | Betaxolol | imazalil |
| Prostaglandins E | titanium dioxide | Benzethonium |
| chloroxylenol | Mycophenolic Acid | Hydrogel |
| troglitazone | pioglitazone | tomatidine |
| oxiconazole | 8-(3-Chlorostyryl)-1,3,7-trimethylxanthine | 15-deoxy-delta(12,14)-prostaglandin J2 |
| Thiostrepton | Methylcholanthrene | Dinoprostone |
| Ibuprofen | lycorine | Gentian Violet |
| 1,2,3-trichloropropane | Itraconazole | Isoproterenol |
| Etodolac | Ketoconazole | Acetylmuramyl-Alanyl-Isoglutamine |
| Sulindac | Zidovudine | Hydrocortisone |
| pramoxine | Vinblastine | telmisartan |
| Estradiol | Fenoprofen | Adenosine-5'-(N-ethylcarboxamide) |
| Phenoxybenzamine | Isotretinoin | Fluocinolone Acetonide |
| Droperidol | atorvastatin | Foscarnet |
| Topotecan | arsenic trioxide | MRK 003 |
| Hemicholinium 3 | Ethylnitrosourea | Immunoglobulins, Intravenous |
| Acetaminophen | Valproic Acid | Methylnitrosourea |
| BCG Vaccine | carvedilol | Primaquine |
| Chlorhexidine | Chlorambucil | Ketorolac |
| gliquidone | Ceftazidime | ranolazine |
| Apazone | withaferin A | Dexamethasone |
| Finasteride | Thioguanine | Methyldopa |
| Cholera Toxin | Coumarins | 4-hydroxytamoxifen |
| Ethylene Glycol | Antigen-Antibody Complex | zardaverine |
| Nitrendipine | Methotrexate | Chorionic Gonadotropin |
| Dichlororibofuranosylbenzimidazole | Cetylpyridinium | Growth Hormone |
| Nystatin | Cortisone | Indomethacin |

TABLE S1-continued

Molecules that regulate genes or gene products relevant to proline transport and metabolism.

| | | |
|---|---|---|
| Carbon Tetrachloride | Chlorpromazine | Methoxsalen |
| fazarabine | Ambroxol | Busulfan |
| Fluconazole | Cytarabine | Digoxin |
| infliximab | lornoxicam | Diclofenac |
| cinchonine | Enoxacin | Naproxen |
| Monocrotaline | monobenzone | Remoxipride |
| Lovastatin | nimesulide | Cefuroxime |
| Ultraviolet Rays | Dobutamine | 4-octylphenol |
| riddelliine | fluvastatin | Pyrilamine |
| indole-3-carbinol | Dinoprost | monophosphoryl lipid A |
| sapphyrin | Roflumilast | Albendazole |
| Baclofen | Norethindrone | benazepril |
| phenothiazine | irbesartan | Azithromycin |
| cerivastatin | phosphonoacetamide | Disulfiram |
| Tocainide | marinobufagenin | Vanadates |
| troglitazone | pioglitazone | tomatidine |
| Tetrachlorodibenzodioxin | Dexfenfluramine | Betamethasone |
| tenidap | sparfloxacin | Poly I-C |
| 4-(N-methyl-N-nitrosamino)-1-(3-pyridyl)-1-butanone | Mebendazole | 3,3',5-triiodothyroacetic acid |
| Debrisoquin | Strophanthidin | senecionine |
| Ethinyl Estradiol | lanatoside C | Ethoxyquin |
| Fluphenazine | meloxicam | Hydroxyurea |
| shikonin | Diflunisal | alginic acid |
| Glafenine | Zalcitabine | Palmitic Acid |
| Prednisone | Simvastatin | 2-(1H-indazol-4-yl)-6-(4-methanesulfonylpiperazin-1-ylmethyl)-4-morpholin-4-ylthieno(3,2-d)pyrimidine |
| sunitinib | erlotinib | Azathioprine |
| Fenoterol | Mifepristone | geldanamycin |
| Hyaluronic Acid | Gonadotropins | Trimetazidine |
| Cimetidine | Tetrahydrocannabinol | Pravastatin |
| 1,10-phenanthroline | trichostatin A | lomefloxacin |
| beta-Naphthoflavone | Econazole | Estrogens |
| piperlonguminine | Ergocalciferols | tracazolate |
| Doxorubicin | Bisacodyl | Lamivudine |
| glycidol | Forskolin | acidocin CH5, *Lactobacillus acidophilus* |
| NSC 652287 | Cisplatin | pepstatin |
| Spiperone | Tryptophan | Kanamycin |
| vorinostat | valsartan | Lithium |
| hydroquinone | Streptomycin | 17-(allylamino)-17-demethoxygeldanamycin |
| sodium selenate | Amiodarone | Dicumarol |
| Carmustine | Metoprolol | acadesine |
| Genistein | gefitinib | Tubocurarine |
| Papaverine | Methyl Methanesulfonate | Physostigmine |
| Clofibrate | Doxazosin | Risperidone |
| Ranitidine | apicidin | Citalopram |
| fasudil | 4-methyl-N-(3-(4-methylimidazol-1-yl)-5-(trifluoromethyl)phenyl)-3-((4-pyridin-3-ylpyrimidin-2-yl)amino)benzamide | Betahistine |
| ellipticine | Miconazole | Digitoxin |
| troglitazone | pioglitazone | tomatidine |
| Diltiazem | Thiethylperazine | Chlorpyrifos |
| Furazolidone | LBH589 | diphenylpyraline |
| dasatinib | Dactinomycin | Puromycin |
| Furosemide | Promethazine | Lomustine |
| hesperetin | Mitomycin | Pyrogallol |
| Altretamine | linezolid | N-Methyl-3,4-methylenedioxyamphetamine |
| Tranylcypromine | Vitamin E | monorden |
| Ouabain | Paclitaxel | Caffeine |
| isoascorbic acid | ciprofibrate | Netilmicin |
| Azauridine | Nimodipine | pirinixic acid |
| Chloramphenicol | lysophosphatidic acid | Enalapril |
| mono-(2-ethylhexyl)phthalate | Dicyclomine | Cycloheximide |
| Imipramine | Buspirone | Alpha-Amanitin |
| Theophylline | Probucol | pralidoxime |
| Fluorouracil | irinotecan | sorafenib |
| bortezomib | | |

| W1. Molecules that upregulate TMEM27: | | |
|---|---|---|
| Mitomycin | resveratrol | cidofovir |
| NG-Nitroarginine Methyl Ester | Neomycin | Neostigmine |

TABLE S1-continued

Molecules that regulate genes or gene products relevant to proline transport and metabolism.

| | | |
|---|---|---|
| Lorazepam | flubendazole | Methocarbamol |
| Methylnitrosourea | hydrazine | Fenbendazole |
| fluvastatin | Cetylpyridinium | geraniol |
| PK 11195 | Promazine | Cymarine |
| Oxytetracycline | PI103 | testosterone 17 beta-cypionate |
| atorvastatin | Mycophenolic Acid | Famotidine |
| norethindrone acetate | salicylamide | diphenidol |
| Nitrendipine | Enterobactin | Clomipramine |
| Poly I-C | Doxorubicin | closantel |
| artemisinine | ipriflavone | Bromisovalum |
| nateglinide | Daunorubicin | Clotrimazole |
| Alprazolam | Verapamil | oxcarbazepine |
| pralidoxime | Galantamine | balsalazide |
| Nizatidine | sulfathiazole | Diazepam |
| benazepril | Moclobemide | 3-hydroxyacetanilide |
| Testosterone | Labetalol | Flunarizine |
| Baclofen | Ethinyl Estradiol | Tramadol |
| Cisplatin | Piracetam | 4,4'-diaminodiphenylmethane |
| Mitomycin | resveratrol | cidofovir |
| Tranexamic Acid | Diethylstilbestrol | Aflatoxin B1 |
| gabapentin | Methimazole | Benzo(a)pyrene |
| Hemin | Paroxetine | Clofibrate |
| olanzapine | oxybutynin | Zinc Oxide |
| 6-Mercaptopurine | Aclarubicin | Pentoxifylline |
| Finasteride | Clofibric Acid | 2-(1H-indazol-4-yl)-6-(4-methanesulfonylpiperazin-1-ylmethyl)-4-morpholin-4-ylthieno(3,2-d)pyrimidine |
| Prazosin | Stanozolol | Cimetidine |
| Busulfan | nimesulide | Simvastatin |
| Metoprolol | Secobarbital | Benzalkonium Compounds |
| Tamoxifen | Mifepristone | Amlodipine |
| Sulindac | anastrozole | Sotalol |
| Propranolol | Chloroform | Clemastine |
| Clarithromycin | Amitriptyline | quetiapine |
| geldanamycin | Prednisolone | Thiabendazole |
| moxonidine | cerivastatin | valsartan |
| Captopril | Alpha-Amanitin | Procaine |
| Spironolactone | motexafin gadolinium | Itraconazole |
| Miconazole | Econazole | Cytokines |
| leflunomide | Dimethyl Sulfoxide | erlotinib |
| Calcium | Acetaminophen | Hydroxyurea |
| Etoposide | Ethylene Glycol | Bezafibrate |
| Clobetasol | Indomethacin | Diethylhexyl Phthalate |
| Clonidine | Methotrexate | Enterotoxins |
| 2-amino-1-methyl-6-phenylimidazo(4,5-b)pyridine | Mercuric Chloride | Glycine |
| Ketoconazole | Sumatriptan | Aspirin |
| Pemoline | Chlorambucil | Fenoprofen |
| Equilin | Cyproheptadine | dibenzazepine |
| Lovastatin | Griseofulvin | Diclofenac |
| Cyclosporine | decitabine | Zinc |
| zomepirac | Carmustine | aceclofenac |
| Chlormadinone Acetate | Ibuprofen | Aminocaproic Acids |
| meloxicam | Fluphenazine | Ergocalciferols |
| Clomiphene | ochratoxin A | dexibuprofen |
| Roxarsone | Chloramphenicol | Norethindrone |
| Ribavirin | withaferin A | Diflunisal |
| Mitomycin | resveratrol | cidofovir |
| Ritonavir | Azacitidine | Sulfadimethoxine |
| enrofloxacin | Fenofibrate | monastrol |
| trichostatin A | vinylidene chloride | blebbistatin |
| Doxycycline | Vincristine | Naproxen |
| Dantrolene | Ethanol | Ramipril |
| Piroxicam | Carbamazepine | Tretinoin |
| Bromhexine | 17-(allylamino)-17-demethoxygeldanamycin | fulvestrant |
| Gemfibrozil | Carboplatin | Hydrochloric Acid |
| candesartan | Soman | Dinoprost |
| Cycloheximide | Netilmicin | Folic Acid |
| HI 6 | Sirolimus | Dimethylformamide |
| zileuton | Hydrochlorothiazide | bevacizumab |
| methylatropine | Tetracycline | pantoprazole |
| lapatinib | Quercetin | Thapsigargin |
| rofecoxib | Carbon Tetrachloride | oxaliplatin |
| Rotenone | valdecoxib | Azathioprine |
| Nicotine | Tacrine | Lactic Acid |
| Epirubicin | vorinostat | bortezomib |

TABLE S1-continued

Molecules that regulate genes or gene products relevant to proline transport and metabolism.

| | | |
|---|---|---|
| quelamycin | Fluconazole | Penicillamine |
| U 0126 | Progesterone | infliximab |
| Acetazolamide | Isotretinoin | Risperidone |
| Chlorpromazine | 4-(5-benzo(1,3)dioxol-5-yl-4-pyridin-2-yl-1H-imidazol-2-yl)benzamide | X-Rays |
| Bleomycin | | |

W2. Molecules that downregulate TMEM27:

| | | |
|---|---|---|
| oxfendazole | Oxyquinoline | Estriol |
| meropenem | chloroxylenol | Cyproterone Acetate |
| sorafenib | cyclonite | Nystatin |
| Trichloroacetic Acid | Aztreonam | pramoxine |
| Atropine | daidzein | Gentamicins |
| Menthol | Am 580 | bromodichloromethane |
| Melphalan | Fonofos | Promegestone |
| bisphenol A | Acyclovir | Bacitracin |
| sulconazole | Noscapine | Estradiol |
| Allopurinol | gefitinib | Lead |
| VX | Acetylmuramyl-Alanyl-Isoglutamine | chlorinated dibenzofurans |
| Valproic Acid | famciclovir | Fluocinolone Acetonide |
| oxfendazole | Oxyquinoline | Estriol |
| lead acetate | 4'-N-benzoylstaurosporine | 2-dichlorobenzene |
| Genistein | Diethylnitrosamine | Aphidicolin |
| hydroquinone | beta-cyclodextrin-benzaldehyde | sodium arsenite |
| SU 5402 | shikonin | Paclitaxel |
| Cephaloridine | tianeptine | compactin |
| CPG-oligonucleotide | 1,2,3-trichloropropane | 3-deazaneplanocin |
| fragment C, human serum albumin | Pravastatin | Theophylline |
| Ifosfamide | Acetylcysteine | enzastaurin |
| linalool | Thioguanine | triadimefon |
| gatifloxacin | oxaprozin | penciclovir |
| Dexamethasone | Ouabain | Perhexiline |
| Chorionic Gonadotropin | Vancomycin | lead tetraacetate |
| Metribolone | Trichloroethylene | trovafloxacin |
| Benzethonium | pioglitazone | Insulin |
| 4-nonylphenol | Flurbiprofen | Colchicine |
| Fluoxetine | Camptothecin | Cadmium |
| Cyclophosphamide | sulforafan | Monocrotaline |
| Papaverine | Danazol | Luteinizing Hormone |
| Trimethadione | Omeprazole | Fluorouracil |
| Medroxyprogesterone Acetate | Isoniazid | Disopyramide |
| aristolochic acid I | Ultraviolet Rays | Dihydrotestosterone |
| Flutamide | Methylprednisolone | rosiglitazone |
| Triiodothyronine | Bithionol | Caffeine |
| Amiodarone | Rifampin | Phenacetin |
| Tetradecanoylphorbol Acetate | Phenobarbital | Tetrachlorodibenzodioxin |

X1. Molecules that upregulate ACE2:

| | | |
|---|---|---|
| Oxytetracycline | Ethylene Dibromide | erlotinib |
| Calcium | diperodon | N-methylolacrylamide |
| Y 27632 | Fursultiamin | hydroxyachillin |
| Sulfisoxazole | Bendroflumethiazide | Terbutaline |
| Aflatoxins | Trichlormethiazide | quintozene |
| althiazide | naphthalan | Pyrogens |
| Poly I-C | acetylleucine | epitiostanol |
| 2-(4-morpholinoanilino)-6-cyclohexylaminopurine | Cytarabine | Colistin |
| 2-dichlorobenzene | Cytochalasin D | cidofovir |
| Trichloroepoxypropane | Pregnenolone | Demeclocycline |
| apratoxin A | Sulfamethazine | Humic Substances |
| Oxytetracycline | Ethylene Dibromide | erlotinib |
| Piperacillin | 4-dichlorobenzene | Dequalinium |
| Cefmetazole | ethaverine | SC 514 |
| fosfosal | vinpocetine | carbetapentane |
| Ozone | canadine | diphemanil methylsulfate |
| 1,2-dilinolenoyl-3-(4-aminobutyryl)propane-1,2,3-triol | Doxorubicin | Reserpine |
| 4-hydroxy-2-nonenal | Cinoxacin | cinchonine |
| Testosterone | Methylene Chloride | bromobenzene |
| Captopril | N-nitrosomorpholine | tyloxapol |
| Ethambutol | oxybutynin | Ipratropium |
| sertaconazole | Isoflurane | Tetradecanoylphorbol Acetate |
| Tranylcypromine | Monocrotaline | solasodine |
| Oxytocin | Cefotaxime | citiolone |
| flunisolide | Tamoxifen | Propidium |
| Amrinone | Ethanol | gefitinib |

TABLE S1-continued

Molecules that regulate genes or gene products relevant to proline transport and metabolism.

| | | |
|---|---|---|
| Biotin | Daunorubicin | Sulfamethoxypyridazine |
| Thioacetamide | Gossypol | monobenzone |
| carcinine | Ribavirin | Roxithromycin |
| bevacizumab | Phentolamine | Lobeline |
| Bromocriptine | wortmannin | Flunarizine |
| vorinostat | medrysone | 16-ketoestradiol |
| Ampicillin | Dextran Sulfate | dexibuprofen |
| Clobetasol | Mitomycin | Alpha-Amanitin |
| Tretinoin | Sulfamethoxazole | Paroxetine |
| aluminum sulfate | oxidized-L-alpha-1-palmitoyl-2-arachidonoyl-sn-glycero-3-phosphorylcholine | Dehydroepiandrosterone |
| vinclozolin | triptolide | decitabine |
| Dexamethasone | peginterferon alfa-2a | Epitestosterone |
| 4-hydroxytamoxifen | Nitrofurantoin | Cholecalciferol |
| blebbistatin | trichostatin A | Azacitidine |
| Diquat | Procainamide | Forskolin |
| Cyclophosphamide | 1-Methyl-4-phenyl-1,2,3,6-tetrahydropyridine | torsemide |
| mycophenolate mofetil | Hydroxyzine | Aflatoxin B1 |
| Mycophenolic Acid | Oxyquinoline | Hydralazine |
| LBH589 | Hemin | pralidoxime |
| Mebendazole | Cephalothin | celecoxib |
| Hydrochloric Acid | fulvestrant | docetaxel |
| Oxytetracycline | Ethylene Dibromide | erlotinib |
| pioglitazone | Enalapril | Chitosan |
| Rifampin | Carbamazepine | Dactinomycin |
| Genistein | Diazepam | Nifedipine |
| Cycloheximide | Lactic Acid | Diethylhexyl Phthalate |
| Bezafibrate | Atropine | Promethazine |
| Metformin | Formaldehyde | Isoproterenol |
| Asbestos | | |

X2. Molecules that downregulate ACE2:

| | | |
|---|---|---|
| sunitinib | polidocanol | VX |
| sorafenib | ubiquinol | Dichlorvos |
| naphthalene | 2-methoxyestradiol | Azoxymethane |
| Ganciclovir | shikonin | 1,5-naphthalenediamine |
| 6-bromoindirubin-3'-oxime | 1-amino-2,4-dibromoanthraquinone | Tacrolimus |
| Benzalkonium Compounds | Hydrogel | Niacinamide |
| Bleomycin | ferric nitrilotriacetate | Malathion |
| Shiga Toxin | Folic Acid | tris(2,3-dibromopropyl)phosphate |
| Lead | bromodichloromethane | Clodronic Acid |
| Furosemide | heliotrine | Quercetin |
| enrofloxacin | perfluorooctane sulfonic acid | Choline |
| Norfloxacin | valdecoxib | Lindane |
| testosterone 17 beta-cypionate | Allopurinol | DDT |
| Tetrachloroethylene | Ultraviolet Rays | Cadmium |
| Acrolein | lead tetraacetate | 4'-N-benzoylstaurosporine |
| Cyclosporine | imatinib | Propylthiouracil |
| Sulindac | SB 203580 | versipelostatin |
| Dihydrotestosterone | Diazinon | Cisplatin |
| sulmazole | Methapyrilene | Eugenol |
| Terfenadine | Enterotoxins | Diethylstilbestrol |
| Fluocinolone Acetonide | R 848 | Methimazole |
| enterotoxin B, staphylococcal | Theophylline | Netilmicin |
| aristolochic acid I | cyclonite | Flurbiprofen |
| chlorinated dibenzofurans | SU 5402 | infliximab |
| Estradiol | Tacrine | oxaprozin |
| Bromisovalum | Ethylnitrosourea | Papaverine |
| Tetrachlorodibenzodioxin | Dinitrofluorobenzene | Deoxyglucose |
| Prednisolone | Capsaicin | Sirolimus |
| Praziquantel | Acetaminophen | fluvastatin |
| atorvastatin | Phosgene | Fluoxetine |
| sunitinib | polidocanol | VX |
| CPG-oligonucleotide | Bacitracin | 4-(4-fluorophenyl)-2-(4-hydroxyphenyl)-5-(4-pyridyl) imidazole |
| Ethionine | Paclitaxel | rosiglitazone |
| U 0126 | trovafloxacin | Valproic Acid |
| Carboplatin | lapatinib | Isotretinoin |
| Azathioprine | Epirubicin | Naproxen |
| leflunomide | Lovastatin | bicalutamide |
| Isoniazid | Particulate Matter | Methotrexate |
| 17-(allylamino)-17-demethoxygeldanamycin | Colchicine | Vinblastine |

TABLE S1-continued

Molecules that regulate genes or gene products relevant to proline transport and metabolism.

| | | |
|---|---|---|
| Insulin | X-Rays | 2-(4-morpholinyl)-8-phenyl-4H-1-benzopyran-4-one |
| irinotecan | oxaliplatin | bisphenol A |
| arsenic trioxide | Cardiotoxins | Progesterone |
| Hydrocortisone | Cortisone | Danazol |
| Mifepristone | 1-Methyl-3-isobutylxanthine | Risperidone |
| Phenobarbital | Trimethadione | Omeprazole |
| Ifosfamide | Chlorambucil | Benzo(a)pyrene |
| Etoposide | Doxycycline | Diclofenac |
| Gemfibrozil | Hydrogen Peroxide | |

Y1. Molecules that upregulate PPAR-α:

| | | |
|---|---|---|
| Fenofibrate | N-Ac-CHAVC-NH2 | ferulic acid |
| ibufenac | Teicoplanin | 1-hydroxycholecalciferol |
| N,N'-diphenyl-4-phenylenediamine | eperisone | tranilast |
| temafloxacin | cetraxate | bromfenac |
| Ciprofloxacin | Fludrocortisone | sparfloxacin |
| Zalcitabine | Sotalol | amitraz |
| benoxaprofen | Amlodipine | Dipyrone |
| piclamilast | trovafloxacin | 1,1,1-trichloroethane |
| oxfendazole | Safrole | Acetylcysteine |
| Nafenopin | Butyric Acid | Rifabutin |
| rabeprazole | Spironolactone | Ketorolac |
| sodium arsenite | 1-(2-cyano-3,12-dioxooleana-1,9-dien-28-oyl) imidazole | methylparaben |
| Ethylestrenol | Cinnarizine | methyl salicylate |
| Sulindac | Ibuprofen | zomepirac |
| Erythromycin Ethylsuccinate | Cefsulodin | ONO 2235 |
| Fenofibrate | N-Ac-CHAVC-NH2 | ferulic acid |
| pantoprazole | Lomustine | Bromisovalum |
| Citric Acid | ipriflavone | Melatonin |
| phenylhydrazine | anastrozole | Omeprazole |
| Busulfan | zileuton | 2-Acetylaminofluorene |
| Roflumilast | beta-Naphthoflavone | Bupropion |
| hydrazine | sulfathiazole | troglitazone |
| Ergocalciferols | Sulfaphenazole | bromodichloromethane |
| Disulfiram | Azathioprine | geraniol |
| rosiglitazone | Carbamazepine | Rolipram |
| Cetylpyridinium | Perhexiline | Ethanol |
| Tacrine | Stanozolol | Amiodarone |
| Fenbendazole | Thioguanine | phenothiazine |
| Raloxifene | Erythromycin | Methylcholanthrene |
| Diethylnitrosamine | 2-nitrofluorene | flubendazole |
| bisphenol A | Ticrynafen | Methyldopa |
| Digoxin | Auranofin | zopiclone |
| sildenafil | balsalazide | Praziquantel |
| Diclofenac | Clomipramine | Propanil |
| pioglitazone | rofecoxib | Promethazine |
| Amantadine | lead acetate | Acetaminophen |
| Clofibric Acid | Pravastatin | Epitestosterone |
| Norethindrone | harman | Phenacetin |
| Nevirapine | Valproic Acid | Foscarnet |
| oxcarbazepine | deferiprone | Acetazolamide |
| Clonazepam | Neomycin | lead tetraacetate |
| imiquimod | Epirubicin | Niacinamide |
| Thiabendazole | erlotinib | Tocainide |
| zaleplon | 6-Mercaptopurine | Lovastatin |
| salicylamide | Mefenamic Acid | Ethylene Glycol |
| Aminoglutethimide | hexachloroethane | Alprazolam |
| Fluphenazine | 1,2-dilinolenoyl-3-(4-aminobutyryl)propane-1,2,3-triol | Clotrimazole |
| Clarithromycin | Indomethacin | Lidocaine |
| Methapyrilene | Griseofulvin | torsemide |
| Etoposide | 4,4'-diaminodiphenylmethane | Bithionol |
| nimesulide | Triacetin | Nisoldipine |
| Dexamethasone | Ketoconazole | 3-hydroxyacetanilide |
| terbinafine | Finasteride | Mifepristone |
| imatinib | Neostigmine | lamotrigine |
| Fenofibrate | N-Ac-CHAVC-NH2 | ferulic acid |
| MRK 003 | Citalopram | 4-biphenylamine |
| Oxymetazoline | Bezafibrate | Naproxen |
| Ofloxacin | gefitinib | Estradiol |
| Nifedipine | Sulfisoxazole | Trichloroethylene |
| fipronil | Albendazole | cryptoxanthin |
| Dimethylformamide | norethindrone acetate | Carmustine |
| Fluconazole | celecoxib | Dicloxacillin |
| Pyrogallol | Enoxacin | Bromhexine |

TABLE S1-continued

Molecules that regulate genes or gene products relevant to proline transport and metabolism.

| | | |
|---|---|---|
| Tolazamide | geldanamycin | Oxytetracycline |
| aluminum sulfate | Nitrofurantoin | Itraconazole |
| Aclarubicin | gamma-Tocopherol | Minoxidil |
| Chloroform | Choline | Caffeine |
| 4-nonylphenol | Simazine | Acyclovir |
| Streptomycin | compactin | Moxisylyte |
| tenofovir | Pyrazinamide | dexamisole |
| irinotecan | Ticlopidine | bicalutamide |
| Ivermectin | garcinol | Practolol |
| Econazole | Chlorpromazine | ovalicin |
| Gemfibrozil | closantel | Simvastatin |
| mosapride | Morphine | Sertraline |
| tosufloxacin | Gliclazide | Dexfenfluramine |
| Indinavir | Fenoprofen | trilinolein |
| fluvastatin | Curcumin | vinylidene chloride |
| Doxycycline | leflunomide | Menthol |
| diisopropyl methylphosphonate | diloxanide furoate | abamectin |
| Roxarsone | artemisinine | Staurosporine |
| Levamisole | bromobenzene | phenacemide |
| crotamiton | Metoclopramide | Propylthiouracil |
| Cytarabine | Mannitol | Miconazole |
| Gentamicins | Isoproterenol | 1-methyl-6-methoxy-dihydro-beta-carboline |
| Metronidazole | Diethylhexyl Phthalate | Pentoxifylline |
| Dichlorvos | Cefaclor | Tetrachlorodibenzodioxin |
| Benzocaine | dexchlorpheniramine | 4,5-dianilinophthalimide |
| Luteinizing Hormone | Niacin | Trichloroepoxypropane |
| ergocryptine | ponasterone A | diindolylmethane |
| ciprofibrate | Brefeldin A | Chlorambucil |
| Diazepam | Megestrol Acetate | Rolitetracycline |
| Carbon Tetrachloride | alpha-Tocopherol | Azithromycin |
| Fenofibrate | N-Ac-CHAVC-NH2 | ferulic acid |
| Quercetin | Thalidomide | Dimethylnitrosamine |
| Concanavalin A | Carbimazole | Trimethadione |
| Fluoxetine | Progesterone | Prednisone |
| nateglinide | fomepizole | Cobalt |
| Pemoline | Phenol | venlafaxine |
| Ketoprofen | dironyl | Chlorpyrifos |
| pimecrolimus | meloxicam | Cefuroxime |
| Nitrazepam | benziodarone | Lincomycin |
| acyline | valdecoxib | Cefotetan |
| 1,2,3-trichloropropane | 4-dichlorobenzene | Mexiletine |
| 17-(allylamino)-17-demethoxygeldanamycin | Ethambutol | Halothane |
| laudanosine | fazarabine | Cephalexin |
| Methylnitrosourea | Clofibrate | Am 580 |
| Aspirin | quetiapine | 2,4-diaminotoluene |
| bevacizumab | Mesna | Carboplatin |
| Eugenol | 2-(4-morpholinyl)-8-phenyl-4H-1-benzopyran-4-one | Hydroxyurea |
| 1-(5-Isoquinolinesulfonyl)-2-Methylpiperazine | bafilomycin A | Bisoprolol |
| N-(2-cyclohexyloxy-4-nitrophenyl)methanesulfonamide | Ritodrine | Ranitidine |
| atorvastatin | Dicyclomine | Levobunolol |
| Dipyridamole | Diazinon | Genistein |
| HC toxin | desloratadine | Puromycin |
| Labetalol | Zidovudine | scriptaid |
| 2-(1H-indazol-4-yl)-6-(4-methanesulfonylpiperazin-1-ylmethyl)-4-morpholin-4-ylthieno(3,2-d)pyrimidine | lansoprazole | Amitriptyline |
| Captopril | 2,2'-(hydroxynitrosohydrazono)bis-ethanamine | Doxepin |
| bromopride | vorinostat | gabapentin |
| CEP 14083 | Cimetidine | Enalapril |
| Diltiazem | Methyl Methanesulfonate | phenethyl isothiocyanate |
| chlorcyclizine | tenidap | Lamivudine |
| hydroquinone | efavirenz | Isocarboxazid |
| Fenofibrate | N-Ac-CHAVC-NH2 | ferulic acid |
| Colchicine | 6-hydroxy-2,5,7,8-tetramethylchroman-2-carboxylic acid | Clindamycin |
| Carbachol | pirinixic acid | Diflunisal |
| Cisapride | Cyclophosphamide | Flurbiprofen |
| Pentobarbital | Bromocriptine | Rifampin |
| 8-Bromo Cyclic Adenosine Monophosphate | benzyloxycarbonylleucyl-leucyl-leucine aldehyde | Zimeldine |

TABLE S1-continued

Molecules that regulate genes or gene products relevant to proline transport and metabolism.

| | | |
|---|---|---|
| LBH589 | Norfloxacin | Lisinopril |
| Atovaquone | Iproniazid | Isoniazid |
| letrozole | N-acetylsphingosine | Promazine |
| Vidarabine | Heparin | 8-aminohexylamino CAMP |
| Propranolol | Flupenthixol | Fluorouracil |
| Droperidol | Amanitins | marimastat |
| Netilmicin | Cyproheptadine | Pergolide |
| 1-Methyl-4-phenyl-1,2,3,6-tetrahydropyridine | Ethionamide | apicidin |
| Losartan | Atropine | Mebendazole |
| Secobarbital | Saquinavir | Topotecan |
| Sulpiride | Azauridine | Clonidine |
| sorafenib | Oxyquinoline | Terbutaline |
| Hydrochlorothiazide | dasatinib | gemcitabine |
| Calcitriol | | |

Y2. Molecules that downregulate PPAR-α:

| | | |
|---|---|---|
| Primidone | Trichloroacetic Acid | Proglumide |
| Tinidazole | tropisetron | Naloxone |
| Streptozocin | Capsaicin | artemether |
| Etodolac | Hexachlorophene | Ethisterone |
| Gentian Violet | bestatin | Phenobarbital |
| glimepiride | Tetracycline | vinorelbine |
| Okadaic Acid | Carotenoids | paricalcitol |
| Shiga Toxin | valacyclovir | Cortisone |
| isopyrin | versipelostatin | marinobufagenin |
| Altretamine | oxiconazole | Salicylic Acid |
| Ifosfamide | Cyproterone Acetate | Sulfamethoxazole |
| Cardiotoxins | Caerulein | Dextran Sulfate |
| fludarabine | senecionine | Methylcellulose |
| Amoxapine | idebenone | aceclofenac |
| Primidone | Trichloroacetic Acid | Proglumide |
| Aminosalicylic Acid | Paclitaxel | Doxapram |
| Tunicamycin | arsenic trioxide | Cyclosporine |
| Methiocarb | Antipyrine | Phenformin |
| Benzethonium | olanzapine | anisindione |
| lacidipine | Heptachlor Epoxide | 3-deazaneplanocin |
| Nystatin | Phalloidine | 4-octylphenol |
| Buformin | pristane | n-hexanal |
| Rotenone | Aflatoxins | Lithium Carbonate |
| Ethylnitrosourea | Papaverine | sunitinib |
| decitabine | Chloroquine | blebbistatin |
| Dimenhydrinate | lomefloxacin | Piperonyl Butoxide |
| famciclovir | doxofylline | nimetazepam |
| Isotretinoin | Norepinephrine | shikonin |
| Stavudine | Methoxsalen | Plicamycin |
| Vinblastine | Kinetin | Clemastine |
| trichostatin A | Deoxyglucose | Cholecalciferol |
| Glycine | enterotoxin I, staphylococcal | Allopurinol |
| Tranexamic Acid | bamipine | Tacrolimus |
| MF59 oil emulsion | Azacitidine | cerivastatin |
| Tretinoin | 4-hydroxy-2-nonenal | beta-glycerophosphoric acid |
| Chlormadinone Acetate | Dihydrotestosterone | Mestranol |
| candesartan | Glycerol | Canavanine |
| benazepril | Vancomycin | Estriol |
| Furosemide | Phytohemagglutinins | Benzo(a)pyrene |
| Botulinum Toxins | Nadolol | Mitomycin |
| monastrol | Azoxymethane | Aminocaproic Acids |
| picotamide | Immunoglobulin M | polidocanol |
| Ondansetron | Methotrexate | Bacitracin |
| Insulin | procyanidin | loxoprofen |
| isoascorbic acid | Chlorhexidine | Antimycin A |
| Tetradecanoylphorbol Acetate | naphthalene | Lead |
| infliximab | Nimodipine | adalimumab |
| cineole | Theophylline | Bleomycin |
| buflomedil | Aflatoxin B1 | Mianserin |
| bis(tri-n-butyltin)oxide | Glipizide | cilostazol |
| Lorazepam | Vecuronium Bromide | carvedilol |
| Dimethyl Sulfoxide | Amiloride | Malathion |
| Ascorbic Acid | Vincristine | Tiapamil Hydrochloride |
| Primidone | Trichloroacetic Acid | Proglumide |
| Ethionine | 4-amino-6-hydrazino-7-beta-D-ribofuranosyl-7H-pyrrolo(2,3-d)-pyrimidine-5-carboxamide | Buthionine Sulfoximine |
| valsartan | Echinomycin | Phenylephrine |
| Cycloheximide | Y 27632 | Reserpine |
| Isradipine | Digitoxin | Melphalan |

TABLE S1-continued

Molecules that regulate genes or gene products relevant to proline transport and metabolism.

| | | |
|---|---|---|
| cyanoginosin LR | Pregnenolone Carbonitrile | tenoxicam |
| SU 5402 | Penicillamine | Acarbose |
| Dactinomycin | fasudil | clopidogrel |
| Palmitic Acid | Paroxetine | U 0126 |
| Loratadine | Nitrendipine | Chlordiazepoxide |
| Prochlorperazine | SC 514 | Terfenadine |
| Nitric Oxide | Ritonavir | Gallamine Triethiodide |
| Emetine | Ramipril | Tubocurarine |
| Guanethidine | Verapamil | Prazosin |
| Luteolin | Buspirone | enzastaurin |
| Inosine Monophosphate | Diphenhydramine | Flunarizine |
| Camptothecin | resveratrol | Galantamine |
| Vitamin E | Haloperidol | Clozapine |
| Kainic Acid | SB 203580 | Atenolol |
| pralidoxime | Vitamin K 3 | Ionomycin |
| Deferoxamine | 4-(5-benzo(1,3)dioxol-5-yl-4-pyridin-2-yl-1H-imidazol-2-yl)benzamide | bortezomib |
| Nocodazole | | |

All patents, patent applications, and publications cited herein are incorporated herein by reference in their entirety as if recited in full herein.

The invention being thus described, it will be obvious that the same may be varied in many ways. Such variations are not to be regarded as a departure from the spirit and scope of the invention and all such modifications are intended to be included within the scope of the following claims.

CITED DOCUMENTS

1. Allen N C, et al. Systematic meta-analyses and field synopsis of genetic association studies in schizophrenia: the SzGene database. Nat Genet 2008; 40(7):827-34
2. Baker K D, Skuse D H. Adolescents and young adults with 22q11 deletion syndrome: psychopathology in an at-risk group. Br J Psychiatry 2005; 186:115-20
3. Baxter C F, et al. High proline levels in the brains of mice as related to specific learning deficits. Pharmacol Biochem Behav 1985; 22(6):1053-9
4. Bender H U, et al. Functional consequences of PRODH missense mutations. Am J Hum Genet 2005; 76:409-20
5. Bilder R M, et al. The catechol-O-methyltransferase polymorphism: relations to the tonic-phasic dopamine hypothesis and neuropsychiatric phenotypes. Neuropsychopharmacology 2004; 29(11):1943-61
6. Blanchard J J, et al. Toward the next generation of negative symptom assessments: the collaboration to advance negative symptom assessment in schizophrenia. Schizophr Bull 2011; 37(2):291-9
7. Chen J, et al. Functional analysis of genetic variation in catechol-O-methyltransferase (COMT): effects on mRNA, protein, and enzyme activity in postmortem human brain. Am J Hum Genet 2004; 75(5):807-21
8. Clelland C L, et al. Evidence for association of hyperprolinemia with schizophrenia and a measure of clinical outcome. Schizophr Res 2011; 131(1-3):139-45
9. Clelland C L, et al. Evidence that COMT genotype and proline interact on negative-symptom outcomes in schizophrenia and bipolar disorder. Translational Psychiatry 2016. In press 10. Cohen S M, Nadler J V. Proline-induced inhibition of glutamate release in hippocampal area CA1. Brain Res 1997; 769:333-9
11. Cohen S M, Nadler J V. Proline-induced potentiation of glutamate transmission. Brain Res 1997; 761:271-82
12. Crabtree G W, et al. Cytosolic Accumulation of L-Proline Disrupts GABA-Ergic Transmission through GAD Blockade. Cell Rep 2016 Oct. 4; 17(2):570-582
13. Dingman W, Sporn M B. The penetration of proline and proline derivatives into brain. J Neurochem 1959; 4(2): 148-53
14. Donnelly C L, McEvoy J P, Wilson W H, Narasimhachari N. (1996) A study of the potential confounding effects of diet, caffeine, nicotine and lorazepam on the stability of plasma and urinary homovanillic acid levels in patients with schizophrenia. Biol Psychiatry. December 15; 40(12):1218-21
15. Drake R E, Mueser K T. Co-occurring alcohol use disorder and schizophrenia. Alcohol Research & Health 2002; 26(2): 99-102
16. Drew L J, et al. The 22q11.2 microdeletion: fifteen years of insights into the genetic and neural complexity of psychiatric disorders. Int J Dev Neurosci 2011; 29(3): 259-81
17. Efrom M L. Familial hyperprolinemia. Report of a second case, associated with congenital renal malformations, hereditary hematuria and mild mental retardation, with demonstration of an enzyme defect. N Engl J Med 1965; 272:1243-54
18. Fernandez-Garcimartin H, et al. Is it possible to combine different psychotic symptom scales in bipolar disorder? Psychiatry Res 2014; 220(3):1090-3
19. Fine S E, et al. Autism spectrum disorders and symptoms in children with molecularly confirmed 22q11.2 deletion syndrome. J Autism Dev Disord 2005; 35(4):461-70
20. Goghari V M, Sponheim S R. Differential association of the COMT Val158Met polymorphism with clinical phenotypes in schizophrenia and bipolar disorder. Schizophr Res 2008; 103(1-3):186-91
21. Gogos J A, et al. The gene encoding proline dehydrogenase modulates sensorimotor gating in mice. Nat Genet 1999; 21(4):434-9
22. Gothelf D, et al. Obsessive-compulsive disorder in patients with velocardiofacial (22q11 deletion) syndrome. Am J Med Genet B Neuropsychiatr Genet. 2004; 126B (1):99-105
23. Grainger D J, Aitken S. A microtitre format assay for proline in human serum or plasma. Clin Chim Acta. 2004; 343(1-2):1 13-8
24. Guillot C R, et al. COMT Associations with Disordered Gambling and Drinking Measures. J Gambl Stud. 2015 June; 31(2): 513-524

25. Hashimoto K, et al. Decreased serum levels of D-serine in patients with schizophrenia: evidence in support of the N-methyl-D-aspartate receptor hypofunction hypothesis of schizophrenia. Arch Gen Psychiatry 2003 June; 60(6): 572-6
26. Huber-Smith M J, Nesse R, Mazhar M, McCann D S. (1986) Evaluation of plasma 3-methoxy-4-hydroxyphenylglycol. J Chromatogr. 1986 Apr. 25; 377:91-9
27. Imaizumi, A., Adachi, Y., Kawaguchi, T. et al. Genetic basis for plasma amino acid concentrations based on absolute quantification: a genome-wide association study in the Japanese population. Eur J Hum Genet 27, 621-630 (2019)
28. Inoue H, et al. Determination of total hydroxyproline and proline in human serum and urine by HPLC with fluorescence detection. Biol Pharm Bull. 1996; 19(2):163-6
29. Jacquet H, et al. Hyperprolinemia is a risk factor for schizoaffective disorder. Mol Psychiatry 2005; 10(5):479-85
30. Jimenez-Jimenez F J, et al. Neurotransmitter amino acids in cerebrospinal fluid of patients with Alzheimer's disease. J Neural Transm (Vienna) 1998; 105(2-3):269-77
31. Joober R, et al. Catechol-O-methyltransferase Val-108/158-Met gene variants associated with performance on the Wisconsin Card Sorting Test. Arch Gen Psychiatry 2002; 59(7):662-3
32. Kane J, et al. Clozapine for the treatment-resistant schizophrenic. A double-blind comparison with chlorpromazine. Arch Gen Psychiatry 1988; 45(9):789-96
33. Karayiorgou M, et al. 22q11.2 microdeletions: linking DNA structural variation to brain dysfunction and schizophrenia. Nat Rev Neurosci 2010; 11:402-16
34. Lachman H M, et al. Human catechol-O-methyltransferase pharmacogenetics: description of a functional polymorphism and its potential application to neuropsychiatric disorders. Pharmacogenetics 1996; 6(3):243-50
35. Le Boucher J, Charret C, Coudray-Lucas C, Giboudeau J, Cynober L. Amino acid determination in biological fluids by automated ion-exchange chromatography: performance of Hitachi L-8500A. Clin Chem. 1997; 43(8 Pt 1):1421-8
36. Lewis D A, et al. Dopamine transporter immunoreactivity in monkey cerebral cortex: regional, laminar, and ultrastructural localization. J Comp Neurol 2001; 432(1): 119-36
37. Liang S, et al. Determination of proline in human serum by a robust LC-MS/MS method: application to identification of human metabolites as candidate biomarkers for esophageal cancer early detection and risk stratification. Biomed. Chromatogr. 2015, 29:570-577
38. Lindenmayer J P, et al. Dimensions of psychosis in patients with bipolar mania as measured by the positive and negative syndrome scale. Psychopathology 2008; 41(4):264-70
39. Lorenz M, Paul F, Moobed M, Baumann G, Zimmermann B F, Stangl K, Stangl V. (2014) The activity of catechol-O-methyltransferase (COMT) is not impaired by high doses of epigallocatechin-3-gallate (EGCG) in vivo. Eur J Pharmacol. 2014 Oct. 5; 740:645-51. doi: 10.1016/j.ejphar.2014.06.014. Epub 2014 Jun. 24
40. Luykx J J, et al. D-amino acid aberrations in cerebrospinal fluid and plasma of smokers. Neuropsychopharmacology 2013 September; 38(10):2019-26
41. Luykx J J, et al. Genome-wide association study of NMDA receptor coagonists in human cerebrospinal fluid and plasma. Mol Psychiatry. 2015; doi: 10.1038/mp.2014.190
42. Masuda M, Tsunoda M, Yusa Y, Yamada S, Imai K. (2002) Assay of catechol-O-methyltransferase activity in human erythrocytes using norepinephrine as a natural substrate. Ann Clin Biochem. November; 39(Pt 6):589-94
43. McBride K L, Belmont J W, O'Brien W E, Amin T J, Carter S, Lee B H. (2007) Heritability of plasma amino acid levels in different nutritional states. Mol Genet Metab; 90(2):217-20
44. Mohammad M G et al. Immune cell trafficking from the brain maintains CNS immune tolerance. J Clin Invest. 2014 March; 124(3):1228-41. doi: 10.1172/JCI71544.Nadler J V. Sodium-dependent proline uptake in the rat hippocampal formation: association with ipsilateral-commissural projections of CA3 pyramidal cells. J Neurochem 1987; 49:1155-60
45. Nackley A G, Shabalina S A, Tchivileva I E, Satterfield K, Korchynskyi O, Makarov S S, Maixner W, Diatchenko L. (2006) Human catechol-O-methyltransferase haplotypes modulate protein expression by altering mRNA secondary structure. Science. December 22; 314(5807): 1930-3
46. Nickolson V J. "On" and "off" responses of K+-induced synaptosomal proline release: involvement of the sodium pump. J Neurochem 1982; 38:289-92
47. Orešič M, et al. Metabolome in schizophrenia and other psychotic disorders: a general population-based study. Genome Med 2011; 3(3):19
48. Paterlini M, et al. Transcriptional and behavioral interaction between 22q11.2 orthologs modulates schizophrenia-related phenotypes in mice. Nat Neurosci 2005; 8(11): 1586-94
49. Phang J M, et al. Disorders of proline and hydroxyproline metabolism, in Metabolic and molecular basis of inherited disease. New York, McGraw-Hill Press, 2001, pp 1821-1838
50. Pomara N, et al. Glutamate and other CSF amino acids in Alzheimer's disease. Am J Psychiatry 1992 February; 149(2):251-4
51. Raux G, et al. Involvement of hyperprolinemia in cognitive and psychiatric features of the 22q11 deletion syndrome. Hum Mol Genet 2007; 16(1):83-91
52. Renick S E, et al. The mammalian brain high-affinity L-proline transporter is enriched preferentially in synaptic vesicles in a subpopulation of excitatory nerve terminals in rat forebrain. J Neurosci 1999; 19:21-33
53. Rhee E P, et al. A genome-wide association study of the human metabolome in a community-based cohort. Cell Metab 2013 Jul. 2; 18(1):130-43.
54. Scholl-Bürgi S, et al. The relation of cerebrospinal fluid and plasma glycine levels in propionic acidaemia, a 'ketotic hyperglycinaemia'. J Inherit Metab Dis 2008 June; 31(3):395-8
55. Segall S K, Nackley A G, Diatchenko L, Lariviere W R, Lu X, Marron J S, Grabowski-Boase L, Walker J R, Slade G, Gauthier J, Bailey J S, Steffy B M, Maynard T M, Tarantino L M, Wiltshire T. (2010) Comt1 genotype and expression predicts anxiety and nociceptive sensitivity in inbred strains of mice. Genes Brain Behav. November; 9(8):933-46. doi: 10.1111/j.1601-183X.2010.00633.x
56. Shifman S, et al. A highly significant association between a COMT haplotype and schizophrenia. Am J Hum Genet 2002; 71(6):1296-302
57. Shifman S, et al. COMT: a common susceptibility gene in bipolar disorder and schizophrenia. Am J Med Genet B Neuropsychiatr Genet 2004; 128B(1):61-4

58. Sonne S C, Brady K T. Bipolar Disorder and Alcoholism. NIAAA publication 2002 November; http://pubs.niaaa.nih.gov/publications/arh26-2/103-108.htm
59. Tomiya M, et al. Alterations in serum amino acid concentrations in male and female schizophrenic patients. Clin Chim Acta 2007; 380(1-2):186-90
60. Tunbridge E M, et al. Catechol-o-methyltransferase, cognition, and psychosis: Val158Met and beyond. Biol Psychiatry 2006; 60:141-151
61. Vorstman J A, et al. Proline affects brain function in 22q11D S children with the low activity COMT 158 allele. Neuropsychopharmacology 2009; 34(3):739-46
62. Wu, G. Determination of proline by reversed-phase high-performance liquid chromatography with automated pre-column o-phthaldialdehyde derivatization. Journal of Chromatography A. Volume 641, Issue 1, 1993, Pages 168-175.
63. Yoneda Y, Roberts E. A new synaptosomal biosynthetic pathway of proline from ornithine and its negative feedback inhibition by proline. Brain Res 1982; 239:479-88
64. Zarchi O, et al. Schizophrenia-like neurophysiological abnormalities in 22q11.2 deletion syndrome and their association to COMT and PRODH genotypes. J Psychiatr Res 2013; 47(11):1623-9

What is claimed is:

1. A method for predicting the clinical response of a subject with a disorder to a solute carrier (SLC) modulator comprising:
   a) obtaining a biological sample from the subject;
   b) determining the identity of the allele(s) of the $Val^{158/108}Met$ locus associated with the COMT gene in the sample;
   wherein the presence of Val/Val is indicative of a subject who will benefit from an SLC modulator that increases proline levels, and wherein the presence of at least one Met allele is indicative of a subject who will benefit from an SLC modulator that decreases proline levels; and
   c) administering, if appropriate based on the results of step b), an effective amount of an SLC modulator to the subject to achieve an appropriate clinical response,
   wherein the disorder is selected from the group consisting of schizophrenia, bipolar disorder, schizophrenia spectrum and other psychotic disorders, 22q11.2 deletion syndrome, depressive disorders, mood disorders, Alzheimer's disease, substance use disorders, ethanol use disorders, addictive disorders, anxiety disorders, obsessive-compulsive disorders, and trauma and stressor-related disorders.

2. The method of claim 1, wherein the SLC to be modulated is selected from the group consisting of SLC6A7, SLC6A17, SLC6A20, SLC6A9, SLC7A11, SLC1A1, SLC1A2, SLC1A3, SLC1A4, SLC1A5, SLC1A6, SLC3A2, SLC7A5, SLC7A8, SLC7A13, SLC7A10, SLC17A6, SLC17A7, SLC17A8, SLC32A1, SLC36A1, SLC36A2, SLC36A4, SLC38A2, SLC38A4, SLC38A9, SLC6A1, SLC6A13, SLC6A11, SLC6A12, SLC6A5, SLC6A14, SLC6A15, SLC6A18, SLC6A19, and combinations thereof.

3. The method of claim 2, wherein the SLC to be modulated is SLC6A7.

4. The method of claim 1, wherein the SLC modulator that increases proline levels is an SLC6A7 modulator selected from the group consisting of LX-6171, Benztropine, LP-403812, 2',3,3',4',5-pentachloro-4-hydroxybiphenyl, Dronabinol, ethanol, N-Methyl-3,4-methylenedioxyamphetamine, Methionine-enkephalin, [D-Ser²]Leu-enkephalin-Thr, Leucine enkephalin, (des-Tyr)-Leucine enkephalin, Leucine enkephalinamide, [D-ser²]Leu-enkephalin-Thr, [D-Ala2, D-Leu5]Leu-enkephalin, GGFL, YGGFL, YGGFM, GFL, GGFL-NH2, YGGFLR, YGGFLRRI (dynorphin A1-8), GGFLRRI (des-Tyr-dynorphinA1-8), L-pipecolate (PIP), L-norleucine, sarcosine, Ammonium Chloride, bisphenol A, Copper, Morphine, Nicotine, Propylthiouracil, pyrachlostrobin, Imatinib mesylate, Fluoxetine, miR-205, microRNA-140, Imatinib, and combinations thereof.

5. The method of claim 4, wherein the SLC6A7 modulator is selected from the group consisting of LX-6171, Benztropine, LP-403812, and combinations thereof.

6. The method of claim 4, wherein the SLC6A7 modulator is LX-6171.

7. The method of claim 1, further comprising determining a proline level in the subject and adjusting a treatment protocol for the subject based on the determined proline level.

8. The method of claim 1, wherein the disorder is schizophrenia.

9. The method of claim 1, wherein the disorder is bipolar disorder.

10. The method of claim 1, wherein the biological sample is selected from the group consisting of a blood sample, a biopsy sample, a plasma sample, a saliva sample, a tissue sample, a serum sample, a tear sample, a sweat sample, a skin sample, a cell sample, a hair sample, an excretion sample, a waste sample, a bodily fluid sample, a nail sample, a cheek swab, a cheek cell sample, and a mucous sample.

* * * * *

UNITED STATES PATENT AND TRADEMARK OFFICE
CERTIFICATE OF CORRECTION

| | | |
|---|---|---|
| PATENT NO. | : 11,814,681 B2 | Page 1 of 1 |
| APPLICATION NO. | : 16/805410 | |
| DATED | : November 14, 2023 | |
| INVENTOR(S) | : Catherine L. Clelland and James D. Clelland | |

It is certified that error appears in the above-identified patent and that said Letters Patent is hereby corrected as shown below:

In the Specification

In Column 1, immediately before the heading "FIELD OF THE INVENTION", please insert the following heading and paragraph:
--GOVERNMENT FUNDING
This invention was made with government support under grant no. MH100219 awarded by the National Institutes of Health. The government has certain rights in the invention.--

Signed and Sealed this
Twenty-sixth Day of December, 2023

*Katherine Kelly Vidal*

Katherine Kelly Vidal
*Director of the United States Patent and Trademark Office*